US012685772B2

(12) United States Patent
Okano et al.

(10) Patent No.: US 12,685,772 B2
(45) Date of Patent: Jul. 21, 2026

(54) METHODS FOR TREATING CAPRIN-1 EXPRESSING CANCERS

(71) Applicant: TORAY INDUSTRIES, INC., Tokyo (JP)

(72) Inventors: Fumiyoshi Okano, Kamakura (JP); Daisuke Akazawa, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 669 days.

Patent file contains an affidavit/declaration under 37 CFR 1.130(b).

(21) Appl. No.: 17/910,532

(22) PCT Filed: Mar. 11, 2021

(86) PCT No.: PCT/JP2021/009796
§ 371 (c)(1),
(2) Date: Sep. 9, 2022

(87) PCT Pub. No.: WO2021/182571
PCT Pub. Date: Sep. 16, 2021

(65) Prior Publication Data
US 2023/0165957 A1    Jun. 1, 2023

(30) Foreign Application Priority Data

Mar. 12, 2020    (JP) ................................. 2020-043019

(51) Int. Cl.
| *A61K 39/395* | (2006.01) |
| *A61K 31/7068* | (2006.01) |
| *A61K 33/243* | (2019.01) |
| *A61P 35/04* | (2006.01) |

(52) U.S. Cl.
CPC ...... *A61K 39/3955* (2013.01); *A61K 31/7068* (2013.01); *A61K 33/243* (2019.01); *A61P 35/04* (2018.01)

(58) Field of Classification Search
CPC ............ A61K 39/3955; A61K 31/7068; A61K 33/243; C07K 2317/24
See application file for complete search history.

(56) References Cited

U.S. PATENT DOCUMENTS

| 5,595,756 | A | 1/1997 | Bally et al. |
| 8,709,418 | B2 * | 4/2014 | Okano ................ C07K 16/3015 530/389.7 |
| 8,828,398 | B2 * | 9/2014 | Kobayashi .............. A61P 35/02 424/139.1 |
| 8,911,740 | B2 * | 12/2014 | Saito ................ A61K 39/39533 424/139.1 |
| 8,937,160 | B2 * | 1/2015 | Kobayashi ............. C07K 16/30 530/387.1 |
| 9,115,200 | B2 * | 8/2015 | Okano ................ C07K 16/3053 |

| 9,175,074 | B2 | 11/2015 | Okano et al. |
| 9,180,187 | B2 * | 11/2015 | Ido ........................... A61P 35/02 |
| 9,180,188 | B2 * | 11/2015 | Kobayashi .............. A61P 43/00 |
| 9,181,334 | B2 * | 11/2015 | Kobayashi ....... A61K 39/39558 |
| 9,181,348 | B2 | 11/2015 | Kobayashi et al. |
| 9,260,513 | B2 | 2/2016 | Kobayashi et al. |
| 9,266,958 | B2 | 2/2016 | Kobayashi et al. |
| 9,273,128 | B2 | 3/2016 | Okano et al. |
| 9,273,130 | B2 * | 3/2016 | Kobayashi .............. A61P 43/00 |
| 9,412,192 | B2 | 8/2016 | Mandel et al. |
| 9,416,192 | B2 | 8/2016 | Okano et al. |
| 9,416,193 | B2 * | 8/2016 | Saito ............... A61K 39/39558 |
| 9,428,581 | B2 | 8/2016 | Saito et al. |
| 9,473,993 | B2 | 10/2016 | Sachs et al. |
| 9,573,993 | B2 * | 2/2017 | Okano ................... C07K 16/18 |
| 9,862,774 | B2 * | 1/2018 | Okano ................... A61P 35/00 |
| 9,982,059 | B2 | 5/2018 | Okano et al. |
| 10,946,093 | B2 | 3/2021 | Junttila |
| 12,274,745 | B2 | 4/2025 | Okano et al. |
| 2005/0019845 | A1 | 1/2005 | Harkins et al. |
| 2011/0256144 | A1 | 10/2011 | Okano et al. |
| 2012/0294860 | A1 | 11/2012 | Ido et al. |
| 2012/0301471 | A1 | 11/2012 | Kobayashi et al. |
| 2012/0321641 | A1 | 12/2012 | Okano et al. |
| 2013/0045210 | A1 | 2/2013 | Kobayashi et al. |
| 2013/0071398 | A1 | 3/2013 | Saito et al. |
| 2014/0154261 | A1 | 6/2014 | Okano et al. |

(Continued)

FOREIGN PATENT DOCUMENTS

| EP | 2 322 221 A1 | 5/2011 |
| EP | 2 324 842 A1 | 5/2011 |

(Continued)

OTHER PUBLICATIONS

Lloyd et al., Protein Engineering, Design & Selection 22:159-168, 2009. (Year: 2009).*
https://en.wikipedia.org/wiki/List_of_cancer_types—accessed May 22, 2020. (Year: 2020).*
https://www.cancer.gov/about-cancer/understanding/what-is-cancer; accessed May 22, 2020. (Year: 2020).*
Http://www.cancer.gov/about-cancer/understanding/what-is-cancer; accessed May 22, 2020 (Year: 2020).*

(Continued)

*Primary Examiner* — Elly-Gerald Stoica

(74) *Attorney, Agent, or Firm* — Birch, Stewart, Kolasch & Birch, LLP

(57) ABSTRACT

An object of the present invention is to provide a medicament for treatment and/or prevention of cancer. The present invention provides a medicament for treatment and/or prevention of cancer in a cancer patient with a previous history of another cancer treatment, comprising an antibody or a fragment thereof having an immunological reactivity with CAPRIN-1 protein, and a pyrimidine-based drug and cisplatin together or separately in combination.

11 Claims, No Drawings

Specification includes a Sequence Listing.

(56) References Cited

U.S. PATENT DOCUMENTS

| | | |
|---|---|---|
| 2014/0178373 A1 | 6/2014 | Kobayashi et al. |
| 2014/0186359 A1 | 7/2014 | Okano et al. |
| 2014/0193434 A1 | 7/2014 | Kobayashi et al. |
| 2014/0199311 A1 | 7/2014 | Kobayashi et al. |
| 2014/0271634 A1 | 9/2014 | Sliwkowski et al. |
| 2015/0004171 A1 | 1/2015 | Kobayashi et al. |
| 2015/0044221 A1 | 2/2015 | Kobayashi et al. |
| 2015/0050283 A1 | 2/2015 | Okano et al. |
| 2015/0299314 A1 | 10/2015 | Saito et al. |
| 2016/0297889 A1 | 10/2016 | Okano et al. |
| 2016/0354499 A1 | 12/2016 | Ghanbari et al. |
| 2017/0002090 A1 | 1/2017 | Wang et al. |
| 2017/0095571 A1 | 4/2017 | Ponte et al. |
| 2018/0000865 A1 | 1/2018 | Weissman et al. |
| 2018/0094322 A1 | 4/2018 | Dalerba et al. |
| 2018/0169230 A1 | 6/2018 | Adams et al. |
| 2018/0312603 A1 | 11/2018 | Okano et al. |
| 2018/0362443 A1 | 12/2018 | Lavallee et al. |
| 2020/0054762 A1 | 2/2020 | Okano et al. |
| 2021/0121562 A1 | 4/2021 | Okano et al. |
| 2022/0072167 A1 | 3/2022 | Ludwig et al. |
| 2023/0129035 A1 | 4/2023 | Okano et al. |
| 2023/0139178 A1 | 5/2023 | Okano |
| 2023/0140155 A1 | 5/2023 | Okano |
| 2023/0159635 A1 | 5/2023 | Okano |
| 2023/0165957 A1 | 6/2023 | Okano et al. |
| 2025/0228937 A1 | 7/2025 | Okano et al. |

FOREIGN PATENT DOCUMENTS

| | | |
|---|---|---|
| EP | 2 532 367 A1 | 12/2012 |
| EP | 2 301 528 B1 | 4/2013 |
| EP | 2 818 481 A1 | 12/2014 |
| EP | 2 818 482 A1 | 12/2014 |
| EP | 2 832 365 A1 | 2/2015 |
| EP | 2 832 366 A1 | 2/2015 |
| EP | 2 818 481 B1 | 8/2019 |
| EP | 3 777 888 A1 | 2/2021 |
| EP | 4 119 156 A1 | 1/2023 |
| EP | 4 119 158 A1 | 1/2023 |
| JP | 2005-512961 A | 5/2005 |
| JP | 2007-527403 A | 9/2007 |
| JP | 2015-502958 A | 1/2015 |
| JP | 2015-127308 A | 7/2015 |
| JP | 2017-510548 A | 4/2017 |
| JP | 2017-535548 A | 11/2017 |
| JP | 2018-502892 A | 2/2018 |
| JP | 2018-516263 A | 6/2018 |
| JP | 2018-518476 A | 7/2018 |
| JP | 2018-527383 A | 9/2018 |
| JP | 2019-504029 A | 2/2019 |
| JP | 2019-527698 A | 10/2019 |
| JP | 2022-516170 A | 2/2022 |
| KR | 10-2014-0130670 A | 11/2014 |
| WO | WO 03/024442 A2 | 3/2003 |
| WO | WO 2009/142810 A2 | 11/2009 |
| WO | WO 2010/016526 A1 | 2/2010 |
| WO | WO 2010/080345 A1 | 7/2010 |
| WO | WO 2011/096517 A1 | 8/2011 |
| WO | WO 2011/096519 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/096535 A1 | 8/2011 |
| WO | WO 2013/018883 A1 | 2/2013 |
| WO | WO 2013/018889 A1 | 2/2013 |
| WO | WO 2013/018891 A1 | 2/2013 |
| WO | WO 2013/018892 A1 | 2/2013 |
| WO | WO 2013/018894 A1 | 2/2013 |
| WO | WO 2013/086260 A2 | 6/2013 |
| WO | WO 2013/125630 A1 | 8/2013 |
| WO | WO 2013/125636 A1 | 8/2013 |
| WO | WO 2013/125654 A1 | 8/2013 |
| WO | WO 2013/147176 A1 | 10/2013 |
| WO | WO 2014/195852 A1 | 12/2014 |
| WO | WO 2015/020212 A1 | 2/2015 |
| WO | WO 2015/112749 A2 | 7/2015 |
| WO | WO 2016/004875 A1 | 1/2016 |
| WO | WO 2016/077227 A2 | 5/2016 |
| WO | WO 2016/193955 A1 | 12/2016 |
| WO | WO 2017/031367 A1 | 2/2017 |
| WO | WO 2017/112838 A1 | 6/2017 |
| WO | WO 2018/023197 A1 | 2/2018 |
| WO | WO 2018/079740 A1 | 5/2018 |
| WO | WO 2018/213302 A1 | 11/2018 |
| WO | WO 2018/234879 A1 | 12/2018 |
| WO | WO 2019/155448 A1 | 8/2019 |
| WO | WO 2019/189780 A1 | 10/2019 |
| WO | WO 2020/000704 A1 | 1/2020 |
| WO | WO 2021/154761 A1 | 8/2021 |
| WO | WO 2021/182570 A1 | 9/2021 |
| WO | WO 2021/182571 A1 | 9/2021 |
| WO | WO 2021/182572 A1 | 9/2021 |
| WO | WO 2021/182573 A1 | 9/2021 |
| WO | WO 2021/182574 A1 | 9/2021 |
| WO | WO 2022/270523 A1 | 12/2022 |
| WO | WO 2022/270524 A1 | 12/2022 |
| WO | WO 2023/008459 A1 | 2/2023 |
| WO | WO 2023/008461 A1 | 2/2023 |
| WO | WO 2023/008462 A1 | 2/2023 |
| WO | WO 2023/033129 A1 | 3/2023 |
| WO | WO 2025/058000 A1 | 3/2025 |

OTHER PUBLICATIONS

"A Study of TRK-950 in Combinations With Anti-Cancer Treatment Regimens in Patients With Advanced Solid Tumors," ClinicalTrials.gov, NCT03872947, Mar. 13, 2019, pp. 1-10.

"A Study of TRK-950 in Combinations With Anti-Cancer Treatment Regimens in Patients With Advanced Solid Tumors," ClinicalTrials.gov, NCT03872947, Unique Protocol ID 950P1V02, Aug. 28, 2019, 12 pages total.

Extended European Search Report for European Application No. 21767020.7, dated Apr. 8, 2024.

Extended European Search Report for European Application No. 21768178.2, dated Apr. 9, 2024.

Extended European Search Report for European Application No. 21768433.1, dated Feb. 28, 2024.

Hanna et al., "A Ph-Ib study of TRK-950 combined with anti-cancer treatment regimens in patients with advanced solid tumors," European Journal of Cancer, 34th EORTC-NCI-AACR Symposium, vol. 174S1, Oct. 26, 2022, pp. S32-S33.

Banerjee et al., "Benefits and Pitfalls of a Glycosylation Inhibitor Tunicamycin in the Therapeutic Implication of Cancers," Cells, vol. 13, No. 5, XP093285590, Feb. 25, 2024, pp. 1-16.

Esko et al., "Chapter 40—Natural and Synthetic Inhibitors of Glycosylation," Essentials of Glycobiology, XP093285359, Jan. 1, 1999, pp. 1-18.

Extended European Search Report for European Application No. 22849522.2, dated Jul. 14, 2025.

Han et al., "Tunicamycin enhances the antitumor activity of trastuzumab on breast cancer in vitro and in vivo," Oncotarget, vol. 6, No. 36, XP093285591, Oct. 12, 2015, pp. 38912-38925.

Korean Office Action for Korean Application No. 10-2020-7028602, dated Oct. 25, 2024.

"A Study of TRK-950 in Combinations With Anti-Cancer Treatment Regimens in Patients With Advanced Solid Tumors", ClinicalTrials.gov, [online], Mar. 13, 2019, total 12 pages.

"A Study of TRK-950 in Combinations With Anti-Cancer Treatment Regimens in Patients With Advanced Solid Tumors", ClinicalTrials.gov, Mar. 13, 2019, total 12 pages. https://Clinicaltrials.gov/ct2/show/NCT03872947?term=TRK-950&draw=2&rank=2.

International Search Report, issued in PCT/JP2021/009796, PCT/ISA/210, dated Apr. 20, 2021.

Peyton et al., "Downstaging and Survival Outcomes Associated With Neoadjuvant Chemotherapy Regimens Among Patients Treated With Cystectomy for Muscle-Invasive Bladder Cancer", JAMA Oncology, 2018, vol. 4, No. 11, p. 1535-1542.

Shroff et al., "Gemcitabine, Cisplatin, and nab-Paclitaxel for the Treatment of Advanced Biliary Tract Cancers A Phase 2 Clinical Trial", JAMA Oncology, 2019, vol. 5, No. 6, p. 824-830.

(56)			References Cited

OTHER PUBLICATIONS

Written Opinion of the International Searching Authority, issued in PCT/JP2021/009796, PCT/ISA/237, dated Apr. 20, 2021.

Australian Office Action for Australian Application No. 2019242520, dated Feb. 17, 2025.

"Imiquimod and Pembrolizumab in Treating Patients With Stage IIIB-IV Melanoma," ClinicalTrials.gov, Sep. 8, 2017, 9 pages total.

Aghajanian et al., "OCEANS: A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer," Journal of Clinical Oncology, vol. 30, No. 17, 2012, pp. 2039-2045.

Alt et al., "Enfortumab Vedotin in urothelial cancer," Therapeutic Advances in Urology, vol. 12, 2020, pp. 1-10.

Anonymous, "History of Changes for Study: NCT03276832, Imiquimod and Pembrolizumab in Treating Patients With Stage IIIB-IV Melanoma", ClinicalTrials.gov, Dec. 20, 2017, pp. 1-5.

Auerbach et al., "Angiogenesis assays; Problems and pitfalls," Cancer and Metastasis Reviews, vol. 19, 2000, pp. 167-172.

Barth et al., "Prognostic Factors in 1,521 Melanoma Patients With Distant Metastases," Journal of the American College of Surgeons, vol. 181, No. 3, 1995, pp. 193-201.

Berman et al., "Novel Dermatologic Uses of the Immune Response Modifier Imiquimod 5% Cream", Skin Therapy Letter, vol. 7, No. 9, 2002, pp. 1-6.

Brown et al., "Tolerance to Single, but Not Multiple, Amino Acid Replacements in Antibody VH CDR2—A Means of Minimizing B Cell Wastage from Somatic Hypermutation?," Journal of Immunology, vol. 156; 1996, pp. 3285-3291.

Campione et al., "Lack of efficacy of imiquimod in patients with basal cell carcinoma previously treated with rituximab for B cell lymphoma: two case reports," Journal of Medical Case Reports, vol. 10, No. 57, 2016, pp. 1-3.

Christiansen et al., "Biological impediments to monoclonal antibody-based cancer immunotherapy," Molecular Cancer Therapeutics, vol. 3, No. 11, 2004, pp. 1493-1501.

Ciardiello et al., "Antitumor Activity of Sequential Treatment with Topotecan and Anti-Epidermal Growth Factor Receptor Monoclonal Antibody C225," Clinical Cancer Research, vol. 5, No. 4, 1999, pp. 909-916.

Cohen et al., "Treatment of Extramammary Paget Disease with Topical Imiquimod Cream: Case Report and Literature Review," Southern Medical Journal, vol. 99, pp. 396-402.

Colombo et al., "Treatment of recurrent ovarian cancer relapsing 6-12 months post platinum-based chemotherapy," Critical Reviews in Oncology/Hematology, vol. 64, 2007, pp. 129-138.

Corraliza-Gorjón et al., "New Strategies Using Antibody Combinations to Increase Cancer Treatment Effectiveness," Frontiers in Immunology, vol. 8, 2017, pp. 1-31.

Douillard et al., "Irinotecan combined with fluorouracil compared with fluorouracil alone as first-line treatment for metastatic colorectal cancer: a multicentre randomised trial," The Lancet, vol. 355, 2000, pp. 1041-1047.

Dummer et al., "Imiquimod in basal cell carcinoma: how does it work?," British Journal of Dermatology, vol. 149; Suppl. 66, 2003, pp. 57-58.

Extended European Search Report for European Application No. 19774904.7, dated Oct. 29, 2021.

Ferrandina et al., "Phase III Trial of Gemcitabine Compared With Pegylated Liposomal Doxorubicin in Progressive or Recurrent Ovarian Cancer," Journal of Clinical Oncology, vol. 26, No. 6, 2008, pp. 890-896.

Gordon et al., "Recurrent Epithelial Ovarian Carcinoma: A Randomized Phase III Study of Pegylated Liposomal Doxorubicin Versus Topotecan," Journal of Clinical Oncology, vol. 19, No. 14, 2001, pp. 3312-3322.

Greenshields et al., "Imiquimod induces reactive oxygen species- and caspase-independent cell cycle arrest and apoptosis in MDA-MB-468 breast cancer cells," Molecular Cancer Therapeutics, vol. 8, Issue 12, supplement, abstract C88, 2009, 2 pages total.

Gura, "Systems for Identifying New Drugs Are Often Faulty," Science, vol. 278, 1997, pp. 1041-1042.

Hammond et al., "Pharmacologic resistance in colorectal cancer: a review," Therapeutic Advances in Medical Oncology, vol. 8, No. 1, 2016, pp. 57-84.

Henriques et al., "Imiquimod in the Treatment of Breast Cancer Skin Metastasis," Journal of Clinical Oncology, vol. 32, No. 8, 2014, pp. e22-e25.

Hogenesch et al., "Challenges in pre-clinical testing of anti-cancer drugs in cell culture and in animal models," Journal of Controlled Release, vol. 164, No. 2, 2012, pp. 183-186.

Hou et al., "Tunicamycin Potentiates Cisplatin Anticancer Efficacy through the DPAGT1/Akt/ABCG2 Pathway in Mouse Xenograft Models of Human Hepatocellular Carcinoma," Molecular Cancer Therapeutics, vol. 12, No. 12, 2013, pp. 2874-2884.

Imai, "HDAC inhibitors for treatment of multiple myeloma," Hematology, vol. 78, No. 1, 2019, pp. 18-24, with a partial English translation.

International Search Report for International Application No. PCT/JP2019/014044, dated May 21, 2019.

International Search Report for International Application No. PCT/JP2021/009795, dated Apr. 20, 2021.

International Search Report for International Application No. PCT/JP2021/009797, dated Apr. 20, 2021.

International Search Report for International Application No. PCT/JP2021/009798, dated Apr. 20, 2021.

International Search Report for International Application No. PCT/JP2021/009799, dated Apr. 20, 2021.

International Search Report for International Application No. PCT/JP2022/024812, dated Sep. 13, 2022.

International Search Report for International Application No. PCT/JP2022/024814, dated Sep. 13, 2022.

International Search Report for International Application No. PCT/JP2022/028871, dated Sep. 27, 2022.

International Search Report for International Application No. PCT/JP2022/028877, dated Oct. 18, 2022.

International Search Report for International Application No. PCT/JP2022/028878, dated Oct. 18, 2022.

Ishida et al., "Regimen Selection for First-line FOLFIRI and FOLFOX Based on UGT1A1 Genotype and Physical Background is Feasible in Japanese Patients with Advanced Colorectal Cancer," Japanese Journal of Clinical Oncology, vol. 41, No. 5, 2011, pp. 617-623.

Ishii; "MEK/RAF, Big-name cancer molecular targets that have finally came—R&D of MAPK pathway inhibitors," Folia Pharmacologica Japonica, vol. 141, 2013, pp. 15-21, with an English translation.

Jain et al., "Current ADC Linker Chemistry," Pharmaceutical Research, vol. 32, 2015, pp. 3526-3540.

Jain, "Barriers to Drug Delivery in Solid Tumors," Scientific American, 1994, pp. 58-65.

Joseph et al., "Treatment of in-transit and metastatic melanoma in two patients treated with ipilimumab and topical imiquimod," Melanoma Research, vol. 26, No. 4, 2016, pp. 409-412.

Kadowaki et al., "Multicenter phase I/II study of nivolumab combined with paclitaxel plus ramucirumab as the second-line treatment in patients with advanced gastric cancer", the ESMO World Congress on Gastrointestinal Cancer 2019, Abstract #SO-001, 1 page total.

Kitchen et al., "Comment on The efficacy and toxicity of gemcitabine, carboplatin and bevacizumab in metastatic breast cancer," British Journal of Cancer, vol. 109, 2013, pp. 526-528.

Komiyama et al., "Japan Society of Gynecologic Oncology guidelines 2015 for the treatment of ovarian cancer including primary peritoneal cancer and fallopian tube cancer," International Journal of Clinical Oncology, vol. 21, 2016, pp. 435-446.

Kussie et al., "A Single Engineered Amino Acid Substitution Changes Antibody Fine Specificity," Journal of Immunology, vol. 152, 1994, pp. 146-152.

Larkin et al., "Five-Year Survival with Combined Nivolumab and Ipilimumuab in Advanced Melanoma," New England Journal of Medicine, vol. 381, 2019, pp. 1535-1546.

(56)                 References Cited

OTHER PUBLICATIONS

Lee et al., "Targeting MAPK Signaling in Cancer: Mechanisms of Drug Resistance and Sensitivity," International Journal of Molecular Sciences, vol. 21, 2020, pp. 1-29.

Li et al., "Glycosylation and stabilization of programmed death ligand-1 suppresses T-cell activity," Nature Communications, vol. 7, 2016, pp. 1-11.

Li et al., "HDACs and HDAC Inhibitors in Cancer Development and Therapy," Cold Spring Harbor Perspectives in Medicine, vol. 6, 2016, pp. 1-34.

Lito et al., "Tumor adaptation and resistance to RAF inhibitors," Nature Medicine, vol. 19, No. 11, 2013, pp. 1401-1409.

Liu et al., "BRAF/MEK inhibitors promote CD47 expression that is reversible by ERK inhibition in melanoma," Oncotarget, vol. 8, No. 41, 2017, pp. 69477-69492.

Mereiter et al., "Glycosylation in the Era of Cancer-Targeted Therapy: Where Are We Heading?," Cancer Cell, vol. 36, 2019, pp. 6-16.

Metzger-Filho et al., "Dissecting the Heterogeneity of Triple-Negative Breast Cancer," Journal of Clinical Oncology, vol. 30, 2012, pp. 1879-1887.

Mitachi et al., "DPAGT1 Inhibitors of Capuramycin Analogues and Their Antimigratory Activities of Solid Tumors," Journal of Medicinal Chemistry, vol. 63, 2020, pp. 10855-10878.

Omura et al., "Phase III Trial of Paclitaxel at Two Dose Levels, the Higher Dose Accompanied by Filgrastim at Two Dose Levels in Platinum-Pretreated Epithelial Ovarian Cancer: An Intergroup Study," Journal of Clinical Oncology, vol. 21, No. 15, 2003, pp. 2843-2848.

Park et al., "A short guide to histone deacetylases including recent progress on class II enzymes," Experimental & Molecular Medicine, vol. 52, 2020, pp. 204-212.

Peyssonnaux et al., "The Raf/MEK/ERK pathway: new concepts of activation," Biology of the Cell, vol. 93, 2001, pp. 53-62.

Pfisterer et al., "Bevacizumab and platinum-based combinations for recurrent ovarian cancer: a randomised, open-label, phase 3 trial," Lancet Oncology, vol. 21, 2020, pp. 699-709.

Pujade-Lauraine et al., "Bevacizumab Combined With Chemotherapy for: Platinum-Resistant Recurrent Ovarian Cancer: The AURELIA Open-Label Randomized Phase III Trial," Journal of Clinical Oncology, vol. 32, No. 13, 2014, pp. 1302-1308.

Rose et al., "Prolonged Oral Etoposide as Second-Line Therapy for Platinum-Resistant and Platinum-Sensitive Ovarian Carcinoma: A Gynecologic Oncology Group Study," Journal of Clinical Oncology, vol. 16, No. 2, 1998, pp. 405-410.

Rowinsky et al., "Review of Phase I Clinical Studies With Topotecan," Seminars in Oncology, vol. 24, No. 6, 1997, pp. S20-3-S20-10.

Salazar et al., "Topical Imiquimod Plus Nab-paclitaxel for Breast Cancer Cutaneous Metastases—A Phase 2 Clinical Trial," JAMA Oncology, vol. 3, No. 7, 2017, pp. 969-973.

Siegel et al., "Colorectal Cancer Statistics, 2014," CA: A Cancer Journal for Clinicians, vol. 64, 2014, pp. 104-117.

Sporn et al., "Chemoprevention of cancer," Carcinogenesis, vol. 21, No. 3, 2000, pp. 525-530.

Study NCT03276832. National Cancer Institute (NCI): Imiquimod and Pembrolizumab in Treating Patients With Stage IIIB-IV Melanoma—ClinicalTrials.gov, Dec. 20, 2017 (v2), URL: https://clinicaltrials.gov/ct2/history/NCT03276832?V_2=View#StudyPageTop.

Sun et al., "Targeting glycosylated PD-1 induces potent anti-tumor immunity," Cancer Research, vol. 80, No. 11, 2020, pp. 2298-2310.

Suraweera et al., "Combination Therapy With Histone Deacetylase Inhibitors (HDACi) for the Treatment of Cancer: Achieving the Full Therapeutic Potential of HDACi," Frontiers in Oncology, vol. 8, 2018, pp. 1-15.

Thomas et al., "Antibody-drug conjugates for cancer therapy," Lancet Oncology, vol. 17, No. 6, 2016, pp. e254-e262.

Topp et al., "Antibody transport in cultured tumor cell layers," Journal of Controlled Release, vol. 53, 1998, pp. 15-23.

Vajdos et al., "Comprehensive Functional Maps of the Antigen-binding Site of an Anti-ErbB2 Antibody Obtained with Shotgun Scanning Mutagenesis," Journal of Molecular Biology, vol. 320, 2002, pp. 415-428.

Wilke et al., "Ramucirumab plus paclitaxel versus placebo plus paclitaxel in patients with previously treated advanced gastric or gastro-oesophageal junction adenocarcinoma (RAINBOW): a double-blind, randomised phase 3 trial," Lancet Oncology, vol. 15, 2014, pp. 1224-1235.

Wojtowicz et al., "Inhibition of protein glycosylation reverses the MDR phenotype of cancer cell lines," Biomedicine & Pharmacotherapy, vol. 74, 2015, pp. 49-56.

Wu et al., "Tunicamycin specifically aggravates ER stress and overcomes chemoresistance in multidrug-resistant gastric cancer cells by inhibiting N-glycosylation," Journal of Experimental & Clinical Cancer Research, vol. 37, No. 272, 2018, pp. 1-12.

Yuan et al., "The MAPK and AMPK signalings: interplay and implication in targeted cancer therapy," Journal of Hematology & Oncology, vol. 13, No. 113, 2020, pp. 1-19.

Zechmeister, "Progress in the Chemistry of Organic Natural Products," Springer Chemistry, 1997, 86 pages total.

International Search Report for International Application No. PCT/JP2023/024125, dated Sep. 12, 2023.

Ha et al., "Mycophenolic acid inhibits mesangial cell activation through p38 MAPK inhibition," Life Sciences, vol. 79, 2006, pp. 1561-1567.

Hatzivassiliou et al., "Mechanism of MEK inhibition determines efficacy in mutant KRAS- versus BRAF-driven cancers," Nature, vol. 501, 2013, pp. 1-5 (6 pages total).

Li et al., "MEK Inhibitor Augments Antitumor Activity of B7-H3-Redirected Bispecific Antibody," Frontiers in Oncology, vol. 10, Article 1527, Aug. 25, 2020, pp. 1-15.

Moreno et al., "Combined treatment with dabrafenib and trametinib with immune-stimulating antibodies for BRAF mutant melanoma," Oncoimmunology, vol. 5, Issue 7, Jul. 2016, pp. e1052212-1-e1052212-8.

Partial Supplementary European Search Report for European Application No. 22828439.4, dated Jun. 20, 2025.

Partial Supplementary European Search Report for European Application No. 22849523.0, dated Jun. 20, 2025.

Toray Industries, "A Study of TRK-950 in Combinations With Anti-Cancer Treatment Regimens in Patients With Advanced Solid Tumors," ClinicalTrials.gov, NCT03872947, Mar. 27, 2020, pp. 1-19.

Xie et al., "Systemic treatment options for advanced biliary tract carcinoma," The Japanese Society of Gastroenterology, vol. 55, 2020, pp. 944-957.

Chan et al., "Bevacizumab in combination with taxanes for the first-line treatment of metastatic breast cancer," Annals of Oncology, vol. 21, 2010, pp. 2305-2315.

Extended European Search Report for European Application No. 22828440.2, dated May 27, 2025.

Okano et al., "Identification of Membrane-expressed CAPRIN-1 as a Novel and Universal Cancer Target, and Generation of a Therapeutic Anti-CAPRIN-1 Antibody TRK-950," Cancer Research Communications, vol. 3, No. 4, XP093277915, Apr. 2023, pp. 640-658.

U.S. Office Action for U.S. Appl. No. 17/910,538, dated Jun. 4, 2025.

U.S. Office Action for U.S. Appl. No. 17/910,544, dated Jun. 17, 2025.

Vanderbeeken et al., "Topoisomerase Inhibitors in Metastatic Breast Cancer: Overview of Current Practice and Future Development," Current Breast Cancer Reports, vol. 5, XP035340237, 2013, pp. 31-41.

Amodio et al., "EGFR Blockade Reverts Resistance to KRASG12C Inhibition in Colorectal Cancer," Cancer Discovery, vol. 10, No. 8, Aug. 1, 2020, XP093240715, pp. 1129-1139.

Du et al., "Inhibition of ERAD synergizes with FTS to eradicate pancreatic cancer cells," BMC Cancer, vol. 21, No. 1, Mar. 6, 2021, XP093320397, pp. 1-13.

Extended European Search Report for European Application No. 22849523.0, dated Oct. 15, 2025.

(56)         References Cited

OTHER PUBLICATIONS

Golas et al., "SKI-606, a Src/Abl Inhibitor with In vivo Activity in Colon Tumor Xenograft Models," Cancer Research, vol. 65, No. 12, Jun. 15, 2005, XP002413906, pp. 5358-5364.

Hochster et al., "Phase II study of selumetinib (AZD6244, ARRY-142886) plus irinotecan as second-line therapy in patients with K-RAS mutated colorectal cancer," Cancer Chemotherapy and Pharmacology, vol. 75, No. 1, Oct. 17, 2024, XP035416470, pp. 17-23.

Jain et al., "Inotuzumab ozogamicin with bosutinib for relapsed or refractory Philadelphia chromosome positive acute lymphoblastic leukemia or lymphoid blast phase of chronic myeloid leukemia," American Journal of Hematology, vol. 96, No. 8, May 28, 2021, XP071632592, pp. 1000-1007.

Kim et al., "Targeting KRAS(G12C): From Inhibitory Mechanism to Modulation of Antitumor Effects in Patients," Cell, vol. 183, No. 4, Nov. 12, 2020, XP086341442, pp. 850-859.

Kunnimalaiyaan et al., "Neuroendocrine tumor cell growth inhibition by ZM336372 through alterations in multiple signaling pathways," Surgery, vol. 142, No. 6, Dec. 6, 2007, XP022421337, pp. 959-964.

Liang et al., "SCH 66336 (LONAFARNIB), A Farnesyl Transferase Inhibitor, Demonstrates Enhanced Antitumor Efficacy in Combination with the Alkylating Agents Temozolomide, Cisplatin, and carboplatin," American Association for Cancer Research, vol. 44, 2nd Edition, Jul. 1, 2003, XP001246805, p. 158.

Pal et al., "Stem-like colorectal cancer cell lines show response to the ERK1/2 inhibitor, SCH772984, alone and in combination with neratinib," EMBASE, Accession No. EMB-619155942, Jul. 1, 2017, XP093320559, pp. 1-4.

Sanz-Garcia et al., "BRAF mutant colorectal cancer: prognosis, treatment, and new perspectives," Annals of Oncology, vol. 28, No. 11, Nov. 1, 2017, XP093320434, pp. 2648-2657.

U.S. Office Action for U.S. Appl. No. 17/910,549, dated Nov. 13, 2025.

Wong et al., "Lonafarnib for cancer and progeria," Expert Opinion on Investigational Drugs, vol. 21, No. 7, May 24, 2012, XP093320714, pp. 1043-1055.

Abdelaziz et al., "A purified and lyophilized Pseudomonas aeruginosa derived pyocyanin induces promising apoptotic and necrotic activities against MCF-7 human breast adenocarcinoma," Microbial Cell Factories, vol. 21, Article 262, 2022, pp. 1-16.

Aikawa et al., "Cell death induced by dorsomorphin in adult T-cell leukemia/lymphoma is AMPK-independent," The FEBS Journal, vol. 287, No. 18, 2020, pp. 4005-4015.

Duffy et al., "GSK3 Inhibitors Regulate MYCN mRNA Levels and Reduce Neuroblastoma Cell Viability through Multiple Mechanisms, Including p53 and Wnt Signaling," Molecular Cancer Therapeutics, vol. 13, No. 2, Feb. 2014, pp. 454-467.

English translation of the International Search Report for International Application No. PCT/JP2024/012990, dated Jun. 18, 2024.

Gong et al., "Caprin-1 is a novel microRNA-223 target for regulation the proliferation and invasion of human breast cancer cells," Biomedicine & Pharmacotherapy, vol. 67, No. 7, 2013, pp. 629-636.

He et al., "Baicalein and Ly294002 induces liver cancer cells apoptosis via regulating phosphatidyl inositol 3-kinase/Akt signaling pathway," Journal of Cancer Research and Therapeutics, vol. 14, Supplement Issue 2, 2018, pp. S519-S525.

Katoh, "Canonical and non-canonical WNT signaling in cancer stem cells and their niches: Cellular heterogeneity, omics reprogramming, targeted therapy and tumor plasticity (Review)," International Journal of Oncology, vol. 51, No. 5, 2017, pp. 1357-1369.

Liu et al., "The AMPK Inhibitor Compound C Is a Potent AMPK-Independent Antiglioma Agent," Molecular Cancer Therapeutics, vol. 13, No. 3, Mar. 2014, pp. 596-605.

Shin, "Laboratory of Molecular and Cellular Biology, Graduate School of Biostudies," Overview of Graduate School and Faculty of Pharmaceutical Sciences, Kyoto University, Sep. 2018, p. 43 (4 pages total), with partial English translation.

Wang et al., "Dynasore-induced potent ubiquitylation of the exon 19 deletion mutant of epidermal growth factor receptor suppresses cell growth and migration in non-small cell lung cancer," International Journal of Biochemistry and Cell Biology, vol. 105, 2018, pp. 1-12.

Wehbe et al., "Pifithrin-σ Enhances Chemosensitivity by a p38 Mitogen-Activated Protein Kinase-Dependent Modulation of the Eukaryotic Initiation Factor 4E in Malignant Cholangiocytes," The Journal of Pharmacology and Experimental Therapeutics, vol. 319, No. 3, 2006, pp. 1153-1161.

Yin et al., "Glycogen Synthase Kinase 3β Inhibition as a Therapeutic Approach in the Treatment of Endometrial Cancer," International Journal of Molecular Sciences, vol. 14, No. 8, Aug. 12, 2013, pp. 16617-16637.

Yue et al., "Gain-of-function mutant p53 activates small GTPase Rac1 through SUMOylation to promote tumor progression," Genes & Development, vol. 31, No. 16, 2017, pp. 1641-1654 (15 pages total).

"A Study of TRK-950 in Combinations With Anti-Cancer Treatment Regimens in Patients With Advanced Solid Tumors," National Library of Medicine, ClinicalTrials.gov, NCT03872947, Version 1, Mar. 13, 2019, pp. 1-18.

Azmy et al., "Gemcitabine Plus Carboplatin in Patients with Advanced Hepatocellular Carcinoma: Results of a Phase II Study," ISRN Oncology, vol. 2012, Article ID 420931, 2012, pp. 1-5.

Eisenhauer et al., "A phase II study of gemcitabine, carboplatin and bevacizumab for the treatment of platinum-sensitive recurrent ovarian cancer," Gynecologic Oncology, vol. 134, 2014, pp. 262-266.

Pignata et al., "Treatment of recurrent ovarian cancer," Annals of Oncology, vol. 28 (Supplement 8), Nov. 2017, pp. viii51-viii56.

Suresh et al., "Gemcitabine and carboplatin in the treatment of metastatic cholangiocarcinoma and gallbladder cancer," Journal of Clinical Oncology, vol. 25, No. 18 Suppl, 2007, pp. 1-2, abstract provided only.

U.S. Office Action for U.S. Appl. No. 17/910,544, dated Sep. 17, 2025.

"A Study of TRK-950 in Combinations With Anti-Cancer Treatment Regimens in Patients With Advanced Solid Tumors," National Library of Medicine, ClinicalTrials.gov ID-NCT03872947, Aug. 3, 2025, 24 pages total.

Australian Office Action for Australian Application No. 2019242520, dated Jan. 16, 2026.

Korean Office Action for Korean Application No. 10-2022-7035177, dated Jan. 9, 2026.

Lipman et al., "Monoclonal Versus Polyclonal Antibodies: Distinguishing Characteristics, Applications, and Information Resources," ILAR Journal, vol. 46, No. 3, 2005, pp. 258-268.

Pfisterer et al., "Gemcitabine Plus Carboplatin Compared With Carboplatin in Patients With Platinum-Sensitive Recurrent Ovarian Cancer: An Intergroup Trial of the AGO-OVAR, the NCIC CTG, and EORTC GCG," Journal of Clinical Oncology, vol. 24, No. 29, Oct. 10, 2006, pp. 4699-4707.

English translation of the International Search Report for International Application No. PCT/JP2024/032627, dated Dec. 3, 2024.

Lewington et al., "Bone-Seeking Radionuclides for Therapy," The Journal of Nuclear Medicine, vol. 46, No. 1 (Suppl), Jan. 2005, pp. 38S-47S.

Reubi et al., "Candidates for Peptide Receptor Radiotherapy Today and in the Future," The Journal of Nuclear Medicine, vol. 46, No. 1 (Suppl), Jan. 2005, pp. 67S-75S.

"Cancer Risk and Prevention," American Cancer Society, https://www.cancer.org/cancer/risk-prevention.html, Nov. 13, 2025, pp. 1-7.

Edwards et al., "The Remarkable Flexibility of the Human Antibody Repertoire; Isolation of Over One Thousand Different Antibodies to a Single Protein, BLyS," Journal of Molecular Biology, vol. 334, 2003, pp. 103-118.

Muro et al., "Irinotecan plus S-1 (IRIS) versus fluorouracil and folinic acid plus irinotecan (FOLFIRI) as second-line chemotherapy for metastatic colorectal cancer: a randomised phase 2/3 non-inferiority study (FIRIS study)," www.thelancet.com/oncology, vol. 11, Sep. 2010, pp. 853-860.

(56) References Cited

OTHER PUBLICATIONS

Schultheis et al., "Regorafenib in combination with FOLFOX or FOLFIRI as first- or second-line treatment of colorectal cancer: results of a multicenter, phase Ib study," Annals of Oncology, vol. 24, 2013, pp. 1560-1567.

Sela-Culang et al., "The structural basis of antibody-antigen recognition," Frontiers in Immunology, vol. 4, Article 302, Oct. 2013, pp. 1-13.

U.S. Office Action for U.S. Appl. No. 17/910,522, dated Nov. 28, 2025.

\* cited by examiner

```
                        SEQUENCE LISTING

<160> NUMBER OF SEQ ID NOS: 309

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)

<400> SEQUENCE: 1
cagagggctg ctggctggct aagtccctcc cgctcccggc tctcgcctca ctaggagcgg      60
```

-continued

```
ctctcggtgc agcgggacag ggcgaagcgg cctgcgccca cggagcgcgc gacactgccc      120
ggaagggacc gccaccccttg cccccctcagc tgcccactcg tgatttccag cggcctccgc      180 gcgcgcacg atg ccc tcg gcc acc agc cac agc ggg agc ggc agc aag tcg      231
          Met Pro Ser Ala Thr Ser His Ser Gly Ser Gly Ser Lys Ser
            1               5                  10 tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac      375
Gly Ala Val Gln Thr Glu Ala Met Lys Gln Ile Leu Gly Val Ile Asp
            50                  55                  60 aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
            65                  70                  75 cag gaa cga atg aac aaa ggg gaa agg ctt aat caa gat cag ctg gat      471
Gln Glu Arg Met Asn Lys Gly Glu Arg Leu Asn Gln Asp Gln Leu Asp
        80                  85                  90 gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa      615
Ile Lys Lys Thr Ala Arg Arg Glu Gln Leu Met Arg Glu Glu Ala Glu
            130                 135                 140 cag aaa cgt tta aaa act gta ctt gag cta cag tat gtt ttg gac aaa      663
Gln Lys Arg Leu Lys Thr Val Leu Glu Leu Gln Tyr Val Leu Asp Lys
        145                 150                 155 ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
    160                 165                 170 gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag      807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
            210                 215                 220 aaa cct gta tgt gga acc acc tat aaa gtt cta aag gaa att gtt gag      903
Lys Pro Val Cys Gly Thr Thr Tyr Lys Val Leu Lys Glu Ile Val Glu
        225                 230                 235 cgt gtt ttt cag tca aac tac ttt gac agc acc cac aac cac cag aat      951
Arg Val Phe Gln Ser Asn Tyr Phe Asp Ser Thr His Asn His Gln Asn
    240                 245                 250 ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa      1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa      1095
Ser Glu Val Glu Ser Thr Glu Tyr Val Asn Arg Gln Phe Met Ala Glu
```

-continued

```
                  290                    295                    300
aca cag ttc acc agt ggt gaa aag gag cag gta gat gag tgg aca gtt    1143
Thr Gln Phe Thr Ser Gly Glu Lys Glu Gln Val Asp Glu Trp Thr Val
            305                    310                    315 gaa acg gtt gag gtg gta aat tca ctc cag cag caa cct cag gct gca    1191
Glu Thr Val Glu Val Val Asn Ser Leu Gln Gln Gln Pro Gln Ala Ala
        320                    325                    330 tcc cct tca gta cca gag ccc cac tct ttg act cca gtg gct cag gca    1239
Ser Pro Ser Val Pro Glu Pro His Ser Leu Thr Pro Val Ala Gln Ala
335                    340                    345                    350 gat ccc ctt gtg aga aga cag cga gta caa gac ctt atg gca caa atg    1287
Asp Pro Leu Val Arg Arg Gln Arg Val Gln Asp Leu Met Ala Gln Met
                355                    360                    365 cag ggt ccc tat aat ttc ata cag gat tca atg ctg gat ttt gaa aat    1335
Gln Gly Pro Tyr Asn Phe Ile Gln Asp Ser Met Leu Asp Phe Glu Asn
            370                    375                    380 cag aca ctt gat cct gcc att gta tct gca cag cct atg aat cca aca    1383
Gln Thr Leu Asp Pro Ala Ile Val Ser Ala Gln Pro Met Asn Pro Thr
        385                    390                    395 caa aac atg gac atg ccc cag ctg gtt tgc cct cca gtt cat tct gaa    1431
Gln Asn Met Asp Met Pro Gln Leu Val Cys Pro Pro Val His Ser Glu
        400                    405                    410 tct aga ctt gct cag cct aat caa gtt cct gta caa cca gaa gcg aca    1479
Ser Arg Leu Ala Gln Pro Asn Gln Val Pro Val Gln Pro Glu Ala Thr
415                    420                    425                    430 cag gtt cct ttg gta tca tcc aca agt gag ggg tac aca gca tct caa    1527
Gln Val Pro Leu Val Ser Ser Thr Ser Glu Gly Tyr Thr Ala Ser Gln
                435                    440                    445 ccc ttg tac cag cct tct cat gct aca gag caa cga cca cag aag gaa    1575
Pro Leu Tyr Gln Pro Ser His Ala Thr Glu Gln Arg Pro Gln Lys Glu
            450                    455                    460 cca att gat cag att cag gca aca atc tct tta aat aca gac cag act    1623
Pro Ile Asp Gln Ile Gln Ala Thr Ile Ser Leu Asn Thr Asp Gln Thr
        465                    470                    475 aca gca tca tca tcc ctt cct gct gcg tct cag cct caa gta ttt cag    1671
Thr Ala Ser Ser Ser Leu Pro Ala Ala Ser Gln Pro Gln Val Phe Gln
        480                    485                    490 gct ggg aca agc aaa cct tta cat agc agt gga atc aat gta aat gca    1719
Ala Gly Thr Ser Lys Pro Leu His Ser Ser Gly Ile Asn Val Asn Ala
495                    500                    505                    510 gct cca ttc caa tcc atg caa acg gtg ttc aat atg aat gcc cca gtt    1767
Ala Pro Phe Gln Ser Met Gln Thr Val Phe Asn Met Asn Ala Pro Val
                515                    520                    525 cct cct gtt aat gaa cca gaa act tta aaa cag caa aat cag tac cag    1815
Pro Pro Val Asn Glu Pro Glu Thr Leu Lys Gln Gln Asn Gln Tyr Gln
            530                    535                    540 gcc agt tat aac cag agc ttt tct agt cag cct cac caa gta gaa caa    1863
Ala Ser Tyr Asn Gln Ser Phe Ser Ser Gln Pro His Gln Val Glu Gln
            545                    550                    555 aca gag ctt cag caa gaa cag ctt caa aca gtg gtt ggc act tac cat    1911
Thr Glu Leu Gln Gln Glu Gln Leu Gln Thr Val Val Gly Thr Tyr His
            560                    565                    570 ggt tcc cca gac cag tcc cat caa gtg act ggt aac cac cag cag cct    1959
Gly Ser Pro Asp Gln Ser His Gln Val Thr Gly Asn His Gln Gln Pro
575                    580                    585                    590 cct cag cag aac act gga ttt cca cgt agc aat cag ccc tat tac aat    2007
Pro Gln Gln Asn Thr Gly Phe Pro Arg Ser Asn Gln Pro Tyr Tyr Asn
                595                    600                    605 agt cgt ggt gtg tct cgt gga ggc tcc cgt ggt gct aga ggc ttg atg    2055
```

-continued

```
Ser Arg Gly Val Ser Arg Gly Gly Ser Arg Gly Ala Arg Gly Leu Met
            610             615             620 aat gga tac cgg ggc cct gcc aat gga ttc aga gga gga tat gat ggt        2103
Asn Gly Tyr Arg Gly Pro Ala Asn Gly Phe Arg Gly Gly Tyr Asp Gly
            625             630             635 tac cgc cct tca ttc tct aac act cca aac agt ggt tat aca cag tct        2151
Tyr Arg Pro Ser Phe Ser Asn Thr Pro Asn Ser Gly Tyr Thr Gln Ser
            640             645             650 cag ttc agt gct ccc cgg gat tac tct ggc tat caa cgg gat gga tat        2199
Gln Phe Ser Ala Pro Arg Asp Tyr Ser Gly Tyr Gln Arg Asp Gly Tyr
655                 660             665                 670 cag cag aat ttc aag cga ggc tct ggg cag agt gga cca cgg gga gcc        2247
Gln Gln Asn Phe Lys Arg Gly Ser Gly Gln Ser Gly Pro Arg Gly Ala
                675             680             685 cca cga ggt cgt gga ggg ccc cca aga ccc aac aga ggg atg ccg caa        2295
Pro Arg Gly Arg Gly Gly Pro Pro Arg Pro Asn Arg Gly Met Pro Gln
            690             695             700 atg aac act cag caa gtg aat taa tctgattcac aggattatgt ttaatcgcca        2349
Met Asn Thr Gln Gln Val Asn
            705 aaaacacact ggccagtgta ccataatatg ttaccagaag agttattatc tatttgttct        2409 ccctttcagg aaacttattg taaagggact gttttcatcc cataaagaca ggactacaat        2469 tgtcagcttt ctattacctg gatatggaag gaaactattt ttactctgca tgttctgtcc        2529 taagcgtcat cttgagcctt gcacatgata ctcagattcc tcacccttgc ttaggagtaa        2589 aacaatatac tttacagggt gataataatc tccatagtta tttgaagtgg cttgaaaaag        2649 gcaagattga cttttatgac attggataaa atctacaaat cagccctcga gttattcaat        2709 gataactgac aaactaaatt atttccctag aaaggaagat gaaaggagtg gagtgtggtt        2769 tggcagaaca actgcatttc acagcttttc cagttaaatt ggagcactga acgttcagat        2829 gcataccaaa ttatgcatgg gtcctaatca cacatataag gctggctacc agctttgaca        2889 cagcactgtt catctggcca acaactgtg gttaaaaaca catgtaaaat gctttttaac        2949 agctgatact gtataagaca aagccaagat gcaaaattag ctttgattg gcactttttg        3009 aaaaatatgc aacaaatatg ggatgtaatc cggatggccg cttctgtact taatgtgaaa        3069 tatttagata cctttttgaa cacttaacag tttctttgag acaatgactt ttgtaaggat        3129 tggtactatc tatcattcct tatgacatgt acattgtctg tcactaatcc ttggattтttg        3189 ctgtattgtc acctaaattg gtacaggtac tgatgaaaat ctctagtgga taatcataac        3249 actctcggtc acatgttttt ccttcagctt gaaagctttt ttttaaaagg aaaagatacc        3309 aaatgcctgc tgctaccacc cтttтtcaatt gctatctttt gaaaggcacc agtatgtgtt        3369 ttagattgat ttccctgttt cagggaaatc acgacagta gtttcagttc tgatggtata        3429 agcaaaacaa ataaaacgtt tataaaagtt gtatcttgaa acactggtgt tcaacagcta        3489 gcagcttatg tgattcaccc catgccacgt tagtgtcaca aattttatgg tttatctcca        3549 gcaacatttc tctagtactt gcacttatta tcttttgtct aatttaacct taactgaatt        3609 ctccgtttct cctggaggca tttatattca gtgataattc cttcccttag atgcataggg        3669 agagtctcta aatttgatgg aaatggacac ttgagtagtg acttagcctt atgtactctg        3729 ttggaatttg tgctagcagt ttgagcacta gttctgtgtg cctaggaagt taatgctgct        3789 tattgtctca ttctgacttc atggagaatt aatcccacct ttaagcaaag gctactaagt        3849 taatggtatt ttctgtgcag aaattaaatt ttattтttcag catttagccc aggaattctt        3909
```

-continued

```
ccagtaggtg ctcagctatt taaaaacaaa actattctca aacattcatc attagacaac      3969
tggagttttt gctggttttg taacctacca aaatggatag gctgttgaac attccacatt      4029
caaaagtttt gtagggtggt gggaaatggg ggatcttcaa tgtttatttt aaaataaaat      4089
aaaataagtt cttgactttt ctcatgtgtg gttgtggtac atcatattgg aagggttaac      4149
ctgttacttt ggcaaatgag tatttttttg ctagcacctc cccttgcgtg ctttaaatga      4209
catctgcctg ggatgtacca caaccatatg ttacctgtat cttaggggaa tggataaaat      4269
atttgtggtt tactgggtaa tccctagatg atgtatgctt gcagtcctat ataaaactaa      4329
atttgctatc tgtgtagaaa ataatttcat gacatttaca atcaggactg aagtaagttc      4389
ttcacacagt gacctctgaa tcagtttcag agaagggatg ggggagaaaa tgccttctag      4449
gttttgaact tctatgcatt agtgcagatg ttgtgaatgt gtaaaggtgt tcatagtttg      4509
actgtttcta tgtatgtttt ttcaaagaat tgttcctttt tttgaactat aatttttctt      4569
tttttggtta ttttaccatc acagtttaaa tgtatatctt ttatgtctct actcagacca      4629
tatttttaaa ggggtgcctc attatggggc agagaacttt tcaataagtc tcattaagat      4689
ctgaatcttg gttctaagca ttctgtataa tatgtgattg cttgtcctag ctgcagaagg      4749
ccttttgttt ggtcaaatgc atattttagc agagtttcaa ggaaatgatt gtcacacatg      4809
tcactgtagc ctcttggtgt agcaagctca catacaaaat acttttgtat atgcataata      4869
taaatcatct catgtggata tgaaacttct tttttaaaac ttaaaaaggt agaatgttat      4929
tgattacctt gattagggca gttttatttc cagatcctaa taattcctaa aaaatatgga      4989
aaagtttttt ttcaatcatt gtaccttgat attaaaacaa atatcctta agtatttcta      5049 atcagttagc ttctacagtt cttttgtctc cttttatatg cagctcttac gtgggagact      5109
tttccactta aaggagacat agaatgtgtg cttattctca gaaggttcat taactgaggt      5169
gatgagttaa caactagttg agcagtcagc ttcctaagtg ttttaggaca tttgttcatt      5229
atattttccg tcatataact agaggaagtg gaatgcagat aagtgccgaa ttcaaaccct      5289
tcattttatg tttaagctcc tgaatctgca ttccacttgg gttgttttta agcattctaa      5349
attttagttg attataagtt agatttcaca gaatcagtat tgcccttgat cttgtccttt      5409
ttatggagtt aacggggagg aagacccctc aggaaaacga aagtaaattg ttaaggctca      5469
tcttcatacc tttttccatt ttgaatccta caaaaatact gcaaaagact agtgaatgtt      5529
taaaattaca ctagattaaa taatatgaaa gtc                                  5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Gly Ala Ala Ala Pro Ala Ser Gln His Pro Ala Thr Gly Thr Gly Ala
        35                  40                  45

Val Gln Thr Glu Ala Met Lys Gln Ile Leu Gly Val Ile Asp Lys Lys
    50                  55                  60

Leu Arg Asn Leu Glu Lys Lys Lys Gly Lys Leu Asp Asp Tyr Gln Glu
65                  70                  75                  80
```

-continued

```
Arg Met Asn Lys Gly Glu Arg Leu Asn Gln Asp Gln Leu Asp Ala Val
            85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
            115                 120                 125

Lys Thr Ala Arg Arg Glu Gln Leu Met Arg Glu Glu Ala Glu Gln Lys
        130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
            180                 185                 190

Val Asp Pro Glu Arg Asp Met Ser Leu Arg Leu Asn Glu Gln Tyr Glu
            195                 200                 205

His Ala Ser Ile His Leu Trp Asp Leu Leu Glu Gly Lys Glu Lys Pro
        210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
            260                 265                 270

Pro Glu Ala Glu Pro Glu Pro Ala Glu Glu Tyr Thr Glu Gln Ser Glu
            275                 280                 285

Val Glu Ser Thr Glu Tyr Val Asn Arg Gln Phe Met Ala Glu Thr Gln
        290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
            340                 345                 350

Leu Val Arg Arg Gln Arg Val Gln Asp Leu Met Ala Gln Met Gln Gly
            355                 360                 365

Pro Tyr Asn Phe Ile Gln Asp Ser Met Leu Asp Phe Glu Asn Gln Thr
        370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
            435                 440                 445

Tyr Gln Pro Ser His Ala Thr Glu Gln Arg Pro Gln Lys Glu Pro Ile
        450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
```

-continued

```
                500               505               510

Phe Gln Ser Met Gln Thr Val Phe Asn Met Asn Ala Pro Val Pro Pro
        515               520               525

Val Asn Glu Pro Glu Thr Leu Lys Gln Gln Asn Gln Tyr Gln Ala Ser
    530               535               540

Tyr Asn Gln Ser Phe Ser Ser Gln Pro His Gln Val Glu Gln Thr Glu
545               550               555               560

Leu Gln Gln Glu Gln Leu Gln Thr Val Val Gly Thr Tyr His Gly Ser
                565               570               575

Pro Asp Gln Ser His Gln Val Thr Gly Asn His Gln Gln Pro Pro Gln
            580               585               590

Gln Asn Thr Gly Phe Pro Arg Ser Asn Gln Pro Tyr Tyr Asn Ser Arg
        595               600               605

Gly Val Ser Arg Gly Gly Ser Arg Gly Ala Arg Gly Leu Met Asn Gly
    610               615               620

Tyr Arg Gly Pro Ala Asn Gly Phe Arg Gly Gly Tyr Asp Gly Tyr Arg
625               630               635               640

Pro Ser Phe Ser Asn Thr Pro Asn Ser Gly Tyr Thr Gln Ser Gln Phe
                645               650               655

Ser Ala Pro Arg Asp Tyr Ser Gly Tyr Gln Arg Asp Gly Tyr Gln Gln
            660               665               670

Asn Phe Lys Arg Gly Ser Gly Gln Ser Gly Pro Arg Gly Ala Pro Arg
        675               680               685

Gly Arg Gly Gly Pro Pro Arg Pro Asn Arg Gly Met Pro Gln Met Asn
    690               695               700

Thr Gln Gln Val Asn
705
```

```
<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<400> SEQUENCE: 3
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc      180 gcgcgcacg atg ccc tcg gcc acc agc cac agc ggg agc ggc agc aag tcg     231
            Met Pro Ser Ala Thr Ser His Ser Gly Ser Gly Ser Lys Ser
                1               5                   10 tcc gga ccg cca ccg ccg tcg ggt tcc tcc ggg agt gag gcg gcc gcg     279
Ser Gly Pro Pro Pro Pro Ser Gly Ser Ser Gly Ser Glu Ala Ala Ala
15                  20                  25                  30 gga gcc ggg gcc gcc gcg ccg gct tct cag cac ccc gca acc ggc acc     327
Gly Ala Gly Ala Ala Ala Pro Ala Ser Gln His Pro Ala Thr Gly Thr
                35                  40                  45 ggc gct gtc cag acc gag gcc atg aag cag att ctc ggg gtg atc gac     375
Gly Ala Val Gln Thr Glu Ala Met Lys Gln Ile Leu Gly Val Ile Asp
            50                  55                  60 aag aaa ctt cgg aac ctg gag aag aaa aag ggt aag ctt gat gat tac     423
Lys Lys Leu Arg Asn Leu Glu Lys Lys Lys Gly Lys Leu Asp Asp Tyr
        65                  70                  75 cag gaa cga atg aac aaa ggg gaa agg ctt aat caa gat cag ctg gat     471
```

-continued

```
Gln Glu Arg Met Asn Lys Gly Glu Arg Leu Asn Gln Asp Gln Leu Asp
    80              85                  90 gcc gtt tct aag tac cag gaa gtc aca aat aat ttg gag ttt gca aaa        519
Ala Val Ser Lys Tyr Gln Glu Val Thr Asn Asn Leu Glu Phe Ala Lys
95                  100                 105                 110 gaa tta cag agg agt ttc atg gca cta agt caa gat att cag aaa aca        567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa        615
Ile Lys Lys Thr Ala Arg Arg Glu Gln Leu Met Arg Glu Glu Ala Glu
                130                 135                 140 cag aaa cgt tta aaa act gta ctt gag cta cag tat gtt ttg gac aaa        663
Gln Lys Arg Leu Lys Thr Val Leu Glu Leu Gln Tyr Val Leu Asp Lys
                145                 150                 155 ttg gga gat gat gaa gtg cgg act gac ctg aaa caa ggt ttg aat gga        711
Leu Gly Asp Asp Glu Val Arg Thr Asp Leu Lys Gln Gly Leu Asn Gly
    160                 165                 170 gtg cca ata ttg tcc gaa gag gag ttg tca ttg ttg gat gaa ttc tat        759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag        807
Lys Leu Val Asp Pro Glu Arg Asp Met Ser Leu Arg Leu Asn Glu Gln
                195                 200                 205 tat gaa cat gcc tcc att cac ctg tgg gac ctg ctg gaa ggg aag gaa        855
Tyr Glu His Ala Ser Ile His Leu Trp Asp Leu Leu Glu Gly Lys Glu
                210                 215                 220 aaa cct gta tgt gga acc acc tat aaa gtt cta aag gaa att gtt gag        903
Lys Pro Val Cys Gly Thr Thr Tyr Lys Val Leu Lys Glu Ile Val Glu
                225                 230                 235 cgt gtt ttt cag tca aac tac ttt gac agc acc cac aac cac cag aat        951
Arg Val Phe Gln Ser Asn Tyr Phe Asp Ser Thr His Asn His Gln Asn
    240                 245                 250 ggg ctg tgt gag gaa gaa gag gca gcc tca gca cct gca gtt gaa gac        999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa       1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa       1095
Ser Glu Val Glu Ser Thr Glu Tyr Val Asn Arg Gln Phe Met Ala Glu
                290                 295                 300 aca cag ttc acc agt ggt gaa aag gag cag gta gat gag tgg aca gtt       1143
Thr Gln Phe Thr Ser Gly Glu Lys Glu Gln Val Asp Glu Trp Thr Val
    305                 310                 315 gaa acg gtt gag gtg gta aat tca ctc cag cag caa cct cag gct gca       1191
Glu Thr Val Glu Val Val Asn Ser Leu Gln Gln Gln Pro Gln Ala Ala
    320                 325                 330 tcc cct tca gta cca gag ccc cac tct ttg act cca gtg gct cag gca       1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg       1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat       1335
Gln Gly Pro Tyr Asn Phe Ile Gln Asp Ser Met Leu Asp Phe Glu Asn
                370                 375                 380 cag aca ctt gat cct gcc att gta tct gca cag cct atg aat cca aca       1383
Gln Thr Leu Asp Pro Ala Ile Val Ser Ala Gln Pro Met Asn Pro Thr
                385                 390                 395
```

-continued

```
caa aac atg gac atg ccc cag ctg gtt tgc cct cca gtt cat tct gaa      1431
Gln Asn Met Asp Met Pro Gln Leu Val Cys Pro Pro Val His Ser Glu
    400             405             410 tct aga ctt gct cag cct aat caa gtt cct gta caa cca gaa gcg aca      1479
Ser Arg Leu Ala Gln Pro Asn Gln Val Pro Val Gln Pro Glu Ala Thr
415             420             425             430 cag gtt cct ttg gta tca tcc aca agt gag ggg tac aca gca tct caa      1527
Gln Val Pro Leu Val Ser Ser Thr Ser Glu Gly Tyr Thr Ala Ser Gln
            435             440             445 ccc ttg tac cag cct tct cat gct aca gag caa cga cca cag aag gaa      1575
Pro Leu Tyr Gln Pro Ser His Ala Thr Glu Gln Arg Pro Gln Lys Glu
        450             455             460 cca att gat cag att cag gca aca atc tct tta aat aca gac cag act      1623
Pro Ile Asp Gln Ile Gln Ala Thr Ile Ser Leu Asn Thr Asp Gln Thr
        465             470             475 aca gca tca tca tcc ctt cct gct gcg tct cag cct caa gta ttt cag      1671
Thr Ala Ser Ser Ser Leu Pro Ala Ala Ser Gln Pro Gln Val Phe Gln
    480             485             490 gct ggg aca agc aaa cct tta cat agc agt gga atc aat gta aat gca      1719
Ala Gly Thr Ser Lys Pro Leu His Ser Ser Gly Ile Asn Val Asn Ala
495             500             505             510 gct cca ttc caa tcc atg caa acg gtg ttc aat atg aat gcc cca gtt      1767
Ala Pro Phe Gln Ser Met Gln Thr Val Phe Asn Met Asn Ala Pro Val
            515             520             525 cct cct gtt aat gaa cca gaa act tta aaa cag caa aat cag tac cag      1815
Pro Pro Val Asn Glu Pro Glu Thr Leu Lys Gln Gln Asn Gln Tyr Gln
            530             535             540 gcc agt tat aac cag agc ttt tct agt cag cct cac caa gta gaa caa      1863
Ala Ser Tyr Asn Gln Ser Phe Ser Ser Gln Pro His Gln Val Glu Gln
        545             550             555 aca gag ctt cag caa gaa cag ctt caa aca gtg gtt ggc act tac cat      1911
Thr Glu Leu Gln Gln Glu Gln Leu Gln Thr Val Val Gly Thr Tyr His
        560             565             570 ggt tcc cca gac cag tcc cat caa gtg act ggt aac cac cag cag cct      1959
Gly Ser Pro Asp Gln Ser His Gln Val Thr Gly Asn His Gln Gln Pro
575             580             585             590 cct cag cag aac act gga ttt cca cgt agc aat cag ccc tat tac aat      2007
Pro Gln Gln Asn Thr Gly Phe Pro Arg Ser Asn Gln Pro Tyr Tyr Asn
            595             600             605 agt cgt ggt gtg tct cgt gga ggc tcc cgt ggt gct aga ggc ttg atg      2055
Ser Arg Gly Val Ser Arg Gly Gly Ser Arg Gly Ala Arg Gly Leu Met
            610             615             620 aat gga tac cgg ggc cct gcc aat gga ttc aga gga gga tat gat ggt      2103
Asn Gly Tyr Arg Gly Pro Ala Asn Gly Phe Arg Gly Gly Tyr Asp Gly
        625             630             635 tac cgc cct tca ttc tct aac act cca aac agt ggt tat aca cag tct      2151
Tyr Arg Pro Ser Phe Ser Asn Thr Pro Asn Ser Gly Tyr Thr Gln Ser
    640             645             650 cag ttc agt gct ccc cgg gat tac tct ggc tat caa cgg gat gga tat      2199
Gln Phe Ser Ala Pro Arg Asp Tyr Ser Gly Tyr Gln Arg Asp Gly Tyr
655             660             665             670 cag cag aat ttc aag cga ggc tct ggg cag agt gga cca cgg gga gcc      2247
Gln Gln Asn Phe Lys Arg Gly Ser Gly Gln Ser Gly Pro Arg Gly Ala
            675             680             685 cca cga ggt aat att ttg tgg tgg tga tcctagctcc taagtggagc           2294
Pro Arg Gly Asn Ile Leu Trp Trp
            690 ttctgttctg gccttggaag agctgttaat agtctgcatg ttaggaatac atttatcctt   2354 tccagacttg ttgctaggga ttaaatgaaa tgctctgttt ctaaaactta atcttggacc   2414
```

```
caaattttaa tttttgaatg atttaatttt ccctgttact atataaactg tcttgaaaac    2474
tagaacatat tctcttctca gaaaaagtgt ttttccaact gaaaattatt tttcaggtcc    2534
taaaacctgc taaatgtttt taggaagtac ttactgaaac attttgtaa gacatttttg     2594 gaatgagatt gaacatttat ataaatttat tattcctctt tcattttttt gaaacatgcc    2654
tattatattt tagggccaga cacccttaa tggccggata agccatagtt aacatttaga     2714
gaaccattta gaagtgatag aactaatgga atttgcaatg cctttttggac ctctattagt   2774 gatataaata tcaagttatt tctgactttt aaacaaaact cccaaattcc taacttattg    2834
agctatactt aaaaaaaatt acaggtttag agagtttttt gttttttcttt tactgttgga   2894 aaactacttc ccattttggc aggaagttaa cctatttaac aattagagct agcatttcat    2954
gtagtctgaa attctaaatg gttctctgat ttgagggagg ttaaacatca aacaggtttc    3014
ctctattggc cataacatgt ataaaatgtg tgttaaggag gaattacaac gtactttgat    3074
ttgaatacta gtagaaactg gccaggaaaa aggtacattt ttctaaaaat taatggatca    3134
cttgggaatt actgacttga ctagaagtat caaaggatgt ttgcatgtga atgtgggtta    3194
tgttctttcc caccttgtag catattcgat gaaagttgag ttaactgata gctaaaaatc    3254
tgttttaaca gcatgtaaaa agttatttta tctgttaaaa gtcattatac agttttgaat    3314
gttatgtagt ttcttttttaa cagtttaggt aataaggtct gttttcattc tggtgctttt   3374
attaattttg atagtatgat gttacttact actgaaatgt aagctagagt gtacactaga    3434
atgtaagctc catgagagca ggtaccttgt ctgtcttctc tgctgtatct attcccaacg    3494
cttgatgatg gtgcctggca catagtaggc actcaataaa tatttgttga atgaatgaa     3553
```

<210> SEQ ID NO 4
<211> LENGTH: 694
<212> TYPE: PRT
<213> ORGANISM: Homo sapiens

<400> SEQUENCE: 4

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30

Gly Ala Ala Ala Pro Ala Ser Gln His Pro Ala Thr Gly Thr Gly Ala
            35                  40                  45

Val Gln Thr Glu Ala Met Lys Gln Ile Leu Gly Val Ile Asp Lys Lys
        50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
            100                 105                 110

Gln Arg Ser Phe Met Ala Leu Ser Gln Asp Ile Gln Lys Thr Ile Lys
        115                 120                 125

Lys Thr Ala Arg Arg Glu Gln Leu Met Arg Glu Glu Ala Glu Gln Lys
        130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175
```

```
Ile Leu Ser Glu Glu Glu Leu Ser Leu Leu Asp Glu Phe Tyr Lys Leu
            180                     185                 190

Val Asp Pro Glu Arg Asp Met Ser Leu Arg Leu Asn Glu Gln Tyr Glu
            195                     200                 205

His Ala Ser Ile His Leu Trp Asp Leu Leu Glu Gly Lys Glu Lys Pro
            210                     215                 220

Val Cys Gly Thr Thr Tyr Lys Val Leu Lys Glu Ile Val Glu Arg Val
225                         230                 235                 240

Phe Gln Ser Asn Tyr Phe Asp Ser Thr His Asn His Gln Asn Gly Leu
                245                     250                 255

Cys Glu Glu Glu Glu Ala Ala Ser Ala Pro Ala Val Glu Asp Gln Val
            260                     265                 270

Pro Glu Ala Glu Pro Glu Pro Ala Glu Glu Tyr Thr Glu Gln Ser Glu
            275                     280                 285

Val Glu Ser Thr Glu Tyr Val Asn Arg Gln Phe Met Ala Glu Thr Gln
            290                     295                 300

Phe Thr Ser Gly Glu Lys Glu Gln Val Asp Glu Trp Thr Val Glu Thr
305                         310                 315                 320

Val Glu Val Val Asn Ser Leu Gln Gln Gln Pro Gln Ala Ala Ser Pro
                325                     330                 335

Ser Val Pro Glu Pro His Ser Leu Thr Pro Val Ala Gln Ala Asp Pro
                340                     345                 350

Leu Val Arg Arg Gln Arg Val Gln Asp Leu Met Ala Gln Met Gln Gly
                355                     360                 365

Pro Tyr Asn Phe Ile Gln Asp Ser Met Leu Asp Phe Glu Asn Gln Thr
            370                     375                 380

Leu Asp Pro Ala Ile Val Ser Ala Gln Pro Met Asn Pro Thr Gln Asn
385                         390                 395                 400

Met Asp Met Pro Gln Leu Val Cys Pro Pro Val His Ser Glu Ser Arg
                405                     410                 415

Leu Ala Gln Pro Asn Gln Val Pro Val Gln Pro Glu Ala Thr Gln Val
            420                     425                 430

Pro Leu Val Ser Ser Thr Ser Glu Gly Tyr Thr Ala Ser Gln Pro Leu
            435                     440                 445

Tyr Gln Pro Ser His Ala Thr Glu Gln Arg Pro Gln Lys Glu Pro Ile
            450                     455                 460

Asp Gln Ile Gln Ala Thr Ile Ser Leu Asn Thr Asp Gln Thr Thr Ala
465                         470                 475                 480

Ser Ser Ser Leu Pro Ala Ala Ser Gln Pro Gln Val Phe Gln Ala Gly
                485                     490                 495

Thr Ser Lys Pro Leu His Ser Ser Gly Ile Asn Val Asn Ala Ala Pro
            500                     505                 510

Phe Gln Ser Met Gln Thr Val Phe Asn Met Asn Ala Pro Val Pro Pro
            515                     520                 525

Val Asn Glu Pro Glu Thr Leu Lys Gln Gln Asn Gln Tyr Gln Ala Ser
            530                     535                 540

Tyr Asn Gln Ser Phe Ser Ser Gln Pro His Gln Val Glu Gln Thr Glu
545                         550                 555                 560

Leu Gln Gln Glu Gln Leu Gln Thr Val Val Gly Thr Tyr His Gly Ser
                565                     570                 575

Pro Asp Gln Ser His Gln Val Thr Gly Asn His Gln Gln Pro Pro Gln
            580                     585                 590
```

-continued

```
Gln Asn Thr Gly Phe Pro Arg Ser Asn Gln Pro Tyr Tyr Asn Ser Arg
        595             600             605

Gly Val Ser Arg Gly Gly Ser Arg Gly Ala Arg Gly Leu Met Asn Gly
    610             615             620

Tyr Arg Gly Pro Ala Asn Gly Phe Arg Gly Gly Tyr Asp Gly Tyr Arg
625             630             635             640

Pro Ser Phe Ser Asn Thr Pro Asn Ser Gly Tyr Thr Gln Ser Gln Phe
            645             650             655

Ser Ala Pro Arg Asp Tyr Ser Gly Tyr Gln Arg Asp Gly Tyr Gln Gln
            660             665             670

Asn Phe Lys Arg Gly Ser Gly Gln Ser Gly Pro Arg Gly Ala Pro Arg
            675             680             685

Gly Asn Ile Leu Trp Trp
    690
```

```
<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)

<400> SEQUENCE: 5
```

```
gtcacaaata acttggagtt tgcaaaagaa ttacagagga gtttc atg gca tta agt       57
                                                 Met Ala Leu Ser
                                                  1 caa gat att cag aaa aca ata aag aag act gca cgt cgg gag cag ctt       105
Gln Asp Ile Gln Lys Thr Ile Lys Lys Thr Ala Arg Arg Glu Gln Leu
 5               10              15              20 atg aga gag gaa gcg gaa caa aaa cgt tta aaa act gta ctt gag ctc       153
Met Arg Glu Glu Ala Glu Gln Lys Arg Leu Lys Thr Val Leu Glu Leu
             25              30              35 cag tat gtt ttg gac aaa ttg gga gat gat gaa gtg aga act gac ctg       201
Gln Tyr Val Leu Asp Lys Leu Gly Asp Asp Glu Val Arg Thr Asp Leu
         40              45              50 aag caa ggt ttg aat gga gtg cca ata ttg tct gaa gaa gaa ttg tcg       249
Lys Gln Gly Leu Asn Gly Val Pro Ile Leu Ser Glu Glu Glu Leu Ser
         55              60              65 ttg ttg gat gaa ttc tac aaa tta gca gac cct gaa cgg gac atg agc       297
Leu Leu Asp Glu Phe Tyr Lys Leu Ala Asp Pro Glu Arg Asp Met Ser
     70              75              80 ttg agg ttg aat gag cag tat gaa cat gct tcc att cac ctg tgg gac       345
Leu Arg Leu Asn Glu Gln Tyr Glu His Ala Ser Ile His Leu Trp Asp
 85              90              95              100 ttg ctg gaa gga aag gaa aag tct gta tgt gga aca acc tat aaa gca       393
Leu Leu Glu Gly Lys Glu Lys Ser Val Cys Gly Thr Thr Tyr Lys Ala
            105             110             115 cta aag gaa att gtt gag cgt gtt ttc cag tca aat tac ttt gac agc       441
Leu Lys Glu Ile Val Glu Arg Val Phe Gln Ser Asn Tyr Phe Asp Ser
            120             125             130 act cac aac cac cag aat ggg cta tgt gag gaa gaa gag gca gcc tca       489
Thr His Asn His Gln Asn Gly Leu Cys Glu Glu Glu Glu Ala Ala Ser
            135             140             145 gca cct aca gtt gaa gac cag gta gct gaa gct gag cct gag cca gca       537
Ala Pro Thr Val Glu Asp Gln Val Ala Glu Ala Glu Pro Glu Pro Ala
    150             155             160 gaa gaa tac act gaa caa agt gaa gtt gaa tca aca gag tat gta aat       585
Glu Glu Tyr Thr Glu Gln Ser Glu Val Glu Ser Thr Glu Tyr Val Asn
165             170             175             180
```

-continued

```
aga caa ttt atg gca gaa aca cag ttc agc agt ggt gaa aag gag cag        633
Arg Gln Phe Met Ala Glu Thr Gln Phe Ser Ser Gly Glu Lys Glu Gln
            185               190               195 gta gat gag tgg acg gtc gaa aca gtg gag gtg gtg aat tca ctc cag        681
Val Asp Glu Trp Thr Val Glu Thr Val Glu Val Val Asn Ser Leu Gln
            200               205               210 cag caa cct cag gct gcg tct cct tca gta cca gag ccc cac tct ttg        729
Gln Gln Pro Gln Ala Ala Ser Pro Ser Val Pro Glu Pro His Ser Leu
            215               220               225 act ccg gtg gct cag gca gat ccc ctt gtg aga aga cag cga gtc cag        777
Thr Pro Val Ala Gln Ala Asp Pro Leu Val Arg Arg Gln Arg Val Gln
            230               235               240 gac ctt atg gcg cag atg cag ggg ccc tat aat ttc ata cag gat tca        825
Asp Leu Met Ala Gln Met Gln Gly Pro Tyr Asn Phe Ile Gln Asp Ser
245               250               255               260 atg ctg gat ttt gaa aac cag aca ctc gat cct gcc att gta tct gca        873
Met Leu Asp Phe Glu Asn Gln Thr Leu Asp Pro Ala Ile Val Ser Ala
            265               270               275 cag cct atg aat ccg aca caa aac atg gac atg ccc cag ctg gtt tgc        921
Gln Pro Met Asn Pro Thr Gln Asn Met Asp Met Pro Gln Leu Val Cys
            280               285               290 cct cca gtt cat tct gaa tct aga ctt gct caa cct aat caa gtt cct        969
Pro Pro Val His Ser Glu Ser Arg Leu Ala Gln Pro Asn Gln Val Pro
            295               300               305 gta caa cca gaa gct aca cag gtt cct ttg gtt tca tcc aca agt gag       1017
Val Gln Pro Glu Ala Thr Gln Val Pro Leu Val Ser Ser Thr Ser Glu
            310               315               320 ggg tat aca gca tct caa ccc ttg tac cag cct tct cat gct aca gag       1065
Gly Tyr Thr Ala Ser Gln Pro Leu Tyr Gln Pro Ser His Ala Thr Glu
325               330               335               340 caa cga cca caa aag gaa cca att gac cag att cag gca aca atc tct       1113
Gln Arg Pro Gln Lys Glu Pro Ile Asp Gln Ile Gln Ala Thr Ile Ser
            345               350               355 tta aat aca gac cag act aca gcg tca tca tcc ctt ccg gct gct tct       1161
Leu Asn Thr Asp Gln Thr Thr Ala Ser Ser Ser Leu Pro Ala Ala Ser
            360               365               370 cag cct cag gta ttc cag gct ggg aca agc aaa cca tta cat agc agt       1209
Gln Pro Gln Val Phe Gln Ala Gly Thr Ser Lys Pro Leu His Ser Ser
            375               380               385 gga atc aat gta aat gca gct cca ttc caa tcc atg caa acg gtg ttc       1257
Gly Ile Asn Val Asn Ala Ala Pro Phe Gln Ser Met Gln Thr Val Phe
            390               395               400 aat atg aat gcc cca gtt cct cct gtt aat gaa cca gaa act ttg aaa       1305
Asn Met Asn Ala Pro Val Pro Pro Val Asn Glu Pro Glu Thr Leu Lys
405               410               415               420 caa caa aat cag tac cag gcc agt tat aac cag agc ttt tct agt cag       1353
Gln Gln Asn Gln Tyr Gln Ala Ser Tyr Asn Gln Ser Phe Ser Ser Gln
            425               430               435 cct cac caa gta gaa caa aca gag gga tgc cgc aaa tga acactcagca       1402
Pro His Gln Val Glu Gln Thr Glu Gly Cys Arg Lys
            440               445 agtgaattaa tctgattcac aggattatgt ttaaacgcca aaaacacact ggccagtgta    1462
ccataatatg ttaccagaag agttattatc tatttgttct ccctttcagg aaacttattg    1522
taaagggact gttttcatcc cataaagaca ggactacaat tgtcagcttt atattacctg    1582
gaaaaaaaaa aaaaaaaaa aaa                                             1605
```

<210> SEQ ID NO 6

-continued

```
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
            115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
            195                 200                 205

Asn Ser Leu Gln Gln Gln Pro Gln Ala Ala Ser Pro Ser Val Pro Glu
            210                 215                 220

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
                245                 250                 255

Ile Gln Asp Ser Met Leu Asp Phe Glu Asn Gln Thr Leu Asp Pro Ala
                260                 265                 270

Ile Val Ser Ala Gln Pro Met Asn Pro Thr Gln Asn Met Asp Met Pro
            275                 280                 285

Gln Leu Val Cys Pro Pro Val His Ser Glu Ser Arg Leu Ala Gln Pro
    290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
            355                 360                 365

Pro Ala Ala Ser Gln Pro Gln Val Phe Gln Ala Gly Thr Ser Lys Pro
    370                 375                 380

Leu His Ser Ser Gly Ile Asn Val Asn Ala Ala Pro Phe Gln Ser Met
```

-continued

```
385               390               395               400
Gln Thr Val Phe Asn Met Asn Ala Pro Val Pro Pro Val Asn Glu Pro
              405               410               415

Glu Thr Leu Lys Gln Gln Asn Gln Tyr Gln Ala Ser Tyr Asn Gln Ser
              420               425               430

Phe Ser Ser Gln Pro His Gln Val Glu Gln Thr Glu Gly Cys Arg Lys
              435               440               445

<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)

<400> SEQUENCE: 7 atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
              20                  25                  30 ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
              35                  40                  45 cac ccc gcg acc ggc acc ggc gct gtc cag acc gag gcc atg aag cag      192
His Pro Ala Thr Gly Thr Gly Ala Val Gln Thr Glu Ala Met Lys Gln
      50                  55                  60 atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                  85                  90                  95 aat caa gat cag ctg gat gcc gta tct aag tac cag gaa gtc aca aat      336
Asn Gln Asp Gln Leu Asp Ala Val Ser Lys Tyr Gln Glu Val Thr Asn
              100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
              115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
      130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                  165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
              180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
              195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
      210                 215                 220 ttg ctg gaa gga aag gaa aag tct gta tgt gga aca acc tat aaa gca      720
```

-continued

```
Leu Leu Glu Gly Lys Glu Lys Ser Val Cys Gly Thr Thr Tyr Lys Ala
225             230                 235                 240 cta aag gaa att gtt gag cgt gtt ttc cag tca aat tac ttt gac agc        768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca        816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca        864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat        912
Glu Glu Tyr Thr Glu Gln Ser Glu Val Glu Ser Thr Glu Tyr Val Asn
        290                 295                 300 aga caa ttt atg gca gaa aca cag ttc agc agt ggt gaa aag gag cag        960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag       1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg       1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag       1104
Thr Pro Val Ala Gln Ala Asp Pro Leu Val Arg Arg Gln Arg Val Gln
            355                 360                 365 gac ctt atg gcg cag atg cag ggg ccc tat aat ttc ata cag gat tca       1152
Asp Leu Met Ala Gln Met Gln Gly Pro Tyr Asn Phe Ile Gln Asp Ser
        370                 375                 380 atg ctg gat ttt gaa aac cag aca ctc gat cct gcc att gta tct gca       1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc       1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct       1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag       1344
Val Gln Pro Glu Ala Thr Gln Val Pro Leu Val Ser Ser Thr Ser Glu
            435                 440                 445 ggg tat aca gca tct caa ccc ttg tac cag cct tct cat gct aca gag       1392
Gly Tyr Thr Ala Ser Gln Pro Leu Tyr Gln Pro Ser His Ala Thr Glu
        450                 455                 460 caa cga cca caa aag gaa cca att gac cag att cag gca aca atc tct       1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct       1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt       1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc       1584
Gly Ile Asn Val Asn Ala Ala Pro Phe Gln Ser Met Gln Thr Val Phe
            515                 520                 525 aat atg aat gcc cca gtt cct cct gtt aat gaa cca gaa act ttg aaa       1632
Asn Met Asn Ala Pro Val Pro Pro Val Asn Glu Pro Glu Thr Leu Lys
        530                 535                 540
```

```
caa caa aat cag tac cag gcc agt tat aac cag agc ttt tct agt cag        1680
Gln Gln Asn Gln Tyr Gln Ala Ser Tyr Asn Gln Ser Phe Ser Ser Gln
545             550                 555                 560 cct cac caa gta gaa caa aca gac ctt cag caa gaa cag ctt caa aca        1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act        1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc        1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt        1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc        1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac        1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc        2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag        2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc        2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa              2154
Asn Arg Gly Met Pro Gln Met Asn Thr Gln Gln Val Asn
705                 710                 715 tctgattcac aggattatgt ttaaacgcca aaaacacact ggccagtgta ccataatatg        2214
ttaccagaag agttattatc tatttgttct ccctttcagg aaacttattg taaagggact        2274
gttttcatcc cataaagaca ggactacaat tgtcagcttt atattacctg gatatggaag        2334
gaaactattt ttattctgca tgttcttcct aagcgtcatc ttgagccttg cacatgatac        2394
tcagattcct caccccttgct taggagtaaa acataataca ctttacaggg tgatatctcc        2454
atagttattt gaagtggctt ggaaaaagca agattaactt ctgacattgg ataaaaatca        2514
acaaatcagc cctagagtta ttcaaatggt aattgacaaa aactaaaata tttcccttcg        2574
agaaggagtg gaatgtggtt tggcagaaca actgcatttc acagctttc cggttaaatt        2634 ggagcactaa acgtttagat gcataccaaa ttatgcatgg gcccttaata taaaaggctg        2694
gctaccagct ttgacacagc actattcatc ctctggccaa acaactgtgg ttaaacaaca        2754
catgtaaatt gctttttaac agctgatact ataataagac aaagccaaaa tgcaaaaatt        2814
gggctttgat tggcactttt tgaaaaatat gcaacaaata tgggatgtaa tctggatggc        2874
cgcttctgta cttaatgtga agtatttaga tacctttttg aacacttaac agtttcttct        2934
gacaatgact tttgtaagga ttggtactat ctatcattcc ttataatgta cattgtctgt        2994
cactaatcct cagatcttgc tgtattgtca cctaaattgg tacaggtact gatgaaaata        3054
tctaatggat aatcataaca ctcttggtca catgtttttc ctgcagcctg aaggttttta        3114
aaagaaaaag atatcaaatg cctgctgcta ccacccttt aaattgctat cttttgaaaa        3174
gcaccagtat gtgtttttaga ttgatttccc tattttaggg aaatgacaga cagtagtttc        3234
```

```
agttctgatg gtataagcaa aacaaataaa acatgtttat aaaagttgta tcttgaaaca    3294
ctggtgttca acagctagca gcttatgtgg ttcaccccat gcattgttag tgtttcagat    3354
tttatggtta tctccagcag ctgtttctgt agtacttgca tttatctttt gtctaaccct    3414
aatattctca cggaggcatt tatattcaaa gtggtgatcc cttcacttag acgcataggg    3474
agagtcacaa gtttgatgaa gaggacagtg tagtaattta tatgctgttg gaatttgtgc    3534
tagcagtttg agcactagtt ctgtgtgcct atgaacttaa tgctgcttgt catattccac    3594
tttgacttca tggagaatta atcccatcta ctcagcaaag gctatactaa tactaagtta    3654
atggtatttt ctgtgcagaa attgaatttt gtttttattag catttagcta aggaattttt    3714
ccagtaggtg ctcagctact aaagaaaaac aaaaacaaga cacaaaacta ttctcaaaca    3774
ttcattgtta gacaactgga gtttttgctg gtttttgtaac ctactaaaat ggataggctg    3834
ttgaacattc cacattcaaa agtttttttgt agggtggtgg ggaaggggg gtgtcttcaa    3894 tgtttatttt aaaataaaat aagttcttga cttttctcat gtgtggttgt ggtacatcat    3954
attggaaggg ttatctgttt acttttgcaa atgagtattt ctcttgctag cacctcccgt    4014
tgtgcgcttt aaatgacatc tgcctgggat gtaccacaac catatgttag ctgtatttta    4074
tggggaatag ataaaatatt cgtggtttat tgggtaatcc ctagatgtgt atgcttacaa    4134
tcctatatat aaaactaaat                                                 4154
```

<210> SEQ ID NO 8
<211> LENGTH: 717
<212> TYPE: PRT
<213> ORGANISM: Canis familiaris

<400> SEQUENCE: 8

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
        195                 200                 205
```

-continued

```
Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                260             265                 270

Ala Pro Thr Val Glu Asp Gln Val Ala Glu Ala Glu Pro Glu Pro Ala
            275                 280                 285

Glu Glu Tyr Thr Glu Gln Ser Glu Val Glu Ser Thr Glu Tyr Val Asn
    290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335

Gln Gln Pro Gln Ala Ala Ser Pro Ser Val Pro Glu Pro His Ser Leu
                340                 345                 350

Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
    370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
                420                 425                 430

Val Gln Pro Glu Ala Thr Gln Val Pro Leu Val Ser Ser Thr Ser Glu
            435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Ser Leu Pro Ala Ala Ser
                485                 490                 495

Gln Pro Gln Val Phe Gln Ala Gly Thr Ser Lys Pro Leu His Ser Ser
                500                 505                 510

Gly Ile Asn Val Asn Ala Ala Pro Phe Gln Ser Met Gln Thr Val Phe
            515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
    595                 600                 605

Ser Gln Pro Tyr Tyr Asn Ser Arg Gly Val Ser Arg Gly Gly Ser Arg
    610                 615                 620
```

-continued

```
Gly Ala Arg Gly Leu Met Asn Gly Tyr Arg Gly Pro Ala Asn Gly Phe
625             630             635             640

Arg Gly Gly Tyr Asp Gly Tyr Arg Pro Ser Phe Ser Asn Thr Pro Asn
                645             650             655

Ser Gly Tyr Thr Gln Ser Gln Phe Ser Ala Pro Arg Asp Tyr Ser Gly
            660             665             670

Tyr Gln Arg Asp Gly Tyr Gln Gln Asn Phe Lys Arg Gly Ser Gly Gln
        675             680             685

Ser Gly Pro Arg Gly Ala Pro Arg Gly Arg Gly Gly Pro Pro Arg Pro
    690             695             700

Asn Arg Gly Met Pro Gln Met Asn Thr Gln Gln Val Asn
705             710             715
```

```
<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)

<400> SEQUENCE: 9 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
            35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
        50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat     336
Asn Gln Asp Gln Leu Asp Ala Val Ser Lys Tyr Gln Glu Val Thr Asn
                100                 105                 110 aac ttg gag ttt gca aaa gaa tta cag agg agt ttc atg gca tta agt     384
Asn Leu Glu Phe Ala Lys Glu Leu Gln Arg Ser Phe Met Ala Leu Ser
            115                 120                 125 caa gat att cag aaa aca ata aag aag act gca cgt cgg gag cag ctt     432
Gln Asp Ile Gln Lys Thr Ile Lys Lys Thr Ala Arg Arg Glu Gln Leu
        130                 135                 140 atg aga gag gaa gcg gaa caa aaa cgt tta aaa act gta ctt gag ctc     480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg     528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg     576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc     624
Leu Leu Asp Glu Phe Tyr Lys Leu Ala Asp Pro Glu Arg Asp Met Ser
```

-continued

```
              195                   200                   205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                   215                   220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                   230                   235                   240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                  245                   250                   255 act cac aac cac cag aat ggg cta tgt gag gaa gaa gag gca gcc tca      816
Thr His Asn His Gln Asn Gly Leu Cys Glu Glu Glu Glu Ala Ala Ser
                  260                   265                   270 gca cct aca gtt gaa gac cag gta gct gaa gct gag cct gag cca gca      864
Ala Pro Thr Val Glu Asp Gln Val Ala Glu Ala Glu Pro Glu Pro Ala
                  275                   280                   285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                   295                   300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                   310                   315                   320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                  325                   330                   335 cag caa cct cag gct gcg tct cct tca gta cca gag ccc cac tct ttg     1056
Gln Gln Pro Gln Ala Ala Ser Pro Ser Val Pro Glu Pro His Ser Leu
                  340                   345                   350 act ccg gtg gct cag gca gat ccc ctt gtg aga aga cag cga gtc cag     1104
Thr Pro Val Ala Gln Ala Asp Pro Leu Val Arg Arg Gln Arg Val Gln
                  355                   360                   365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                   375                   380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                   390                   395                   400 cag cct atg aat ccg aca caa aac atg gac atg ccc cag ctg gtt tgc     1248
Gln Pro Met Asn Pro Thr Gln Asn Met Asp Met Pro Gln Leu Val Cys
                  405                   410                   415 cct cca gtt cat tct gaa tct aga ctt gct caa cct aat caa gtt cct     1296
Pro Pro Val His Ser Glu Ser Arg Leu Ala Gln Pro Asn Gln Val Pro
                  420                   425                   430 gta caa cca gaa gct aca cag gtt cct ttg gtt tca tcc aca agt gag     1344
Val Gln Pro Glu Ala Thr Gln Val Pro Leu Val Ser Ser Thr Ser Glu
                  435                   440                   445 ggg tat aca gca tct caa ccc ttg tac cag cct tct cat gct aca gag     1392
Gly Tyr Thr Ala Ser Gln Pro Leu Tyr Gln Pro Ser His Ala Thr Glu
    450                   455                   460 caa cga cca caa aag gaa cca att gac cag att cag gca aca atc tct     1440
Gln Arg Pro Gln Lys Glu Pro Ile Asp Gln Ile Gln Ala Thr Ile Ser
465                   470                   475                   480 tta aat aca gac cag act aca gcg tca tca tcc ctt ccg gct gct tct     1488
Leu Asn Thr Asp Gln Thr Thr Ala Ser Ser Ser Leu Pro Ala Ala Ser
                  485                   490                   495 cag cct cag gta ttc cag gct ggg aca agc aaa cca tta cat agc agt     1536
Gln Pro Gln Val Phe Gln Ala Gly Thr Ser Lys Pro Leu His Ser Ser
                  500                   505                   510 gga atc aat gta aat gca gct cca ttc caa tcc atg caa acg gtg ttc     1584
```

```
Gly Ile Asn Val Asn Ala Ala Pro Phe Gln Ser Met Gln Thr Val Phe
    515                 520                 525 aat atg aat gcc cca gtt cct cct gtt aat gaa cca gaa act ttg aaa      1632
Asn Met Asn Ala Pro Val Pro Pro Val Asn Glu Pro Glu Thr Leu Lys
    530                 535                 540 caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act      1776
Val Val Gly Thr Tyr His Gly Ser Gln Asp Gln Pro His Gln Val Thr
                580                 585                 590 ggt aac cat cag cag cct ccc cag cag aac act gga ttt cca cgt agc      1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
        610                 615                 620 ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
                660                 665                 670 tat cag cgg gat gga tat cag cag aat ttc aag cga ggc tct ggg cag      2064
Tyr Gln Arg Asp Gly Tyr Gln Gln Asn Phe Lys Arg Gly Ser Gly Gln
                675                 680                 685 agt gga cca cgg gga gcc cca cga ggt aat att ttg tgg tgg tga          2109
Ser Gly Pro Arg Gly Ala Pro Arg Gly Asn Ile Leu Trp Trp
        690                 695                 700 tcctagctcc taagtggagc ttctgttctg gccttggaag agctgttcca tagtctgcat     2169
gtaggttaca tgttaggaat acatttatca ttaccagact tgttgctagg gattaaatga     2229
aatgctctgt ttctaaaact tctcttgaac ccaaatttaa ttttttgaat gactttccct     2289
gttactatat aaattgtctt gaaaactaga acatttctcc tcctcagaaa aagtgttttt     2349
ccaactgcaa attattttttc aggtcctaaa acctgctaaa tgtttttagg aagtacttac     2409
tgaaacattt ttgtaagaca tttttggaat gagattgaac atttatataa atttattatt     2469
attcctcttt cattttttgaa catgcatatt atatttttagg gtcagaaatc ctttaatggc     2529
caaataagcc atagttacat ttagagaacc atttagaagt gatagaacta actgaaattt     2589
caatgccttt ggatcattaa tagcgatata aatttcaaat tgtttctgac ttttaaataa     2649
aacatccaaa atcctaacta acttcctgaa ctatatttaa aaattacagg tttaaggagt     2709
ttctggtttt tttttctctta ccataggaaa actgtttcct gtttggccag gaagtcaacc     2769
tgtgtaataa ttagaagtag catttcatat gatctgaagt tctaaatggt tctctgattt     2829
aagggaagtt aaattgaata ggtttcctct agttattggc cataacatgt ataaaatgta     2889
tattaaggag gaatacaaag tactttgatt tcaatgctag tagaaactgg ccagcaaaaa     2949
ggtgcatttt attttttaaat taatggatca cttgggaatt actgacttga agtatcaaag     3009
gatatttgca tgtgaatgtg ggttatgttc tttctcacct tgtagcatat tctatgaaag     3069
```

-continued

```
ttgagttgac tggtagctaa aaatctgttt taacagcatg taaaaagtta ttttatctgt    3129
tacaagtcat tatacaattt tgaatgttat gtagtttctt tttaacagtt taggtaacaa    3189
ggtctgtttt tcattctggt gcttttatta attttgatag tatgatgtta cttactactg    3249
aaatgtaagc tagagtgtac actagaatgt aagctccatg agagcaggta ccttgtctgt    3309
cttcactgct gtatctattt ccaacgcctg atgacagtgc ctgacacata gtaggcactc    3369
aataaatact tgttgaatga atgaatgaat gagtactggt ggaatactcc attagctcta    3429
ctcttctttt agctagagaa catgagcaaa tttgcgcatg acaacttcca ggacaggtga    3489
acactgaaga attgacctct taaacctaat aatgtggtga caagctgccc acatgcttct    3549
tgacttcaga tgaaaatctg cttgaaggca aagcaaataa tatttgaaag aaaaaccaaa    3609
tgccattttt gtcttctagg tcgtggaggg cccccaagac ccaacagagg gatgccgcaa    3669
atgaacactc agcaagtgaa ttaatctgat tcacaggatt atgtttaaac gccaaaaaca    3729
cactggccag tgtaccataa tatgttacca gaagagttat tatctatttg ttctcccttt    3789
caggaaactt attgtaaagg gactgttttc atcccataaa gacaggacta caattgtcag    3849
ctttatatta cctggatatg gaaggaaact attttttattc tgcatgttct tcctaagcgt    3909
catcttgagc cttgcacatg atactcagat tcctcaccct tgcttaggag taaaacataa    3969
tacactttac agggtgatat ctccatagtt atttgaagtg gcttggaaaa agcaagatta    4029
acttctgaca ttggataaaa atcaacaaat cagccctaga gttattcaaa tggtaattga    4089
caaaaactaa aatatttccc ttcgagaagg agtggaatgt ggtttggcag aacaactgca    4149
tttcacagct tttccggtta aattggagca ctaaacgttt agatgcatac caaattatgc    4209 atgggcccctt aatataaaag gctggctacc agctttgaca cagcactatt catcctctgg    4269
ccaaacaact gtggttaaac aacacatgta aattgctttt taacagctga tactataata    4329
agacaaagcc aaaatgcaaa aattgggctt tgattggcac ttttttgaaaa atatgcaaca    4389 aatatgggat gtaatctgga tggccgcttc tgtacttaat gtgaagtatt tagataacct    4449
tttgaacact taacagtttc ttctgacaat gacttttgta aggattggta ctatctatca    4509
ttccttataa tgtacattgt ctgtcactaa tcctcagatc ttgctgtatt gtcacctaaa    4569
ttggtacagg tactgatgaa aatatctaat ggataatcat aacactcttg gtcacatgtt    4629
tttcctgcag cctgaaggtt tttaaaagaa aaagatatca aatgcctgct gctaccaccc    4689
ttttaaattg ctatctttttg aaaagcacca gtatgtgttt tagattgatt tccctatttt    4749
agggaaatga cagacagtag tttcagttct gatggtataa gcaaaacaaa taaaacatgt    4809
ttataaaagt tgtatcttga aacactggtg ttcaacagct agcagcttat gtggttcacc    4869
ccatgcattg ttagtgtttc agattttatg gttatctcca gcagctgttt ctgtagtact    4929
tgcatttatc                                                          4939
```

```
<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
                20                  25                  30

Gly Ala Ala Gly Ala Ala Gly Ala Gly Ala Ala Ala Pro Ala Ser Gln
```

-continued

```
              35               40                45
His Pro Ala Thr Gly Thr Gly Ala Val Gln Thr Glu Ala Met Lys Gln
    50               55               60

Ile Leu Gly Val Ile Asp Lys Lys Leu Arg Asn Leu Glu Lys Lys Lys
65               70               75               80

Gly Lys Leu Asp Asp Tyr Gln Glu Arg Met Asn Lys Gly Glu Arg Leu
                85               90               95

Asn Gln Asp Gln Leu Asp Ala Val Ser Lys Tyr Gln Glu Val Thr Asn
            100              105              110

Asn Leu Glu Phe Ala Lys Glu Leu Gln Arg Ser Phe Met Ala Leu Ser
            115              120              125

Gln Asp Ile Gln Lys Thr Ile Lys Lys Thr Ala Arg Arg Glu Gln Leu
    130              135              140

Met Arg Glu Glu Ala Glu Gln Lys Arg Leu Lys Thr Val Leu Glu Leu
145              150              155              160

Gln Tyr Val Leu Asp Lys Leu Gly Asp Asp Glu Val Arg Thr Asp Leu
                165              170              175

Lys Gln Gly Leu Asn Gly Val Pro Ile Leu Ser Glu Glu Glu Leu Ser
            180              185              190

Leu Leu Asp Glu Phe Tyr Lys Leu Ala Asp Pro Glu Arg Asp Met Ser
            195              200              205

Leu Arg Leu Asn Glu Gln Tyr Glu His Ala Ser Ile His Leu Trp Asp
    210              215              220

Leu Leu Glu Gly Lys Glu Lys Ser Val Cys Gly Thr Thr Tyr Lys Ala
225              230              235              240

Leu Lys Glu Ile Val Glu Arg Val Phe Gln Ser Asn Tyr Phe Asp Ser
                245              250              255

Thr His Asn His Gln Asn Gly Leu Cys Glu Glu Glu Glu Ala Ala Ser
            260              265              270

Ala Pro Thr Val Glu Asp Gln Val Ala Glu Ala Glu Pro Glu Pro Ala
            275              280              285

Glu Glu Tyr Thr Glu Gln Ser Glu Val Glu Ser Thr Glu Tyr Val Asn
    290              295              300

Arg Gln Phe Met Ala Glu Thr Gln Phe Ser Ser Gly Glu Lys Glu Gln
305              310              315              320

Val Asp Glu Trp Thr Val Glu Thr Val Glu Val Val Asn Ser Leu Gln
                325              330              335

Gln Gln Pro Gln Ala Ala Ser Pro Ser Val Pro Glu Pro His Ser Leu
            340              345              350

Thr Pro Val Ala Gln Ala Asp Pro Leu Val Arg Arg Gln Arg Val Gln
            355              360              365

Asp Leu Met Ala Gln Met Gln Gly Pro Tyr Asn Phe Ile Gln Asp Ser
    370              375              380

Met Leu Asp Phe Glu Asn Gln Thr Leu Asp Pro Ala Ile Val Ser Ala
385              390              395              400

Gln Pro Met Asn Pro Thr Gln Asn Met Asp Met Pro Gln Leu Val Cys
                405              410              415

Pro Pro Val His Ser Glu Ser Arg Leu Ala Gln Pro Asn Gln Val Pro
            420              425              430

Val Gln Pro Glu Ala Thr Gln Val Pro Leu Val Ser Ser Thr Ser Glu
            435              440              445

Gly Tyr Thr Ala Ser Gln Pro Leu Tyr Gln Pro Ser His Ala Thr Glu
    450              455              460
```

-continued

```
Gln Arg Pro Gln Lys Glu Pro Ile Asp Gln Ile Gln Ala Thr Ile Ser
465             470             475             480

Leu Asn Thr Asp Gln Thr Thr Ala Ser Ser Ser Leu Pro Ala Ala Ser
                485             490             495

Gln Pro Gln Val Phe Gln Ala Gly Thr Ser Lys Pro Leu His Ser Ser
            500             505             510

Gly Ile Asn Val Asn Ala Ala Pro Phe Gln Ser Met Gln Thr Val Phe
            515             520             525

Asn Met Asn Ala Pro Val Pro Pro Val Asn Glu Pro Glu Thr Leu Lys
        530             535             540

Gln Gln Asn Gln Tyr Gln Ala Ser Tyr Asn Gln Ser Phe Ser Ser Gln
545             550             555             560

Pro His Gln Val Glu Gln Thr Asp Leu Gln Gln Glu Gln Leu Gln Thr
                565             570             575

Val Val Gly Thr Tyr His Gly Ser Gln Asp Gln Pro His Gln Val Thr
                580             585             590

Gly Asn His Gln Gln Pro Pro Gln Gln Asn Thr Gly Phe Pro Arg Ser
            595             600             605

Ser Gln Pro Tyr Tyr Asn Ser Arg Gly Val Ser Arg Gly Gly Ser Arg
        610             615             620

Gly Ala Arg Gly Leu Met Asn Gly Tyr Arg Gly Pro Ala Asn Gly Phe
625             630             635             640

Arg Gly Gly Tyr Asp Gly Tyr Arg Pro Ser Phe Ser Asn Thr Pro Asn
                645             650             655

Ser Gly Tyr Thr Gln Ser Gln Phe Ser Ala Pro Arg Asp Tyr Ser Gly
            660             665             670

Tyr Gln Arg Asp Gly Tyr Gln Gln Asn Phe Lys Arg Gly Ser Gly Gln
            675             680             685

Ser Gly Pro Arg Gly Ala Pro Arg Gly Asn Ile Leu Trp Trp
        690             695             700
```

```
<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)

<400> SEQUENCE: 11
```

```
atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5               10              15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20              25              30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
        35              40              45 cac ccc gcg acc ggc acc ggc gct gtc cag acc gag gcc atg aag cag     192
His Pro Ala Thr Gly Thr Gly Ala Val Gln Thr Glu Ala Met Lys Gln
    50              55              60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65              70              75              80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
```

```
                    85                 90                 95 aat caa gat cag ctg gat gcc gta tct aag tac cag gaa gtc aca aat        336
Asn Gln Asp Gln Leu Asp Ala Val Ser Lys Tyr Gln Glu Val Thr Asn
            100             105             110 aac ttg gag ttt gca aaa gaa tta cag agg agt ttc atg gca tta agt        384
Asn Leu Glu Phe Ala Lys Glu Leu Gln Arg Ser Phe Met Ala Leu Ser
            115             120             125 caa gat att cag aaa aca ata aag aag act gca cgt cgg gag cag ctt        432
Gln Asp Ile Gln Lys Thr Ile Lys Lys Thr Ala Arg Arg Glu Gln Leu
            130             135             140 atg aga gag gaa gcg gaa caa aaa cgt tta aaa act gta ctt gag ctc        480
Met Arg Glu Glu Ala Glu Gln Lys Arg Leu Lys Thr Val Leu Glu Leu
145             150             155             160 cag tat gtt ttg gac aaa ttg gga gat gat gaa gtg aga act gac ctg        528
Gln Tyr Val Leu Asp Lys Leu Gly Asp Asp Glu Val Arg Thr Asp Leu
                165             170             175 aag caa ggt ttg aat gga gtg cca ata ttg tct gaa gaa gaa ttg tcg        576
Lys Gln Gly Leu Asn Gly Val Pro Ile Leu Ser Glu Glu Glu Leu Ser
            180             185             190 ttg ttg gat gaa ttc tac aaa tta gca gac cct gaa cgg gac atg agc        624
Leu Leu Asp Glu Phe Tyr Lys Leu Ala Asp Pro Glu Arg Asp Met Ser
                195             200             205 ttg agg ttg aat gag cag tat gaa cat gct tcc att cac ctg tgg gac        672
Leu Arg Leu Asn Glu Gln Tyr Glu His Ala Ser Ile His Leu Trp Asp
            210             215             220 ttg ctg gaa gga aag gaa aag tct gta tgt gga aca acc tat aaa gca        720
Leu Leu Glu Gly Lys Glu Lys Ser Val Cys Gly Thr Thr Tyr Lys Ala
225             230             235             240 cta aag gaa att gtt gag cgt gtt ttc cag tca aat tac ttt gac agc        768
Leu Lys Glu Ile Val Glu Arg Val Phe Gln Ser Asn Tyr Phe Asp Ser
                245             250             255 act cac aac cac cag aat ggg cta tgt gag gaa gaa gag gca gcc tca        816
Thr His Asn His Gln Asn Gly Leu Cys Glu Glu Glu Glu Ala Ala Ser
            260             265             270 gca cct aca gtt gaa gac cag gta gct gaa gct gag cct gag cca gca        864
Ala Pro Thr Val Glu Asp Gln Val Ala Glu Ala Glu Pro Glu Pro Ala
            275             280             285 gaa gaa tac act gaa caa agt gaa gtt gaa tca aca gag tat gta aat        912
Glu Glu Tyr Thr Glu Gln Ser Glu Val Glu Ser Thr Glu Tyr Val Asn
            290             295             300 aga caa ttt atg gca gaa aca cag ttc agc agt ggt gaa aag gag cag        960
Arg Gln Phe Met Ala Glu Thr Gln Phe Ser Ser Gly Glu Lys Glu Gln
305             310             315             320 gta gat gag tgg acg gtc gaa aca gtg gag gtg gtg aat tca ctc cag       1008
Val Asp Glu Trp Thr Val Glu Thr Val Glu Val Val Asn Ser Leu Gln
                325             330             335 cag caa cct cag gct gcg tct cct tca gta cca gag ccc cac tct ttg       1056
Gln Gln Pro Gln Ala Ala Ser Pro Ser Val Pro Glu Pro His Ser Leu
            340             345             350 act ccg gtg gct cag gca gat ccc ctt gtg aga aga cag cga gtc cag       1104
Thr Pro Val Ala Gln Ala Asp Pro Leu Val Arg Arg Gln Arg Val Gln
            355             360             365 gac ctt atg gcg cag atg cag ggg ccc tat aat ttc ata cag gat tca       1152
Asp Leu Met Ala Gln Met Gln Gly Pro Tyr Asn Phe Ile Gln Asp Ser
            370             375             380 atg ctg gat ttt gaa aac cag aca ctc gat cct gcc att gta tct gca       1200
Met Leu Asp Phe Glu Asn Gln Thr Leu Asp Pro Ala Ile Val Ser Ala
385             390             395             400 cag cct atg aat ccg aca caa aac atg gac atg ccc cag ctg gtt tgc       1248
```

```
Gln Pro Met Asn Pro Thr Gln Asn Met Asp Met Pro Gln Leu Val Cys
            405                 410             415 cct cca gtt cat tct gaa tct aga ctt gct caa cct aat caa gtt cct      1296
Pro Pro Val His Ser Glu Ser Arg Leu Ala Gln Pro Asn Gln Val Pro
            420                 425             430 gta caa cca gaa gct aca cag gtt cct ttg gtt tca tcc aca agt gag      1344
Val Gln Pro Glu Ala Thr Gln Val Pro Leu Val Ser Ser Thr Ser Glu
            435                 440             445 ggg tat aca gca tct caa ccc ttg tac cag cct tct cat gct aca gag      1392
Gly Tyr Thr Ala Ser Gln Pro Leu Tyr Gln Pro Ser His Ala Thr Glu
            450                 455             460 caa cga cca caa aag gaa cca att gac cag att cag gca aca atc tct      1440
Gln Arg Pro Gln Lys Glu Pro Ile Asp Gln Ile Gln Ala Thr Ile Ser
465                 470                 475             480 tta aat aca gac cag act aca gcg tca tca tcc ctt ccg gct gct tct      1488
Leu Asn Thr Asp Gln Thr Thr Ala Ser Ser Ser Leu Pro Ala Ala Ser
                485                 490             495 cag cct cag gta ttc cag gct ggg aca agc aaa cca tta cat agc agt      1536
Gln Pro Gln Val Phe Gln Ala Gly Thr Ser Lys Pro Leu His Ser Ser
                500                 505             510 gga atc aat gta aat gca gct cca ttc caa tcc atg caa acg gtg ttc      1584
Gly Ile Asn Val Asn Ala Ala Pro Phe Gln Ser Met Gln Thr Val Phe
            515                 520             525 aat atg aat gcc cca gtt cct cct gtt aat gaa cca gaa act ttg aaa      1632
Asn Met Asn Ala Pro Val Pro Pro Val Asn Glu Pro Glu Thr Leu Lys
            530                 535             540 caa caa aat cag tac cag gcc agt tat aac cag agc ttt tct agt cag      1680
Gln Gln Asn Gln Tyr Gln Ala Ser Tyr Asn Gln Ser Phe Ser Ser Gln
545                 550                 555             560 cct cac caa gta gaa caa aca gac ctt cag caa gaa cag ctt caa aca      1728
Pro His Gln Val Glu Gln Thr Asp Leu Gln Gln Glu Gln Leu Gln Thr
                565                 570             575 gtg gtt ggc act tac cat ggt tcc cag gac cag ccc cac caa gtg act      1776
Val Val Gly Thr Tyr His Gly Ser Gln Asp Gln Pro His Gln Val Thr
                580                 585             590 ggt aac cat cag cag cct ccc cag cag aac act gga ttt cca cgt agc      1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt      1872
Ser Gln Pro Tyr Tyr Asn Ser Arg Gly Val Ser Arg Gly Gly Ser Arg
            610                 615                 620 ggt gct aga ggc tta atg aat gga tac agg ggc cct gcc aat gga ttc      1920
Gly Ala Arg Gly Leu Met Asn Gly Tyr Arg Gly Pro Ala Asn Gly Phe
625                 630                 635             640 aga gga gga tat gat ggt tac cgc cct tca ttc tct aac act cca aac      1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc      2016
Ser Gly Tyr Thr Gln Ser Gln Phe Ser Ala Pro Arg Asp Tyr Ser Gly
                660                 665                 670 tat cag cgg gga tgc cgc aaa tga acactcagca agtgaattaa tctgattcac      2070
Tyr Gln Arg Gly Cys Arg Lys
            675 aggattatgt ttaaacgcca aaaacacact ggccagtgta ccataatatg ttaccagaag      2130 agttattatc tatttgttct ccctttcagg aaacttattg taaagggact gttttcatcc      2190 cataaagaca ggactacaat tgtcagcttt atattacctg gatatggaag gaaactattt      2250 ttattctgca tgttcttcct aagcgtcatc ttgagccttg cacatgatac tcagattcct      2310
```

-continued

```
caccccttgct taggagtaaa acataataca ctttacaggg tgatatctcc atagttattt    2370
gaagtggctt ggaaaaagca agattaactt ctgacattgg ataaaaatca acaaatcagc    2430
cctagagtta ttcaaatggt aattgacaaa aactaaaata tttcccttcg agaaggagtg    2490
gaatgtggtt tggcagaaca actgcatttc acagctttc cggttaaatt ggagcactaa     2550
acgtttagat gcataccaaa ttatgcatgg gcccttaata taaaaggctg gctaccagct    2610
ttgacacagc actattcatc ctctggccaa acaactgtgg ttaaacaaca catgtaaatt    2670 gcttttttaac agctgatact ataataagac aaagccaaaa tgcaaaaatt gggctttgat   2730 tggcacttttt tgaaaaatat gcaacaaata tgggatgtaa tctggatggc cgcttctgta   2790
cttaatgtga agtatttaga tacctttttg aacacttaac agtttcttct gacaatgact    2850
tttgtaagga ttggtactat ctatcattcc ttataatgta cattgtctgt cactaatcct    2910
cagatcttgc tgtattgtca cctaaattgg tacaggtact gatgaaaata tctaatggat    2970
aatcataaca ctcttggtca catgtttttc ctgcagcctg aaggtttta aaagaaaaag     3030 atatcaaatg cctgctgcta ccaccctttt aaattgctat cttttgaaaa gcaccagtat    3090 gtgtttttaga ttgatttccc tattttaggg aaatgacaga cagtagtttc agttctgatg   3150
gtataagcaa aacaaataaa acatgtttat aaaagttgta tcttgaaaca ctggtgttca    3210
acagctagca gcttatgtgg ttcaccccat gcattgttag tgtttcagat tttatggtta    3270
tctccagcag ctgtttctgt agtacttgca tttatc                              3306
```

<210> SEQ ID NO 12
<211> LENGTH: 679
<212> TYPE: PRT
<213> ORGANISM: Canis familiaris

<400> SEQUENCE: 12

```
Met Pro Ser Ala Thr Ser Leu Ser Gly Ser Gly Ser Lys Ser Gly
1               5                   10                  15

Pro Pro Pro Pro Ser Gly Ser Ser Gly Ser Glu Ala Ala Ala Ala Ala
            20                  25                  30

Gly Ala Ala Gly Ala Ala Gly Ala Gly Ala Ala Ala Pro Ala Ser Gln
        35                  40                  45

His Pro Ala Thr Gly Thr Gly Ala Val Gln Thr Glu Ala Met Lys Gln
    50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Glu Leu Ser
            180                 185                 190

Leu Leu Asp Glu Phe Tyr Lys Leu Ala Asp Pro Glu Arg Asp Met Ser
```

-continued

```
                195                 200                 205

Leu Arg Leu Asn Glu Gln Tyr Glu His Ala Ser Ile His Leu Trp Asp
        210                 215                 220

Leu Leu Glu Gly Lys Glu Lys Ser Val Cys Gly Thr Thr Tyr Lys Ala
    225                 230                 235                 240

Leu Lys Glu Ile Val Glu Arg Val Phe Gln Ser Asn Tyr Phe Asp Ser
                    245                 250                 255

Thr His Asn His Gln Asn Gly Leu Cys Glu Glu Glu Ala Ala Ser
                260                 265                 270

Ala Pro Thr Val Glu Asp Gln Val Ala Glu Ala Glu Pro Glu Pro Ala
                275                 280                 285

Glu Glu Tyr Thr Glu Gln Ser Glu Val Glu Ser Thr Glu Tyr Val Asn
        290                 295                 300

Arg Gln Phe Met Ala Glu Thr Gln Phe Ser Ser Gly Glu Lys Glu Gln
    305                 310                 315                 320

Val Asp Glu Trp Thr Val Glu Thr Val Glu Val Val Asn Ser Leu Gln
                    325                 330                 335

Gln Gln Pro Gln Ala Ala Ser Pro Ser Val Pro Glu Pro His Ser Leu
                340                 345                 350

Thr Pro Val Ala Gln Ala Asp Pro Leu Val Arg Arg Gln Arg Val Gln
                355                 360                 365

Asp Leu Met Ala Gln Met Gln Gly Pro Tyr Asn Phe Ile Gln Asp Ser
        370                 375                 380

Met Leu Asp Phe Glu Asn Gln Thr Leu Asp Pro Ala Ile Val Ser Ala
    385                 390                 395                 400

Gln Pro Met Asn Pro Thr Gln Asn Met Asp Met Pro Gln Leu Val Cys
                    405                 410                 415

Pro Pro Val His Ser Glu Ser Arg Leu Ala Gln Pro Asn Gln Val Pro
                420                 425                 430

Val Gln Pro Glu Ala Thr Gln Val Pro Leu Val Ser Ser Thr Ser Glu
                435                 440                 445

Gly Tyr Thr Ala Ser Gln Pro Leu Tyr Gln Pro Ser His Ala Thr Glu
        450                 455                 460

Gln Arg Pro Gln Lys Glu Pro Ile Asp Gln Ile Gln Ala Thr Ile Ser
    465                 470                 475                 480

Leu Asn Thr Asp Gln Thr Thr Ala Ser Ser Ser Leu Pro Ala Ala Ser
                    485                 490                 495

Gln Pro Gln Val Phe Gln Ala Gly Thr Ser Lys Pro Leu His Ser Ser
                500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
        530                 535                 540

Gln Gln Asn Gln Tyr Gln Ala Ser Tyr Asn Gln Ser Phe Ser Ser Gln
    545                 550                 555                 560

Pro His Gln Val Glu Gln Thr Asp Leu Gln Gln Glu Gln Leu Gln Thr
                    565                 570                 575

Val Val Gly Thr Tyr His Gly Ser Gln Asp Gln Pro His Gln Val Thr
                580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
        610                 615                 620
```

-continued

```
Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
                660                 665                 670

Tyr Gln Arg Gly Cys Arg Lys
        675

<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)

<400> SEQUENCE: 13 atg ccg tcg gcc acc agc ctc agc gga agc ggc agc aag tcg tcg ggc       48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg       96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag      144
Gly Ala Ala Gly Ala Ala Gly Ala Gly Ala Ala Ala Pro Ala Ser Gln
            35                  40                  45 cac ccc gcg acc ggc acc ggc gct gtc cag acc gag gcc atg aag cag      192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag      240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
                85                  90                  95 aat caa gat cag ctg gat gcc gta tct aag tac cag gaa gtc aca aat      336
Asn Gln Asp Gln Leu Asp Ala Val Ser Lys Tyr Gln Glu Val Thr Asn
                100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
            115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
        130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
                180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
            195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
        210                 215                 220
```

```
ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
                260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
                275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
        290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
                340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
                355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
        370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct     1296
Pro Pro Val His Ser Glu Ser Arg Leu Ala Gln Pro Asn Gln Val Pro
                420                 425                 430 gta caa cca gaa gct aca cag gtt cct ttg gtt tca tcc aca agt gag     1344
Val Gln Pro Glu Ala Thr Gln Val Pro Leu Val Ser Ser Thr Ser Glu
                435                 440                 445 ggg tat aca gca tct caa ccc ttg tac cag cct tct cat gct aca gag     1392
Gly Tyr Thr Ala Ser Gln Pro Leu Tyr Gln Pro Ser His Ala Thr Glu
        450                 455                 460 caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt     1536
Gln Pro Gln Val Phe Gln Ala Gly Thr Ser Lys Pro Leu His Ser Ser
                500                 505                 510 gga atc aat gta aat gca gct cca ttc caa tcc atg caa acg gtg ttc     1584
Gly Ile Asn Val Asn Ala Ala Pro Phe Gln Ser Met Gln Thr Val Phe
                515                 520                 525 aat atg aat gcc cca gtt cct cct gtt aat gaa cca gaa act ttg aaa     1632
Asn Met Asn Ala Pro Val Pro Pro Val Asn Glu Pro Glu Thr Leu Lys
```

-continued

```
        530            535            540
caa caa aat cag tac cag gcc agt tat aac cag agc ttt tct agt cag    1680
Gln Gln Asn Gln Tyr Gln Ala Ser Tyr Asn Gln Ser Phe Ser Ser Gln
545            550            555            560 cct cac caa gta gaa caa aca gac ctt cag caa gaa cag ctt caa aca    1728
Pro His Gln Val Glu Gln Thr Asp Leu Gln Gln Glu Gln Leu Gln Thr
           565            570            575 gtg gtt ggc act tac cat ggt tcc cag gac cag ccc cac caa gtg act    1776
Val Val Gly Thr Tyr His Gly Ser Gln Asp Gln Pro His Gln Val Thr
           580            585            590 ggt aac cat cag cag cct ccc cag cag aac act gga ttt cca cgt agc    1824
Gly Asn His Gln Gln Pro Pro Gln Gln Asn Thr Gly Phe Pro Arg Ser
           595            600            605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
           610            615            620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625            630            635            640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
           645            650            655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
           660            665            670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
           675            680            685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
           690            695            700 aac aga ggg atg ccg caa atg aac act cag caa gtg aat taa    2154
Asn Arg Gly Met Pro Gln Met Asn Thr Gln Gln Val Asn
705            710            715 tctgattcac aggattatgt ttaaacgcca aaaacacact ggccagtgta ccataatatg    2214
ttaccagaag agttattatc tatttggact gttttcatcc cataaagaca ggactacaat    2274
tgtcagc    2281
```

```
<210> SEQ ID NO 14
<211> LENGTH: 717
<212> TYPE: PRT
<213> ORGANISM: Canis familiaris

<400> SEQUENCE: 14

Met Pro Ser Ala Thr Ser Leu Ser Gly Ser Gly Ser Lys Ser Ser Gly
1               5                  10                 15

Pro Pro Pro Pro Ser Gly Ser Ser Gly Ser Glu Ala Ala Ala Ala
           20                 25                 30

Gly Ala Ala Gly Ala Ala Gly Ala Gly Ala Ala Ala Pro Ala Ser Gln
           35                 40                 45

His Pro Ala Thr Gly Thr Gly Ala Val Gln Thr Glu Ala Met Lys Gln
           50                 55                 60

Ile Leu Gly Val Ile Asp Lys Lys Leu Arg Asn Leu Glu Lys Lys Lys
65                 70                 75                 80

Gly Lys Leu Asp Asp Tyr Gln Glu Arg Met Asn Lys Gly Glu Arg Leu
           85                 90                 95

Asn Gln Asp Gln Leu Asp Ala Val Ser Lys Tyr Gln Glu Val Thr Asn
```

-continued

```
                100               105                 110
Asn Leu Glu Phe Ala Lys Glu Leu Gln Arg Ser Phe Met Ala Leu Ser
            115                 120                 125
Gln Asp Ile Gln Lys Thr Ile Lys Lys Thr Ala Arg Arg Glu Gln Leu
        130                 135                 140
Met Arg Glu Glu Ala Glu Gln Lys Arg Leu Lys Thr Val Leu Glu Leu
145                 150                 155                 160
Gln Tyr Val Leu Asp Lys Leu Gly Asp Asp Glu Val Arg Thr Asp Leu
                165                 170                 175
Lys Gln Gly Leu Asn Gly Val Pro Ile Leu Ser Glu Glu Glu Leu Ser
            180                 185                 190
Leu Leu Asp Glu Phe Tyr Lys Leu Ala Asp Pro Glu Arg Asp Met Ser
        195                 200                 205
Leu Arg Leu Asn Glu Gln Tyr Glu His Ala Ser Ile His Leu Trp Asp
    210                 215                 220
Leu Leu Glu Gly Lys Glu Lys Ser Val Cys Gly Thr Thr Tyr Lys Ala
225                 230                 235                 240
Leu Lys Glu Ile Val Glu Arg Val Phe Gln Ser Asn Tyr Phe Asp Ser
                245                 250                 255
Thr His Asn His Gln Asn Gly Leu Cys Glu Glu Glu Glu Ala Ala Ser
            260                 265                 270
Ala Pro Thr Val Glu Asp Gln Val Ala Glu Ala Glu Pro Glu Pro Ala
        275                 280                 285
Glu Glu Tyr Thr Glu Gln Ser Glu Val Glu Ser Thr Glu Tyr Val Asn
    290                 295                 300
Arg Gln Phe Met Ala Glu Thr Gln Phe Ser Ser Gly Glu Lys Glu Gln
305                 310                 315                 320
Val Asp Glu Trp Thr Val Glu Thr Val Glu Val Val Asn Ser Leu Gln
                325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
        355                 360                 365
Asp Leu Met Ala Gln Met Gln Gly Pro Tyr Asn Phe Ile Gln Asp Ser
    370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                405                 410                 415
Pro Pro Val His Ser Glu Ser Arg Leu Ala Gln Pro Asn Gln Val Pro
            420                 425                 430
Val Gln Pro Glu Ala Thr Gln Val Pro Leu Val Ser Ser Thr Ser Glu
        435                 440                 445
Gly Tyr Thr Ala Ser Gln Pro Leu Tyr Gln Pro Ser His Ala Thr Glu
    450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Ser Leu Pro Ala Ala Ser
            485                 490                 495
Gln Pro Gln Val Phe Gln Ala Gly Thr Ser Lys Pro Leu His Ser Ser
        500                 505                 510
Gly Ile Asn Val Asn Ala Ala Pro Phe Gln Ser Met Gln Thr Val Phe
            515                 520                 525
```

```
Asn Met Asn Ala Pro Val Pro Pro Val Asn Glu Pro Glu Thr Leu Lys
    530                 535             540

Gln Gln Asn Gln Tyr Gln Ala Ser Tyr Asn Gln Ser Phe Ser Ser Gln
545                 550             555             560

Pro His Gln Val Glu Gln Thr Asp Leu Gln Gln Glu Gln Leu Gln Thr
            565             570             575

Val Val Gly Thr Tyr His Gly Ser Gln Asp Gln Pro His Gln Val Thr
            580             585             590

Gly Asn His Gln Gln Pro Pro Gln Gln Asn Thr Gly Phe Pro Arg Ser
            595             600             605

Ser Gln Pro Tyr Tyr Asn Ser Arg Gly Val Ser Arg Gly Gly Ser Arg
    610             615             620

Gly Ala Arg Gly Leu Met Asn Gly Tyr Arg Gly Pro Ala Asn Gly Phe
625                 630             635             640

Arg Gly Gly Tyr Asp Gly Tyr Arg Pro Ser Phe Ser Asn Thr Pro Asn
                645             650             655

Ser Gly Tyr Thr Gln Ser Gln Phe Ser Ala Pro Arg Asp Tyr Ser Gly
            660             665             670

Tyr Gln Arg Asp Gly Tyr Gln Gln Asn Phe Lys Arg Gly Ser Gly Gln
    675             680             685

Ser Gly Pro Arg Gly Ala Pro Arg Gly Arg Gly Gly Pro Pro Arg Pro
    690             695             700

Asn Arg Gly Met Pro Gln Met Asn Thr Gln Gln Val Asn
705             710             715

<210> SEQ ID NO 15
<211> LENGTH: 3386
<212> TYPE: DNA
<213> ORGANISM: Bos taurus
<220> FEATURE:
<221> NAME/KEY: CDS
<222> LOCATION: (82)..(2208)

<400> SEQUENCE: 15
cgcgtctcgc cccgtccacc gattgactcg ccgctcttgt ccttcctccc gctctttctt        60
ctctcccctt acggtttcaa g atg cct tcg gcc acc agc cac agc gga agc       111
                        Met Pro Ser Ala Thr Ser His Ser Gly Ser
                        1               5               10 ggc agc aag tcg tcc gga ccg cca ccg ccg tcg ggt tcc tcc ggg aat       159
Gly Ser Lys Ser Ser Gly Pro Pro Pro Pro Ser Gly Ser Ser Gly Asn
                15              20              25 gag gcg ggg gcc ggg gcc gcc gcg ccg gct tcc caa cac ccc atg acc       207
Glu Ala Gly Ala Gly Ala Ala Ala Pro Ala Ser Gln His Pro Met Thr
            30              35              40 ggc acc ggg gct gtc cag acc gag gcc atg aag cag att ctc ggg gtg       255
Gly Thr Gly Ala Val Gln Thr Glu Ala Met Lys Gln Ile Leu Gly Val
            45              50              55 atc gac aag aaa ctt cgg aac ctg gag aag aaa aag ggc aag ctt gat       303
Ile Asp Lys Lys Leu Arg Asn Leu Glu Lys Lys Lys Gly Lys Leu Asp
    60              65              70 gat tat cag gaa cga atg aac aaa ggg gaa agg ctt aat caa gat cag       351
Asp Tyr Gln Glu Arg Met Asn Lys Gly Glu Arg Leu Asn Gln Asp Gln
75              80              85              90 ctg gat gcc gtg tct aag tac cag gaa gtc aca aat aac ttg gag ttt       399
Leu Asp Ala Val Ser Lys Tyr Gln Glu Val Thr Asn Asn Leu Glu Phe
                95              100             105 gca aaa gaa tta cag agg agt ttc atg gca tta agc caa gat att cag       447
```

-continued

```
Ala Lys Glu Leu Gln Arg Ser Phe Met Ala Leu Ser Gln Asp Ile Gln
            110                 115                 120 aaa aca ata aag aag aca gca cgt cgg gag cag ctt atg aga gag gaa        495
Lys Thr Ile Lys Lys Thr Ala Arg Arg Glu Gln Leu Met Arg Glu Glu
            125                 130                 135 gct gaa cag aaa cgt tta aaa aca gta ctt gag ctg cag tat gtt ttg        543
Ala Glu Gln Lys Arg Leu Lys Thr Val Leu Glu Leu Gln Tyr Val Leu
        140                 145                 150 gac aaa cta gga gat gat gaa gtg aga act gac ctg aag caa ggt ttg        591
Asp Lys Leu Gly Asp Asp Glu Val Arg Thr Asp Leu Lys Gln Gly Leu
155                 160                 165                 170 aat gga gtg cca ata ttg tct gaa gag gag ttg tcg ttg tta gat gag        639
Asn Gly Val Pro Ile Leu Ser Glu Glu Glu Leu Ser Leu Leu Asp Glu
                175                 180                 185 ttc tac aaa tta gca gac cct gaa cga gac atg agc ttg agg ttg aat        687
Phe Tyr Lys Leu Ala Asp Pro Glu Arg Asp Met Ser Leu Arg Leu Asn
            190                 195                 200 gag cag tat gaa cat gcc tcc att cac ctg tgg gac ttg ctg gaa gga        735
Glu Gln Tyr Glu His Ala Ser Ile His Leu Trp Asp Leu Leu Glu Gly
            205                 210                 215 aag gaa aaa cct gta tgt gga aca act tat aaa gct cta aag gaa att        783
Lys Glu Lys Pro Val Cys Gly Thr Thr Tyr Lys Ala Leu Lys Glu Ile
        220                 225                 230 gtt gag cgt gtt ttc cag tca aac tac ttt gac agc acc cac aac cac        831
Val Glu Arg Val Phe Gln Ser Asn Tyr Phe Asp Ser Thr His Asn His
235                 240                 245                 250 cag aat ggt ctg tgt gag gaa gag gag gca gcc tca gca cct aca gtt        879
Gln Asn Gly Leu Cys Glu Glu Glu Glu Ala Ala Ser Ala Pro Thr Val
                255                 260                 265 gaa gac cag gca gct gaa gct gaa cct gag cca gtg gaa gaa tat act        927
Glu Asp Gln Ala Ala Glu Ala Glu Pro Glu Pro Val Glu Glu Tyr Thr
            270                 275                 280 gaa caa aat gag gtt gaa tca aca gag tat gta aat aga caa ttt atg        975
Glu Gln Asn Glu Val Glu Ser Thr Glu Tyr Val Asn Arg Gln Phe Met
            285                 290                 295 gca gaa aca cag ttc agc agt ggt gaa aag gag cag gta gat gat tgg       1023
Ala Glu Thr Gln Phe Ser Ser Gly Glu Lys Glu Gln Val Asp Asp Trp
300                 305                 310 aca gtt gaa aca gtt gag gtg gta aat tca ctc cag cag caa cct cag       1071
Thr Val Glu Thr Val Glu Val Val Asn Ser Leu Gln Gln Gln Pro Gln
315                 320                 325                 330 gct gca tct cct tca gta cca gaa ccc cac tct ttg acc cca gtg gct       1119
Ala Ala Ser Pro Ser Val Pro Glu Pro His Ser Leu Thr Pro Val Ala
                335                 340                 345 caa gcc gat ccc ctc gtg aga aga cag cga gta cag gac ctt atg gca       1167
Gln Ala Asp Pro Leu Val Arg Arg Gln Arg Val Gln Asp Leu Met Ala
                350                 355                 360 caa atg cag ggg ccc tat aat ttc ata cag gat tca atg ttg gat ttt       1215
Gln Met Gln Gly Pro Tyr Asn Phe Ile Gln Asp Ser Met Leu Asp Phe
            365                 370                 375 gaa aac cag aca ctt gat cct gcc att gta tct gca cag ccg atg aat       1263
Glu Asn Gln Thr Leu Asp Pro Ala Ile Val Ser Ala Gln Pro Met Asn
            380                 385                 390 cca gca cag aac atg gac ata ccc cag ctg gtt tgc cct cca gtt cat       1311
Pro Ala Gln Asn Met Asp Ile Pro Gln Leu Val Cys Pro Pro Val His
395                 400                 405                 410 tct gaa tct aga ctt gct caa cct aat caa gtt tct gta cag cca gaa       1359
Ser Glu Ser Arg Leu Ala Gln Pro Asn Gln Val Ser Val Gln Pro Glu
            415                 420                 425
```

-continued

```
gct aca cag gtt cct ttg gtt tca tcc aca agt gag gga tat aca gca    1407
Ala Thr Gln Val Pro Leu Val Ser Ser Thr Ser Glu Gly Tyr Thr Ala
            430              435              440 tct caa ccc ttg tac caa cct tct cat gct act gac caa cga cca caa    1455
Ser Gln Pro Leu Tyr Gln Pro Ser His Ala Thr Asp Gln Arg Pro Gln
            445              450              455 aag gaa ccg att gat cag att cag gcg acg atc tct tta aat aca gac    1503
Lys Glu Pro Ile Asp Gln Ile Gln Ala Thr Ile Ser Leu Asn Thr Asp
        460              465              470 cag act aca gca tca tca tcc ctt cct gct gct tct cag cct caa gtg    1551
Gln Thr Thr Ala Ser Ser Ser Leu Pro Ala Ala Ser Gln Pro Gln Val
475              480              485              490 ttc cag gct ggg aca agc aaa cct tta cat agc agt gga atc aat gta    1599
Phe Gln Ala Gly Thr Ser Lys Pro Leu His Ser Ser Gly Ile Asn Val
            495              500              505 aat gca gct cca ttc caa tcc atg caa acg gta ttc aat atg aat gcc    1647
Asn Ala Ala Pro Phe Gln Ser Met Gln Thr Val Phe Asn Met Asn Ala
            510              515              520 cca gtt cct cct gtt aat gaa cca gaa act tta aaa cag caa aat cag    1695
Pro Val Pro Pro Val Asn Glu Pro Glu Thr Leu Lys Gln Gln Asn Gln
            525              530              535 tac cag gcc agt tac aac cag agc ttt tcc agt cag cct cac caa gta    1743
Tyr Gln Ala Ser Tyr Asn Gln Ser Phe Ser Ser Gln Pro His Gln Val
            540              545              550 gaa caa aca gag ctt cag caa gaa cag ctt caa aca gtg gtt ggc act    1791
Glu Gln Thr Glu Leu Gln Gln Glu Gln Leu Gln Thr Val Val Gly Thr
555              560              565              570 tat cat ggt tct cag gac cag ccc cat caa gtg act ggt aac cac cag    1839
Tyr His Gly Ser Gln Asp Gln Pro His Gln Val Thr Gly Asn His Gln
            575              580              585 cag cct cct cag cag aac act gga ttt cca cgt agc aat cag ccc tat    1887
Gln Pro Pro Gln Gln Asn Thr Gly Phe Pro Arg Ser Asn Gln Pro Tyr
            590              595              600 tac aac agt cgt ggt gtg tct cgt gga ggt tcc cgt ggt gct aga ggc    1935
Tyr Asn Ser Arg Gly Val Ser Arg Gly Gly Ser Arg Gly Ala Arg Gly
            605              610              615 ttg atg aat gga tac aga gga cct gct aat gga ttc aga gga gga tat    1983
Leu Met Asn Gly Tyr Arg Gly Pro Ala Asn Gly Phe Arg Gly Gly Tyr
        620              625              630 gat ggt tac cgc cct tca ttc tct act aac act cca aac agt ggt tat    2031
Asp Gly Tyr Arg Pro Ser Phe Ser Thr Asn Thr Pro Asn Ser Gly Tyr
635              640              645              650 aca caa tct caa ttc agt gct ccc cgg gac tac tct ggc tat cag cgg    2079
Thr Gln Ser Gln Phe Ser Ala Pro Arg Asp Tyr Ser Gly Tyr Gln Arg
            655              660              665 gat gga tat cag cag aat ttc aag cga ggc tct ggg cag agt gga cca    2127
Asp Gly Tyr Gln Gln Asn Phe Lys Arg Gly Ser Gly Gln Ser Gly Pro
            670              675              680 cgg gga gcc cca cga ggt cgt gga ggg ccc cca aga ccc aac aga ggg    2175
Arg Gly Ala Pro Arg Gly Arg Gly Gly Pro Pro Arg Pro Asn Arg Gly
            685              690              695 atg ccg caa atg aac act cag caa gtg aat taa tctgattcac aggattatgt    2228
Met Pro Gln Met Asn Thr Gln Gln Val Asn
        700              705 ttaatcgcca aaaacacact ggccagtgta ccataatatg ttaccagaag agttattatc    2288
tatttgttct ccctttcagg aaacttattg taaagggact gttttcatcc cataaagaca    2348
ggactacaat tgtcagcttt atattacctg gatatggaag gaaactattt ttactctgca    2408
tgttctgtcc taagcgtcat cttgagcctt gcacatgata ctcagattcc tcacccttgc    2468
```

-continued

```
ttaggagtaa aacataatat actttaatgg ggtgatatct ccatagttat ttgaagtggc      2528
ttggataaag caagactgac ttctgacatt ggataaaatc tacaaatcag ccctagagtc      2588
attcagtggt aactgacaaa actaaaatat ttcccttgaa aggaagatgg aaggagtgga      2648
gtgtggtttg gcagaacaac tgcatttcac agctttttcca cttaaattgg agcactgaac      2708
atttagatgc ataccgaatt atgcatgggc cctaatcaca cagacaaggc tggtgccagc      2768
cttaggcttg acacggcagt gttcaccctc tggccagacg actgtggttc aagacacatg      2828
taaattgctt tttaacagct gatactgtat aagacaaagc caaaatgcaa aattaggctt      2888
tgattggcac ttttcgaaaa atatgcaaca attaagggat ataatctgga tggccgcttc      2948
tgtacttaat gtgaaatatt tagatacctt tcaaacactt aacagtttct ttgacaatga      3008
gttttgtaag gattggtagt aaatatcatt ccttatgacg tacattgtct gtcactaatc      3068
cttggatctt gctgtattgt cacctaaatt ggtacaggta ctgatgaaaa tctaatggat      3128
aatcataaca ctcttggtta catgtttttc ctgcagcctg aaagtttttta taagaaaaag      3188 acatcaaatg cctgctgctg ccacccttttt aaattgctat ctttttgaaaa gcaccagtat      3248 gtgttttaga ttgatttccc tattttaggg aaatgacagt cagtagtttc acttctgatg      3308
gtataagcaa acaaataaaa catgtttata aaaaaaaaaa aaaaaaaaaa aaaaaaaaaa      3368
aaaaaaaaaa aaaaaaaa                                                    3386
```

<210> SEQ ID NO 16
<211> LENGTH: 708
<212> TYPE: PRT
<213> ORGANISM: Bos taurus

<400> SEQUENCE: 16

```
Met Pro Ser Ala Thr Ser His Ser Gly Ser Gly Ser Lys Ser Ser Gly
1               5                   10                  15

Pro Pro Pro Pro Ser Gly Ser Ser Gly Asn Glu Ala Gly Ala Gly Ala
            20                  25                  30

Ala Ala Pro Ala Ser Gln His Pro Met Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
        130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
            180                 185                 190

Pro Glu Arg Asp Met Ser Leu Arg Leu Asn Glu Gln Tyr Glu His Ala
            195                 200                 205
```

-continued

```
Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
                260                 265                 270

Ala Glu Pro Glu Pro Val Glu Glu Tyr Thr Glu Gln Asn Glu Val Glu
                275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
                340                 345                 350

Arg Arg Gln Arg Val Gln Asp Leu Met Ala Gln Met Gln Gly Pro Tyr
                355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
                420                 425                 430

Val Ser Ser Thr Ser Glu Gly Tyr Thr Ala Ser Gln Pro Leu Tyr Gln
                435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
                500                 505                 510

Ser Met Gln Thr Val Phe Asn Met Asn Ala Pro Val Pro Pro Val Asn
                515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
                580                 585                 590

Thr Gly Phe Pro Arg Ser Asn Gln Pro Tyr Tyr Asn Ser Arg Gly Val
                595                 600                 605

Ser Arg Gly Gly Ser Arg Gly Ala Arg Gly Leu Met Asn Gly Tyr Arg
    610                 615                 620
```

-continued

```
Gly Pro Ala Asn Gly Phe Arg Gly Gly Tyr Asp Gly Tyr Arg Pro Ser
625             630             635             640

Phe Ser Thr Asn Thr Pro Asn Ser Gly Tyr Thr Gln Ser Gln Phe Ser
                645             650             655

Ala Pro Arg Asp Tyr Ser Gly Tyr Gln Arg Asp Gly Tyr Gln Gln Asn
            660             665             670

Phe Lys Arg Gly Ser Gly Gln Ser Gly Pro Arg Gly Ala Pro Arg Gly
        675             680             685

Arg Gly Gly Pro Pro Arg Pro Asn Arg Gly Met Pro Gln Met Asn Thr
    690             695             700

Gln Gln Val Asn
705
```

```
<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)

<400> SEQUENCE: 17
```

```
atg gag ggc aag ctc gat gat tac caa gag cga atg aac aaa gga gaa        48
Met Glu Gly Lys Leu Asp Asp Tyr Gln Glu Arg Met Asn Lys Gly Glu
1               5                   10                  15 agg ctt aat cag gat cag ctg gat gct gtg tct aag tac cag gaa gtc        96
Arg Leu Asn Gln Asp Gln Leu Asp Ala Val Ser Lys Tyr Gln Glu Val
                20                  25                  30 aca aat aac ttg gag ttt gcg aaa gaa ttg cag agg agt ttc atg gcg       144
Thr Asn Asn Leu Glu Phe Ala Lys Glu Leu Gln Arg Ser Phe Met Ala
            35                  40                  45 ttg agt cag gat att cag aaa aca ata aag aag acg gca cgt cgg gag       192
Leu Ser Gln Asp Ile Gln Lys Thr Ile Lys Lys Thr Ala Arg Arg Glu
        50                  55                  60 cag ctt atg aga gaa gaa gct gaa cag aaa cgt tta aaa act gta ctt       240
Gln Leu Met Arg Glu Glu Ala Glu Gln Lys Arg Leu Lys Thr Val Leu
65                  70                  75                  80 gag ctg cag tat gtt ttg gac aaa ttg gga gat gaa gaa gtg cga act       288
Glu Leu Gln Tyr Val Leu Asp Lys Leu Gly Asp Glu Glu Val Arg Thr
                85                  90                  95 gac ctg aaa caa ggt ttg aat gga gtg cca ata ctc tct gaa gaa gag       336
Asp Leu Lys Gln Gly Leu Asn Gly Val Pro Ile Leu Ser Glu Glu Glu
                100                 105                 110 ttg tcg ctg ttg gat gag ttc tac aag tta gca gac cct gta cgg gac       384
Leu Ser Leu Leu Asp Glu Phe Tyr Lys Leu Ala Asp Pro Val Arg Asp
            115                 120                 125 atg agc ttg agg ttg aat gag cag tat gag cat gcc tcc att cac ctg       432
Met Ser Leu Arg Leu Asn Glu Gln Tyr Glu His Ala Ser Ile His Leu
        130                 135                 140 tgg gac ttg ctg gaa ggg aag gaa aaa tct gtc tgt gga aca acc tat       480
Trp Asp Leu Leu Glu Gly Lys Glu Lys Ser Val Cys Gly Thr Thr Tyr
145                 150                 155                 160 aaa gct ctg agg gaa att gtt gag cgt gtt ttc cag tcc aac tac ttt       528
Lys Ala Leu Arg Glu Ile Val Glu Arg Val Phe Gln Ser Asn Tyr Phe
                165                 170                 175 gac agc acc cac aac cac cag aat ggg ctc tgt gag gag gaa gag gct       576
Asp Ser Thr His Asn His Gln Asn Gly Leu Cys Glu Glu Glu Glu Ala
                180                 185                 190 acc tca gct cca aca gct gaa gac cag gga gct gaa gct gaa cct gag       624
Thr Ser Ala Pro Thr Ala Glu Asp Gln Gly Ala Glu Ala Glu Pro Glu
```

-continued

```
            195                 200                 205
cca gca gaa gaa tac act gaa caa agt gaa gtt gaa tca aca gag tat      672
Pro Ala Glu Glu Tyr Thr Glu Gln Ser Glu Val Glu Ser Thr Glu Tyr
    210                 215                 220 gta aat aga cag ttt atg gca gaa gcg cag ttc agt ggt gag aag gag      720
Val Asn Arg Gln Phe Met Ala Glu Ala Gln Phe Ser Gly Glu Lys Glu
225                 230                 235                 240 cag gtg gat gag tgg aca gtc gag acg gtc gag gtg gta aat tca ctc      768
Gln Val Asp Glu Trp Thr Val Glu Thr Val Glu Val Val Asn Ser Leu
                245                 250                 255 cag cag caa cct cag gct gca tct cct tca gta ccg gag ccc cac tct      816
Gln Gln Gln Pro Gln Ala Ala Ser Pro Ser Val Pro Glu Pro His Ser
                260                 265                 270 ttg act cca gtg gct cag gca gat ccc ctt gtg aga aga cag cga gta      864
Leu Thr Pro Val Ala Gln Ala Asp Pro Leu Val Arg Arg Gln Arg Val
                275                 280                 285 cag gac ctt atg gcg caa atg cag ggg ccc tat aat ttc ata cag gat      912
Gln Asp Leu Met Ala Gln Met Gln Gly Pro Tyr Asn Phe Ile Gln Asp
    290                 295                 300 tca atg ctg gat ttt gaa aac cag aca ctt gat cct gcc att gta tct      960
Ser Met Leu Asp Phe Glu Asn Gln Thr Leu Asp Pro Ala Ile Val Ser
305                 310                 315                 320 gca cag cct atg aat cca gca cag aat atg gac atg ccc cag ctg gtt     1008
Ala Gln Pro Met Asn Pro Ala Gln Asn Met Asp Met Pro Gln Leu Val
                325                 330                 335 tgc cct cca gtt cat gct gaa tct aga ctt gct caa cct aat caa gtt     1056
Cys Pro Pro Val His Ala Glu Ser Arg Leu Ala Gln Pro Asn Gln Val
                340                 345                 350 cct gta caa cca gaa gct aca cag gtt cct ttg gtt tca tcc aca agt     1104
Pro Val Gln Pro Glu Ala Thr Gln Val Pro Leu Val Ser Ser Thr Ser
                355                 360                 365 gag ggg tat aca gca tct cag ccc ttg tac cag cct tct cat gct aca     1152
Glu Gly Tyr Thr Ala Ser Gln Pro Leu Tyr Gln Pro Ser His Ala Thr
    370                 375                 380 gag caa cga ccg caa aag gaa ccg act gac cag atc cag gca aca atc     1200
Glu Gln Arg Pro Gln Lys Glu Pro Thr Asp Gln Ile Gln Ala Thr Ile
385                 390                 395                 400 tct tta aat aca gac cag act aca gca tca tca tcc ctt cct gct gct     1248
Ser Leu Asn Thr Asp Gln Thr Thr Ala Ser Ser Ser Leu Pro Ala Ala
                405                 410                 415 tct cag cct cag gtg ttc cag gct ggg aca agc aaa cct tta cac agc     1296
Ser Gln Pro Gln Val Phe Gln Ala Gly Thr Ser Lys Pro Leu His Ser
                420                 425                 430 agt ggg atc aat gta aat gca gcg cca ttc cag tcc atg caa acg gtg     1344
Ser Gly Ile Asn Val Asn Ala Ala Pro Phe Gln Ser Met Gln Thr Val
                435                 440                 445 ttc aac atg aat gcc ccg gtt cct cct gtt aat gaa cca gaa act tta     1392
Phe Asn Met Asn Ala Pro Val Pro Pro Val Asn Glu Pro Glu Thr Leu
    450                 455                 460 aaa cag caa aat cag tac cag gcc agc tat aac cag agc ttt tcc agt     1440
Lys Gln Gln Asn Gln Tyr Gln Ala Ser Tyr Asn Gln Ser Phe Ser Ser
465                 470                 475                 480 ccg cct cac caa gta gag cag aca gag ctt ccg caa gag cag ctt cag     1488
Pro Pro His Gln Val Glu Gln Thr Glu Leu Pro Gln Glu Gln Leu Gln
                485                 490                 495 acg gtg gtt ggt act tac cat gct tcc caa gac cag ccc cat caa gtg     1536
Thr Val Val Gly Thr Tyr His Ala Ser Gln Asp Gln Pro His Gln Val
                500                 505                 510 acc ggt aac cac cag cag cct ccc cag cag aac act ggg ttt cca cgt     1584
```

```
Thr Gly Asn His Gln Gln Pro Pro Gln Gln Asn Thr Gly Phe Pro Arg
        515                 520                 525 agc agt cag ccc tat tac aac agt cgt ggt gtg tct cgt gga ggc tcc    1632
Ser Ser Gln Pro Tyr Tyr Asn Ser Arg Gly Val Ser Arg Gly Gly Ser
        530                 535                 540 cgt ggt gct aga ggc ttg atg aat gga tac agg ggc cct gcc aat gga    1680
Arg Gly Ala Arg Gly Leu Met Asn Gly Tyr Arg Gly Pro Ala Asn Gly
545                 550                 555                 560 ttc aga gga gga tat gat ggt tac cgc cct tcg ttc tct aac act cca    1728
Phe Arg Gly Gly Tyr Asp Gly Tyr Arg Pro Ser Phe Ser Asn Thr Pro
                565                 570                 575 aac agc ggt tac aca cag tct cag ttc agt gct ccc cgg gac tac tct    1776
Asn Ser Gly Tyr Thr Gln Ser Gln Phe Ser Ala Pro Arg Asp Tyr Ser
                580                 585                 590 ggc tat cag cgg gat gga tat cag cag aat ttc aag cga ggc tct ggg    1824
Gly Tyr Gln Arg Asp Gly Tyr Gln Gln Asn Phe Lys Arg Gly Ser Gly
                595                 600                 605 cag agt gga ccc cgg gga gcc cca cga ggt cgt gga ggg ccc cca aga    1872
Gln Ser Gly Pro Arg Gly Ala Pro Arg Gly Arg Gly Gly Pro Pro Arg
        610                 615                 620 ccc aac aga ggg atg ccg caa atg aac act cag caa gtg aat taa        1917
Pro Asn Arg Gly Met Pro Gln Met Asn Thr Gln Gln Val Asn
625                 630                 635 tctgattcac aggattatct ttaatcgcca aaacacactg gccagtgtac cataatatgt    1977
taccagaaga gttattatct atttgttctc cctttcagga aacttattgt aaagggactg    2037
ttttcatccc ataaagacag gactacagtt gtcagcttta tattacctgg atatggaagg    2097
aaactatttt tactctgcat gttctgtcct aagcgtcatc ttgagccttg cacatgatac    2157
tcagattcct ttcccttgct taggagtaaa acataatata ctttatgggg tgataatatc    2217
tccatagtta tttgaagtgg cttggaaaaa gcaagattga cttttgacat tggataaaat    2277
ctacaaatca gccctagagt ttcatggtca ttcacaaaac taaaatattt cccttgaaag    2337
gaagatggaa ggactggagt gtggtttggc agaacaactg catttcacag cttttcctat    2397
taaattggag cactgaatgt aaatgcata ccaaattatg catgggccct taatcacaca    2457
tacatggcta ccagctttga cacagcacta ttcatcctct ggccaaacga ctgtggttaa    2517
aaacacgtgt aaattgcttt ttaacagctg atactgtaaa agacaaagct aaaatgcaaa    2577
attaggcttt cattggcact tttcgaaaaa tatgcaacaa atttgggatg taatctggat    2637
ggccacttct gtacttaatg tgaagtattt agatacctt ttgaacactt aacagtttct    2697
tcgacaatga cttttgtaag gattggtagt atatatcatt ccttatgaca tacattgtct    2757
gttgctaatc cttggatctt gctgtattgt cacctaaatt ggtacaggta ctgatgaaaa    2817
tctctcatgg ataaacctaa cactcttcgt cacatgtttt tcctgcagcc tgaaggtttt    2877
taaaaggaaa agatatcaaa tgcctgctgc taccacccct ttaaattgct atcttttgaa    2937
aagcaccagt atgtgttttt agattgattt ccctatttta gggaaatgac agtcagtagt    2997
ttcagttctg atggtataag caaagcaaat aaaacgtgtt tataaaagtt gtatcttgaa    3057
acactggtgt tcaacagcta gcagcttctg tggttcaccc cctgccttgt tagtgttacc    3117
catttatggt tatctccagc agcaatttct cta                                 3150
```

<210> SEQ ID NO 18
<211> LENGTH: 638
<212> TYPE: PRT
<213> ORGANISM: Equus caballus

```
<400> SEQUENCE: 18

Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
                20                  25                  30

Thr Asn Asn Leu Glu Phe Ala Lys Glu Leu Gln Arg Ser Phe Met Ala
            35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205

Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Ser Leu Pro Ala Ala
                405                 410                 415
```

-continued

```
Ser Gln Pro Gln Val Phe Gln Ala Gly Thr Ser Lys Pro Leu His Ser
        420             425             430

Ser Gly Ile Asn Val Asn Ala Ala Pro Phe Gln Ser Met Gln Thr Val
        435             440             445

Phe Asn Met Asn Ala Pro Val Pro Pro Val Asn Glu Pro Glu Thr Leu
        450             455             460

Lys Gln Gln Asn Gln Tyr Gln Ala Ser Tyr Asn Gln Ser Phe Ser Ser
465             470             475             480

Pro Pro His Gln Val Glu Gln Thr Glu Leu Pro Gln Glu Gln Leu Gln
            485             490             495

Thr Val Val Gly Thr Tyr His Ala Ser Gln Asp Gln Pro His Gln Val
            500             505             510

Thr Gly Asn His Gln Gln Pro Pro Gln Gln Asn Thr Gly Phe Pro Arg
            515             520             525

Ser Ser Gln Pro Tyr Tyr Asn Ser Arg Gly Val Ser Arg Gly Gly Ser
        530             535             540

Arg Gly Ala Arg Gly Leu Met Asn Gly Tyr Arg Gly Pro Ala Asn Gly
545             550             555             560

Phe Arg Gly Gly Tyr Asp Gly Tyr Arg Pro Ser Phe Ser Asn Thr Pro
            565             570             575

Asn Ser Gly Tyr Thr Gln Ser Gln Phe Ser Ala Pro Arg Asp Tyr Ser
            580             585             590

Gly Tyr Gln Arg Asp Gly Tyr Gln Gln Asn Phe Lys Arg Gly Ser Gly
            595             600             605

Gln Ser Gly Pro Arg Gly Ala Pro Arg Gly Arg Gly Gly Pro Pro Arg
        610             615             620

Pro Asn Arg Gly Met Pro Gln Met Asn Thr Gln Gln Val Asn
625             630             635
```

```
<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)

<400> SEQUENCE: 19
```

```
gctggctggc taagtccctc ccgcgccggc tcttgtccca ctaggagcag ctcagagccg        60
cggggacagg gcgaagcggc ctgcgcccac ggagcgcacg tctctgttct caacgcagca       120
ccacccttgc cccctcggc tgcccactcc agacgtccag cggctccgcg cgcgcacg          178 atg ccc tcg gcc acc agc cac agc gga agc ggc agc aaa tcg tcg gga       226
Met Pro Ser Ala Thr Ser His Ser Gly Ser Gly Ser Lys Ser Ser Gly
1               5               10              15 ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20              25              30 gct gcg ccg gct tct cag cat ccg gca acc ggc acc ggc gcc gtc cag       322
Ala Ala Pro Ala Ser Gln His Pro Ala Thr Gly Thr Gly Ala Val Gln
        35              40              45 acc gag gcc atg aag cag att ctc ggc gta atc gac aag aaa ctt cgg       370
Thr Glu Ala Met Lys Gln Ile Leu Gly Val Ile Asp Lys Lys Leu Arg
    50              55              60 aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
65              70              75              80
```

-continued

```
aat aaa ggg gaa agg ctc aat caa gac cag ctg gat gcc gta tct aag    466
Asn Lys Gly Glu Arg Leu Asn Gln Asp Gln Leu Asp Ala Val Ser Lys
                85              90              95 tac cag gaa gtc aca aat aat ttg gag ttt gca aag gaa tta cag agg    514
Tyr Gln Glu Val Thr Asn Asn Leu Glu Phe Ala Lys Glu Leu Gln Arg
                100             105             110 agt ttc atg gca tta agt caa gat att cag aaa aca ata aag aag aca    562
Ser Phe Met Ala Leu Ser Gln Asp Ile Gln Lys Thr Ile Lys Lys Thr
                115             120             125 gca cgt cgg gaa cag ctt atg aga gaa gaa gca gaa cag aag cgc tta    610
Ala Arg Arg Glu Gln Leu Met Arg Glu Glu Ala Glu Gln Lys Arg Leu
                130             135             140 aaa act gta ctt gag tta cag tat gta ttg gat aag ctg gga gat gat    658
Lys Thr Val Leu Glu Leu Gln Tyr Val Leu Asp Lys Leu Gly Asp Asp
145             150             155             160 gat gtg aga aca gat ctg aaa caa ggt ttg agt gga gtg cca ata ttg    706
Asp Val Arg Thr Asp Leu Lys Gln Gly Leu Ser Gly Val Pro Ile Leu
                165             170             175 tct gag gag gag ttg tca ttg ctg gat gag ttc tac aag ctc gta gat    754
Ser Glu Glu Glu Leu Ser Leu Leu Asp Glu Phe Tyr Lys Leu Val Asp
                180             185             190 cct gag cgt gac atg agt tta agg tta aat gag cag tat gaa cat gcc    802
Pro Glu Arg Asp Met Ser Leu Arg Leu Asn Glu Gln Tyr Glu His Ala
                195             200             205 tca att cac ttg tgg gat ttg ctg gaa ggg aaa gaa aag cct gtg tgt    850
Ser Ile His Leu Trp Asp Leu Leu Glu Gly Lys Glu Lys Pro Val Cys
                210             215             220 gga aca acc tat aaa gct cta aag gaa att gtt gag cgt gtt ttc cag    898
Gly Thr Thr Tyr Lys Ala Leu Lys Glu Ile Val Glu Arg Val Phe Gln
225             230             235             240 tca aac tac ttt gat agc act cac aat cat caa aat ggg ttg tgt gag    946
Ser Asn Tyr Phe Asp Ser Thr His Asn His Gln Asn Gly Leu Cys Glu
                245             250             255 gag gaa gag gcg gct tca gcg ccc aca gtg gag gac cag gta gct gaa    994
Glu Glu Glu Ala Ala Ser Ala Pro Thr Val Glu Asp Gln Val Ala Glu
                260             265             270 gct gaa cct gag cca gcg gaa gaa tac aca gag caa agt gag gtt gaa   1042
Ala Glu Pro Glu Pro Ala Glu Glu Tyr Thr Glu Gln Ser Glu Val Glu
                275             280             285 tca aca gag tat gtc aat agg cag ttc atg gca gaa aca cag ttc agc   1090
Ser Thr Glu Tyr Val Asn Arg Gln Phe Met Ala Glu Thr Gln Phe Ser
                290             295             300 agt ggt gag aag gag caa gtg gat gag tgg aca gtt gaa aca gtt gag   1138
Ser Gly Glu Lys Glu Gln Val Asp Glu Trp Thr Val Glu Thr Val Glu
305             310             315             320 gtt gta aac tca ctc cag cag caa cct cag gct gcg tcc cct tca gtc   1186
Val Val Asn Ser Leu Gln Gln Gln Pro Gln Ala Ala Ser Pro Ser Val
                325             330             335 cca gag ccc cac tct ttg act cca gtg gct cag tca gat cca ctt gtg   1234
Pro Glu Pro His Ser Leu Thr Pro Val Ala Gln Ser Asp Pro Leu Val
                340             345             350 aga agg cag cgt gta caa gat ctt atg gca caa atg caa ggg ccc tat   1282
Arg Arg Gln Arg Val Gln Asp Leu Met Ala Gln Met Gln Gly Pro Tyr
                355             360             365 aat ttc ata cag gat tca atg ttg gat ttt gaa aat cag acg ctt gat   1330
Asn Phe Ile Gln Asp Ser Met Leu Asp Phe Glu Asn Gln Thr Leu Asp
                370             375             380 cct gcc att gta tcc gca cag cct atg aac cct acc cag aac atg gat   1378
Pro Ala Ile Val Ser Ala Gln Pro Met Asn Pro Thr Gln Asn Met Asp
```

-continued

```
385                 390                 395                 400 atg cct cag ctg gtt tgc cct cag gtt cat tct gaa tct aga ctt gcc    1426
Met Pro Gln Leu Val Cys Pro Gln Val His Ser Glu Ser Arg Leu Ala
            405                 410                 415 caa tct aat caa gtt cct gta caa cca gaa gcc aca cag gtt cct ttg    1474
Gln Ser Asn Gln Val Pro Val Gln Pro Glu Ala Thr Gln Val Pro Leu
            420                 425                 430 gtt tca tcc aca agt gag ggg tat aca gca tct cag ccc ttg tac cag    1522
Val Ser Ser Thr Ser Glu Gly Tyr Thr Ala Ser Gln Pro Leu Tyr Gln
            435                 440                 445 cca tct cat gct acg gag cag cgg ccg cag aaa gag cca atg gat cag    1570
Pro Ser His Ala Thr Glu Gln Arg Pro Gln Lys Glu Pro Met Asp Gln
    450                 455                 460 att cag gca aca ata tct ttg aat aca gac cag act aca gca tcc tca    1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt    1666
Ser Leu Pro Ala Ala Ser Gln Pro Gln Val Phe Gln Ala Gly Thr Ser
            485                 490                 495 aaa cct ttg cac agc agt gga atc aat gta aat gca gct cca ttc cag    1714
Lys Pro Leu His Ser Ser Gly Ile Asn Val Asn Ala Ala Pro Phe Gln
            500                 505                 510 tcc atg caa acg gtg ttc aat atg aat gct cca gtc cct cct gct aat    1762
Ser Met Gln Thr Val Phe Asn Met Asn Ala Pro Val Pro Pro Ala Asn
            515                 520                 525 gaa cca gaa acg tta aaa caa cag agt cag tac cag gcc act tat aac    1810
Glu Pro Glu Thr Leu Lys Gln Gln Ser Gln Tyr Gln Ala Thr Tyr Asn
    530                 535                 540 cag agt ttt tcc agt cag cct cac caa gtg gaa caa aca gag ctt caa    1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac    1906
Gln Asp Gln Leu Gln Thr Val Val Gly Thr Tyr His Gly Ser Gln Asp
            565                 570                 575 cag cct cat caa gtg cct ggt aac cac cag caa ccc cca cag cag aac    1954
Gln Pro His Gln Val Pro Gly Asn His Gln Gln Pro Pro Gln Gln Asn
            580                 585                 590 act ggc ttt cca cgt agc agt cag cct tat tac aac agt cgt ggg gta    2002
Thr Gly Phe Pro Arg Ser Ser Gln Pro Tyr Tyr Asn Ser Arg Gly Val
            595                 600                 605 tct cga gga ggg tct cgt ggt gcc aga ggc ttg atg aat gga tac agg    2050
Ser Arg Gly Gly Ser Arg Gly Ala Arg Gly Leu Met Asn Gly Tyr Arg
            610                 615                 620 ggc cct gcc aat gga ttt aga gga gga tat gat ggt tac cgc cct tca    2098
Gly Pro Ala Asn Gly Phe Arg Gly Gly Tyr Asp Gly Tyr Arg Pro Ser
625                 630                 635                 640 ttc tcg aac act cca aac agt ggt tat tca cag tct cag ttc act gct    2146
Phe Ser Asn Thr Pro Asn Ser Gly Tyr Ser Gln Ser Gln Phe Thr Ala
            645                 650                 655 ccc cgg gac tac tct ggt tac cag cgg gat gga tat cag cag aat ttc    2194
Pro Arg Asp Tyr Ser Gly Tyr Gln Arg Asp Gly Tyr Gln Gln Asn Phe
            660                 665                 670 aag cga ggc tct ggg cag agt gga cca cgg gga gcc cca cga ggt cgt    2242
Lys Arg Gly Ser Gly Gln Ser Gly Pro Arg Gly Ala Pro Arg Gly Arg
            675                 680                 685 gga ggg ccc cca aga ccc aac aga ggg atg ccg caa atg aac act cag    2290
Gly Gly Pro Pro Arg Pro Asn Arg Gly Met Pro Gln Met Asn Thr Gln
            690                 695                 700 caa gtg aat taa tgtgatacac aggattatgt ttaatcgcca aaaacacact    2342
Gln Val Asn
```

-continued

```
Gln Val Asn
705 ggccagtgta ccataatatg ttaccagaag agttattatc tatttgttct ccctttcagg    2402 aaacttattg taaagggact gttttcatcc cataaagaca ggactgcaat tgtcagcttt    2462 acattacctg gatatggaag gaaactattt ttattctgca tgttctgtcc taagcgtcat    2522 cttgagcctt gcacacaata caatactcag attcctcacc cttgcttagg agtaaaacat    2582 tatatactta tggggtgata atatctccat agttagttga agtggcttgg aaaaaaaatg    2642 caagattgaa tttttgacct tggataaaat ctacaatcag ccctagaact attcagtggt    2702 aattgacaaa gttaaagcat tttctttgaa aggaagatgg aaggagtgga gtgtggttta    2762 gcaaaactgc atttcatagc tttcccatta aattggagca ccgacagatt aaaagcatac    2822 caaattatgc atgggtcctt actcacacaa gtgaggctgg ctaccagcct tgacatagca    2882 ctcactagtc ttctggccaa acgactgtga ttaaaacaca tgtaaattgc tctttagtag    2942 tggatactgt gtaagacaaa gccaaattgc aaatcaggct ttgattggct cttctggaaa    3002 atatgcatca aatatggggg ataatctgga tgggctgctg ctgtgctcaa tgtgaactat    3062 ttagatacct ttggaacact taacagtttc tctgaacaat gacttacatg gggattggtc    3122 ctgtttgtca ttcctcacca taattgcatt gtcatcacta atccttggat cttgctgtat    3182 tgttactcaa attggtaata ggtactgatg gaaatcgcta atggatggat aatcataaca    3242 cttttggtca catgttttct cctgcagcct gaaagttctt aaagaaaaag atatcaaatg    3302 cctgctgcta ccaccctttt aaattgctat ctttagaaaa gcaccggtat gtgtttttaga    3362 ttcatttccc tgttttaggg aaatgacagg cagtagtttc agttctgatg gcaaaacaaa    3422 taaaaacatg tttctaaaag ttgtatcttg aaacactggt gttcaacagc tagcagctaa    3482 agtaattcaa cccatgcatt gctagtgtca cagcctttgg ttatgtctag tagctgtttc    3542 tgaagtattt tcatttatct tttgtcaaat ttaaccctgt ttgaattctc tcctttcctc    3602 aaggagacac ttatgttcaa agtgttgatt ctttgcctta ggtgcataga gagtagacag    3662 tttggagatg gaaaggttag cagtgactta gccatatgtt ctgtgttgga atttgtgcta    3722 gcagtttgag cactagctct gcgtgcctat gaactgaatg ctgcttgtcc cattccattt    3782 tatgtcatgg agaaataatt ccacttggta acacaaaggc taagttaatg ttattttctg    3842 tacagaaatt aaattttact tttagccttt tgtaaacttt tttttttttt ttccaagccg    3902 gtatcagcta ctcaaaacaa ttctcagata ttcatcatta gacaactgga gtttttgctg    3962 gttttgtagc ctactaaaac tgctgaggct gttgaacatt ccacattcaa aagtttttgta    4022 gggtggtgga taatggggaa gcttcaatgt ttattttaaa ataaataaaa taagttcttg    4082 acttttctca tgtgtggtta tggtacatca tattggaagg gttatctgtt tacttttgcc    4142 aagactattt tgccagcacc tacacttgtg tgctttaaaa gacaactacc tgggatgtac    4202 cacaaccata tgttaattgt attttattgg gatggataaa atgtttgtgg tttattggat    4262 aatccctaga tggtgtgtta cgtgtgtaga atataatttt atgatagtaa gaaagcaaaa    4322 ttgaagaaaa taagtttagt attgaatttg agttctgaag tgaattcagg gaatgtctca    4382 cgtttcgggc ttctacccaa agtgtagggc agaaggtgta aaagttgttt gtagtttgac    4442 ttgtttattt tttaagttgc ttattccttt caacagcaac atatcattag ctgtcattct    4502 accattgcag ttctagtgag tttttaacgtc tgcattcaag actgtttttaa aagcaacctc    4562 actggacaga gaactgctaa agtcttttcc ttaagatctg agtctttgtt actcagtatc    4622
```

-continued

```
ttctataata tgcaaatgct tgtctagagg cagaagacct tttgtttggt caagtgtgta    4682
ttttaccaga gtacagggaa ctgatggtcc tacatgtctc ttagtgtagt aagactataa    4742
aatcttttgt acatgcacaa ttcacagtat gtttagatac cacgtgtata atgccccccc    4802
ctcccccagg tagcatgcca ttgatgactt tttgcttagg gccattttat taccagggcc    4862
ttaatattcc taaaaagatg attttttttc atcctttctc ctcttttgat cattgtatct    4922
tgatattaaa aacatgacct tccaatgatt gtagtaaatt aacttctata gttcttttgt    4982
ctctatatgt attcatatat atgctattgt atagagactt caaggagaca tggagatgca    5042
tgcttattct caggttcatt cactaaggtg cttggcagac aaccagtttc taagtgcaga    5102
atgtagttaa gcagcttcat atatgtgcca ggcaatttgt tttgttaaat tttcatctac    5162
ttaaggaaat agggtattgt agcttaggct gatcataccc ttcatttcaa ccttaagctc    5222
tcaacctgca tccatccgac ttgagctatt aagtacttta gttttatcga gtataagtta    5282
acagaaaaag taaattaagc tttgccttta ctattttgaa tttatataca ttctggaaaa    5342
acttagaaac tgttgtatat ttcattagat taaattatat gaaaatgtga ttgtttatag    5402
caaagcctgt gagttgcata cacccctaagg aaaactcctt aagtgctcct tgaagagaga    5462
agaaacaatt ctgggtctgg tcttttttaag aacaaagcta gactactgta tgttagcact    5522
gtacattaat agtctgttgt gaagcttgag cagtttcctg catagccttg atccttcacc    5582
gttggcattg aaaatagcag tatccctgat gtacttaaaa cttaaagtca ggttttggta    5642
tatttatttg taagtcttaa tttcctctaa atactatatc tctttagcga gacaacctga    5702
aatttattag cacatttggg tatctcttgc ttggcattat ggccagtgtt aactattcag    5762
tggtgaaaaa attacccctc aagacactgg agtgacccca gatgtgtgta gtaagtggca    5822
tggttcaact gtgtggttaa tgataaatat atgacttagt cggtatgatc tggaaagact    5882
tgattgaaag ataattcagc tgacataagg atgagtgagg agtggcaaac tggataaaag    5942
agtcaagaga cctgtattcc agtgactcct gtttttgttta agcattagca agatctgtct    6002
ggggaaactg gatagggcag ttttcttcca tgtttagttt ttgtctcaac atttggaagc    6062
tattgaaggt tttaaaatgg tgtgtattgt ttttttttgg ggggggggtg gccagaatag    6122
tgggtcatct aataaaactg ccatttaaaa gatcaaaaaa aaaaaaaaaa aaaaaaaaa     6181
```

<210> SEQ ID NO 20
<211> LENGTH: 707
<212> TYPE: PRT
<213> ORGANISM: Mus musculus

<400> SEQUENCE: 20

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
```

-continued

```
             100               105               110
Ser Phe Met Ala Leu Ser Gln Asp Ile Gln Lys Thr Ile Lys Lys Thr
         115               120               125

Ala Arg Arg Glu Gln Leu Met Arg Glu Glu Ala Glu Gln Lys Arg Leu
     130               135               140

Lys Thr Val Leu Glu Leu Gln Tyr Val Leu Asp Lys Leu Gly Asp Asp
145               150               155               160

Asp Val Arg Thr Asp Leu Lys Gln Gly Leu Ser Gly Val Pro Ile Leu
                 165               170               175

Ser Glu Glu Glu Leu Ser Leu Leu Asp Glu Phe Tyr Lys Leu Val Asp
             180               185               190

Pro Glu Arg Asp Met Ser Leu Arg Leu Asn Glu Gln Tyr Glu His Ala
         195               200               205

Ser Ile His Leu Trp Asp Leu Leu Glu Gly Lys Glu Lys Pro Val Cys
     210               215               220

Gly Thr Thr Tyr Lys Ala Leu Lys Glu Ile Val Glu Arg Val Phe Gln
225               230               235               240

Ser Asn Tyr Phe Asp Ser Thr His Asn His Gln Asn Gly Leu Cys Glu
                 245               250               255

Glu Glu Glu Ala Ala Ser Ala Pro Thr Val Glu Asp Gln Val Ala Glu
             260               265               270

Ala Glu Pro Glu Pro Ala Glu Glu Tyr Thr Glu Gln Ser Glu Val Glu
         275               280               285

Ser Thr Glu Tyr Val Asn Arg Gln Phe Met Ala Glu Thr Gln Phe Ser
     290               295               300

Ser Gly Glu Lys Glu Gln Val Asp Glu Trp Thr Val Glu Thr Val Glu
305               310               315               320

Val Val Asn Ser Leu Gln Gln Gln Pro Gln Ala Ala Ser Pro Ser Val
                 325               330               335

Pro Glu Pro His Ser Leu Thr Pro Val Ala Gln Ser Asp Pro Leu Val
             340               345               350

Arg Arg Gln Arg Val Gln Asp Leu Met Ala Gln Met Gln Gly Pro Tyr
         355               360               365

Asn Phe Ile Gln Asp Ser Met Leu Asp Phe Glu Asn Gln Thr Leu Asp
     370               375               380

Pro Ala Ile Val Ser Ala Gln Pro Met Asn Pro Thr Gln Asn Met Asp
385               390               395               400

Met Pro Gln Leu Val Cys Pro Gln Val His Ser Glu Ser Arg Leu Ala
                 405               410               415

Gln Ser Asn Gln Val Pro Val Gln Pro Glu Ala Thr Gln Val Pro Leu
             420               425               430

Val Ser Ser Thr Ser Glu Gly Tyr Thr Ala Ser Gln Pro Leu Tyr Gln
         435               440               445

Pro Ser His Ala Thr Glu Gln Arg Pro Gln Lys Glu Pro Met Asp Gln
     450               455               460

Ile Gln Ala Thr Ile Ser Leu Asn Thr Asp Gln Thr Thr Ala Ser Ser
465               470               475               480

Ser Leu Pro Ala Ala Ser Gln Pro Gln Val Phe Gln Ala Gly Thr Ser
                 485               490               495

Lys Pro Leu His Ser Ser Gly Ile Asn Val Asn Ala Ala Pro Phe Gln
             500               505               510

Ser Met Gln Thr Val Phe Asn Met Asn Ala Pro Val Pro Pro Ala Asn
         515               520               525
```

-continued

```
Glu Pro Glu Thr Leu Lys Gln Gln Ser Gln Tyr Gln Ala Thr Tyr Asn
    530             535             540

Gln Ser Phe Ser Ser Gln Pro His Gln Val Glu Gln Thr Glu Leu Gln
545             550             555             560

Gln Asp Gln Leu Gln Thr Val Val Gly Thr Tyr His Gly Ser Gln Asp
                565             570             575

Gln Pro His Gln Val Pro Gly Asn His Gln Gln Pro Pro Gln Gln Asn
                580             585             590

Thr Gly Phe Pro Arg Ser Ser Gln Pro Tyr Tyr Asn Ser Arg Gly Val
                595             600             605

Ser Arg Gly Gly Ser Arg Gly Ala Arg Gly Leu Met Asn Gly Tyr Arg
    610             615             620

Gly Pro Ala Asn Gly Phe Arg Gly Gly Tyr Asp Gly Tyr Arg Pro Ser
625             630             635             640

Phe Ser Asn Thr Pro Asn Ser Gly Tyr Ser Gln Ser Gln Phe Thr Ala
                645             650             655

Pro Arg Asp Tyr Ser Gly Tyr Gln Arg Asp Gly Tyr Gln Gln Asn Phe
                660             665             670

Lys Arg Gly Ser Gly Gln Ser Gly Pro Arg Gly Ala Pro Arg Gly Arg
                675             680             685

Gly Gly Pro Pro Arg Pro Asn Arg Gly Met Pro Gln Met Asn Thr Gln
    690             695             700

Gln Val Asn
705

<210> SEQ ID NO 21
<211> LENGTH: 6141
<212> TYPE: DNA
<213> ORGANISM: Mus musculus
<220> FEATURE:
<221> NAME/KEY: CDS
<222> LOCATION: (139)..(2262)

<400> SEQUENCE: 21
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                  Met Pro Ser Ala Thr Ser His Ser Gly Ser Gly
                  1               5                   10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15              20              25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
            30              35              40 acc ggc gcc gtc cag acc gag gcc atg aag cag att ctc ggc gta atc      315
Thr Gly Ala Val Gln Thr Glu Ala Met Lys Gln Ile Leu Gly Val Ile
            45              50              55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60              65              70              75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80              85              90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
                95              100             105
```

```
aag gaa tta cag agg agt ttc atg gca tta agt caa gat att cag aaa      507
Lys Glu Leu Gln Arg Ser Phe Met Ala Leu Ser Gln Asp Ile Gln Lys
            110                 115                 120 aca ata aag aag aca gca cgt cgg gaa cag ctt atg aga gaa gaa gca      555
Thr Ile Lys Lys Thr Ala Arg Arg Glu Gln Leu Met Arg Glu Glu Ala
            125                 130                 135 gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc      699
Gly Val Pro Ile Leu Ser Glu Glu Glu Leu Ser Leu Leu Asp Glu Phe
                175                 180                 185 tac aag ctc gta gat cct gag cgt gac atg agt tta agg tta aat gag      747
Tyr Lys Leu Val Asp Pro Glu Arg Asp Met Ser Leu Arg Leu Asn Glu
            190                 195                 200 cag tat gaa cat gcc tca att cac ttg tgg gat ttg ctg gaa ggg aaa      795
Gln Tyr Glu His Ala Ser Ile His Leu Trp Asp Leu Leu Glu Gly Lys
            205                 210                 215 gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
                255                 260                 265 gac cag gta gct gaa gct gaa cct gag cca gcg gaa gaa tac aca gag      987
Asp Gln Val Ala Glu Ala Glu Pro Glu Pro Ala Glu Glu Tyr Thr Glu
            270                 275                 280 caa agt gag gtt gaa tca aca gag tat gtc aat agg cag ttc atg gca      1035
Gln Ser Glu Val Glu Ser Thr Glu Tyr Val Asn Arg Gln Phe Met Ala
285                 290                 295 gaa aca cag ttc agc agt ggt gag aag gag caa gtg gat gag tgg aca      1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct      1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag      1179
Ala Ser Pro Ser Val Pro Glu Pro His Ser Leu Thr Pro Val Ala Gln
                335                 340                 345 tca gat cca ctt gtg aga agg cag cgt gta caa gat ctt atg gca caa      1227
Ser Asp Pro Leu Val Arg Arg Gln Arg Val Gln Asp Leu Met Ala Gln
            350                 355                 360 atg caa ggg ccc tat aat ttc ata cag gat tca atg ttg gat ttt gaa      1275
Met Gln Gly Pro Tyr Asn Phe Ile Gln Asp Ser Met Leu Asp Phe Glu
            365                 370                 375 aat cag acg ctt gat cct gcc att gta tcc gca cag cct atg aac cct      1323
Asn Gln Thr Leu Asp Pro Ala Ile Val Ser Ala Gln Pro Met Asn Pro
380                 385                 390                 395 acc cag aac atg gat atg cct cag ctg gtt tgc cct cag gtt cat tct      1371
Thr Gln Asn Met Asp Met Pro Gln Leu Val Cys Pro Gln Val His Ser
                400                 405                 410 gaa tct aga ctt gcc caa tct aat caa gtt cct gta caa cca gaa gcc      1419
Glu Ser Arg Leu Ala Gln Ser Asn Gln Val Pro Val Gln Pro Glu Ala
```

-continued

```
                415                 420                 425
aca cag gtt cct ttg gtt tca tcc aca agt gag ggg tat aca gca tct    1467
Thr Gln Val Pro Leu Val Ser Ser Thr Ser Glu Gly Tyr Thr Ala Ser
        430                 435                 440 cag ccc ttg tac cag cca tct cat gct acg gag cag cgg ccg cag aaa    1515
Gln Pro Leu Tyr Gln Pro Ser His Ala Thr Glu Gln Arg Pro Gln Lys
        445                 450                 455 gag cca atg gat cag att cag gca aca ata tct ttg aat aca gac cag    1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc    1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat    1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca    1707
Ala Ala Pro Phe Gln Ser Met Gln Thr Val Phe Asn Met Asn Ala Pro
            510                 515                 520 gtc cct cct gct aat gaa cca gaa acg tta aaa caa cag agt cag tac    1755
Val Pro Pro Ala Asn Glu Pro Glu Thr Leu Lys Gln Gln Ser Gln Tyr
        525                 530                 535 cag gcc act tat aac cag agt ttt tcc agt cag cct cac caa gtg gaa    1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac    1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa    1899
His Gly Ser Gln Asp Gln Pro His Gln Val Pro Gly Asn His Gln Gln
                575                 580                 585 ccc cca cag cag aac act ggc ttt cca cgt agc agt cag cct tat tac    1947
Pro Pro Gln Gln Asn Thr Gly Phe Pro Arg Ser Ser Gln Pro Tyr Tyr
            590                 595                 600 aac agt cgt ggg gta tct cga gga ggg tct cgt ggt gcc aga ggc ttg    1995
Asn Ser Arg Gly Val Ser Arg Gly Gly Ser Arg Gly Ala Arg Gly Leu
        605                 610                 615 atg aat gga tac agg ggc cct gcc aat gga ttt aga gga gga tat gat    2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag    2091
Gly Tyr Arg Pro Ser Phe Ser Asn Thr Pro Asn Ser Gly Tyr Ser Gln
            640                 645                 650 tct cag ttc act gct ccc cgg gac tac tct ggt tac cag cgg gat gga    2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga    2187
Tyr Gln Gln Asn Phe Lys Arg Gly Ser Gly Gln Ser Gly Pro Arg Gly
            670                 675                 680 gcc cca cga ggt cgt gga ggg ccc cca aga ccc aac aga ggg atg ccg    2235
Ala Pro Arg Gly Arg Gly Gly Pro Pro Arg Pro Asn Arg Gly Met Pro
            685                 690                 695 caa atg aac act cag caa gtg aat taa tgtgatacac aggattatgt         2282
Gln Met Asn Thr Gln Gln Val Asn
700                 705 ttaatcgcca aaaacacact ggccagtgta ccataatatg ttaccagaag agttattatc   2342
tatttgttct cccctttcagg aaacttattg taaagggact gttttcatcc cataaagaca   2402
ggactgcaat tgtcagcttt acattacctg gatatggaag gaaactattt ttattctgca   2462
```

-continued

```
tgttctgtcc taagcgtcat cttgagcctt gcacacaata caatactcag attcctcacc    2522
cttgcttagg agtaaaacat tatatactta tggggtgata atatctccat agttagttga    2582
agtggcttgg aaaaaaaatg caagattgaa tttttgacct tggataaaat ctacaatcag    2642
ccctagaact attcagtggt aattgacaaa gttaaagcat tttctttgaa aggaagatgg    2702
aaggagtgga gtgtggttta gcaaaactgc atttcatagc tttcccatta aattggagca    2762
ccgacagatt aaaagcatac caaattatgc atgggtcctt actcacacaa gtgaggctgg    2822
ctaccagcct tgacatagca ctcactagtc ttctggccaa acgactgtga ttaaaacaca    2882
tgtaaattgc tctttagtag tggatactgt gtaagacaaa gccaaattgc aaatcaggct    2942
ttgattggct cttctggaaa atatgcatca aatatggggg ataatctgga tgggctgctg    3002
ctgtgctcaa tgtgaactat ttagatacct ttggaacact taacagtttc tctgaacaat    3062
gacttacatg gggattggtc ctgtttgtca ttcctcacca taattgcatt gtcatcacta    3122
atccttggat cttgctgtat tgttactcaa attggtaata ggtactgatg gaaatcgcta    3182
atggatggat aatcataaca cttttggtca catgttttct cctgcagcct gaaagttctt    3242
aaagaaaaag atatcaaatg cctgctgcta ccacccttt aaattgctat ctttagaaaa    3302
gcaccggtat gtgttttaga ttcatttccc tgttttaggg aaatgacagg cagtagtttc    3362
agttctgatg gcaaaacaaa taaaaacatg tttctaaaag ttgtatcttg aaacactggt    3422
gttcaacagc tagcagctaa agtaattcaa cccatgcatt gctagtgtca cagcctttgg    3482
ttatgtctag tagctgtttc tgaagtattt tcatttatct tttgtcaaat ttaaccctgt    3542
ttgaattctc tcctttcctc aaggagacac ttatgttcaa agtgttgatt ctttgcctta    3602
ggtgcataga gagtagacag tttggagatg gaaaggttag cagtgactta gccatatgtt    3662
ctgtgttgga atttgtgcta gcagtttgag cactagctct gcgtgcctat gaactgaatg    3722
ctgcttgtcc cattccattt tatgtcatgg agaaataatt ccacttggta acacaaaggc    3782
taagttaatg ttattttctg tacagaaatt aaattttact tttagccttt tgtaaacttt    3842 ttttttttt ttccaagccg gtatcagcta ctcaaaacaa ttctcagata ttcatcatta    3902
gacaactgga gtttttgctg gttttgtagc ctactaaaac tgctgaggct gttgaacatt    3962
ccacattcaa aagttttgta gggtggtgga taatggggaa gcttcaatgt ttattttaaa    4022
ataaataaaa taagttcttg acttttctca tgtgtggtta tggtacatca tattggaagg    4082
gttatctgtt tacttttgcc aagactattt tgccagcacc tacacttgtg tgctttaaaa    4142
gacaactacc tgggatgtac cacaaccata tgttaattgt attttattgg gatggataaa    4202
atgtttgtgg tttattggat aatccctaga tggtgtgtta cgtgtgtaga atataatttt    4262
atgatagtaa gaaagcaaaa ttgaagaaaa taagtttagt attgaatttg agttctgaag    4322
tgaattcagg gaatgtctca cgtttcgggc ttctacccaa agtgtagggc agaaggtgta    4382
aaagttgttt gtagtttgac ttgtttattt tttaagttgc ttattccttt caacagcaac    4442
atatcattag ctgtcattct accattgcag ttctagtgag ttttaacgtc tgcattcaag    4502
actgttttaa aagcaacctc actggacaga gaactgctaa agtcttttcc ttaagatctg    4562
agtctttgtt actcagtatc ttctataata tgcaaatgct tgtctagagg cagaagacct    4622
tttgtttggt caagtgtgta ttttaccaga gtacagggaa ctgatggtcc tacatgtctc    4682
ttagtgtagt aagactataa aatcttttgt acatgcacaa ttcacagtat gtttagatac    4742
cacgtgtata atgcccccccc ctccccaggg tagcatgcca ttgatgactt tttgcttagg    4802
```

-continued

```
gccattttat taccagggcc ttaatattcc taaaaagatg attttttttc atcctttctc      4862
ctcttttgat cattgtatct tgatattaaa aacatgacct tccaatgatt gtagtaaatt      4922
aacttctata gttcttttgt ctctatatgt attcatatat atgctattgt atagagactt      4982
caaggagaca tggagatgca tgcttattct caggttcatt cactaaggtg cttggcagac      5042
aaccagtttc taagtgcaga atgtagttaa gcagcttcat atatgtgcca ggcaatttgt      5102
tttgttaaat tttcatctac ttaaggaaat agggtattgt agcttaggct gatcataccc      5162
ttcatttcaa ccttaagctc tcaacctgca tccatccgac ttgagctatt aagtacttta      5222
gttttatcga gtataagtta acagaaaaag taaattaagc tttgccttta ctattttgaa      5282
tttatataca ttctggaaaa acttagaaac tgttgtatat ttcattagat taaattatat      5342
gaaaatgtga ttgtttatag caaagcctgt gagttgcata caccctaagg aaaactcctt      5402
aagtgctcct tgaagagaga agaaacaatt ctgggtctgg tcttttttaag aacaaagcta     5462 gactactgta tgttagcact gtacattaat agtctgttgt gaagcttgag cagtttcctg      5522
catagccttg atccttcacc gttggcattg aaaatagcag tatccctgat gtacttaaaa      5582
cttaaagtca ggttttggta tatttatttg taagtcttaa tttcctctaa atactatatc      5642
tctttagcga gacaacctga aatttattag cacatttggg tatctcttgc ttggcattat      5702
ggccagtgtt aactattcag tggtgaaaaa attacccctc aagacactgg agtgacccca      5762
gatgtgtgta gtaagtggca tggttcaact gtgtggttaa tgataaatat atgacttagt      5822
cggtatgatc tggaaagact tgattgaaag ataattcagc tgacataagg atgagtgagg      5882
agtggcaaac tggataaaag agtcaagaga cctgtattcc agtgactcct gttttgttta      5942
agcattagca agatctgtct ggggaaactg gatagggcag ttttcttcca tgtttagttt      6002
ttgtctcaac atttggaagc tattgaaggt tttaaaatgg tgtgtattgt ttttttttgg      6062
ggggggggtg gccagaatag tgggtcatct aataaaactg ccatttaaaa gatcaaaaaa      6122
aaaaaaaaaa aaaaaaaa                                                    6141
```

```
<210> SEQ ID NO 22
<211> LENGTH: 707
<212> TYPE: PRT
<213> ORGANISM: Mus musculus

<400> SEQUENCE: 22

Met Pro Ser Ala Thr Ser His Ser Gly Ser Gly Ser Lys Ser Ser Gly
1               5                   10                  15

Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
```

```
         130                135                140
Lys Thr Val Leu Glu Leu Gln Tyr Val Leu Asp Lys Leu Gly Asp Asp
145                150                155                160

Asp Val Arg Thr Asp Leu Lys Gln Gly Leu Ser Gly Val Pro Ile Leu
                165                170                175

Ser Glu Glu Glu Leu Ser Leu Leu Asp Glu Phe Tyr Lys Leu Val Asp
                180                185                190

Pro Glu Arg Asp Met Ser Leu Arg Leu Asn Glu Gln Tyr Glu His Ala
                195                200                205

Ser Ile His Leu Trp Asp Leu Leu Glu Gly Lys Glu Lys Pro Val Cys
                210                215                220

Gly Thr Thr Tyr Lys Ala Leu Lys Glu Ile Val Glu Arg Val Phe Gln
225                230                235                240

Ser Asn Tyr Phe Asp Ser Thr His Asn His Gln Asn Gly Leu Cys Glu
                245                250                255

Glu Glu Glu Ala Ala Ser Ala Pro Thr Val Glu Asp Gln Val Ala Glu
                260                265                270

Ala Glu Pro Glu Pro Ala Glu Glu Tyr Thr Glu Gln Ser Glu Val Glu
                275                280                285

Ser Thr Glu Tyr Val Asn Arg Gln Phe Met Ala Glu Thr Gln Phe Ser
                290                295                300

Ser Gly Glu Lys Glu Gln Val Asp Glu Trp Thr Val Glu Thr Val Glu
305                310                315                320

Val Val Asn Ser Leu Gln Gln Gln Pro Gln Ala Ala Ser Pro Ser Val
                325                330                335

Pro Glu Pro His Ser Leu Thr Pro Val Ala Gln Ser Asp Pro Leu Val
                340                345                350

Arg Arg Gln Arg Val Gln Asp Leu Met Ala Gln Met Gln Gly Pro Tyr
                355                360                365

Asn Phe Ile Gln Asp Ser Met Leu Asp Phe Glu Asn Gln Thr Leu Asp
                370                375                380

Pro Ala Ile Val Ser Ala Gln Pro Met Asn Pro Thr Gln Asn Met Asp
385                390                395                400

Met Pro Gln Leu Val Cys Pro Gln Val His Ser Glu Ser Arg Leu Ala
                405                410                415

Gln Ser Asn Gln Val Pro Val Gln Pro Glu Ala Thr Gln Val Pro Leu
                420                425                430

Val Ser Ser Thr Ser Glu Gly Tyr Thr Ala Ser Gln Pro Leu Tyr Gln
                435                440                445

Pro Ser His Ala Thr Glu Gln Arg Pro Gln Lys Glu Pro Met Asp Gln
                450                455                460

Ile Gln Ala Thr Ile Ser Leu Asn Thr Asp Gln Thr Thr Ala Ser Ser
465                470                475                480

Ser Leu Pro Ala Ala Ser Gln Pro Gln Val Phe Gln Ala Gly Thr Ser
                485                490                495

Lys Pro Leu His Ser Ser Gly Ile Asn Val Asn Ala Ala Pro Phe Gln
                500                505                510

Ser Met Gln Thr Val Phe Asn Met Asn Ala Pro Val Pro Pro Ala Asn
                515                520                525

Glu Pro Glu Thr Leu Lys Gln Gln Ser Gln Tyr Gln Ala Thr Tyr Asn
                530                535                540

Gln Ser Phe Ser Ser Gln Pro His Gln Val Glu Gln Thr Glu Leu Gln
545                550                555                560
```

-continued

```
Gln Asp Gln Leu Gln Thr Val Val Gly Thr Tyr His Gly Ser Gln Asp
            565             570             575

Gln Pro His Gln Val Pro Gly Asn His Gln Gln Pro Pro Gln Gln Asn
            580             585             590

Thr Gly Phe Pro Arg Ser Ser Gln Pro Tyr Tyr Asn Ser Arg Gly Val
            595             600             605

Ser Arg Gly Gly Ser Arg Gly Ala Arg Gly Leu Met Asn Gly Tyr Arg
            610             615             620

Gly Pro Ala Asn Gly Phe Arg Gly Gly Tyr Asp Gly Tyr Arg Pro Ser
625             630             635             640

Phe Ser Asn Thr Pro Asn Ser Gly Tyr Ser Gln Ser Gln Phe Thr Ala
            645             650             655

Pro Arg Asp Tyr Ser Gly Tyr Gln Arg Asp Gly Tyr Gln Gln Asn Phe
            660             665             670

Lys Arg Gly Ser Gly Gln Ser Gly Pro Arg Gly Ala Pro Arg Gly Arg
            675             680             685

Gly Gly Pro Pro Arg Pro Asn Arg Gly Met Pro Gln Met Asn Thr Gln
            690             695             700

Gln Val Asn
705
```

```
<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)

<400> SEQUENCE: 23
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc       171
                    Met Pro Ser Ala Thr Ser His Ser Gly Ser Gly
                    1               5                   10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
            30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
            45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
            95                  100                 105 aag gaa tta cag agg agt ttc atg gca tta agt caa gat att cag aaa      507
Lys Glu Leu Gln Arg Ser Phe Met Ala Leu Ser Gln Asp Ile Gln Lys
            110                 115                 120 aca ata aag aag aca gca cgt cgg gaa cag ctt atg aga gaa gaa gca      555
```

-continued

```
Thr Ile Lys Lys Thr Ala Arg Arg Glu Gln Leu Met Arg Glu Glu Ala
    125                 130                 135 gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc      699
Gly Val Pro Ile Leu Ser Glu Glu Glu Leu Ser Leu Leu Asp Glu Phe
                175                 180                 185 tac aag ctc gta gat cct gag cgt gac atg agt tta agg tta aat gag      747
Tyr Lys Leu Val Asp Pro Glu Arg Asp Met Ser Leu Arg Leu Asn Glu
            190                 195                 200 cag tat gaa cat gcc tca att cac ttg tgg gat ttg ctg gaa ggg aaa      795
Gln Tyr Glu His Ala Ser Ile His Leu Trp Asp Leu Leu Glu Gly Lys
        205                 210                 215 gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa      891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
                255                 260                 265 gac cag gta gct gaa gct gaa cct gag cca gcg gaa gaa tac aca gag      987
Asp Gln Val Ala Glu Ala Glu Pro Glu Pro Ala Glu Glu Tyr Thr Glu
                270                 275                 280 caa agt gag gtt gaa tca aca gag tat gtc aat agg cag ttc atg gca     1035
Gln Ser Glu Val Glu Ser Thr Glu Tyr Val Asn Arg Gln Phe Met Ala
        285                 290                 295 gaa aca cag ttc agc agt ggt gag aag gag caa gtg gat gag tgg aca     1083
Glu Thr Gln Phe Ser Ser Gly Glu Lys Glu Gln Val Asp Glu Trp Thr
300                 305                 310                 315 gtt gaa aca gtt gag gtt gta aac tca ctc cag cag caa cct cag gct     1131
Val Glu Thr Val Glu Val Val Asn Ser Leu Gln Gln Gln Pro Gln Ala
                320                 325                 330 gcg tcc cct tca gtc cca gag ccc cac tct ttg act cca gtg gct cag     1179
Ala Ser Pro Ser Val Pro Glu Pro His Ser Leu Thr Pro Val Ala Gln
                335                 340                 345 tca gat cca ctt gtg aga agg cag cgt gta caa gat ctt atg gca caa     1227
Ser Asp Pro Leu Val Arg Arg Gln Arg Val Gln Asp Leu Met Ala Gln
            350                 355                 360 atg caa ggg ccc tat aat ttc ata cag acg ctt gat cct gcc att gta     1275
Met Gln Gly Pro Tyr Asn Phe Ile Gln Thr Leu Asp Pro Ala Ile Val
        365                 370                 375 tcc gca cag cct atg aac cct acc cag aac atg gat atg cct cag ctg     1323
Ser Ala Gln Pro Met Asn Pro Thr Gln Asn Met Asp Met Pro Gln Leu
380                 385                 390                 395 gtt tgc cct cag gtt cat tct gaa tct aga ctt gcc caa tct aat caa     1371
Val Cys Pro Gln Val His Ser Glu Ser Arg Leu Ala Gln Ser Asn Gln
                400                 405                 410 gtt cct gta caa cca gaa gcc aca cag gtt cct ttg gtt tca tcc aca     1419
Val Pro Val Gln Pro Glu Ala Thr Gln Val Pro Leu Val Ser Ser Thr
            415                 420                 425 agt gag ggg tat aca gca tct cag ccc ttg tac cag cca tct cat gct     1467
Ser Glu Gly Tyr Thr Ala Ser Gln Pro Leu Tyr Gln Pro Ser His Ala
            430                 435                 440
```

-continued

```
acg gag cag cgg ccg cag aaa gag cca atg gat cag att cag gca aca    1515
Thr Glu Gln Arg Pro Gln Lys Glu Pro Met Asp Gln Ile Gln Ala Thr
    445             450             455 ata tct ttg aat aca gac cag act aca gca tcc tca tcc ctt cct gct    1563
Ile Ser Leu Asn Thr Asp Gln Thr Thr Ala Ser Ser Ser Leu Pro Ala
460             465             470             475 gct tct cag cct caa gtg ttc cag gct ggg aca agt aaa cct ttg cac    1611
Ala Ser Gln Pro Gln Val Phe Gln Ala Gly Thr Ser Lys Pro Leu His
            480             485             490 agc agt gga atc aat gta aat gca gct cca ttc cag tcc atg caa acg    1659
Ser Ser Gly Ile Asn Val Asn Ala Ala Pro Phe Gln Ser Met Gln Thr
        495             500             505 gtg ttc aat atg aat gct cca gtc cct cct gct aat gaa cca gaa acg    1707
Val Phe Asn Met Asn Ala Pro Val Pro Pro Ala Asn Glu Pro Glu Thr
        510             515             520 tta aaa caa cag agt cag tac cag gcc act tat aac cag agt ttt tcc    1755
Leu Lys Gln Gln Ser Gln Tyr Gln Ala Thr Tyr Asn Gln Ser Phe Ser
    525             530             535 agt cag cct cac caa gtg gaa caa aca gag ctt caa caa gac caa ctg    1803
Ser Gln Pro His Gln Val Glu Gln Thr Glu Leu Gln Gln Asp Gln Leu
540             545             550             555 caa acg gtg gtt ggc act tac cat gga tcc cag gac cag cct cat caa    1851
Gln Thr Val Val Gly Thr Tyr His Gly Ser Gln Asp Gln Pro His Gln
            560             565             570 gtg cct ggt aac cac cag caa ccc cca cag cag aac act ggc ttt cca    1899
Val Pro Gly Asn His Gln Gln Pro Pro Gln Gln Asn Thr Gly Phe Pro
            575             580             585 cgt agc agt cag cct tat tac aac agt cgt ggg gta tct cga gga ggg    1947
Arg Ser Ser Gln Pro Tyr Tyr Asn Ser Arg Gly Val Ser Arg Gly Gly
        590             595             600 tct cgt ggt gcc aga ggc ttg atg aat gga tac agg ggc cct gcc aat    1995
Ser Arg Gly Ala Arg Gly Leu Met Asn Gly Tyr Arg Gly Pro Ala Asn
    605             610             615 gga ttt aga gga gga tat gat ggt tac cgc cct tca ttc tcg aac act    2043
Gly Phe Arg Gly Gly Tyr Asp Gly Tyr Arg Pro Ser Phe Ser Asn Thr
620             625             630             635 cca aac agt ggt tat tca cag tct cag ttc act gct ccc cgg gac tac    2091
Pro Asn Ser Gly Tyr Ser Gln Ser Gln Phe Thr Ala Pro Arg Asp Tyr
            640             645             650 tct ggt tac cag cgg gat gga tat cag cag aat ttc aag cga ggc tct    2139
Ser Gly Tyr Gln Arg Asp Gly Tyr Gln Gln Asn Phe Lys Arg Gly Ser
            655             660             665 ggg cag agt gga cca cgg gga gcc cca cga ggt cgt gga ggg ccc cca    2187
Gly Gln Ser Gly Pro Arg Gly Ala Pro Arg Gly Arg Gly Gly Pro Pro
            670             675             680 aga ccc aac aga ggg atg ccg caa atg aac act cag caa gtg aat taa    2235
Arg Pro Asn Arg Gly Met Pro Gln Met Asn Thr Gln Gln Val Asn
    685             690             695 tgtgatacac aggattatgt ttaatcgcca aaaacacact ggccagtgta ccataatatg    2295
ttaccagaag agttattatc tatttgttct ccctttcagg aaacttattg taaagggact    2355
gttttcatcc cataaagaca ggactgcaat tgtcagcttt acattacctg gatatggaag    2415
gaaactattt ttattctgca tgttctgtcc taagcgtcat cttgagcctt gcacacaata    2475
caatactcag attcctcacc cttgcttagg agtaaaacat tatatactta tggggtgata    2535
atatctccat agttagttga agtggcttgg aaaaaaaatg caagattgaa tttttgacct    2595
tggataaaat ctacaatcag ccctagaact attcagtggt aattgacaaa gttaaagcat    2655
tttctttgaa aggaagatgg aaggagtgga gtgtggttta gcaaaactgc atttcatagc    2715
```

-continued

```
tttcccatta aattggagca ccgacagatt aaaagcatac caaattatgc atgggtcctt      2775
actcacacaa gtgaggctgg ctaccagcct tgacatagca ctcactagtc ttctggccaa      2835
acgactgtga ttaaaacaca tgtaaattgc tctttagtag tggatactgt gtaagacaaa      2895
gccaaattgc aaatcaggct ttgattggct cttctggaaa atatgcatca aatatggggg      2955
ataatctgga tgggctgctg ctgtgctcaa tgtgaactat ttagatacct ttggaacact      3015
taacagtttc tctgaacaat gacttacatg gggattggtc ctgtttgtca ttcctcacca      3075
taattgcatt gtcatcacta atccttggat cttgctgtat tgttactcaa attggtaata      3135
ggtactgatg gaaatcgcta atggatggat aatcataaca cttttggtca catgttttct      3195
cctgcagcct gaaagttctt aaagaaaaag atatcaaatg cctgctgcta ccacccttt      3255 aaattgctat ctttagaaaa gcaccggtat gtgtttaga ttcatttccc tgttttaggg      3315
aaatgacagg cagtagtttc agttctgatg gcaaacaaa taaaaacatg tttctaaaag      3375
ttgtatcttg aaacactggt gttcaacagc tagcagctaa agtaattcaa cccatgcatt      3435
gctagtgtca cagcctttgg ttatgtctag tagctgtttc tgaagtattt tcatttatct      3495
tttgtcaaat ttaaccctgt ttgaattctc tcctttcctc aaggagacac ttatgttcaa      3555
agtgttgatt ctttgcctta ggtgcataga gagtagacag tttggagatg gaaaggttag      3615
cagtgactta gccatatgtt ctgtgttgga atttgtgcta gcagtttgag cactagctct      3675
gcgtgcctat gaactgaatg ctgcttgtcc cattccattt tatgtcatgg agaaataatt      3735
ccacttggta acacaaaggc taagttaatg ttattttctg tacagaaatt aaatttact      3795 tttagcctt tgtaaacttt tttttttttt ttccaagccg gtatcagcta ctcaaaacaa      3855
ttctcagata ttcatcatta gacaactgga gtttttgctg gttttgtagc ctactaaaac      3915
tgctgaggct gttgaacatt ccacattcaa aagtttgta gggtggtgga taatgggga      3975 gcttcaatgt ttattttaaa ataaataaaa taagttcttg acttttctca tgtgtggtta      4035
tggtacatca tattggaagg gttatctgtt tacttttgcc aagactattt tgccagcacc      4095
tacacttgtg tgctttaaaa gacaactacc tgggatgtac cacaaccata tgttaattgt      4155
attttattgg gatggataaa atgtttgtgg tttattggat aatccctaga tggtgtgtta      4215
cgtgtgtaga atataatttt atgatagtaa gaaagcaaaa ttgaagaaaa taagtttagt      4275
attgaatttg agttctgaag tgaattcagg gaatgtctca cgtttcgggc ttctacccaa      4335
agtgtagggc agaaggtgta aaagttgttt gtagtttgac ttgtttattt tttaagttgc      4395
ttattccttt caacagcaac atatcattag ctgtcattct accattgcag ttctagtgag      4455
ttttaacgtc tgcattcaag actgttttaa aagcaacctc actggacaga gaactgctaa      4515 agtctttttcc ttaagatctg agtctttgtt actcagtatc ttctataata tgcaaatgct      4575
tgtctagagg cagaagacct tttgtttggt caagtgtgta ttttaccaga gtacagggaa      4635
ctgatggtcc tacatgtctc ttagtgtagt aagactataa aatcttttgt acatgcacaa      4695
ttcacagtat gtttagatac cacgtgtata atgcccccccc ctccccagg tagcatgcca      4755 ttgatgactt tttgcttagg gccatttat taccagggcc ttaatattcc taaaaagatg      4815 atttttttc atcctttctc ctcttttgat cattgtatct tgatattaaa aacatgacct      4875
tccaatgatt gtagtaaatt aacttctata gttctttgt ctctatatgt attcatatat      4935
atgctattgt atagagactt caaggagaca tggagatgca tgcttattct caggttcatt      4995
cactaaggtg cttggcagac aaccagtttc taagtgcaga atgtagttaa gcagcttcat      5055
```

-continued

```
atatgtgcca ggcaatttgt tttgttaaat tttcatctac ttaaggaaat agggtattgt    5115
agcttaggct gatcataccc ttcatttcaa ccttaagctc tcaacctgca tccatccgac    5175
ttgagctatt aagtacttta gttttatcga gtataagtta acagaaaaag taaattaagc    5235
tttgccttta ctattttgaa tttatataca ttctggaaaa acttagaaac tgttgtatat    5295
ttcattagat taaattatat gaaaatgtga ttgtttatag caaagcctgt gagttgcata    5355
caccctaagg aaaactcctt aagtgctcct tgaagagaga agaaacaatt ctgggtctgg    5415 tcttttttaag aacaaagcta gactactgta tgttagcact gtacattaat agtctgttgt    5475
gaagcttgag cagtttcctg catagccttg atccttcacc gttggcattg aaaatagcag    5535
tatccctgat gtacttaaaa cttaaagtca ggttttggta tatttatttg taagtcttaa    5595
tttcctctaa atactatatc tctttagcga gacaacctga aatttattag cacatttggg    5655
tatctcttgc ttggcattat ggccagtgtt aactattcag tggtgaaaaa attacccctc    5715
aagacactgg agtgaccoca gatgtgtgta gtaagtggca tggttcaact gtgtggttaa    5775
tgataaatat atgacttagt cggtatgatc tggaaagact tgattgaaag ataattcagc    5835
tgacataagg atgagtgagg agtggcaaac tggataaaag agtcaagaga cctgtattcc    5895
agtgactcct gttttgttta agcattagca agatctgtct ggggaaactg gatagggcag    5955
ttttcttcca tgtttagttt ttgtctcaac atttggaagc tattgaaggt tttaaaatgg    6015
tgtgtattgt ttttttttgg ggggggggtg gccagaatag tgggtcatct aataaaactg    6075
ccatttaaaa gatcaaaaaa aaaaaaaaaa aaaaaaaaa                            6114
```

```
<210> SEQ ID NO 24
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
        130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190
```

```
Pro Glu Arg Asp Met Ser Leu Arg Leu Asn Glu Gln Tyr Glu His Ala
    195             200             205
Ser Ile His Leu Trp Asp Leu Leu Glu Gly Lys Glu Lys Pro Val Cys
    210             215             220
Gly Thr Thr Tyr Lys Ala Leu Lys Glu Ile Val Glu Arg Val Phe Gln
225             230             235             240
Ser Asn Tyr Phe Asp Ser Thr His Asn His Gln Asn Gly Leu Cys Glu
            245             250             255
Glu Glu Glu Ala Ala Ser Ala Pro Thr Val Glu Asp Gln Val Ala Glu
            260             265             270
Ala Glu Pro Glu Pro Ala Glu Glu Tyr Thr Glu Gln Ser Glu Val Glu
    275             280             285
Ser Thr Glu Tyr Val Asn Arg Gln Phe Met Ala Glu Thr Gln Phe Ser
    290             295             300
Ser Gly Glu Lys Glu Gln Val Asp Glu Trp Thr Val Glu Thr Val Glu
305             310             315             320
Val Val Asn Ser Leu Gln Gln Gln Pro Gln Ala Ala Ser Pro Ser Val
            325             330             335
Pro Glu Pro His Ser Leu Thr Pro Val Ala Gln Ser Asp Pro Leu Val
            340             345             350
Arg Arg Gln Arg Val Gln Asp Leu Met Ala Gln Met Gln Gly Pro Tyr
    355             360             365
Asn Phe Ile Gln Thr Leu Asp Pro Ala Ile Val Ser Ala Gln Pro Met
    370             375             380
Asn Pro Thr Gln Asn Met Asp Met Pro Gln Leu Val Cys Pro Gln Val
385             390             395             400
His Ser Glu Ser Arg Leu Ala Gln Ser Asn Gln Val Pro Val Gln Pro
            405             410             415
Glu Ala Thr Gln Val Pro Leu Val Ser Ser Thr Ser Glu Gly Tyr Thr
            420             425             430
Ala Ser Gln Pro Leu Tyr Gln Pro Ser His Ala Thr Glu Gln Arg Pro
    435             440             445
Gln Lys Glu Pro Met Asp Gln Ile Gln Ala Thr Ile Ser Leu Asn Thr
    450             455             460
Asp Gln Thr Thr Ala Ser Ser Ser Leu Pro Ala Ala Ser Gln Pro Gln
465             470             475             480
Val Phe Gln Ala Gly Thr Ser Lys Pro Leu His Ser Ser Gly Ile Asn
            485             490             495
Val Asn Ala Ala Pro Phe Gln Ser Met Gln Thr Val Phe Asn Met Asn
            500             505             510
Ala Pro Val Pro Pro Ala Asn Glu Pro Glu Thr Leu Lys Gln Gln Ser
            515             520             525
Gln Tyr Gln Ala Thr Tyr Asn Gln Ser Phe Ser Ser Gln Pro His Gln
    530             535             540
Val Glu Gln Thr Glu Leu Gln Gln Asp Gln Leu Gln Thr Val Val Gly
545             550             555             560
Thr Tyr His Gly Ser Gln Asp Gln Pro His Gln Val Pro Gly Asn His
            565             570             575
Gln Gln Pro Pro Gln Gln Asn Thr Gly Phe Pro Arg Ser Ser Gln Pro
            580             585             590
Tyr Tyr Asn Ser Arg Gly Val Ser Arg Gly Gly Ser Arg Gly Ala Arg
            595             600             605
```

```
Gly Leu Met Asn Gly Tyr Arg Gly Pro Ala Asn Gly Phe Arg Gly Gly
    610                 615                 620

Tyr Asp Gly Tyr Arg Pro Ser Phe Ser Asn Thr Pro Asn Ser Gly Tyr
625                 630                 635                 640

Ser Gln Ser Gln Phe Thr Ala Pro Arg Asp Tyr Ser Gly Tyr Gln Arg
                645                 650                 655

Asp Gly Tyr Gln Gln Asn Phe Lys Arg Gly Ser Gly Gln Ser Gly Pro
                660                 665                 670

Arg Gly Ala Pro Arg Gly Arg Gly Gly Pro Pro Arg Pro Asn Arg Gly
                675                 680                 685

Met Pro Gln Met Asn Thr Gln Gln Val Asn
    690                 695

<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)

<400> SEQUENCE: 25
gctggctggc taagtccctc ccgcgccggc tcttgtccca ctaggagcag ctcagagccg        60
cggggacagg gcgaagcggc ctgcgcccac ggagcgcacg tctctgttct caacgcagca       120
ccacccttgc cccctcggc tgcccactcc agacgtccag cggctccgcg cgcgcacg          178 atg ccc tcg gcc acc agc cac agc gga agc ggc agc aaa tcg tcg gga        226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca        274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag        322
Ala Ala Pro Ala Ser Gln His Pro Ala Thr Gly Thr Gly Ala Val Gln
            35                  40                  45 acc gag gcc atg aag cag att ctc ggc gta atc gac aag aaa ctt cgg        370
Thr Glu Ala Met Lys Gln Ile Leu Gly Val Ile Asp Lys Lys Leu Arg
        50                  55                  60 aac ctg gag aag aaa aag ggt aaa ctt gat gat tac cag gaa cga atg        418
Asn Leu Glu Lys Lys Lys Gly Lys Leu Asp Asp Tyr Gln Glu Arg Met
65                  70                  75                  80 aat aaa ggg gaa agg ctc aat caa gac cag ctg gat gcc gta tct aag        466
Asn Lys Gly Glu Arg Leu Asn Gln Asp Gln Leu Asp Ala Val Ser Lys
                85                  90                  95 tac cag gaa gtc aca aat aat ttg gag ttt gca aag gaa tta cag agg        514
Tyr Gln Glu Val Thr Asn Asn Leu Glu Phe Ala Lys Glu Leu Gln Arg
                100                 105                 110 agt ttc atg gca tta agt caa gat att cag aaa aca ata aag aag aca        562
Ser Phe Met Ala Leu Ser Gln Asp Ile Gln Lys Thr Ile Lys Lys Thr
            115                 120                 125 gca cgt cgg gaa cag ctt atg aga gaa gaa gca gaa cag aag cgc tta        610
Ala Arg Arg Glu Gln Leu Met Arg Glu Glu Ala Glu Gln Lys Arg Leu
        130                 135                 140 aaa act gta ctt gag tta cag tat gta ttg gat aag ctg gga gat gat        658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg        706
Asp Val Arg Thr Asp Leu Lys Gln Gly Leu Ser Gly Val Pro Ile Leu
                165                 170                 175
```

```
tct gag gag gag ttg tca ttg ctg gat gag ttc tac aag ctc gta gat      754
Ser Glu Glu Glu Leu Ser Leu Leu Asp Glu Phe Tyr Lys Leu Val Asp
            180                 185                 190 cct gag cgt gac atg agt tta agg tta aat gag cag tat gaa cat gcc      802
Pro Glu Arg Asp Met Ser Leu Arg Leu Asn Glu Gln Tyr Glu His Ala
        195                 200                 205 tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
    210                 215                 220 gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240 tca aac tac ttt gat agc act cac aat cat caa aat ggg ttg tgt gag      946
Ser Asn Tyr Phe Asp Ser Thr His Asn His Gln Asn Gly Leu Cys Glu
                245                 250                 255 gag gaa gag gcg gct tca gcg ccc aca gtg gag gac cag gta gct gaa      994
Glu Glu Glu Ala Ala Ser Ala Pro Thr Val Glu Asp Gln Val Ala Glu
            260                 265                 270 gct gaa cct gag cca gcg gaa gaa tac aca gag caa agt gag gtt gaa     1042
Ala Glu Pro Glu Pro Ala Glu Glu Tyr Thr Glu Gln Ser Glu Val Glu
        275                 280                 285 tca aca gag tat gtc aat agg cag ttc atg gca gaa aca cag ttc agc     1090
Ser Thr Glu Tyr Val Asn Arg Gln Phe Met Ala Glu Thr Gln Phe Ser
    290                 295                 300 agt ggt gag aag gag caa gtg gat gag tgg aca gtt gaa aca gtt gag     1138
Ser Gly Glu Lys Glu Gln Val Asp Glu Trp Thr Val Glu Thr Val Glu
305                 310                 315                 320 gtt gta aac tca ctc cag cag caa cct cag gct gcg tcc cct tca gtc     1186
Val Val Asn Ser Leu Gln Gln Gln Pro Gln Ala Ala Ser Pro Ser Val
                325                 330                 335 cca gag ccc cac tct ttg act cca gtg gct cag tca gat cca ctt gtg     1234
Pro Glu Pro His Ser Leu Thr Pro Val Ala Gln Ser Asp Pro Leu Val
            340                 345                 350 aga agg cag cgt gta caa gat ctt atg gca caa atg caa ggg ccc tat     1282
Arg Arg Gln Arg Val Gln Asp Leu Met Ala Gln Met Gln Gly Pro Tyr
        355                 360                 365 aat ttc ata cag gat tca atg ttg gat ttt gaa aat cag acg ctt gat     1330
Asn Phe Ile Gln Asp Ser Met Leu Asp Phe Glu Asn Gln Thr Leu Asp
    370                 375                 380 cct gcc att gta tcc gca cag cct atg aac cct acc cag aac atg gat     1378
Pro Ala Ile Val Ser Ala Gln Pro Met Asn Pro Thr Gln Asn Met Asp
385                 390                 395                 400 atg cct cag ctg gtt tgc cct cag gtt cat tct gaa tct aga ctt gcc     1426
Met Pro Gln Leu Val Cys Pro Gln Val His Ser Glu Ser Arg Leu Ala
                405                 410                 415 caa tct aat caa gtt cct gta caa cca gaa gcc aca cag gtt cct ttg     1474
Gln Ser Asn Gln Val Pro Val Gln Pro Glu Ala Thr Gln Val Pro Leu
            420                 425                 430 gtt tca tcc aca agt gag ggg tat aca gca tct cag ccc ttg tac cag     1522
Val Ser Ser Thr Ser Glu Gly Tyr Thr Ala Ser Gln Pro Leu Tyr Gln
        435                 440                 445 cca tct cat gct acg gag cag cgg ccg cag aaa gag cca atg gat cag     1570
Pro Ser His Ala Thr Glu Gln Arg Pro Gln Lys Glu Pro Met Asp Gln
    450                 455                 460 att cag gca aca ata tct ttg aat aca gac cag act aca gca tcc tca     1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt     1666
Ser Leu Pro Ala Ala Ser Gln Pro Gln Val Phe Gln Ala Gly Thr Ser
                485                 490                 495
```

```
aaa cct ttg cac agc agt gga atc aat gta aat gca gct cca ttc cag    1714
Lys Pro Leu His Ser Ser Gly Ile Asn Val Asn Ala Ala Pro Phe Gln
        500                 505                 510 tcc atg caa acg gtg ttc aat atg aat gct cca gtc cct cct gct aat    1762
Ser Met Gln Thr Val Phe Asn Met Asn Ala Pro Val Pro Pro Ala Asn
        515                 520                 525 gaa cca gaa acg tta aaa caa cag agt cag tac cag gcc act tat aac    1810
Glu Pro Glu Thr Leu Lys Gln Gln Ser Gln Tyr Gln Ala Thr Tyr Asn
        530                 535                 540 cag agt ttt tcc agt cag cct cac caa gtg gaa caa aca gag ctt caa    1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac    1906
Gln Asp Gln Leu Gln Thr Val Val Gly Thr Tyr His Gly Ser Gln Asp
                565                 570                 575 cag cct cat caa gtg cct ggt aac cac cag caa ccc cca cag cag aac    1954
Gln Pro His Gln Val Pro Gly Asn His Gln Gln Pro Pro Gln Gln Asn
                580                 585                 590 act ggc ttt cca cgt agc agt cag cct tat tac aac agt cgt ggg gta    2002
Thr Gly Phe Pro Arg Ser Ser Gln Pro Tyr Tyr Asn Ser Arg Gly Val
                595                 600                 605 tct cga gga ggg tct cgt ggt gcc aga ggc ttg atg aat gga tac agg    2050
Ser Arg Gly Gly Ser Arg Gly Ala Arg Gly Leu Met Asn Gly Tyr Arg
        610                 615                 620 ggc cct gcc aat gga ttt aga gga gga tat gat ggt tac cgc cct tca    2098
Gly Pro Ala Asn Gly Phe Arg Gly Gly Tyr Asp Gly Tyr Arg Pro Ser
625                 630                 635                 640 ttc tcg aac act cca aac agt ggt tat tca cag tct cag ttc act gct    2146
Phe Ser Asn Thr Pro Asn Ser Gly Tyr Ser Gln Ser Gln Phe Thr Ala
                645                 650                 655 ccc cgg gac tac tct ggt tac cag cgg gat gga tat cag cag aat ttc    2194
Pro Arg Asp Tyr Ser Gly Tyr Gln Arg Asp Gly Tyr Gln Gln Asn Phe
                660                 665                 670 aag cga ggc tct ggg cag agt gga cca cgg gga gcc cca cga ggt aat    2242
Lys Arg Gly Ser Gly Gln Ser Gly Pro Arg Gly Ala Pro Arg Gly Asn
                675                 680                 685 ata ttg tgg tgg tga tcctagctcc tatgtggagc ttctgttctg gccttggaag    2297
Ile Leu Trp Trp
        690 aactgttcat agtccgcatg taggttacat gttaggaata catttatctt ttccagactt    2357 gttgctaaag attaaatgaa atgctctgtt tctaaaattt catcttgaat ccaaatttta    2417 attttgaat gactttccct gctgttgtct tcaaaatcag aacattttct ctgcctcaga    2477 aaagcgtttt tccaactgga aatttatttt tcaggtctta aaacctgcta aatgttttta    2537 ggaagtacct actgaaactt tttgtaagac attttggaa cgagcttgaa catttatata    2597 aatttattac cctctttgat ttttgaaaca tgcatattat atttaggctg agaagccctt    2657 caaatggcca gataagccac agttttagct agagaaccat ttagaattga cataactaat    2717 ctaaacttga acacttttag gaccaatgtt agtgttctaa ataccaacat atttctgatg    2777 tttaaacaga tctcccaaat tcttaggacc ttgatgtcat taaaatttag aatgacaagc    2837 ttaagaggct ttagtttcat ttgtttttca agtaatgaaa aataatttct tacatgggca    2897 gatagttaat ttgttgaaca attacaggta gcatttcatg taatctgatg ttctaaatgg    2957 ttctcttatt gaaggaggtt aaagaattag gtttcttaca gtttttggct ggccatgaca    3017 tgtataaaat gtatattaag gaggaattat aaagtacttt aatttgaatg ctagtggcaa    3077
```
ttgatcatta agaaagtact ttaaagcaaa aggttaatgg gtcatctggg aaaaatactg        3137
aagtatcaaa ggtatttgca tgtgaatgtg ggttatgttc ttctatccca ccttgtagca        3197
tattctatga aagttgagtt aaatgatagc taaaatatct gtttcaacag catgtaaaaa        3257
gttattttaa ctgttacaag tcattataca attttgaatg ttctgtagtt tcttttaac         3317 agtttaggta caaaggtctg ttttcattct ggtgcttttt attaattttg atagtatgat        3377
gtcacttcct attgaaatgt aagctagcgt gtaccttaga atgtgagctc catgagagca        3437
ggtaccttgt ttgtcttcac tgctgtatct attcccaacg cctcatgaca gtgcctggca        3497
catagtaggc actcaataaa tacttgttga atgaatgaaa aaaaaaaaaa a                 3548

<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
        130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser

-continued
_____

```
           290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
                340                 345                 350

Arg Arg Gln Arg Val Gln Asp Leu Met Ala Gln Met Gln Gly Pro Tyr
                355                 360                 365

Asn Phe Ile Gln Asp Ser Met Leu Asp Phe Glu Asn Gln Thr Leu Asp
                370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
                420                 425                 430

Val Ser Ser Thr Ser Glu Gly Tyr Thr Ala Ser Gln Pro Leu Tyr Gln
                435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
                500                 505                 510

Ser Met Gln Thr Val Phe Asn Met Asn Ala Pro Val Pro Pro Ala Asn
                515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Pro Gln Gln Asn
                580                 585                 590

Thr Gly Phe Pro Arg Ser Ser Gln Pro Tyr Tyr Asn Ser Arg Gly Val
                595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
                660                 665                 670

Lys Arg Gly Ser Gly Gln Ser Gly Pro Arg Gly Ala Pro Arg Gly Asn
                675                 680                 685

Ile Leu Trp Trp
    690
```

<210> SEQ ID NO 27

```
<211> LENGTH: 3508
<212> TYPE: DNA
<213> ORGANISM: Mus musculus
<220> FEATURE:
<221> NAME/KEY: CDS
<222> LOCATION: (139)..(2217)

<400> SEQUENCE: 27
cccaccgcgc gcgcgcgtag ccgcctgccc gcccgcccgc tgcgcgtttt gtcccgcgtc          60 tctcccgtc cgtctcctga cttgctggtc ttgtccttcc ctcccgcttt tttcctctcc          120
tctcttctcg gtctaaag atg ccc tcg gcc acc agc cac agc gga agc ggc          171
                    Met Pro Ser Ala Thr Ser His Ser Gly Ser Gly
                    1               5                   10 agc aaa tcg tcg gga ccg ccg ccg ccg tcc ggt tcc tcc ggg agt gag          219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc          267
Ala Ala Ala Gly Ala Ala Ala Pro Ala Ser Gln His Pro Ala Thr Gly
                30                  35                  40 acc ggc gcc gtc cag acc gag gcc atg aag cag att ctc ggc gta atc          315
Thr Gly Ala Val Gln Thr Glu Ala Met Lys Gln Ile Leu Gly Val Ile
        45                  50                  55 gac aag aaa ctt cgg aac ctg gag aag aaa aag ggt aaa ctt gat gat          363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg          411
Tyr Gln Glu Arg Met Asn Lys Gly Glu Arg Leu Asn Gln Asp Gln Leu
                80                  85                  90 gat gcc gta tct aag tac cag gaa gtc aca aat aat ttg gag ttt gca          459
Asp Ala Val Ser Lys Tyr Gln Glu Val Thr Asn Asn Leu Glu Phe Ala
                95                  100                 105 aag gaa tta cag agg agt ttc atg gca tta agt caa gat att cag aaa          507
Lys Glu Leu Gln Arg Ser Phe Met Ala Leu Ser Gln Asp Ile Gln Lys
            110                 115                 120 aca ata aag aag aca gca cgt cgg gaa cag ctt atg aga gaa gaa gca          555
Thr Ile Lys Lys Thr Ala Arg Arg Glu Gln Leu Met Arg Glu Glu Ala
        125                 130                 135 gaa cag aag cgc tta aaa act gta ctt gag tta cag tat gta ttg gat          603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt          651
Lys Leu Gly Asp Asp Asp Val Arg Thr Asp Leu Lys Gln Gly Leu Ser
                160                 165                 170 gga gtg cca ata ttg tct gag gag gag ttg tca ttg ctg gat gag ttc          699
Gly Val Pro Ile Leu Ser Glu Glu Glu Leu Ser Leu Leu Asp Glu Phe
                175                 180                 185 tac aag ctc gta gat cct gag cgt gac atg agt tta agg tta aat gag          747
Tyr Lys Leu Val Asp Pro Glu Arg Asp Met Ser Leu Arg Leu Asn Glu
            190                 195                 200 cag tat gaa cat gcc tca att cac ttg tgg gat ttg ctg gaa ggg aaa          795
Gln Tyr Glu His Ala Ser Ile His Leu Trp Asp Leu Leu Glu Gly Lys
        205                 210                 215 gaa aag cct gtg tgt gga aca acc tat aaa gct cta aag gaa att gtt          843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa          891
Glu Arg Val Phe Gln Ser Asn Tyr Phe Asp Ser Thr His Asn His Gln
                240                 245                 250 aat ggg ttg tgt gag gag gaa gag gcg gct tca gcg ccc aca gtg gag          939
Asn Gly Leu Cys Glu Glu Glu Glu Ala Ala Ser Ala Pro Thr Val Glu
```

```
           255              260              265
gac cag gta gct gaa gct gaa cct gag cca gcg gaa gaa tac aca gag    987
Asp Gln Val Ala Glu Ala Glu Pro Glu Pro Ala Glu Glu Tyr Thr Glu
        270              275              280 caa agt gag gtt gaa tca aca gag tat gtc aat agg cag ttc atg gca   1035
Gln Ser Glu Val Glu Ser Thr Glu Tyr Val Asn Arg Gln Phe Met Ala
        285              290              295 gaa aca cag ttc agc agt ggt gag aag gag caa gtg gat gag tgg aca   1083
Glu Thr Gln Phe Ser Ser Gly Glu Lys Glu Gln Val Asp Glu Trp Thr
300              305              310              315 gtt gaa aca gtt gag gtt gta aac tca ctc cag cag caa cct cag gct   1131
Val Glu Thr Val Glu Val Val Asn Ser Leu Gln Gln Gln Pro Gln Ala
                320              325              330 gcg tcc cct tca gtc cca gag ccc cac tct ttg act cca gtg gct cag   1179
Ala Ser Pro Ser Val Pro Glu Pro His Ser Leu Thr Pro Val Ala Gln
            335              340              345 tca gat cca ctt gtg aga agg cag cgt gta caa gat ctt atg gca caa   1227
Ser Asp Pro Leu Val Arg Arg Gln Arg Val Gln Asp Leu Met Ala Gln
        350              355              360 atg caa ggg ccc tat aat ttc ata cag gat tca atg ttg gat ttt gaa   1275
Met Gln Gly Pro Tyr Asn Phe Ile Gln Asp Ser Met Leu Asp Phe Glu
        365              370              375 aat cag acg ctt gat cct gcc att gta tcc gca cag cct atg aac cct   1323
Asn Gln Thr Leu Asp Pro Ala Ile Val Ser Ala Gln Pro Met Asn Pro
380              385              390              395 acc cag aac atg gat atg cct cag ctg gtt tgc cct cag gtt cat tct   1371
Thr Gln Asn Met Asp Met Pro Gln Leu Val Cys Pro Gln Val His Ser
                400              405              410 gaa tct aga ctt gcc caa tct aat caa gtt cct gta caa cca gaa gcc   1419
Glu Ser Arg Leu Ala Gln Ser Asn Gln Val Pro Val Gln Pro Glu Ala
            415              420              425 aca cag gtt cct ttg gtt tca tcc aca agt gag ggg tat aca gca tct   1467
Thr Gln Val Pro Leu Val Ser Ser Thr Ser Glu Gly Tyr Thr Ala Ser
            430              435              440 cag ccc ttg tac cag cca tct cat gct acg gag cag cgg ccg cag aaa   1515
Gln Pro Leu Tyr Gln Pro Ser His Ala Thr Glu Gln Arg Pro Gln Lys
        445              450              455 gag cca atg gat cag att cag gca aca ata tct ttg aat aca gac cag   1563
Glu Pro Met Asp Gln Ile Gln Ala Thr Ile Ser Leu Asn Thr Asp Gln
460              465              470              475 act aca gca tcc tca tcc ctt cct gct gct tct cag cct caa gtg ttc   1611
Thr Thr Ala Ser Ser Ser Leu Pro Ala Ala Ser Gln Pro Gln Val Phe
                480              485              490 cag gct ggg aca agt aaa cct ttg cac agc agt gga atc aat gta aat   1659
Gln Ala Gly Thr Ser Lys Pro Leu His Ser Ser Gly Ile Asn Val Asn
            495              500              505 gca gct cca ttc cag tcc atg caa acg gtg ttc aat atg aat gct cca   1707
Ala Ala Pro Phe Gln Ser Met Gln Thr Val Phe Asn Met Asn Ala Pro
        510              515              520 gtc cct cct gct aat gaa cca gaa acg tta aaa caa cag agt cag tac   1755
Val Pro Pro Ala Asn Glu Pro Glu Thr Leu Lys Gln Gln Ser Gln Tyr
        525              530              535 cag gcc act tat aac cag agt ttt tcc agt cag cct cac caa gtg gaa   1803
Gln Ala Thr Tyr Asn Gln Ser Phe Ser Ser Gln Pro His Gln Val Glu
540              545              550              555 caa aca gag ctt caa caa gac caa ctg caa acg gtg gtt ggc act tac   1851
Gln Thr Glu Leu Gln Gln Asp Gln Leu Gln Thr Val Val Gly Thr Tyr
            560              565              570 cat gga tcc cag gac cag cct cat caa gtg cct ggt aac cac cag caa   1899
```

-continued

```
His Gly Ser Gln Asp Gln Pro His Gln Val Pro Gly Asn His Gln Gln
            575             580             585 ccc cca cag cag aac act ggc ttt cca cgt agc agt cag cct tat tac      1947
Pro Pro Gln Gln Asn Thr Gly Phe Pro Arg Ser Ser Gln Pro Tyr Tyr
            590             595             600 aac agt cgt ggg gta tct cga gga ggg tct cgt ggt gcc aga ggc ttg      1995
Asn Ser Arg Gly Val Ser Arg Gly Gly Ser Arg Gly Ala Arg Gly Leu
            605             610             615 atg aat gga tac agg ggc cct gcc aat gga ttt aga gga gga tat gat      2043
Met Asn Gly Tyr Arg Gly Pro Ala Asn Gly Phe Arg Gly Gly Tyr Asp
620             625             630             635 ggt tac cgc cct tca ttc tcg aac act cca aac agt ggt tat tca cag      2091
Gly Tyr Arg Pro Ser Phe Ser Asn Thr Pro Asn Ser Gly Tyr Ser Gln
            640             645             650 tct cag ttc act gct ccc cgg gac tac tct ggt tac cag cgg gat gga      2139
Ser Gln Phe Thr Ala Pro Arg Asp Tyr Ser Gly Tyr Gln Arg Asp Gly
            655             660             665 tat cag cag aat ttc aag cga ggc tct ggg cag agt gga cca cgg gga      2187
Tyr Gln Gln Asn Phe Lys Arg Gly Ser Gly Gln Ser Gly Pro Arg Gly
            670             675             680 gcc cca cga ggt aat ata ttg tgg tgg tga tcctagctcc tatgtggagc        2237
Ala Pro Arg Gly Asn Ile Leu Trp Trp
685             690 ttctgttctg gccttggaag aactgttcat agtccgcatg taggttacat gttaggaata    2297
catttatctt ttccagactt gttgctaaag attaaatgaa atgctctgtt tctaaaattt    2357
catcttgaat ccaaatttta attttgaat gactttccct gctgttgtct tcaaaatcag     2417
aacattttct ctgcctcaga aaagcgtttt tccaactgga aatttatttt tcaggtctta    2477
aaacctgcta aatgtttta ggaagtacct actgaaactt tttgtaagac attttttggaa    2537 cgagcttgaa catttatata aatttattac cctctttgat ttttgaaaca tgcatattat    2597
atttaggctg agaagcccTt caaatggcca gataagccac agtttttagct agagaaccat   2657 ttagaattga cataactaat ctaaacttga acacttttag gaccaatgtt agtgttctaa    2717
ataccaacat atttctgatg tttaaacaga tctcccaaat tcttaggacc ttgatgtcat    2777
taaaatttag aatgacaagc ttaagaggct ttagtttcat ttgttttttca agtaatgaaa   2837 aataatttct tacatgggca gatagttaat ttgttgaaca attacaggta gcatttcatg    2897
taatctgatg ttctaaatgg ttctcttatt gaaggaggtt aaagaattag gtttcttaca    2957
gtttttggct ggccatgaca tgtataaaat gtatattaag gaggaattat aaagtacttt    3017
aatttgaatg ctagtggcaa ttgatcatta agaaagtact ttaaagcaaa aggttaatgg    3077
gtcatctggg aaaaatactg aagtatcaaa ggtatttgca tgtgaatgtg ggttatgttc    3137
ttctatccca ccttgtagca tattctatga aagttgagtt aaatgatagc taaaatatct    3197
gtttcaacag catgtaaaaa gttattttaa ctgttacaag tcattataca attttgaatg    3257
ttctgtagtt tcttttttaac agtttaggta caaaggtctg ttttcattct ggtgcttttt   3317
attaattttg atagtatgat gtcacttcct attgaaatgt aagctagcgt gtaccttaga    3377
atgtgagctc catgagagca ggtaccttgt ttgtcttcac tgctgtatct attcccaacg    3437
cctcatgaca gtgcctggca catagtaggc actcaataaa tacttgttga atgaatgaaa    3497
aaaaaaaaaa a                                                         3508
```

<210> SEQ ID NO 28
<211> LENGTH: 692
<212> TYPE: PRT

<213> ORGANISM: Mus musculus

<400> SEQUENCE: 28

```
Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
        130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
        210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
        370                 375                 380

Pro Ala Ile Val Ser Ala Gln Pro Met Asn Pro Thr Gln Asn Met Asp
385                 390                 395                 400
```

-continued

```
Met Pro Gln Leu Val Cys Pro Gln Val His Ser Glu Ser Arg Leu Ala
            405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
            435                 440                 445

Pro Ser His Ala Thr Glu Gln Arg Pro Gln Lys Glu Pro Met Asp Gln
        450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
            485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
            515                 520                 525

Glu Pro Glu Thr Leu Lys Gln Gln Ser Gln Tyr Gln Ala Thr Tyr Asn
        530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
            565                 570                 575

Gln Pro His Gln Val Pro Gly Asn His Gln Gln Pro Pro Gln Gln Asn
            580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
        610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
            645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
            675                 680                 685

Ile Leu Trp Trp
    690
```

```
<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)

<400> SEQUENCE: 29 atg ccc tcg gct acc aac ggc acc atg gcg agc agc agc ggg aag gcg        48
Met Pro Ser Ala Thr Asn Gly Thr Met Ala Ser Ser Ser Gly Lys Ala
1               5                   10                  15 ggc ccg ggc ggc aac gag cag gcc ccg gcg gcg gca gcg gcg gcc ccg        96
Gly Pro Gly Gly Asn Glu Gln Ala Pro Ala Ala Ala Ala Ala Ala Pro
                20                  25                  30 cag gcg tcg ggc ggc agc atc acc tcg gtt cag acc gag gcc atg aag       144
Gln Ala Ser Gly Gly Ser Ile Thr Ser Val Gln Thr Glu Ala Met Lys
            35                  40                  45
```

```
cag atc ttg gga gtg atc gac aaa aag ctc cgc aac ctc gag aag aaa      192
Gln Ile Leu Gly Val Ile Asp Lys Lys Leu Arg Asn Leu Glu Lys Lys
    50              55              60 aag agc aaa ctt gac gat tac cag gaa cga atg aac aag ggg gaa cgt      240
Lys Ser Lys Leu Asp Asp Tyr Gln Glu Arg Met Asn Lys Gly Glu Arg
65              70              75              80 cta aat caa gat caa ctg gat gca gtg tca aaa tac cag gaa gtg aca      288
Leu Asn Gln Asp Gln Leu Asp Ala Val Ser Lys Tyr Gln Glu Val Thr
            85              90              95 aat aac ctg gaa ttc gct aaa gaa ctg cag agg agc ttt atg gca ctg      336
Asn Asn Leu Glu Phe Ala Lys Glu Leu Gln Arg Ser Phe Met Ala Leu
        100             105             110 agc caa gat atc cag aaa aca ata aaa aag acg gct cgc agg gag cag      384
Ser Gln Asp Ile Gln Lys Thr Ile Lys Lys Thr Ala Arg Arg Glu Gln
        115             120             125 ctg atg aga gaa gag gct gag cag aag cgt tta aag act gtg cta gag      432
Leu Met Arg Glu Glu Ala Glu Gln Lys Arg Leu Lys Thr Val Leu Glu
    130             135             140 ctg cag ttc att ttg gac aag ttg ggt gac gat gaa gtg cgc agt gac      480
Leu Gln Phe Ile Leu Asp Lys Leu Gly Asp Asp Glu Val Arg Ser Asp
145             150             155             160 ttg aaa caa gga tca aat gga gta ccg gta ctg aca gag gag gaa ctg      528
Leu Lys Gln Gly Ser Asn Gly Val Pro Val Leu Thr Glu Glu Glu Leu
                165             170             175 aca atg ctg gat gaa ttt tac aag cta gtt tac cct gaa agg gac atg      576
Thr Met Leu Asp Glu Phe Tyr Lys Leu Val Tyr Pro Glu Arg Asp Met
            180             185             190 aac atg agg ttg aat gag cag tat gag caa gca tct gtt cac ctg tgg      624
Asn Met Arg Leu Asn Glu Gln Tyr Glu Gln Ala Ser Val His Leu Trp
        195             200             205 gac tta ctg gaa ggg aag gaa aaa ccc gtt tgt gga aca acc tat aaa      672
Asp Leu Leu Glu Gly Lys Glu Lys Pro Val Cys Gly Thr Thr Tyr Lys
    210             215             220 gcc ctg aag gag gtt gtt gaa cgt att ctt caa act agt tac ttt gat      720
Ala Leu Lys Glu Val Val Glu Arg Ile Leu Gln Thr Ser Tyr Phe Asp
225             230             235             240 agc acc cat aac cat cag aac ggg tta tgt gag gaa gaa gag gca gca      768
Ser Thr His Asn His Gln Asn Gly Leu Cys Glu Glu Glu Glu Ala Ala
                245             250             255 ccc aca cct gca gta gaa gac act gta gca gaa gct gag cct gat cca      816
Pro Thr Pro Ala Val Glu Asp Thr Val Ala Glu Ala Glu Pro Asp Pro
            260             265             270 gca gaa gaa ttt act gaa cct act gaa gtt gaa tcg act gag tat gta      864
Ala Glu Glu Phe Thr Glu Pro Thr Glu Val Glu Ser Thr Glu Tyr Val
        275             280             285 aac aga caa ttc atg gca gag act cag ttc agc agt agt gag aag gaa      912
Asn Arg Gln Phe Met Ala Glu Thr Gln Phe Ser Ser Ser Glu Lys Glu
        290             295             300 cag gta gat gag tgg aca gtt gaa acg gtt gag gtt gta aat tca ctg      960
Gln Val Asp Glu Trp Thr Val Glu Thr Val Glu Val Val Asn Ser Leu
305             310             315             320 cag caa caa aca caa gct aca tct cct cca gtt cct gaa cct cat aca     1008
Gln Gln Gln Thr Gln Ala Thr Ser Pro Pro Val Pro Glu Pro His Thr
                325             330             335 ctc act act gtg gct caa gca gat cct ctt gtt aga aga cag aga gta     1056
Leu Thr Thr Val Ala Gln Ala Asp Pro Leu Val Arg Arg Gln Arg Val
            340             345             350 cag gac ctt atg gcc cag atg cag ggt cca tat aac ttc atg cag gac     1104
Gln Asp Leu Met Ala Gln Met Gln Gly Pro Tyr Asn Phe Met Gln Asp
```

```
             355                   360                   365 tct atg ctg gag ttt gag aac cag aca ctt gat cct gcc att gta tct    1152
Ser Met Leu Glu Phe Glu Asn Gln Thr Leu Asp Pro Ala Ile Val Ser
    370                   375                   380 gca cag ccc atg aat cca gca cag aat ttg gac atg ccg caa atg gtc    1200
Ala Gln Pro Met Asn Pro Ala Gln Asn Leu Asp Met Pro Gln Met Val
385                   390                   395                   400 tgc cct cca gtt cat act gag tca aga ctt gcc cag cct aat caa gtt    1248
Cys Pro Pro Val His Thr Glu Ser Arg Leu Ala Gln Pro Asn Gln Val
                405                   410                   415 cct gtg caa cca gaa gct acg cag gtt ccc ttg gtt tca tct aca agt    1296
Pro Val Gln Pro Glu Ala Thr Gln Val Pro Leu Val Ser Ser Thr Ser
                420                   425                   430 gag gga tat aca gcc tcc cag ccc atg tat cag cct tct cat acc aca    1344
Glu Gly Tyr Thr Ala Ser Gln Pro Met Tyr Gln Pro Ser His Thr Thr
            435                   440                   445 gag caa cgg cca cag aag gaa tcc att gac cag att cag gct tca atg    1392
Glu Gln Arg Pro Gln Lys Glu Ser Ile Asp Gln Ile Gln Ala Ser Met
    450                   455                   460 tca ctg aat gca gac cag acc ccg tca tca tca tca ctt ccc act gca    1440
Ser Leu Asn Ala Asp Gln Thr Pro Ser Ser Ser Ser Leu Pro Thr Ala
465                   470                   475                   480 tcc cag ccg caa gtt ttc caa gct gga tct agc aaa cct ttg cat agc    1488
Ser Gln Pro Gln Val Phe Gln Ala Gly Ser Ser Lys Pro Leu His Ser
                485                   490                   495 agc gga atc aat gtt aat gca gct cca ttc caa tcc atg caa aca gta    1536
Ser Gly Ile Asn Val Asn Ala Ala Pro Phe Gln Ser Met Gln Thr Val
                500                   505                   510 ttc aac atg aat gca cct gtt cct cct gtt aat gag cca gaa gcc ctt    1584
Phe Asn Met Asn Ala Pro Val Pro Pro Val Asn Glu Pro Glu Ala Leu
            515                   520                   525 aag caa caa aat cag tac cag gcc agt tac aac cag agt ttc tcc aat    1632
Lys Gln Gln Asn Gln Tyr Gln Ala Ser Tyr Asn Gln Ser Phe Ser Asn
    530                   535                   540 cag cca cac caa gta gaa caa tca gat ctt cag caa gaa cag ctc cag    1680
Gln Pro His Gln Val Glu Gln Ser Asp Leu Gln Gln Glu Gln Leu Gln
545                   550                   555                   560 aca gtg gtt ggt act tac cat ggt tct ccg gac cag acc cat caa gtg    1728
Thr Val Val Gly Thr Tyr His Gly Ser Pro Asp Gln Thr His Gln Val
                565                   570                   575 gca gga aac cac cag caa cct ccc cag cag aat act gga ttt cca cgc    1776
Ala Gly Asn His Gln Gln Pro Pro Gln Gln Asn Thr Gly Phe Pro Arg
            580                   585                   590 aac agt cag cct tat tac aac agt cgg gga gtg tct cgt ggt gga tca    1824
Asn Ser Gln Pro Tyr Tyr Asn Ser Arg Gly Val Ser Arg Gly Gly Ser
            595                   600                   605 cgt ggg act cgt gga ttg atg aat ggt tac agg gga cct gca aat gga    1872
Arg Gly Thr Arg Gly Leu Met Asn Gly Tyr Arg Gly Pro Ala Asn Gly
        610                   615                   620 ttt aga gga gga tat gat ggc tac cgt cct tca ttt tcc aac act ccg    1920
Phe Arg Gly Gly Tyr Asp Gly Tyr Arg Pro Ser Phe Ser Asn Thr Pro
625                   630                   635                   640 aac agt ggt tac acg cag ccc caa ttt aat gct cct cga gat tat tca    1968
Asn Ser Gly Tyr Thr Gln Pro Gln Phe Asn Ala Pro Arg Asp Tyr Ser
                645                   650                   655 aac tac cag cgg gat gga tat cag cag aac ttc aaa cgt ggt tct gga    2016
Asn Tyr Gln Arg Asp Gly Tyr Gln Gln Asn Phe Lys Arg Gly Ser Gly
                660                   665                   670 caa agt ggg cct cgg gga gct cct cga ggt cgt gga ggg ccc cca aga    2064
```

-continued

```
Gln Ser Gly Pro Arg Gly Ala Pro Arg Gly Arg Gly Gly Pro Pro Arg
        675             680             685 cca aac aga ggg atg cct caa atg aac gct cag caa gtg aat taa        2109
Pro Asn Arg Gly Met Pro Gln Met Asn Ala Gln Gln Val Asn
        690             695             700

<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110

Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
    130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
            180                 185                 190

Asn Met Arg Leu Asn Glu Gln Tyr Glu Gln Ala Ser Val His Leu Trp
        195                 200                 205

Asp Leu Leu Glu Gly Lys Glu Lys Pro Val Cys Gly Thr Thr Tyr Lys
    210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
        275                 280                 285

Asn Arg Gln Phe Met Ala Glu Thr Gln Phe Ser Ser Ser Glu Lys Glu
        290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
```

```
              340             345             350

Gln Asp Leu Met Ala Gln Met Gln Gly Pro Tyr Asn Phe Met Gln Asp
        355             360             365

Ser Met Leu Glu Phe Glu Asn Gln Thr Leu Asp Pro Ala Ile Val Ser
        370             375             380

Ala Gln Pro Met Asn Pro Ala Gln Asn Leu Asp Met Pro Gln Met Val
385             390             395             400

Cys Pro Pro Val His Thr Glu Ser Arg Leu Ala Gln Pro Asn Gln Val
            405             410             415

Pro Val Gln Pro Glu Ala Thr Gln Val Pro Leu Val Ser Ser Thr Ser
        420             425             430

Glu Gly Tyr Thr Ala Ser Gln Pro Met Tyr Gln Pro Ser His Thr Thr
        435             440             445

Glu Gln Arg Pro Gln Lys Glu Ser Ile Asp Gln Ile Gln Ala Ser Met
        450             455             460

Ser Leu Asn Ala Asp Gln Thr Pro Ser Ser Ser Ser Leu Pro Thr Ala
465             470             475             480

Ser Gln Pro Gln Val Phe Gln Ala Gly Ser Ser Lys Pro Leu His Ser
            485             490             495

Ser Gly Ile Asn Val Asn Ala Ala Pro Phe Gln Ser Met Gln Thr Val
            500             505             510

Phe Asn Met Asn Ala Pro Val Pro Pro Val Asn Glu Pro Glu Ala Leu
            515             520             525

Lys Gln Gln Asn Gln Tyr Gln Ala Ser Tyr Asn Gln Ser Phe Ser Asn
        530             535             540

Gln Pro His Gln Val Glu Gln Ser Asp Leu Gln Gln Glu Gln Leu Gln
545             550             555             560

Thr Val Val Gly Thr Tyr His Gly Ser Pro Asp Gln Thr His Gln Val
            565             570             575

Ala Gly Asn His Gln Gln Pro Pro Gln Gln Asn Thr Gly Phe Pro Arg
            580             585             590

Asn Ser Gln Pro Tyr Tyr Asn Ser Arg Gly Val Ser Arg Gly Gly Ser
        595             600             605

Arg Gly Thr Arg Gly Leu Met Asn Gly Tyr Arg Gly Pro Ala Asn Gly
        610             615             620

Phe Arg Gly Gly Tyr Asp Gly Tyr Arg Pro Ser Phe Ser Asn Thr Pro
625             630             635             640

Asn Ser Gly Tyr Thr Gln Pro Gln Phe Asn Ala Pro Arg Asp Tyr Ser
            645             650             655

Asn Tyr Gln Arg Asp Gly Tyr Gln Gln Asn Phe Lys Arg Gly Ser Gly
            660             665             670

Gln Ser Gly Pro Arg Gly Ala Pro Arg Gly Arg Gly Gly Pro Pro Arg
            675             680             685

Pro Asn Arg Gly Met Pro Gln Met Asn Ala Gln Gln Val Asn
    690             695             700
```

<210> SEQ ID NO 31
<211> LENGTH: 63
<212> TYPE: PRT
<213> ORGANISM: Homo sapiens

<400> SEQUENCE: 31

```
Glu Glu Tyr Thr Glu Gln Ser Glu Val Glu Ser Thr Glu Tyr Val Asn
1               5               10              15
```

```
Arg Gln Phe Met Ala Glu Thr Gln Phe Thr Ser Gly Glu Lys Glu Gln
              20                  25                  30

Val Asp Glu Trp Thr Val Glu Thr Val Glu Val Val Asn Ser Leu Gln
        35                  40                  45

Gln Gln Pro Gln Ala Ala Ser Pro Ser Val Pro Glu Pro His Ser
    50                  55                  60

<210> SEQ ID NO 32
<211> LENGTH: 18
<212> TYPE: PRT
<213> ORGANISM: Homo sapiens

<400> SEQUENCE: 32

Val Phe Asn Met Asn Ala Pro Val Pro Pro Val Asn Glu Pro Glu Thr
1               5                   10                  15

Leu Lys

<210> SEQ ID NO 33
<211> LENGTH: 16
<212> TYPE: PRT
<213> ORGANISM: Homo sapiens

<400> SEQUENCE: 33

Ala Thr Gln Val Pro Leu Val Ser Ser Thr Ser Glu Gly Tyr Thr Ala
1               5                   10                  15

<210> SEQ ID NO 34
<211> LENGTH: 25
<212> TYPE: PRT
<213> ORGANISM: Homo sapiens

<400> SEQUENCE: 34

Gln Ile Leu Gly Val Ile Asp Lys Lys Leu Arg Asn Leu Glu Lys Lys
1               5                   10                  15

Lys Gly Lys Leu Asp Asp Tyr Gln Glu
            20                  25

<210> SEQ ID NO 35
<211> LENGTH: 23
<212> TYPE: PRT
<213> ORGANISM: Homo sapiens

<400> SEQUENCE: 35

Pro Arg Gly Arg Gly Gly Pro Pro Arg Pro Asn Arg Gly Met Pro Gln
1               5                   10                  15

Met Asn Thr Gln Gln Val Asn
            20

<210> SEQ ID NO 36
<211> LENGTH: 5
<212> TYPE: PRT
<213> ORGANISM: Gallus gallus

<400> SEQUENCE: 36

Ser Tyr Gln Met Asn
1               5

<210> SEQ ID NO 37
<211> LENGTH: 17
<212> TYPE: PRT
<213> ORGANISM: Gallus gallus

<400> SEQUENCE: 37
```

-continued

Ala Ile Asn Lys Phe Gly Asn Ser Thr Gly His Gly Ala Ala Val Lys
1               5                   10                  15

Gly

<210> SEQ ID NO 38
<211> LENGTH: 19
<212> TYPE: PRT
<213> ORGANISM: Gallus gallus

<400> SEQUENCE: 38

His Ala Tyr Gly Tyr Cys Gly Ser Gly Thr Trp Cys Ala Ala Gly Glu
1               5                   10                  15

Ile Asp Ala

<210> SEQ ID NO 39
<211> LENGTH: 128
<212> TYPE: PRT
<213> ORGANISM: Gallus gallus

<400> SEQUENCE: 39

Ala Val Thr Leu Asp Glu Ser Gly Gly Gly Leu Gln Met Ser Arg Gly
1               5                   10                  15

Gly Leu Ser Leu Val Cys Lys Ala Ser Gly Phe Asp Phe Ser Ser Tyr
            20                  25                  30

Gln Met Asn Trp Ile Arg Gln Ala Pro Gly Lys Gly Leu Glu Phe Val
            35                  40                  45

Ala Ala Ile Asn Lys Phe Gly Asn Ser Thr Gly His Gly Ala Ala Val
    50                  55                  60

Lys Gly Arg Val Thr Ile Ser Arg Asp Asn Gly Gln Ser Thr Val Arg
65                  70                  75                  80

Leu Gln Leu Asn Asn Leu Arg Ala Glu Asp Thr Ala Ile Tyr Phe Cys
                85                  90                  95

Thr Lys His Ala Tyr Gly Tyr Cys Gly Ser Gly Thr Trp Cys Ala Ala
            100                 105                 110

Gly Glu Ile Asp Ala Trp Gly His Gly Thr Glu Val Ile Val Ser Ser
            115                 120                 125

<210> SEQ ID NO 40
<211> LENGTH: 9
<212> TYPE: PRT
<213> ORGANISM: Gallus gallus

<400> SEQUENCE: 40

Ser Gly Gly Gly Ser Tyr Ser Tyr Gly
1               5

<210> SEQ ID NO 41
<211> LENGTH: 7
<212> TYPE: PRT
<213> ORGANISM: Gallus gallus

<400> SEQUENCE: 41

Asn Asn Lys Arg Pro Ser Asp
1               5

<210> SEQ ID NO 42
<211> LENGTH: 10
<212> TYPE: PRT
<213> ORGANISM: Gallus gallus -continued

```
<400> SEQUENCE: 42

Ser Gly Asp Ser Thr Asp Thr Ala Val Phe
1               5                   10

<210> SEQ ID NO 43
<211> LENGTH: 108
<212> TYPE: PRT
<213> ORGANISM: Gallus gallus

<400> SEQUENCE: 43

Gln Ala Ala Ser Thr Gln Pro Ser Ser Val Ser Ala Asn Pro Gly Glu
1               5                   10                  15

Thr Val Glu Ile Thr Cys Ser Gly Gly Gly Ser Tyr Ser Tyr Gly Trp
            20                  25                  30

Phe Gln Gln Lys Ser Pro Gly Ser Ala Pro Val Thr Val Ile Tyr Tyr
        35                  40                  45

Asn Asn Lys Arg Pro Ser Asp Ile Pro Ser Arg Phe Ser Gly Ser Lys
    50                  55                  60

Ser Gly Ser Thr Gly Thr Leu Thr Ile Thr Gly Val Gln Ala Asp Asp
65                  70                  75                  80

Glu Ala Val Tyr Tyr Cys Gly Ser Gly Asp Ser Thr Asp Thr Ala Val
                85                  90                  95

Phe Gly Ala Gly Thr Thr Leu Thr Val Leu Gly Gln
            100                 105

<210> SEQ ID NO 44
<211> LENGTH: 5
<212> TYPE: PRT
<213> ORGANISM: Rabbit

<400> SEQUENCE: 44

Ser His Ser Leu Gly
1               5

<210> SEQ ID NO 45
<211> LENGTH: 16
<212> TYPE: PRT
<213> ORGANISM: Rabbit

<400> SEQUENCE: 45

Asp Ile Arg Ser Gly Gly Ser Ala Tyr Tyr Ala Asn Trp Ala Lys Gly
1               5                   10                  15

<210> SEQ ID NO 46
<211> LENGTH: 13
<212> TYPE: PRT
<213> ORGANISM: Rabbit

<400> SEQUENCE: 46

Thr Asn Gly Pro Ser Asp Leu Thr Asn Arg Leu Asp Leu
1               5                   10

<210> SEQ ID NO 47
<211> LENGTH: 121
<212> TYPE: PRT
<213> ORGANISM: Homo sapiens

<400> SEQUENCE: 47

Glu Gln Ser Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
```

-continued

```
                20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
                100                 105                 110

Gln Gly Thr Leu Val Thr Val Ser Ser
            115                 120

<210> SEQ ID NO 48
<211> LENGTH: 13
<212> TYPE: PRT
<213> ORGANISM: Rabbit

<400> SEQUENCE: 48

Gln Ala Ser Gln Ser Leu Tyr Asn Asn Glu Asn Leu Ala
1               5                   10

<210> SEQ ID NO 49
<211> LENGTH: 7
<212> TYPE: PRT
<213> ORGANISM: Rabbit

<400> SEQUENCE: 49

Gly Ala Ser Thr Leu Ala Ser
1               5

<210> SEQ ID NO 50
<211> LENGTH: 13
<212> TYPE: PRT
<213> ORGANISM: Rabbit

<400> SEQUENCE: 50

Leu Gly Glu Phe Ser Cys Gly Ser Ala Asp Cys Phe Ala
1               5                   10

<210> SEQ ID NO 51
<211> LENGTH: 112
<212> TYPE: PRT
<213> ORGANISM: Homo sapiens

<400> SEQUENCE: 51

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
                20                  25                  30

Asn Leu Ala Trp Phe Gln Gln Lys Pro Gly Lys Val Pro Lys Arg Leu
            35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95
```

```
Ser Ala Asp Cys Phe Ala Phe Gly Gly Gly Thr Lys Val Glu Ile Lys
            100                 105                 110
```

```
<210> SEQ ID NO 52
<211> LENGTH: 4
<212> TYPE: PRT
<213> ORGANISM: Gallus gallus

<400> SEQUENCE: 52

Phe Asp Met Gly
1
```

```
<210> SEQ ID NO 53
<211> LENGTH: 17
<212> TYPE: PRT
<213> ORGANISM: Gallus gallus

<400> SEQUENCE: 53

Gln Ile Asn Asp Ala Gly Ser Arg Thr Trp Tyr Ala Thr Ala Val Lys
1               5                   10                  15

Gly
```

```
<210> SEQ ID NO 54
<211> LENGTH: 12
<212> TYPE: PRT
<213> ORGANISM: Gallus gallus

<400> SEQUENCE: 54

Gly Ser Gly Tyr Val Gly Ala Gly Ala Ile Asp Ala
1               5                   10
```

```
<210> SEQ ID NO 55
<211> LENGTH: 120
<212> TYPE: PRT
<213> ORGANISM: Gallus gallus

<400> SEQUENCE: 55

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Phe
            20                  25                  30

Asp Met Gly Trp Val Arg Gln Ala Pro Gly Lys Gly Leu Glu Phe Val
            35                  40                  45

Ala Gln Ile Asn Asp Ala Gly Ser Arg Thr Trp Tyr Ala Thr Ala Val
        50                  55                  60

Lys Gly Arg Ala Thr Ile Ser Arg Asp Asn Gly Gln Thr Thr Val Arg
65                  70                  75                  80

Leu Gln Leu Asn Asn Leu Arg Ala Glu Asp Thr Gly Thr Tyr Tyr Cys
                85                  90                  95

Thr Arg Gly Ser Gly Tyr Val Gly Ala Gly Ala Ile Asp Ala Trp Gly
            100                 105                 110

His Gly Thr Glu Val Ile Val Ser
        115                 120
```

```
<210> SEQ ID NO 56
<211> LENGTH: 8
<212> TYPE: PRT
<213> ORGANISM: Gallus gallus

<400> SEQUENCE: 56

Ser Gly Gly Ser Gly Tyr Tyr Gly
```

-continued

```
1               5

<210> SEQ ID NO 57
<211> LENGTH: 7
<212> TYPE: PRT
<213> ORGANISM: Gallus gallus

<400> SEQUENCE: 57

Asn Asp Lys Arg Pro Ser Asp
1               5

<210> SEQ ID NO 58
<211> LENGTH: 10
<212> TYPE: PRT
<213> ORGANISM: Gallus gallus

<400> SEQUENCE: 58

Arg Tyr Asp Ser Thr Asp Ser Gly Ile Phe
1               5                   10

<210> SEQ ID NO 59
<211> LENGTH: 105
<212> TYPE: PRT
<213> ORGANISM: Gallus gallus

<400> SEQUENCE: 59

Ala Ala Leu Thr Gln Pro Ser Ser Val Ser Ala Asn Pro Gly Glu Thr
1               5                   10                  15

Val Lys Ile Thr Cys Ser Gly Gly Ser Gly Tyr Tyr Gly Trp Tyr Gln
                20                  25                  30

Gln Gln Lys Ser Pro Gly Ser Ala Pro Val Thr Val Ile Tyr Gln Asn
        35                  40                  45

Asp Lys Arg Pro Ser Asp Ile Pro Ser Arg Phe Ser Gly Ser Gly Ser
    50                  55                  60

Gly Ser Thr Asn Thr Leu Thr Ile Thr Gly Val Gln Ala Glu Asp Glu
65                  70                  75                  80

Ala Val Tyr Phe Cys Gly Arg Tyr Asp Ser Thr Asp Ser Gly Ile Phe
                85                  90                  95

Gly Ala Gly Thr Thr Leu Thr Val Leu
            100                 105

<210> SEQ ID NO 60
<211> LENGTH: 6
<212> TYPE: PRT
<213> ORGANISM: Oryctolagus cuniculus

<400> SEQUENCE: 60

Gly Ser Tyr Tyr Met Ser
1               5

<210> SEQ ID NO 61
<211> LENGTH: 17
<212> TYPE: PRT
<213> ORGANISM: Oryctolagus cuniculus

<400> SEQUENCE: 61

Tyr Ile Tyr Ile Gly Asp Gly Val Thr Ala Tyr Ala Asn Trp Ala Lys
1               5                   10                  15

Gly

<210> SEQ ID NO 62
```

-continued

```
<211> LENGTH: 4
<212> TYPE: PRT
<213> ORGANISM: Oryctolagus cuniculus

<400> SEQUENCE: 62

Gly Asn Lys Leu
1

<210> SEQ ID NO 63
<211> LENGTH: 112
<212> TYPE: PRT
<213> ORGANISM: Oryctolagus cuniculus

<400> SEQUENCE: 63

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Gly Ser Tyr
            20                  25                  30

Tyr Met Ser Trp Val Arg Gln Ala Pro Gly Lys Gly Leu Glu Trp Ile
        35                  40                  45

Ala Tyr Ile Tyr Ile Gly Asp Gly Val Thr Ala Tyr Ala Asn Trp Ala
    50                  55                  60

Lys Gly Arg Phe Thr Ile Ser Lys Ala Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Gly Asn Lys Leu Trp Gly Pro Gly Thr Leu Val Thr Val Ser Ser
            100                 105                 110

<210> SEQ ID NO 64
<211> LENGTH: 11
<212> TYPE: PRT
<213> ORGANISM: Oryctolagus cuniculus

<400> SEQUENCE: 64

Gln Ala Ser Gln Ser Ile Ser Ser Tyr Leu Ala
1               5                   10

<210> SEQ ID NO 65
<211> LENGTH: 7
<212> TYPE: PRT
<213> ORGANISM: Oryctolagus cuniculus

<400> SEQUENCE: 65

Asp Ala Ser Asn Leu Asp Ser
1               5

<210> SEQ ID NO 66
<211> LENGTH: 14
<212> TYPE: PRT
<213> ORGANISM: Oryctolagus cuniculus

<400> SEQUENCE: 66

Gln Cys Thr Ala Val Ser Ser Ala Thr Ile Tyr Gly Asn Ala
1               5                   10

<210> SEQ ID NO 67
<211> LENGTH: 112
<212> TYPE: PRT
<213> ORGANISM: Oryctolagus cuniculus

<400> SEQUENCE: 67
```

-continued

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Arg Leu Ile
            35                  40                  45

Tyr Asp Ala Ser Asn Leu Asp Ser Gly Val Pro Ser Arg Phe Lys Gly
        50                  55                  60

Ser Gly Ser Gly Thr Asp Phe Thr Ile Thr Ile Ser Asp Leu Glu Cys
65                  70                  75                  80

Ala Asp Ala Ala Thr Tyr Tyr Cys Gln Cys Thr Ala Val Ser Ser Ala
                85                  90                  95

Thr Ile Tyr Gly Asn Ala Phe Gly Gly Gly Thr Glu Val Val Val Lys
            100                 105                 110

<210> SEQ ID NO 68
<211> LENGTH: 127
<212> TYPE: PRT
<213> ORGANISM: Gallus gallus

<400> SEQUENCE: 68

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Gly Tyr
                20                  25                  30

Asp Met Leu Trp Val Arg Gln Ala Pro Gly Lys Gly Leu Glu Trp Val
            35                  40                  45

Ala Gly Ile Gly Ser Thr Gly Gly Gly Thr Asp Tyr Gly Ala Ala Val
        50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Val Ala Gly Gly Cys Asn Ser Gly Tyr Cys Arg Asp Ser Pro
            100                 105                 110

Gly Ser Ile Asp Ala Trp Gly His Gly Thr Glu Val Ile Val Ser
            115                 120                 125

<210> SEQ ID NO 69
<211> LENGTH: 107
<212> TYPE: PRT
<213> ORGANISM: Gallus gallus

<400> SEQUENCE: 69

Ala Val Thr Gln Gln Pro Ala Ser Val Ser Ala Asn Pro Gly Glu Thr
1               5                   10                  15

Val Lys Ile Thr Cys Ser Gly Gly Gly Ser Arg Asn Tyr Tyr Gly Trp
                20                  25                  30

Tyr Gln Gln Lys Ser Pro Gly Ser Val Pro Val Thr Val Ile Tyr Tyr
            35                  40                  45

Asp Asp Gln Arg Pro Ser Asn Ile Pro Ser Arg Phe Ser Gly Ala Leu
        50                  55                  60

Ser Gly Ser Thr Ser Thr Leu Thr Ile Thr Gly Val Gln Ala Asp Asp
65                  70                  75                  80

Glu Ala Val Tyr Phe Cys Gly Ser Ala Asp Ser Asn Thr Tyr Glu Gly
                85                  90                  95

-continued

```
Ser Phe Gly Ala Gly Thr Thr Leu Thr Val Leu
            100             105
```

<210> SEQ ID NO 70
<211> LENGTH: 148
<212> TYPE: PRT
<213> ORGANISM: Mus musculus

<400> SEQUENCE: 70

```
Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
            85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
            115                 120                 125

Trp Gly Gln Gly Thr Leu Val Thr Val Ser Ala Ala Lys Thr Thr Pro
    130                 135                 140

Pro Ser Val Tyr
145
```

<210> SEQ ID NO 71
<211> LENGTH: 105
<212> TYPE: PRT
<213> ORGANISM: Mus musculus

<400> SEQUENCE: 71

```
Gly Leu Phe Cys Ser Val Glu Arg Cys His Tyr Gln Leu Gln Ser Ser
1               5                   10                  15

Gln Asn Leu Leu Ser Ile Val Asn Arg Tyr His Tyr Met Ser Gly Asn
            20                  25                  30

Pro Pro Lys Leu Leu Val Tyr Pro Ala Leu Leu Ile Tyr Glu Ala Ser
        35                  40                  45

Ile Thr Lys Ser Cys Val Pro Asp Arg Phe Thr Arg Ser Gly Ser Gly
    50                  55                  60

Thr Asn Phe Thr Leu Thr Ile Asn Phe Val His Ala Asp Asp Leu Ile
65                  70                  75                  80

Phe Tyr Tyr Cys Gln His Asn Arg Gly Ser Phe Leu Pro Ser Ser Ser
            85                  90                  95

Val Gln Val Pro Arg Arg Arg Ser Asn
            100                 105
```

<210> SEQ ID NO 72
<211> LENGTH: 109
<212> TYPE: PRT
<213> ORGANISM: Mus musculus

<400> SEQUENCE: 72

```
Pro Arg Ala Ser Leu Gly Val Ser Glu Thr Leu Leu Cys Thr Ser Gly
```

-continued

```
1               5                   10                  15
Phe Thr Phe Thr Asp Tyr Tyr Met Ser Trp Val Arg Gln Pro Pro Gly
                20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
                100                 105
```

```
<210> SEQ ID NO 73
<211> LENGTH: 94
<212> TYPE: PRT
<213> ORGANISM: Mus musculus

<400> SEQUENCE: 73
```

```
Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
                20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
        50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90
```

```
<210> SEQ ID NO 74
<211> LENGTH: 118
<212> TYPE: PRT
<213> ORGANISM: Mus musculus

<400> SEQUENCE: 74
```

```
Ala Ala Glu Leu Val Arg Pro Gly Thr Ser Val Lys Val Ser Cys Lys
1               5                   10                  15

Ala Ser Gly Tyr Ala Phe Thr Asn Tyr Leu Ile Val Trp Ile Lys Gln
                20                  25                  30

Arg Pro Gly Gln Gly Leu Glu Trp Ile Gly Val Ile Ser Pro Gly Ser
        35                  40                  45

Gly Gly Thr Asn Tyr Asn Glu Lys Phe Lys Gly Lys Ala Ile Leu Thr
        50                  55                  60

Ala Asp Lys Ser Ser Ser Thr Ala Tyr Met Gln Leu Ser Ser Leu Thr
65                  70                  75                  80

Ser Asp Glu Phe Ala Val Tyr Phe Cys Ala Arg Glu Lys Ile Tyr Asp
                85                  90                  95

Asp Tyr Tyr Glu Gly Tyr Phe Asp Val Trp Gly Ala Gly Pro Arg His
                100                 105                 110

Leu Leu Ala Ser Leu Ser
        115
```

-continued

<210> SEQ ID NO 75
<211> LENGTH: 107
<212> TYPE: PRT
<213> ORGANISM: Mus musculus

<400> SEQUENCE: 75

Gly Thr Arg Cys Asp Ile Arg Leu Thr Gln Thr Thr Ser Ser Leu Ser
1               5                   10                  15

Ala Ser Leu Gly Asp Arg Val Thr Ile Ser Cys Ser Ala Ser Leu Gly
            20                  25                  30

Ile Gly Asn Tyr Leu Asn Trp Tyr Gln Gln Lys Pro Asp Gly Thr Val
        35                  40                  45

Lys Leu Leu Ile Tyr Tyr Thr Ser Asn Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Pro Glu Asp Ile Ala Thr Tyr Tyr Cys Gln His Tyr Ser
                85                  90                  95

Lys Leu Pro Leu Thr Phe Gly Ala Gly Pro Ser
            100                 105

<210> SEQ ID NO 76
<211> LENGTH: 113
<212> TYPE: PRT
<213> ORGANISM: Mus musculus

<400> SEQUENCE: 76

Gly Ala Glu Leu Val Arg Ser Gly Ala Ser Val Lys Met Ser Cys Lys
1               5                   10                  15

Ala Ser Gly Tyr Ser Phe Thr Asp Tyr Asn Met Tyr Trp Val Lys Gln
            20                  25                  30

Thr Pro Gly Gln Gly Leu Glu Trp Ile Gly Tyr Ile Tyr Pro Gly Asn
        35                  40                  45

Gly Gly Thr Asn Tyr Asn Gln Lys Phe Lys Gly Lys Ala Thr Leu Thr
    50                  55                  60

Ala Asp Thr Ser Ser Ser Thr Ala Tyr Met Gln Ile Ser Ser Leu Thr
65                  70                  75                  80

Ser Glu Asp Ser Ala Val Tyr Phe Cys Ala Arg Asp Tyr Asp Asp Gly
                85                  90                  95

Gly Tyr Ala Met Asp Tyr Trp Gly Gln Gly Thr Thr Val Thr Val Ser
            100                 105                 110

Ser

<210> SEQ ID NO 77
<211> LENGTH: 117
<212> TYPE: PRT
<213> ORGANISM: Mus musculus

<400> SEQUENCE: 77

Leu Leu Leu Trp Leu Thr Gly Ala Arg Cys Asp Ile Gln Met Thr Gln
1               5                   10                  15

Ser Pro Ala Ser Leu Ser Ala Ser Val Gly Glu Thr Val Thr Ile Thr
            20                  25                  30

Cys Arg Ala Ser Gly Asn Ile His Asn Tyr Leu Thr Trp Tyr Gln Gln
        35                  40                  45

Lys Gln Gly Lys Ser Pro Gln Leu Leu Val Tyr Asn Ala Lys Thr Leu
    50                  55                  60

```
Ala Asp Gly Val Pro Ser Arg Phe Ser Gly Ser Gly Ser Gly Thr Gln
65                  70                  75                  80

Tyr Ser Leu Lys Ile Asn Arg Leu Gln Pro Glu Asp Phe Gly Ser Tyr
                85                  90                  95

Tyr Cys Gln His Phe Trp Asn Ile Pro Trp Thr Phe Gly Gly Gly Thr
                100                 105                 110

Lys Leu Asn Ser Arg
            115

<210> SEQ ID NO 78
<211> LENGTH: 114
<212> TYPE: PRT
<213> ORGANISM: Mus musculus

<400> SEQUENCE: 78

Asp Ala Glu Leu Val Lys Pro Gly Ala Ser Val Lys Ile Ser Cys Lys
1               5                   10                  15

Ala Ser Gly Tyr Thr Phe Thr Asp His Ser Ile His Trp Val Gln Gln
                20                  25                  30

Lys Pro Glu Gln Gly Leu Glu Trp Ile Gly Tyr Ile Ser Pro Gly Asn
            35                  40                  45

Gly Asn Ile Lys Tyr Asn Glu Lys Phe Lys Gly Lys Ala Thr Leu Thr
        50                  55                  60

Ala Asp Lys Ser Ser Ser Thr Ala Tyr Met Gln Leu Asn Ser Leu Thr
65                  70                  75                  80

Ser Glu Asp Ser Ala Val Tyr Phe Cys Lys Arg Ser Leu Gly Arg Gly
                85                  90                  95

Gly Pro Tyr Tyr Phe Asp Tyr Trp Gly Gln Gly Thr Thr Val Thr Val
                100                 105                 110

Ser Ser

<210> SEQ ID NO 79
<211> LENGTH: 108
<212> TYPE: PRT
<213> ORGANISM: Mus musculus

<400> SEQUENCE: 79

Asp Ile Val Leu Thr Gln Ala Ala Pro Ser Leu Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Arg Glu Tyr Pro Val Thr Phe Gly Ser Gly Pro Asn
                100                 105

<210> SEQ ID NO 80
<211> LENGTH: 111
<212> TYPE: PRT
<213> ORGANISM: Mus musculus

<400> SEQUENCE: 80
```

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Ser Tyr Tyr Trp Tyr Phe Asp Val Trp Ala Gln Asp His Val
            100                 105                 110

<210> SEQ ID NO 81
<211> LENGTH: 109
<212> TYPE: PRT
<213> ORGANISM: Mus musculus

<400> SEQUENCE: 81

Ile Val Met Thr Gln Ala Ala Phe Ser Asn Pro Val Thr Leu Gly Thr
1               5                   10                  15

Ser Ala Ser Ile Ser Cys Arg Ser Ser Lys Asn Leu Leu His Ser Asn
                20                  25                  30

Gly Ile Thr Tyr Leu Tyr Trp Tyr Leu Gln Arg Pro Gly Gln Ser Pro
        35                  40                  45

Gln Leu Leu Ile Tyr Arg Val Ser Asn Leu Ala Ser Gly Val Pro Asn
    50                  55                  60

Arg Phe Ser Gly Ser Glu Ser Gly Thr Asp Phe Thr Leu Arg Ile Ser
65                  70                  75                  80

Arg Val Glu Ala Glu Asp Val Gly Val Tyr Tyr Cys Ala Gln Leu Leu
                85                  90                  95

Glu Leu Pro Tyr Thr Ser Glu Gly Thr Lys Arg Trp Glu
            100                 105

<210> SEQ ID NO 82
<211> LENGTH: 109
<212> TYPE: PRT
<213> ORGANISM: Mus musculus

<400> SEQUENCE: 82

Gly Gly Gly Leu Val Lys Pro Gly Gly Ser Leu Lys Leu Ser Cys Ala
1               5                   10                  15

Ala Ser Gly Phe Ala Phe Ser Ser Tyr Asp Met Ser Trp Ile Arg Gln
                20                  25                  30

Thr Pro Glu Lys Arg Leu Glu Trp Val Ala Tyr Ile Ser Ser Gly Ala
        35                  40                  45

Gly Ser Thr Tyr Tyr Pro Asp Thr Val Lys Gly Arg Phe Thr Val Ser
    50                  55                  60

Arg Asp Asn Ala Lys Asn Thr Leu Tyr Leu Gln Met Ser Ser Leu Lys
65                  70                  75                  80

Ser Glu Asp Thr Ala Met Tyr Tyr Cys Ala Arg His Phe Tyr Arg Phe
                85                  90                  95

Asp Tyr Trp Gly Gln Gly Thr Thr Val Thr Val Ser Ser
            100                 105
```

-continued

<210> SEQ ID NO 83
<211> LENGTH: 113
<212> TYPE: PRT
<213> ORGANISM: Mus musculus

<400> SEQUENCE: 83

Leu Leu Leu Cys Val Ser Gly Ala Pro Gly Ser Ile Val Met Thr Gln
1               5                   10                  15

Thr Pro Lys Phe Leu Leu Val Ser Ala Gly Asp Arg Ile Thr Ile Thr
            20                  25                  30

Cys Lys Ala Ser Gln Ser Val Ser Asn Asp Val Ala Trp Tyr Gln Gln
        35                  40                  45

Lys Pro Gly Gln Ser Pro Lys Leu Leu Ile Tyr Tyr Ala Ser Asn Arg
    50                  55                  60

Tyr Thr Gly Val Pro Asp Arg Phe Thr Gly Ser Gly Tyr Gly Thr Asp
65                  70                  75                  80

Phe Thr Phe Thr Ile Ser Thr Val Gln Ala Glu Asp Leu Ala Val Tyr
                85                  90                  95

Phe Cys Gln Gln Asp Asp Arg Phe Pro Leu Thr Phe Gly Ala Gly Pro
            100                 105                 110

Ser

<210> SEQ ID NO 84
<211> LENGTH: 112
<212> TYPE: PRT
<213> ORGANISM: Mus musculus

<400> SEQUENCE: 84

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Thr Gly Ala Trp Phe Ala Tyr Trp Ala Lys Asp Ser Ser Arg His
            100                 105                 110

<210> SEQ ID NO 85
<211> LENGTH: 107
<212> TYPE: PRT
<213> ORGANISM: Mus musculus

<400> SEQUENCE: 85

Gly Val Glu Gly Asp Ile Val Met Thr Gln Ser His Lys Phe Met Ser
1               5                   10                  15

Thr Ser Val Gly Asp Arg Val Ser Ile Thr Cys Lys Ala Ser Gln Asp
            20                  25                  30

Val Gly Thr Ala Val Ala Trp Tyr Gln Gln Lys Pro Gly Gln Ser Pro
        35                  40                  45

Lys Leu Leu Ile Tyr Trp Ala Ser Thr Arg His Thr Gly Val Pro Asp

-continued

```
            50              55              60

Arg Phe Thr Gly Ser Gly Ser Gly Thr Asp Phe Thr Leu Thr Ile Ser
65              70              75              80

Asn Val Gln Ser Glu Asp Leu Ala Asp Tyr Phe Cys Gln Gln Tyr Ser
                85              90              95

Ser Tyr Pro Leu Thr Phe Gly Ala Gly Pro Ser
            100             105

<210> SEQ ID NO 86
<211> LENGTH: 118
<212> TYPE: PRT
<213> ORGANISM: Mus musculus

<400> SEQUENCE: 86

Gly Gly Gly Leu Val Gln Pro Gly Gly Ser Met Lys Val Ser Cys Val
1               5               10              15

Ala Ser Gly Phe Ser Phe Ile Asp Phe Trp Met Asn Trp Val Arg Gln
                20              25              30

Ser Pro Glu Lys Gly Leu Glu Trp Val Ala Glu Ile Arg Leu Lys Ser
            35              40              45

Asn Asn Tyr Ala Thr His Tyr Ala Glu Ser Val Lys Gly Arg Phe Thr
        50              55              60

Ile Ser Arg Asp Asp Ser Lys Ser Ser Val Tyr Leu Gln Met Asn Asn
65              70              75              80

Leu Arg Pro Glu Asp Thr Gly Ile Tyr Tyr Cys Thr Ser Leu Phe Tyr
                85              90              95

Tyr Tyr Asp Gly Thr Ser Gly Phe Ala Tyr Trp Gly Gln Gly Thr Thr
            100             105             110

Val Thr Val Leu Leu Lys
        115

<210> SEQ ID NO 87
<211> LENGTH: 109
<212> TYPE: PRT
<213> ORGANISM: Mus musculus

<400> SEQUENCE: 87

Asp Ile Val Met Thr Gln Ser Pro Ser Ser Leu Thr Val Thr Ala Gly
1               5               10              15

Glu Lys Val Thr Met His Cys Lys Ser Ser Gln Ser Leu Leu Asn Ser
                20              25              30

Gly Asp Gln Lys Asn Tyr Leu Thr Trp Tyr Gln Gln Lys Pro Gly Gln
            35              40              45

Pro Pro Lys Leu Leu Ile Tyr Trp Ala Ser Thr Arg Glu Ser Gly Val
        50              55              60

Pro Asp Arg Phe Thr Gly Ser Gly Ser Gly Thr Asp Phe Thr Leu Thr
65              70              75              80

Ile Ser Ser Val Gln Ala Glu Asp Leu Ala Val Tyr Tyr Cys Gln Asn
                85              90              95

Asp Tyr Asp Tyr Pro Leu Thr Phe Gly Ala Gly Pro Ser
            100             105

<210> SEQ ID NO 88
<211> LENGTH: 148
<212> TYPE: PRT
<213> ORGANISM: Mus musculus

<400> SEQUENCE: 88
```

```
Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
                20                  25                  30

Pro Gly Ala Ser Val Lys Ile Ser Cys Lys Ala Ser Gly Tyr Thr Phe
            35                  40                  45

Thr Asp Tyr Asn Met Asp Trp Val Lys Gln Ser His Gly Lys Ser Leu
        50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
                100                 105                 110

Tyr Tyr Cys Ala Arg Ser Arg Ser Tyr Asp Tyr Glu Gly Phe Ala Tyr
            115                 120                 125

Trp Gly Gln Gly Thr Leu Val Thr Val Ser Ala Ala Lys Thr Thr Pro
    130                 135                 140

Pro Ser Val Tyr
145
```

```
<210> SEQ ID NO 89
<211> LENGTH: 139
<212> TYPE: PRT
<213> ORGANISM: Mus musculus

<400> SEQUENCE: 89
```

```
Met Ser Val Leu Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
            35                  40                  45

Ile His Asn Tyr Leu Ala Trp Tyr Gln Gln Lys Gln Gly Lys Ser Pro
        50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
                100                 105                 110

Ser Thr Leu Thr Phe Gly Ala Gly Thr Lys Leu Glu Leu Lys Arg Ala
            115                 120                 125

Asp Ala Ala Pro Thr Val Ser Asn Pro Tyr Asp
    130                 135
```

```
<210> SEQ ID NO 90
<211> LENGTH: 100
<212> TYPE: PRT
<213> ORGANISM: Mus musculus

<400> SEQUENCE: 90
```

```
Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
                20                  25                  30
```

-continued

```
Asn Pro Tyr Asn Gly Gly Thr Ser Tyr Asn Gln Lys Phe Lys Gly Lys
        35              40              45

Ala Thr Leu Thr Val Asp Lys Ser Ser Ser Thr Ala Tyr Met Glu Leu
    50              55              60

Leu Ser Leu Thr Ser Glu Asp Ser Ala Val Tyr Tyr Cys Ala Arg Trp
65              70              75              80

Gly Val Trp Ser Ala Met Asp Tyr Trp Gly Gln Gly Thr Thr Val Thr
                85              90              95

Val Ser Ser Lys
            100
```

<210> SEQ ID NO 91
<211> LENGTH: 90
<212> TYPE: PRT
<213> ORGANISM: Mus musculus

<400> SEQUENCE: 91

```
Asp Arg Val Ser Ile Thr Cys Lys Ala Ser Gln Asn Val Arg Thr Ala
1               5               10              15

Val Ala Trp Tyr Gln Gln Lys Pro Arg Gln Ser Pro Lys Ala Leu Ile
                20              25              30

Tyr Leu Ala Ser Asn Arg Asp Thr Gly Leu Pro Asp Arg Phe Pro Gly
        35              40              45

Arg Gly Ser Gly Thr Asp Phe Thr Leu Asn Ile Thr Asn Val Gln Ser
    50              55              60

Glu Asp Leu Glu Asp Tyr Phe Cys Leu Gln His Cys Asn Tyr Pro Asn
65              70              75              80

Glu Phe Arg Gly Cys Thr Lys Val Pro Ile
                85              90
```

<210> SEQ ID NO 92
<211> LENGTH: 116
<212> TYPE: PRT
<213> ORGANISM: Mus musculus

<400> SEQUENCE: 92

```
Leu Gln Glu Ser Gly Ala Glu Leu Ala Arg Pro Gly Ala Ser Val Lys
1               5               10              15

Leu Ser Cys Lys Ala Ser Gly Tyr Thr Phe Thr Ser Tyr Trp Met Gln
                20              25              30

Trp Val Lys Gln Arg Pro Gly Gln Gly Leu Glu Trp Ile Gly Ala Ile
        35              40              45

Tyr Pro Gly Asp Gly Asp Thr Arg Tyr Thr Gln Lys Phe Lys Gly Lys
    50              55              60

Ala Thr Leu Thr Ala Asp Lys Ser Ser Ser Thr Ala Tyr Met Gln Leu
65              70              75              80

Ser Ser Leu Ala Ser Glu Asp Ser Ala Val Tyr Tyr Cys Ala Arg Gly
                85              90              95

Glu Tyr Gly Asn Tyr Phe Ala Tyr Trp Gly Gln Gly Thr Thr Val Thr
                100             105             110

Val Ser Ser Asn
        115
```

<210> SEQ ID NO 93
<211> LENGTH: 100
<212> TYPE: PRT
<213> ORGANISM: Mus musculus

<400> SEQUENCE: 93

```
Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
                20                  25                  30

Lys Ser Pro Lys Thr Leu Ile Tyr Arg Ala Asn Arg Leu Val Asp Gly
            35                  40                  45

Val Pro Ser Arg Phe Ser Gly Ser Gly Ser Gly Gln Asp Tyr Ser Leu
        50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
            100
```

<210> SEQ ID NO 94
<211> LENGTH: 108
<212> TYPE: PRT
<213> ORGANISM: Mus musculus

<400> SEQUENCE: 94

```
Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
                20                  25                  30

Trp Ile Gly Arg Ile Asp Pro Ala Asn Gly Asn Thr Lys Tyr Asp Pro
            35                  40                  45

Lys Phe Gln Gly Lys Ala Thr Ile Thr Ala Asp Thr Ser Ser Asn Thr
        50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Tyr Gly Ser Ser Leu Ala Tyr
                85                  90                  95

Trp Gly Gln Gly Thr Thr Val Thr Val Ser Ser Lys
            100                 105
```

<210> SEQ ID NO 95
<211> LENGTH: 104
<212> TYPE: PRT
<213> ORGANISM: Mus musculus

<400> SEQUENCE: 95

```
Glu Phe His Ala Val Ser Leu Gly Gln Arg Ala Thr Ile Ser Cys Arg
1               5                   10                  15

Ala Ser Glu Ser Val Asp Ser Tyr Gly Asn Ser Phe Met His Trp Tyr
                20                  25                  30

Gln Gln Lys Pro Gly Gln Pro Pro Lys Leu Leu Ile Tyr Arg Ala Ser
            35                  40                  45

Asn Leu Glu Ser Gly Ile Pro Ala Arg Phe Ser Gly Ser Gly Ser Arg
        50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95
```

-continued

```
Val Pro Ser Trp Arg Ser Asn Lys
            100

<210> SEQ ID NO 96
<211> LENGTH: 109
<212> TYPE: PRT
<213> ORGANISM: Mus musculus

<400> SEQUENCE: 96

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 97
<211> LENGTH: 94
<212> TYPE: PRT
<213> ORGANISM: Mus musculus

<400> SEQUENCE: 97

Ser Gly Asp Arg Val Ser Leu Ser Cys Arg Ala Ser Gln Ser Ile Ser
1               5                   10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Gly Gly Thr Lys Leu Glu Ile Lys Gln
                85                  90

<210> SEQ ID NO 98
<211> LENGTH: 111
<212> TYPE: PRT
<213> ORGANISM: Mus musculus

<400> SEQUENCE: 98

Pro Ala Cys Leu Pro Gly Gly Ser Leu Arg Leu Ser Cys Ala Thr Ser
1               5                   10                  15

Gly Phe Thr Phe Thr Asp Tyr Tyr Met Ser Trp Val Arg Gln Pro Pro
            20                  25                  30

Gly Lys Ala Leu Glu Trp Leu Gly Phe Ile Arg Asn Lys Ala Asn Gly
            35                  40                  45

Tyr Thr Thr Glu Tyr Ser Ala Ser Val Lys Gly Arg Phe Thr Ile Ser
    50                  55                  60

Arg Asp Asn Ser Gln Ser Ile Leu Tyr Leu Gln Met Asn Thr Leu Arg
```

```
65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
                100                 105                 110

<210> SEQ ID NO 99
<211> LENGTH: 102
<212> TYPE: PRT
<213> ORGANISM: Mus musculus

<400> SEQUENCE: 99

Arg Leu Pro Phe Tyr Ser Leu Glu Gln Arg Ala Thr Ile Ser Tyr Arg
1               5                   10                  15

Ala Ser Lys Asn Val Ser Thr Ser Gly Tyr Ser Tyr Met His Trp Asn
                20                  25                  30

Gln Gln Lys Pro Gly Gln Pro Pro Lys Leu Leu Ile Tyr Leu Val Ser
            35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
                100

<210> SEQ ID NO 100
<211> LENGTH: 101
<212> TYPE: PRT
<213> ORGANISM: Mus musculus

<400> SEQUENCE: 100

Val Ser Cys Lys Ala Ser Gly Tyr Thr Phe Thr Ser Tyr Trp Met His
1               5                   10                  15

Trp Val Lys Gln Arg Pro Gly Gln Gly Leu Glu Trp Ile Gly Met Ile
                20                  25                  30

Asp Pro Ser Asn Ser Glu Thr Arg Leu Asn Gln Lys Phe Lys Asp Lys
            35                  40                  45

Ala Thr Leu Asn Val Asp Lys Ser Ser Asn Thr Ala Tyr Met Gln Leu
    50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
                85                  90                  95

Thr Val Ser Ser Lys
                100

<210> SEQ ID NO 101
<211> LENGTH: 99
<212> TYPE: PRT
<213> ORGANISM: Mus musculus

<400> SEQUENCE: 101

Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
                20                  25                  30
```

-continued

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Glu Asp Ala Ala Thr Tyr Tyr Cys
65                  70                  75                  80

Gln His Ile Arg Glu Leu Thr Arg Ser Glu Glu Val Pro Ser Trp Arg
            85                  90                  95

Ser Asn Lys

<210> SEQ ID NO 102
<211> LENGTH: 110
<212> TYPE: PRT
<213> ORGANISM: Mus musculus

<400> SEQUENCE: 102

Gly Gly Gly Leu Val Lys Pro Gly Gly Ser Leu Lys Leu Ser Cys Ala
1               5                   10                  15

Ala Ser Gly Phe Thr Phe Ser Ser Tyr Gly Met Ser Trp Val Arg Gln
            20                  25                  30

Thr Pro Glu Lys Arg Leu Glu Trp Val Ala Thr Ile Ser Ser Gly Gly
        35                  40                  45

Ser Tyr Thr Tyr Tyr Pro Asp Ser Val Lys Gly Arg Phe Thr Ile Ser
    50                  55                  60

Arg Asp Asn Ala Lys Asn Thr Leu Tyr Leu Gln Met Ser Ser Leu Arg
65                  70                  75                  80

Ser Glu Asp Thr Ala Met Tyr Tyr Cys Ala Ser Leu Ala Ser Tyr Tyr
            85                  90                  95

Phe Asp Tyr Trp Gly Gln Gly Thr Thr Leu Thr Val Ser Ser
            100                 105                 110

<210> SEQ ID NO 103
<211> LENGTH: 113
<212> TYPE: PRT
<213> ORGANISM: Mus musculus

<400> SEQUENCE: 103

Gly Ala Arg Cys Asp Val Gln Met Ile Gln Ser Pro Ser Ser Leu Ser
1               5                   10                  15

Ala Ser Leu Gly Asp Ile Val Thr Met Thr Cys Gln Ala Ser Gln Gly
            20                  25                  30

Thr Ser Ile Asn Leu Asn Trp Phe Gln Gln Lys Pro Gly Lys Ala Pro
        35                  40                  45

Lys Leu Leu Ile Tyr Gly Ala Ser Ser Leu Glu Asp Gly Val Pro Ser
    50                  55                  60

Arg Phe Ser Gly Ser Cys Phe Gly Thr Asp Phe Thr Leu Thr Ile Ser
65                  70                  75                  80

Ser Leu Glu Asp Glu Asp Met Ala Thr Tyr Phe Cys Leu Gln His Ser
            85                  90                  95

Tyr Leu Pro Pro Leu Thr Phe Gly Ala Gly Thr Lys Leu Glu Leu Lys
            100                 105                 110

Arg

<210> SEQ ID NO 104
<211> LENGTH: 111
<212> TYPE: PRT

-continued

```
<213> ORGANISM: Mus musculus

<400> SEQUENCE: 104

Gly Pro Gly Leu Val Gln Pro Ser Gln Ser Leu Ser Ile Thr Cys Thr
1               5                   10                  15

Val Ser Gly Phe Ser Leu Thr Thr Tyr Asp Leu His Trp Val Arg Gln
            20                  25                  30

Ser Pro Gly Lys Gly Leu Glu Trp Leu Gly Val Ile Trp Ser Gly Gly
        35                  40                  45

Ser Thr Asp Tyr Asn Ala Ala Phe Ile Ser Arg Leu Ser Ile Ser Lys
    50                  55                  60

Asp Asn Ser Lys Ser Gln Val Phe Phe Lys Met Asn Ser Leu Gln Ala
65                  70                  75                  80

Asn Asp Thr Ala Ile Tyr Tyr Cys Ala Arg Asn Tyr Gly Tyr Ser Ala
                85                  90                  95

Trp Phe Ala Tyr Trp Gly Gln Gly Thr Leu Val Thr Val Ser Ala
                100                 105                 110

<210> SEQ ID NO 105
<211> LENGTH: 118
<212> TYPE: PRT
<213> ORGANISM: Mus musculus

<400> SEQUENCE: 105

Pro Ala Ser Ser Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
            35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Leu Thr Phe Gly Ala Gly Thr
                100                 105                 110

Lys Leu Glu Leu Lys Arg
            115

<210> SEQ ID NO 106
<211> LENGTH: 114
<212> TYPE: PRT
<213> ORGANISM: Mus musculus

<400> SEQUENCE: 106

Gly Phe Glu Leu Lys Lys Pro Gly Glu Thr Val Lys Ile Ser Cys Lys
1               5                   10                  15

Ala Ser Gly Tyr Thr Phe Thr Ala Tyr Ser Met His Trp Val Lys Gln
            20                  25                  30

Thr Pro Gly Lys Gly Leu Lys Trp Leu Gly Trp Ile Asn Thr Glu Thr
        35                  40                  45

Gly Glu Pro Thr Tyr Thr Asp Asp Phe Lys Gly Arg Phe Thr Phe Ser
    50                  55                  60

Leu Glu Thr Ser Ala Arg Ile Ala Tyr Leu Gln Ile Asn Asp Leu Lys
65                  70                  75                  80
```

-continued

```
Asn Glu Asp Thr Ala Thr Tyr Phe Cys Ala Arg Arg Ile Tyr Tyr Phe
                85                  90                  95

Gly Arg Gly Gly Phe Asp Tyr Trp Gly Gln Gly Thr Thr Val Thr Val
            100                 105                 110

Ser Ser

<210> SEQ ID NO 107
<211> LENGTH: 118
<212> TYPE: PRT
<213> ORGANISM: Mus musculus

<400> SEQUENCE: 107

Pro Ala Ser Ser Ser Asp Val Leu Met Thr Gln Thr Pro Leu Ser Leu
1               5                   10                  15

Pro Val Arg Leu Gly Asp Gln Ser Ser Ile Ser Cys Arg Ser Ser Gln
            20                  25                  30

Ser Ile Val His Ser Asn Gly Asn Thr Tyr Leu Glu Trp Tyr Leu Gln
        35                  40                  45

Lys Pro Gly Gln Ser Pro Lys Leu Leu Ile Tyr Lys Val Ser Asn Arg
    50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Pro Glu Asp Leu Gly Val Tyr
                85                  90                  95

Tyr Cys Phe Gln Gly Ser His Val Pro Tyr Thr Ser Glu Gly Asp Gln
            100                 105                 110

Ala Glu Ile Lys Leu Ala
        115

<210> SEQ ID NO 108
<211> LENGTH: 114
<212> TYPE: PRT
<213> ORGANISM: Mus musculus

<400> SEQUENCE: 108

Gly Gly Gly Leu Val Gln Pro Gly Gly Ser Met Arg Leu Ser Cys Val
1               5                   10                  15

Ala Ser Gly Phe Thr Phe Ser Asn Ser Trp Phe Asn Trp Val Arg Gln
            20                  25                  30

Ser Pro Glu Lys Gly Leu Glu Trp Val Ala Glu Ile Arg Leu Thr Ser
        35                  40                  45

Asp Asn Tyr Ala Ile Tyr Tyr Ala Glu Ser Val Lys Gly Arg Phe Thr
    50                  55                  60

Ile Ser Arg Asp Asp Ser Lys Ser Ser Val Tyr Leu Gln Met Asn Asn
65                  70                  75                  80

Leu Arg Ala Glu Asp Thr Gly Ile Tyr Tyr Cys Thr Arg Pro Glu Thr
                85                  90                  95

Ala Arg Ala Thr Phe Ala Tyr Trp Gly Gln Gly Thr Thr Val Thr Val
            100                 105                 110

Ser Ser

<210> SEQ ID NO 109
<211> LENGTH: 118
<212> TYPE: PRT
<213> ORGANISM: Mus musculus

<400> SEQUENCE: 109
```

```
Pro Ala Ser Thr Ser Asp Val Leu Met Thr Gln Thr Pro Leu Ser Leu
1               5                   10                  15

Pro Val Ser Leu Gly Asp Gln Ala Ser Ile Ser Cys Arg Ser Ser Gln
            20                  25                  30

Ser Ile Val His Ser Asn Gly Asn Thr Tyr Leu Glu Trp Tyr Leu Gln
            35                  40                  45

Lys Pro Gly Gln Ser Pro Lys Val Leu Ile Tyr Lys Val Phe Asn Arg
        50                  55                  60

Phe Ser Gly Val Pro Asp Arg Phe Ser Gly Ser Gly Ser Gly Thr Asp
65                  70                  75                  80

Phe Thr Leu Lys Ile Ser Arg Val Glu Ala Glu Asp Leu Gly Val Tyr
                85                  90                  95

Tyr Cys Phe Gln Gly Ser His Val Pro Arg Thr Phe Gly Gly Gly Thr
            100                 105                 110

Lys Leu Asn Gln Thr Gly
        115
```

<210> SEQ ID NO 110
<211> LENGTH: 111
<212> TYPE: PRT
<213> ORGANISM: Mus musculus

<400> SEQUENCE: 110

```
Gly Pro Asp Leu Val Lys Pro Gly Ala Ser Val Lys Ile Ser Cys Lys
1               5                   10                  15

Ala Ser Gly Tyr Ser Phe Thr Ala Tyr Tyr Met His Trp Val Lys Gln
            20                  25                  30

Ser His Gly Lys Ser Leu Glu Trp Ile Gly Arg Val Asn Pro Asn Asn
            35                  40                  45

Gly Gly Thr Thr Tyr Asn Gln Lys Phe Lys Gly Lys Ala Ile Leu Thr
        50                  55                  60

Val Asp Lys Ser Ser Ser Thr Ala Tyr Met Glu Leu Arg Ser Leu Thr
65                  70                  75                  80

Phe Glu Asp Ser Ala Val Tyr Tyr Cys Ala Arg Arg Ile Tyr Tyr Gly
                85                  90                  95

Tyr Phe Asp Tyr Trp Gly Gln Gly Thr Thr Val Thr Val Ser Ser
            100                 105                 110
```

<210> SEQ ID NO 111
<211> LENGTH: 104
<212> TYPE: PRT
<213> ORGANISM: Mus musculus

<400> SEQUENCE: 111

```
Ala Phe Phe Ala Val Ser Leu Gly Gln Arg Ala Thr Ile Ser Cys Lys
1               5                   10                  15

Ala Ser Gln Ser Val Asp Tyr Asp Gly Asp Ser Tyr Met Asn Trp Tyr
            20                  25                  30

Gln Gln Lys Pro Gly Gln Pro Pro Lys Leu Leu Ile Tyr Val Ala Ser
        35                  40                  45

Asn Leu Glu Ser Gly Val Pro Ala Arg Phe Ser Gly Ser Gly Ser Gly
        50                  55                  60

Thr Asp Phe Thr Leu Asn Ile His Pro Val Glu Glu Glu Asp Ala Ala
65                  70                  75                  80

Thr Tyr Tyr Cys Gln Gln Ser Asn Glu Asp Pro Tyr Thr Phe Gly Gly
                85                  90                  95
```

Gly Thr Lys Leu Glu Ile Lys Gln
        100

<210> SEQ ID NO 112
<211> LENGTH: 106
<212> TYPE: PRT
<213> ORGANISM: Mus musculus

<400> SEQUENCE: 112

Gly Ala Glu Leu Val Lys Pro Gly Ala Ser Val Lys Leu Ser Cys Thr
1               5                   10                  15

Ala Ser Gly Leu Asn Ile Arg Asp Ile Tyr Met His Trp Val Lys Gln
        20                  25                  30

Arg Pro Glu Gln Gly Leu Glu Trp Ile Gly Lys Ile Asp Pro Ala Asn
        35                  40                  45

Gly Asn Thr Lys Tyr Asp Pro Lys Phe Gln Gly Lys Ala Thr Ile Thr
    50                  55                  60

Ala Asp Thr Ser Ser Asn Thr Ala Tyr Val Gln Leu Ser Ser Leu Thr
65                  70                  75                  80

Ser Glu Asp Thr Ala Val Tyr Tyr Cys Ala Gly Thr Gly Asp Tyr Trp
                85                  90                  95

Gly Gln Gly Thr Thr Val Thr Val Ser Ser
            100                 105

<210> SEQ ID NO 113
<211> LENGTH: 112
<212> TYPE: PRT
<213> ORGANISM: Mus musculus

<400> SEQUENCE: 113

Gly Thr Cys Gly Asp Ile Val Met Ser Gln Ser Pro Ser Ser Leu Ala
1               5                   10                  15

Val Ser Ala Gly Glu Lys Val Thr Met Ser Cys Lys Ser Ser Gln Ser
        20                  25                  30

Leu Leu Asn Ser Arg Thr Arg Lys Asn Tyr Leu Ala Trp Val Gln His
        35                  40                  45

Lys Pro Gly Gln Ser Pro Arg Leu Leu Ile Tyr Trp Ala Ser Thr Arg
    50                  55                  60

Glu Ser Gly Val Pro Asp Arg Phe Thr Gly Ser Gly Ser Gly Thr Asp
65                  70                  75                  80

Phe Thr Leu Thr Ile Ser Ser Val Gln Ala Glu Asp Leu Ala Val Tyr
                85                  90                  95

Tyr Cys Arg Gln Ser Tyr Asn Leu Val Thr Phe Gly Ala Gly Pro Ser
            100                 105                 110

<210> SEQ ID NO 114
<211> LENGTH: 112
<212> TYPE: PRT
<213> ORGANISM: Mus musculus

<400> SEQUENCE: 114

Gly Pro Glu Leu Val Lys Pro Gly Ala Ser Val Lys Met Ser Cys Lys
1               5                   10                  15

Ala Ser Gly Tyr Thr Phe Thr Ser Tyr Val Met His Trp Val Lys Gln
        20                  25                  30

Lys Pro Gly Gln Gly Leu Glu Trp Ile Gly Tyr Ile Asn Pro Tyr Asn
        35                  40                  45

-continued

```
Asp Gly Thr Lys Tyr Asn Glu Lys Phe Lys Gly Lys Ala Thr Leu Thr
    50              55              60

Ser Asp Lys Ser Ser Ser Thr Ala Tyr Met Glu Leu Ser Ser Leu Thr
65              70              75              80

Ser Glu Asp Ser Ala Val Tyr Tyr Cys Ala Arg Arg Tyr Tyr Tyr Gly
                85              90              95

Ser Ser Gly Gly Tyr Phe Asp Val Trp Ala Gln Asp His Val Arg Thr
            100             105             110
```

<210> SEQ ID NO 115
<211> LENGTH: 108
<212> TYPE: PRT
<213> ORGANISM: Mus musculus

<400> SEQUENCE: 115

```
Asp Val Gln Ile Thr Gln Ser Pro Ser Tyr Leu Ala Ala Ser Pro Gly
1               5               10              15

Glu Thr Ile Thr Ile Asn Cys Arg Ala Ser Lys Ser Ile Ser Lys Tyr
                20              25              30

Leu Ala Trp Tyr Gln Glu Lys Pro Gly Lys Thr Asn Lys Leu Leu Ile
            35              40              45

Tyr Ser Gly Ser Thr Leu Gln Ser Gly Ile Pro Ser Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Met Tyr Tyr Cys Gln Gln His Asn Glu Tyr Pro Tyr
                85              90              95

Thr Phe Gly Gly Gly Thr Lys Leu Glu Ile Lys Arg
            100             105
```

<210> SEQ ID NO 116
<211> LENGTH: 113
<212> TYPE: PRT
<213> ORGANISM: Mus musculus

<400> SEQUENCE: 116

```
Gly Pro Glu Leu Val Lys Pro Gly Ala Ser Val Lys Ile Ser Cys Lys
1               5               10              15

Ala Ser Gly Tyr Ser Phe Thr Gly Tyr Phe Met Asn Trp Val Met Gln
                20              25              30

Ser His Gly Lys Ser Leu Glu Trp Ile Gly Arg Ile Asn Pro Tyr Asn
            35              40              45

Gly Asp Thr Phe Tyr Asn Gln Lys Phe Lys Gly Lys Ala Thr Leu Thr
    50              55              60

Val Asp Lys Ser Ser Ser Thr Ala His Met Glu Leu Arg Ser Leu Ala
65              70              75              80

Ser Glu Asp Ser Ala Val Tyr Tyr Cys Ala Arg Arg Ile His Tyr Tyr
                85              90              95

Tyr Gly Ser Ser Tyr Tyr Ala Met Asp Tyr Trp Gly Gln Glu Pro His
            100             105             110

His
```

<210> SEQ ID NO 117
<211> LENGTH: 108
<212> TYPE: PRT
<213> ORGANISM: Mus musculus

<400> SEQUENCE: 117

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys Arg
            100                 105

<210> SEQ ID NO 118
<211> LENGTH: 113
<212> TYPE: PRT
<213> ORGANISM: Mus musculus

<400> SEQUENCE: 118

Gly Ala Gly Leu Val Lys Pro Gly Ala Ser Val Lys Leu Ser Cys Lys
1               5                   10                  15

Ala Ser Gly Tyr Thr Phe Thr Glu Tyr Ile Ile His Trp Val Lys Gln
            20                  25                  30

Arg Ser Gly Gln Gly Leu Glu Trp Ile Gly Trp Phe Tyr Pro Gly Ser
        35                  40                  45

Gly Ser Ile Lys Tyr Asn Glu Lys Phe Lys Asp Lys Ala Thr Leu Thr
    50                  55                  60

Ala Asp Lys Ser Ser Ser Thr Val Tyr Met Glu Leu Ser Arg Leu Thr
65                  70                  75                  80

Ser Glu Asp Ser Ala Val Tyr Phe Cys Ala Arg His Glu Val Tyr Tyr
                85                  90                  95

Asp Tyr Asp Lys Ser Met Leu Trp Thr Thr Gly Val Lys Asn Leu Ile
            100                 105                 110

Arg

<210> SEQ ID NO 119
<211> LENGTH: 108
<212> TYPE: PRT
<213> ORGANISM: Mus musculus

<400> SEQUENCE: 119

Ser Pro Ser Ser Leu Ala Val Ser Val Gly Glu Lys Val Thr Met Ser
1               5                   10                  15

Cys Lys Ser Ser Gln Ser Leu Leu Tyr Ser Ser Asn Gln Lys Asn Tyr
            20                  25                  30

Leu Ala Trp Tyr Gln Gln Lys Pro Gly Gln Ser Pro Lys Leu Leu Ile
        35                  40                  45

Tyr Trp Ala Ser Thr Arg Glu Ser Gly Val Pro Asp Arg Phe Thr Gly
    50                  55                  60

Ser Gly Ser Gly Thr Asp Phe Thr Leu Thr Ile Ser Ser Val Lys Ala
65                  70                  75                  80

Glu Asp Leu Ala Val Tyr Tyr Cys Gln Gln Tyr Tyr Ser Tyr Pro Tyr
                85                  90                  95
```

-continued

```
Thr Phe Gly Gly Gly Thr Lys Leu Glu Ile Lys Arg
            100                 105

<210> SEQ ID NO 120
<211> LENGTH: 113
<212> TYPE: PRT
<213> ORGANISM: Mus musculus

<400> SEQUENCE: 120

Gly Ala Glu Leu Val Arg Pro Gly Thr Ser Val Lys Val Ser Cys Lys
1               5                   10                  15

Ala Ser Val Tyr Ala Phe Thr Asn Tyr Leu Ile Glu Trp Val Lys Gln
            20                  25                  30

Arg Pro Gly Gln Gly Leu Glu Trp Ile Gly Val Ile Asn Pro Lys Ser
        35                  40                  45

Gly Gly Thr Lys Tyr Asn Glu Lys Phe Arg Gly Lys Ala Thr Leu Thr
    50                  55                  60

Ala Asp Lys Ser Ser Ser Thr Ala Tyr Met Gln Leu Ser Ser Leu Thr
65                  70                  75                  80

Ser Gly Asp Ser Ala Val Tyr Phe Cys Ala Ile Thr Gly Thr Asp Tyr
                85                  90                  95

Trp Gly Gln Gly Thr Thr Leu Thr Val Ser Ser Ala Lys Thr Thr Pro
            100                 105                 110

Pro

<210> SEQ ID NO 121
<211> LENGTH: 113
<212> TYPE: PRT
<213> ORGANISM: Mus musculus

<400> SEQUENCE: 121

Gln Gly Thr Arg Cys Asp Ile Gln Met Thr Gln Thr Thr Ser Ser Leu
1               5                   10                  15

Ser Ala Ser Leu Gly Asp Arg Val Thr Ile Ser Cys Ser Ala Ser Gln
            20                  25                  30

Gly Ile Asn Asn Tyr Leu Asn Trp Tyr Gln Gln Lys Pro Asp Gly Thr
        35                  40                  45

Val Lys Leu Leu Ile Tyr Tyr Thr Ser Ser Leu Arg Ser Gly Val Pro
    50                  55                  60

Ser Arg Phe Ser Gly Ser Gly Ser Gly Thr Asp Tyr Ser Leu Thr Ile
65                  70                  75                  80

Ser Asn Leu Glu Pro Glu Asp Val Ala Thr Tyr Tyr Cys Gln Gln Tyr
                85                  90                  95

Ser Lys Leu Pro Arg Thr Phe Gly Gly Gly Thr Lys Leu Glu Ile Lys
            100                 105                 110

Arg

<210> SEQ ID NO 122
<211> LENGTH: 121
<212> TYPE: PRT
<213> ORGANISM: Homo sapiens

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30
```

-continued

```
Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
                100                 105                 110

Gln Gly Thr Leu Val Thr Val Ser Ser
        115                 120

<210> SEQ ID NO 123
<211> LENGTH: 112
<212> TYPE: PRT
<213> ORGANISM: Homo sapiens

<400> SEQUENCE: 123

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
                20                  25                  30

Asn Leu Ala Trp Phe Gln Gln Lys Pro Gly Lys Val Pro Lys Arg Leu
        35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
                100                 105                 110

<210> SEQ ID NO 124
<211> LENGTH: 121
<212> TYPE: PRT
<213> ORGANISM: Homo sapiens

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
                20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
                100                 105                 110

Gln Gly Thr Leu Val Thr Val Ser Ser
        115                 120
```

```
<210> SEQ ID NO 125
<211> LENGTH: 112
<212> TYPE: PRT
<213> ORGANISM: Homo sapiens

<400> SEQUENCE: 125

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Leu Tyr Asn Asn Glu
            20                  25                  30

Asn Leu Ala Trp Phe Gln Gln Lys Pro Gly Lys Val Pro Lys Arg Leu
        35                  40                  45

Ile Tyr Gly Ala Ser Thr Leu Ala Ser Gly Val Ser Ser Arg Phe Ser
    50                  55                  60

Gly Ser Gly Ser Gly Thr Glu Phe Thr Leu Thr Ile Ser Ser Leu Gln
65                  70                  75                  80

Cys Glu Asp Phe Ala Ile Tyr Tyr Cys Leu Gly Glu Phe Ser Cys Gly
                85                  90                  95

Ser Ala Asp Cys Phe Ala Phe Gly Gly Gly Thr Lys Val Glu Ile Lys
            100                 105                 110
```

```
<210> SEQ ID NO 126
<211> LENGTH: 121
<212> TYPE: PRT
<213> ORGANISM: Homo sapiens

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
            115                 120
```

```
<210> SEQ ID NO 127
<211> LENGTH: 113
<212> TYPE: PRT
<213> ORGANISM: Homo sapiens

<400> SEQUENCE: 127

Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
```

-continued

```
          50               55               60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys

<210> SEQ ID NO 128
<211> LENGTH: 121
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
                20                  25                  30

Ser Leu Gly Trp Val Arg Gln Ala Pro Gly Lys Gly Leu Glu Trp Ile
            35                  40                  45

Gly Asp Ile Arg Ser Gly Gly Ser Ala Tyr Tyr Ala Asn Trp Ala Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
            115                 120

<210> SEQ ID NO 129
<211> LENGTH: 113
<212> TYPE: PRT
<213> ORGANISM: Homo sapiens

<400> SEQUENCE: 129

Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
                20                  25                  30

Glu Asn Leu Ala Trp Phe Gln Gln Lys Pro Gly Lys Val Pro Lys Arg
            35                  40                  45

Leu Ile Tyr Gly Ala Ser Thr Leu Ala Ser Gly Val Ser Ser Arg Phe
        50                  55                  60

Ser Gly Ser Gly Ser Gly Thr Glu Phe Thr Leu Thr Ile Ser Asn Leu
65                  70                  75                  80

Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys

<210> SEQ ID NO 130
<211> LENGTH: 121
```

-continued

<212> TYPE: PRT
<213> ORGANISM: Homo sapiens

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120

<210> SEQ ID NO 131
<211> LENGTH: 113
<212> TYPE: PRT
<213> ORGANISM: Homo sapiens

<400> SEQUENCE: 131

Glu Ile Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
            20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Thr Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys

<210> SEQ ID NO 132
<211> LENGTH: 121
<212> TYPE: PRT
<213> ORGANISM: Homo sapiens

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser His
            20                  25                  30

Ser Leu Gly Trp Val Arg Gln Ala Pro Gly Lys Gly Leu Glu Trp Ile
        35                  40                  45

Gly Asp Ile Arg Ser Gly Gly Ser Ala Tyr Tyr Ala Asn Trp Ala Lys
    50                  55                  60

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Thr
                85                  90                  95

Arg Thr Asn Gly Pro Ser Asp Leu Thr Asn Arg Leu Asp Leu Trp Gly
            100                 105                 110

Gln Gly Thr Leu Val Thr Val Ser Ser
        115                 120

<210> SEQ ID NO 133
<211> LENGTH: 113
<212> TYPE: PRT
<213> ORGANISM: Homo sapiens

<400> SEQUENCE: 133

Glu Gln Val Leu Thr Gln Ser Pro Ser Ser Leu Ser Ala Ser Val Gly
1               5                   10                  15

Asp Arg Val Thr Ile Asn Cys Gln Ala Ser Gln Ser Leu Tyr Asn Asn
                20                  25                  30

Glu Asn Leu Ala Trp Phe Gln Gln Lys Pro Gly Lys Val Pro Lys Arg
        35                  40                  45

Leu Ile Tyr Gly Ala Ser Thr Leu Ala Ser Gly Val Ser Ser Arg Phe
    50                  55                  60

Ser Gly Ser Gly Ser Gly Thr Glu Phe Thr Leu Thr Ile Ser Asn Leu
65                  70                  75                  80

Gln Pro Glu Asp Phe Ala Ile Tyr Tyr Cys Leu Gly Glu Phe Ser Cys
                85                  90                  95

Gly Ser Ala Asp Cys Phe Ala Phe Gly Gly Gly Thr Lys Val Glu Ile
            100                 105                 110

Lys

<210> SEQ ID NO 134
<211> LENGTH: 5
<212> TYPE: PRT
<213> ORGANISM: Gallus gallus

<400> SEQUENCE: 134

Gly Tyr Asp Met Leu
1               5

<210> SEQ ID NO 135
<211> LENGTH: 17
<212> TYPE: PRT
<213> ORGANISM: Gallus gallus

<400> SEQUENCE: 135

Gly Ile Gly Ser Thr Gly Gly Gly Thr Asp Tyr Gly Ala Ala Val Lys
1               5                   10                  15

Gly

<210> SEQ ID NO 136
<211> LENGTH: 19
<212> TYPE: PRT
<213> ORGANISM: Gallus gallus

<400> SEQUENCE: 136

Val Ala Gly Gly Cys Asn Ser Gly Tyr Cys Arg Asp Ser Pro Gly Ser
1               5                   10                  15
```

Ile Asp Ala

<210> SEQ ID NO 137
<211> LENGTH: 10
<212> TYPE: PRT
<213> ORGANISM: Gallus gallus

<400> SEQUENCE: 137

Ser Gly Gly Gly Ser Arg Asn Tyr Tyr Gly
1               5                   10

<210> SEQ ID NO 138
<211> LENGTH: 7
<212> TYPE: PRT
<213> ORGANISM: Gallus gallus

<400> SEQUENCE: 138

Asp Asp Gln Arg Pro Ser Asn
1               5

<210> SEQ ID NO 139
<211> LENGTH: 11
<212> TYPE: PRT
<213> ORGANISM: Gallus gallus

<400> SEQUENCE: 139

Ser Ala Asp Ser Asn Thr Tyr Glu Gly Ser Phe
1               5                   10

<210> SEQ ID NO 140
<211> LENGTH: 5
<212> TYPE: PRT
<213> ORGANISM: Mus musculus

<400> SEQUENCE: 140

Asp Tyr Asn Met Asp
1               5

<210> SEQ ID NO 141
<211> LENGTH: 17
<212> TYPE: PRT
<213> ORGANISM: Mus musculus

<400> SEQUENCE: 141

Asp Ile Asn Pro Asn Tyr Asp Ser Thr Ser Tyr Asn Gln Lys Phe Lys
1               5                   10                  15

Gly

<210> SEQ ID NO 142
<211> LENGTH: 11
<212> TYPE: PRT
<213> ORGANISM: Mus musculus

<400> SEQUENCE: 142

Ser Arg Ser Tyr Asp Tyr Glu Gly Phe Ala Tyr
1               5                   10

<210> SEQ ID NO 143
<211> LENGTH: 11
<212> TYPE: PRT
<213> ORGANISM: Mus musculus

<400> SEQUENCE: 143

Leu Ser Ile Val Asn Arg Tyr His Tyr Met Ser

-continued

```
1               5                    10
```

```
<210> SEQ ID NO 144
<211> LENGTH: 6
<212> TYPE: PRT
<213> ORGANISM: Mus musculus

<400> SEQUENCE: 144

Glu Ala Ser Ile Thr Lys
1               5

<210> SEQ ID NO 145
<211> LENGTH: 9
<212> TYPE: PRT
<213> ORGANISM: Mus musculus

<400> SEQUENCE: 145

Gln His Asn Arg Gly Ser Phe Leu Pro
1               5

<210> SEQ ID NO 146
<211> LENGTH: 5
<212> TYPE: PRT
<213> ORGANISM: Mus musculus

<400> SEQUENCE: 146

Asp Tyr Tyr Met Ser
1               5

<210> SEQ ID NO 147
<211> LENGTH: 17
<212> TYPE: PRT
<213> ORGANISM: Mus musculus

<400> SEQUENCE: 147

Arg Asn Lys Ala Asn Gly Tyr Thr Thr Glu Tyr Ser Ala Ser Val Lys
1               5                    10                   15

Gly

<210> SEQ ID NO 148
<211> LENGTH: 9
<212> TYPE: PRT
<213> ORGANISM: Mus musculus

<400> SEQUENCE: 148

Ala Arg Ala Asn Trp Ala Phe Asp Tyr
1               5

<210> SEQ ID NO 149
<211> LENGTH: 11
<212> TYPE: PRT
<213> ORGANISM: Mus musculus

<400> SEQUENCE: 149

Arg Ala Ser Gln Ser Ile Ser Asn Tyr Leu His
1               5                    10

<210> SEQ ID NO 150
<211> LENGTH: 7
<212> TYPE: PRT
<213> ORGANISM: Mus musculus

<400> SEQUENCE: 150

Tyr Ala Ser Gln Ser Ile Ser
```

```
1               5

<210> SEQ ID NO 151
<211> LENGTH: 7
<212> TYPE: PRT
<213> ORGANISM: Mus musculus

<400> SEQUENCE: 151

Tyr Ala Ser Gln Ser Ile Ser
1               5

<210> SEQ ID NO 152
<211> LENGTH: 5
<212> TYPE: PRT
<213> ORGANISM: Mus musculus

<400> SEQUENCE: 152

Asn Tyr Leu Ile Val
1               5

<210> SEQ ID NO 153
<211> LENGTH: 17
<212> TYPE: PRT
<213> ORGANISM: Mus musculus

<400> SEQUENCE: 153

Val Ile Ser Pro Gly Ser Gly Gly Thr Asn Tyr Asn Glu Lys Phe Lys
1               5                   10                  15

Gly

<210> SEQ ID NO 154
<211> LENGTH: 11
<212> TYPE: PRT
<213> ORGANISM: Mus musculus

<400> SEQUENCE: 154

Glu Lys Ile Tyr Asp Asp Tyr Tyr Glu Gly Tyr
1               5                   10

<210> SEQ ID NO 155
<211> LENGTH: 15
<212> TYPE: PRT
<213> ORGANISM: Mus musculus

<400> SEQUENCE: 155

Thr Ile Ser Cys Ser Ala Ser Leu Gly Ile Gly Asn Tyr Leu Asn
1               5                   10                  15

<210> SEQ ID NO 156
<211> LENGTH: 7
<212> TYPE: PRT
<213> ORGANISM: Mus musculus

<400> SEQUENCE: 156

Thr Ser Asn Leu His Ser Gly
1               5

<210> SEQ ID NO 157
<211> LENGTH: 9
<212> TYPE: PRT
<213> ORGANISM: Mus musculus

<400> SEQUENCE: 157

His Tyr Ser Lys Leu Pro Leu Thr Phe
```

```
1               5

<210> SEQ ID NO 158
<211> LENGTH: 5
<212> TYPE: PRT
<213> ORGANISM: Mus musculus

<400> SEQUENCE: 158

Asp Tyr Asn Met Tyr
1               5

<210> SEQ ID NO 159
<211> LENGTH: 17
<212> TYPE: PRT
<213> ORGANISM: Mus musculus

<400> SEQUENCE: 159

Tyr Ile Tyr Pro Gly Asn Gly Gly Thr Asn Tyr Asn Gln Lys Phe Lys
1               5                   10                  15

Gly

<210> SEQ ID NO 160
<211> LENGTH: 11
<212> TYPE: PRT
<213> ORGANISM: Mus musculus

<400> SEQUENCE: 160

Asp Tyr Asp Asp Gly Gly Tyr Ala Met Asp Tyr
1               5                   10

<210> SEQ ID NO 161
<211> LENGTH: 15
<212> TYPE: PRT
<213> ORGANISM: Mus musculus

<400> SEQUENCE: 161

Ser Val Gly Glu Thr Val Thr Ile Thr Cys Arg Ala Ser Gly Asn
1               5                   10                  15

<210> SEQ ID NO 162
<211> LENGTH: 7
<212> TYPE: PRT
<213> ORGANISM: Mus musculus

<400> SEQUENCE: 162

Asn Ala Lys Thr Leu Ala Asp
1               5

<210> SEQ ID NO 163
<211> LENGTH: 9
<212> TYPE: PRT
<213> ORGANISM: Mus musculus

<400> SEQUENCE: 163

Gln His Phe Trp Asn Ile Pro Trp Thr
1               5

<210> SEQ ID NO 164
<211> LENGTH: 5
<212> TYPE: PRT
<213> ORGANISM: Mus musculus

<400> SEQUENCE: 164

Asp His Ser Ile His
```

-continued

```
1               5

<210> SEQ ID NO 165
<211> LENGTH: 17
<212> TYPE: PRT
<213> ORGANISM: Mus musculus

<400> SEQUENCE: 165

Tyr Ile Ser Pro Gly Asn Gly Asn Ile Lys Tyr Asn Glu Lys Phe Lys
1               5                   10                  15

Gly

<210> SEQ ID NO 166
<211> LENGTH: 12
<212> TYPE: PRT
<213> ORGANISM: Mus musculus

<400> SEQUENCE: 166

Ser Leu Gly Arg Gly Gly Pro Tyr Tyr Phe Asp Tyr
1               5                   10

<210> SEQ ID NO 167
<211> LENGTH: 16
<212> TYPE: PRT
<213> ORGANISM: Mus musculus

<400> SEQUENCE: 167

Arg Ser Ser Lys Ser Leu Leu His Ser Asn Gly Asn Thr Tyr Leu Tyr
1               5                   10                  15

<210> SEQ ID NO 168
<211> LENGTH: 7
<212> TYPE: PRT
<213> ORGANISM: Mus musculus

<400> SEQUENCE: 168

Arg Met Ser Asn Leu Ala Ser
1               5

<210> SEQ ID NO 169
<211> LENGTH: 9
<212> TYPE: PRT
<213> ORGANISM: Mus musculus

<400> SEQUENCE: 169

Met Gln His Arg Glu Tyr Pro Val Thr
1               5

<210> SEQ ID NO 170
<211> LENGTH: 5
<212> TYPE: PRT
<213> ORGANISM: Mus musculus

<400> SEQUENCE: 170

Ser Tyr Trp Ile Glu
1               5

<210> SEQ ID NO 171
<211> LENGTH: 17
<212> TYPE: PRT
<213> ORGANISM: Mus musculus

<400> SEQUENCE: 171

Glu Ile Leu Pro Gly Ser Gly Ser Thr Asn Tyr Asn Glu Lys Phe Lys
```

-continued

```
1               5                   10                  15

Gly

<210> SEQ ID NO 172
<211> LENGTH: 11
<212> TYPE: PRT
<213> ORGANISM: Mus musculus

<400> SEQUENCE: 172

Tyr Tyr Trp Tyr Phe Asp Val Trp Ala Gln Asp
1               5                   10

<210> SEQ ID NO 173
<211> LENGTH: 15
<212> TYPE: PRT
<213> ORGANISM: Mus musculus

<400> SEQUENCE: 173

Ser Ser Lys Asn Leu Leu His Ser Asn Gly Ile Thr Tyr Leu Tyr
1               5                   10                  15

<210> SEQ ID NO 174
<211> LENGTH: 7
<212> TYPE: PRT
<213> ORGANISM: Mus musculus

<400> SEQUENCE: 174

Arg Val Ser Asn Leu Ala Ser
1               5

<210> SEQ ID NO 175
<211> LENGTH: 9
<212> TYPE: PRT
<213> ORGANISM: Mus musculus

<400> SEQUENCE: 175

Ala Gln Leu Leu Glu Leu Pro Tyr Thr
1               5

<210> SEQ ID NO 176
<211> LENGTH: 5
<212> TYPE: PRT
<213> ORGANISM: Mus musculus

<400> SEQUENCE: 176

Ser Tyr Asp Met Ser
1               5

<210> SEQ ID NO 177
<211> LENGTH: 17
<212> TYPE: PRT
<213> ORGANISM: Mus musculus

<400> SEQUENCE: 177

Tyr Ile Ser Ser Gly Ala Gly Ser Thr Tyr Tyr Pro Asp Thr Val Lys
1               5                   10                  15

Gly

<210> SEQ ID NO 178
<211> LENGTH: 11
<212> TYPE: PRT
<213> ORGANISM: Mus musculus

<400> SEQUENCE: 178
```

-continued

```
His Phe Tyr Arg Phe Asp Tyr Trp Gly Gln Gly
1               5                   10

<210> SEQ ID NO 179
<211> LENGTH: 15
<212> TYPE: PRT
<213> ORGANISM: Mus musculus

<400> SEQUENCE: 179

Ser Ala Gly Asp Arg Ile Thr Ile Thr Cys Lys Ala Ser Gln Ser
1               5                   10                  15

<210> SEQ ID NO 180
<211> LENGTH: 7
<212> TYPE: PRT
<213> ORGANISM: Mus musculus

<400> SEQUENCE: 180

Tyr Ala Ser Asn Arg Tyr Thr
1               5

<210> SEQ ID NO 181
<211> LENGTH: 9
<212> TYPE: PRT
<213> ORGANISM: Mus musculus

<400> SEQUENCE: 181

Gln Gln Asp Asp Arg Phe Pro Leu Thr
1               5

<210> SEQ ID NO 182
<211> LENGTH: 5
<212> TYPE: PRT
<213> ORGANISM: Mus musculus

<400> SEQUENCE: 182

Asn Tyr Gly Met Asn
1               5

<210> SEQ ID NO 183
<211> LENGTH: 17
<212> TYPE: PRT
<213> ORGANISM: Mus musculus

<400> SEQUENCE: 183

Trp Ile Asn Thr Tyr Thr Gly Glu Pro Thr Tyr Ala Asp Asp Phe Lys
1               5                   10                  15

Gly

<210> SEQ ID NO 184
<211> LENGTH: 11
<212> TYPE: PRT
<213> ORGANISM: Mus musculus

<400> SEQUENCE: 184

Gly Ala Trp Phe Ala Tyr Trp Ala Lys Asp Ser
1               5                   10

<210> SEQ ID NO 185
<211> LENGTH: 15
<212> TYPE: PRT
<213> ORGANISM: Mus musculus

<400> SEQUENCE: 185
```

-continued

```
Ser Ile Thr Cys Lys Ala Ser Gln Asp Val Gly Thr Ala Val Ala
1               5                   10                  15

<210> SEQ ID NO 186
<211> LENGTH: 7
<212> TYPE: PRT
<213> ORGANISM: Mus musculus

<400> SEQUENCE: 186

Trp Ala Ser Thr Arg His Thr
1               5

<210> SEQ ID NO 187
<211> LENGTH: 9
<212> TYPE: PRT
<213> ORGANISM: Mus musculus

<400> SEQUENCE: 187

Gln Gln Tyr Ser Ser Tyr Pro Leu Thr
1               5

<210> SEQ ID NO 188
<211> LENGTH: 5
<212> TYPE: PRT
<213> ORGANISM: Mus musculus

<400> SEQUENCE: 188

Asp Phe Trp Met Asn
1               5

<210> SEQ ID NO 189
<211> LENGTH: 19
<212> TYPE: PRT
<213> ORGANISM: Mus musculus

<400> SEQUENCE: 189

Glu Ile Arg Leu Lys Ser Asn Asn Tyr Ala Thr His Tyr Ala Glu Ser
1               5                   10                  15

Val Lys Gly

<210> SEQ ID NO 190
<211> LENGTH: 13
<212> TYPE: PRT
<213> ORGANISM: Mus musculus

<400> SEQUENCE: 190

Leu Phe Tyr Tyr Tyr Asp Gly Thr Ser Gly Phe Ala Tyr
1               5                   10

<210> SEQ ID NO 191
<211> LENGTH: 17
<212> TYPE: PRT
<213> ORGANISM: Mus musculus

<400> SEQUENCE: 191

Lys Ser Ser Gln Ser Leu Leu Asn Ser Gly Asp Gln Lys Asn Tyr Leu
1               5                   10                  15

Thr

<210> SEQ ID NO 192
<211> LENGTH: 7
<212> TYPE: PRT
<213> ORGANISM: Mus musculus
```

-continued

<400> SEQUENCE: 192

Trp Ala Ser Thr Arg Glu Ser
1               5

<210> SEQ ID NO 193
<211> LENGTH: 9
<212> TYPE: PRT
<213> ORGANISM: Mus musculus

<400> SEQUENCE: 193

Gln Asn Asp Tyr Asp Tyr Pro Leu Thr
1               5

<210> SEQ ID NO 194
<211> LENGTH: 5
<212> TYPE: PRT
<213> ORGANISM: Mus musculus

<400> SEQUENCE: 194

Asp Tyr Asn Met Asp
1               5

<210> SEQ ID NO 195
<211> LENGTH: 17
<212> TYPE: PRT
<213> ORGANISM: Mus musculus

<400> SEQUENCE: 195

Asp Ile Asn Pro Asn Tyr Asp Ser Thr Ser Tyr Asn Gln Lys Phe Lys
1               5                   10                  15

Gly

<210> SEQ ID NO 196
<211> LENGTH: 11
<212> TYPE: PRT
<213> ORGANISM: Mus musculus

<400> SEQUENCE: 196

Ser Arg Ser Tyr Asp Tyr Glu Gly Phe Ala Tyr
1               5                   10

<210> SEQ ID NO 197
<211> LENGTH: 11
<212> TYPE: PRT
<213> ORGANISM: Mus musculus

<400> SEQUENCE: 197

Arg Ala Ser Gly Asn Ile His Asn Tyr Leu Ala
1               5                   10

<210> SEQ ID NO 198
<211> LENGTH: 7
<212> TYPE: PRT
<213> ORGANISM: Mus musculus

<400> SEQUENCE: 198

Asn Ala Lys Thr Leu Ala Asp
1               5

<210> SEQ ID NO 199
<211> LENGTH: 8
<212> TYPE: PRT
<213> ORGANISM: Mus musculus -continued

<400> SEQUENCE: 199

Gln His Phe Trp Ser Thr Leu Thr
1               5

<210> SEQ ID NO 200
<211> LENGTH: 5
<212> TYPE: PRT
<213> ORGANISM: Mus musculus

<400> SEQUENCE: 200

Gly Tyr Thr Met Asn
1               5

<210> SEQ ID NO 201
<211> LENGTH: 16
<212> TYPE: PRT
<213> ORGANISM: Mus musculus

<400> SEQUENCE: 201

Asn Pro Tyr Asn Gly Gly Thr Ser Tyr Asn Gln Lys Phe Lys Gly Lys
1               5                   10                  15

<210> SEQ ID NO 202
<211> LENGTH: 9
<212> TYPE: PRT
<213> ORGANISM: Mus musculus

<400> SEQUENCE: 202

Trp Gly Val Trp Ser Ala Met Asp Tyr
1               5

<210> SEQ ID NO 203
<211> LENGTH: 11
<212> TYPE: PRT
<213> ORGANISM: Mus musculus

<400> SEQUENCE: 203

Lys Ala Ser Gln Asn Val Arg Thr Ala Val Ala
1               5                   10

<210> SEQ ID NO 204
<211> LENGTH: 7
<212> TYPE: PRT
<213> ORGANISM: Mus musculus

<400> SEQUENCE: 204

Leu Ala Ser Asn Arg Asp Thr
1               5

<210> SEQ ID NO 205
<211> LENGTH: 9
<212> TYPE: PRT
<213> ORGANISM: Mus musculus

<400> SEQUENCE: 205

Leu Gln His Cys Asn Tyr Pro Asn Glu
1               5

<210> SEQ ID NO 206
<211> LENGTH: 5
<212> TYPE: PRT
<213> ORGANISM: Mus musculus

<400> SEQUENCE: 206

```
Ser Tyr Trp Met Gln
1               5

<210> SEQ ID NO 207
<211> LENGTH: 17
<212> TYPE: PRT
<213> ORGANISM: Mus musculus

<400> SEQUENCE: 207

Ala Ile Tyr Pro Gly Asp Gly Asp Thr Arg Tyr Thr Gln Lys Phe Lys
1               5                   10                  15

Gly

<210> SEQ ID NO 208
<211> LENGTH: 11
<212> TYPE: PRT
<213> ORGANISM: Mus musculus

<400> SEQUENCE: 208

Ala Arg Gly Glu Tyr Gly Asn Tyr Phe Ala Tyr
1               5                   10

<210> SEQ ID NO 209
<211> LENGTH: 11
<212> TYPE: PRT
<213> ORGANISM: Mus musculus

<400> SEQUENCE: 209

Lys Ala Ser Gln Asp Ile Asn Ser Tyr Leu Ser
1               5                   10

<210> SEQ ID NO 210
<211> LENGTH: 7
<212> TYPE: PRT
<213> ORGANISM: Mus musculus

<400> SEQUENCE: 210

Arg Ala Asn Arg Leu Val Asp
1               5

<210> SEQ ID NO 211
<211> LENGTH: 9
<212> TYPE: PRT
<213> ORGANISM: Mus musculus

<400> SEQUENCE: 211

Leu Gln Tyr Asp Glu Phe Pro Leu Thr
1               5

<210> SEQ ID NO 212
<211> LENGTH: 5
<212> TYPE: PRT
<213> ORGANISM: Mus musculus

<400> SEQUENCE: 212

Asp Thr Tyr Met His
1               5

<210> SEQ ID NO 213
<211> LENGTH: 17
<212> TYPE: PRT
<213> ORGANISM: Mus musculus

<400> SEQUENCE: 213
```

```
Arg Ile Asp Pro Ala Asn Gly Asn Thr Lys Tyr Asp Pro Lys Phe Gln
1               5                   10                  15

Gly

<210> SEQ ID NO 214
<211> LENGTH: 14
<212> TYPE: PRT
<213> ORGANISM: Mus musculus

<400> SEQUENCE: 214

Ala Arg Pro Ile His Tyr Tyr Tyr Gly Ser Ser Leu Ala Tyr
1               5                   10

<210> SEQ ID NO 215
<211> LENGTH: 11
<212> TYPE: PRT
<213> ORGANISM: Mus musculus

<400> SEQUENCE: 215

Ser Val Asp Ser Tyr Gly Asn Ser Phe Met His
1               5                   10

<210> SEQ ID NO 216
<211> LENGTH: 7
<212> TYPE: PRT
<213> ORGANISM: Mus musculus

<400> SEQUENCE: 216

Arg Ala Ser Asn Leu Glu Ser
1               5

<210> SEQ ID NO 217
<211> LENGTH: 9
<212> TYPE: PRT
<213> ORGANISM: Mus musculus

<400> SEQUENCE: 217

Gln Gln Ser Asn Glu Asp Pro Gly Arg
1               5

<210> SEQ ID NO 218
<211> LENGTH: 5
<212> TYPE: PRT
<213> ORGANISM: Mus musculus

<400> SEQUENCE: 218

Asp Tyr Tyr Met Ser
1               5

<210> SEQ ID NO 219
<211> LENGTH: 17
<212> TYPE: PRT
<213> ORGANISM: Mus musculus

<400> SEQUENCE: 219

Arg Asn Lys Ala Asn Gly Tyr Thr Thr Glu Tyr Ser Ala Ser Val Lys
1               5                   10                  15

Gly

<210> SEQ ID NO 220
<211> LENGTH: 9
<212> TYPE: PRT
<213> ORGANISM: Mus musculus
```

<400> SEQUENCE: 220

Ala Arg Ala Asn Trp Ala Phe Asp Tyr
1               5

<210> SEQ ID NO 221
<211> LENGTH: 11
<212> TYPE: PRT
<213> ORGANISM: Mus musculus

<400> SEQUENCE: 221

Arg Ala Ser Gln Ser Ile Ser Asn Tyr Leu His
1               5                   10

<210> SEQ ID NO 222
<211> LENGTH: 7
<212> TYPE: PRT
<213> ORGANISM: Mus musculus

<400> SEQUENCE: 222

Tyr Ala Ser Gln Ser Ile Ser
1               5

<210> SEQ ID NO 223
<211> LENGTH: 9
<212> TYPE: PRT
<213> ORGANISM: Mus musculus

<400> SEQUENCE: 223

Gln Gln Ser Asn Ser Trp Pro Tyr Thr
1               5

<210> SEQ ID NO 224
<211> LENGTH: 5
<212> TYPE: PRT
<213> ORGANISM: Mus musculus

<400> SEQUENCE: 224

Asp Tyr Tyr Met Ser
1               5

<210> SEQ ID NO 225
<211> LENGTH: 17
<212> TYPE: PRT
<213> ORGANISM: Mus musculus

<400> SEQUENCE: 225

Arg Asn Lys Ala Asn Gly Tyr Thr Thr Glu Tyr Ser Ala Ser Val Lys
1               5                   10                  15

Gly

<210> SEQ ID NO 226
<211> LENGTH: 12
<212> TYPE: PRT
<213> ORGANISM: Mus musculus

<400> SEQUENCE: 226

Ala Arg Ala Pro Leu Leu Tyr Tyr Ala Met Asp Tyr
1               5                   10

<210> SEQ ID NO 227
<211> LENGTH: 11
<212> TYPE: PRT
<213> ORGANISM: Mus musculus -continued

<400> SEQUENCE: 227

Asn Val Ser Thr Ser Gly Tyr Ser Tyr Met His
1               5                   10

<210> SEQ ID NO 228
<211> LENGTH: 7
<212> TYPE: PRT
<213> ORGANISM: Mus musculus

<400> SEQUENCE: 228

Leu Val Ser Asn Leu Glu Ser
1               5

<210> SEQ ID NO 229
<211> LENGTH: 8
<212> TYPE: PRT
<213> ORGANISM: Mus musculus

<400> SEQUENCE: 229

Gln His Ile Arg Glu Leu Thr Arg
1               5

<210> SEQ ID NO 230
<211> LENGTH: 5
<212> TYPE: PRT
<213> ORGANISM: Mus musculus

<400> SEQUENCE: 230

Ser Tyr Trp Met His
1               5

<210> SEQ ID NO 231
<211> LENGTH: 17
<212> TYPE: PRT
<213> ORGANISM: Mus musculus

<400> SEQUENCE: 231

Met Ile Asp Pro Ser Asn Ser Glu Thr Arg Leu Asn Gln Lys Phe Lys
1               5                   10                  15

Asp

<210> SEQ ID NO 232
<211> LENGTH: 12
<212> TYPE: PRT
<213> ORGANISM: Mus musculus

<400> SEQUENCE: 232

Ala Arg Gly Leu Arg His Tyr Trp Tyr Phe Asp Val
1               5                   10

<210> SEQ ID NO 233
<211> LENGTH: 11
<212> TYPE: PRT
<213> ORGANISM: Mus musculus

<400> SEQUENCE: 233

Ser Val Ser Thr Ser Gly Tyr Ser Tyr Met His
1               5                   10

<210> SEQ ID NO 234
<211> LENGTH: 7
<212> TYPE: PRT
<213> ORGANISM: Mus musculus

```
<400> SEQUENCE: 234

Leu Val Ser Asn Leu Glu Ser
1               5

<210> SEQ ID NO 235
<211> LENGTH: 9
<212> TYPE: PRT
<213> ORGANISM: Mus musculus

<400> SEQUENCE: 235

Gln His Ile Arg Glu Leu Thr Arg Ser
1               5

<210> SEQ ID NO 236
<211> LENGTH: 5
<212> TYPE: PRT
<213> ORGANISM: Mus musculus

<400> SEQUENCE: 236

Ser Tyr Gly Met Ser
1               5

<210> SEQ ID NO 237
<211> LENGTH: 14
<212> TYPE: PRT
<213> ORGANISM: Mus musculus

<400> SEQUENCE: 237

Trp Val Arg Gln Thr Pro Glu Lys Arg Leu Glu Trp Val Ala
1               5                   10

<210> SEQ ID NO 238
<211> LENGTH: 11
<212> TYPE: PRT
<213> ORGANISM: Mus musculus

<400> SEQUENCE: 238

Leu Ala Ser Tyr Tyr Phe Asp Tyr Trp Gly Gln
1               5                   10

<210> SEQ ID NO 239
<211> LENGTH: 15
<212> TYPE: PRT
<213> ORGANISM: Mus musculus

<400> SEQUENCE: 239

Thr Met Thr Cys Gln Ala Ser Gln Gly Thr Ser Ile Asn Leu Asn
1               5                   10                  15

<210> SEQ ID NO 240
<211> LENGTH: 7
<212> TYPE: PRT
<213> ORGANISM: Mus musculus

<400> SEQUENCE: 240

Gly Ala Ser Ser Leu Glu Asp
1               5

<210> SEQ ID NO 241
<211> LENGTH: 11
<212> TYPE: PRT
<213> ORGANISM: Mus musculus

<400> SEQUENCE: 241
```

-continued

```
Leu Gln His Ser Tyr Leu Pro Pro Leu Thr Phe
1               5               10

<210> SEQ ID NO 242
<211> LENGTH: 5
<212> TYPE: PRT
<213> ORGANISM: Mus musculus

<400> SEQUENCE: 242

Thr Tyr Asp Leu His
1               5

<210> SEQ ID NO 243
<211> LENGTH: 16
<212> TYPE: PRT
<213> ORGANISM: Mus musculus

<400> SEQUENCE: 243

Val Ile Trp Ser Gly Gly Ser Thr Asp Tyr Asn Ala Ala Phe Ile Ser
1               5               10              15

<210> SEQ ID NO 244
<211> LENGTH: 11
<212> TYPE: PRT
<213> ORGANISM: Mus musculus

<400> SEQUENCE: 244

Asn Tyr Gly Tyr Ser Ala Trp Phe Ala Tyr Trp
1               5               10

<210> SEQ ID NO 245
<211> LENGTH: 15
<212> TYPE: PRT
<213> ORGANISM: Mus musculus

<400> SEQUENCE: 245

Ala Ser Ile Ser Cys Arg Ser Ser Gln Ser Ile Val His Ser Asn
1               5               10              15

<210> SEQ ID NO 246
<211> LENGTH: 7
<212> TYPE: PRT
<213> ORGANISM: Mus musculus

<400> SEQUENCE: 246

Lys Val Ser Asn Arg Phe Ser
1               5

<210> SEQ ID NO 247
<211> LENGTH: 9
<212> TYPE: PRT
<213> ORGANISM: Mus musculus

<400> SEQUENCE: 247

Phe Gln Gly Ser His Val Pro Leu Thr
1               5

<210> SEQ ID NO 248
<211> LENGTH: 5
<212> TYPE: PRT
<213> ORGANISM: Mus musculus

<400> SEQUENCE: 248

Ala Tyr Ser Met His
```

-continued

```
1               5

<210> SEQ ID NO 249
<211> LENGTH: 17
<212> TYPE: PRT
<213> ORGANISM: Mus musculus

<400> SEQUENCE: 249

Trp Ile Asn Thr Glu Thr Gly Glu Pro Thr Tyr Thr Asp Asp Phe Lys
1               5                   10                  15

Gly

<210> SEQ ID NO 250
<211> LENGTH: 11
<212> TYPE: PRT
<213> ORGANISM: Mus musculus

<400> SEQUENCE: 250

Arg Ile Tyr Tyr Phe Gly Arg Gly Gly Phe Asp
1               5                   10

<210> SEQ ID NO 251
<211> LENGTH: 15
<212> TYPE: PRT
<213> ORGANISM: Mus musculus

<400> SEQUENCE: 251

Ser Ser Ile Ser Cys Arg Ser Ser Gln Ser Ile Val His Ser Asn
1               5                   10                  15

<210> SEQ ID NO 252
<211> LENGTH: 7
<212> TYPE: PRT
<213> ORGANISM: Mus musculus

<400> SEQUENCE: 252

Lys Val Ser Asn Arg Phe Ser
1               5

<210> SEQ ID NO 253
<211> LENGTH: 9
<212> TYPE: PRT
<213> ORGANISM: Mus musculus

<400> SEQUENCE: 253

Phe Gln Gly Ser His Val Pro Tyr Thr
1               5

<210> SEQ ID NO 254
<211> LENGTH: 5
<212> TYPE: PRT
<213> ORGANISM: Mus musculus

<400> SEQUENCE: 254

Asn Ser Trp Phe Asn
1               5

<210> SEQ ID NO 255
<211> LENGTH: 19
<212> TYPE: PRT
<213> ORGANISM: Mus musculus

<400> SEQUENCE: 255

Glu Ile Arg Leu Thr Ser Asp Asn Tyr Ala Ile Tyr Tyr Ala Glu Ser
```

-continued

```
1               5               10              15

Val Lys Gly

<210> SEQ ID NO 256
<211> LENGTH: 11
<212> TYPE: PRT
<213> ORGANISM: Mus musculus

<400> SEQUENCE: 256

Pro Glu Thr Ala Arg Ala Thr Phe Ala Tyr Trp
1               5               10

<210> SEQ ID NO 257
<211> LENGTH: 15
<212> TYPE: PRT
<213> ORGANISM: Mus musculus

<400> SEQUENCE: 257

Ala Ser Ile Ser Cys Arg Ser Ser Gln Ser Ile Val His Ser Asn
1               5               10              15

<210> SEQ ID NO 258
<211> LENGTH: 7
<212> TYPE: PRT
<213> ORGANISM: Mus musculus

<400> SEQUENCE: 258

Lys Val Phe Asn Arg Phe Ser
1               5

<210> SEQ ID NO 259
<211> LENGTH: 9
<212> TYPE: PRT
<213> ORGANISM: Mus musculus

<400> SEQUENCE: 259

Phe Gln Gly Ser His Val Pro Arg Thr
1               5

<210> SEQ ID NO 260
<211> LENGTH: 5
<212> TYPE: PRT
<213> ORGANISM: Mus musculus

<400> SEQUENCE: 260

Ala Tyr Tyr Met His
1               5

<210> SEQ ID NO 261
<211> LENGTH: 17
<212> TYPE: PRT
<213> ORGANISM: Mus musculus

<400> SEQUENCE: 261

Arg Val Asn Pro Asn Asn Gly Gly Thr Thr Tyr Asn Gln Lys Phe Lys
1               5               10              15

Gly

<210> SEQ ID NO 262
<211> LENGTH: 11
<212> TYPE: PRT
<213> ORGANISM: Mus musculus

<400> SEQUENCE: 262
```

-continued

```
Arg Ile Tyr Tyr Gly Tyr Phe Asp Tyr Trp Gly
1               5               10

<210> SEQ ID NO 263
<211> LENGTH: 15
<212> TYPE: PRT
<213> ORGANISM: Mus musculus

<400> SEQUENCE: 263

Lys Ala Ser Gln Ser Val Asp Tyr Asp Gly Asp Ser Tyr Met Asn
1               5               10              15

<210> SEQ ID NO 264
<211> LENGTH: 7
<212> TYPE: PRT
<213> ORGANISM: Mus musculus

<400> SEQUENCE: 264

Val Ala Ser Asn Leu Glu Ser
1               5

<210> SEQ ID NO 265
<211> LENGTH: 9
<212> TYPE: PRT
<213> ORGANISM: Mus musculus

<400> SEQUENCE: 265

Gln Gln Ser Asn Glu Asp Pro Tyr Thr
1               5

<210> SEQ ID NO 266
<211> LENGTH: 4
<212> TYPE: PRT
<213> ORGANISM: Mus musculus

<400> SEQUENCE: 266

Asp Ile Tyr Met
1

<210> SEQ ID NO 267
<211> LENGTH: 17
<212> TYPE: PRT
<213> ORGANISM: Mus musculus

<400> SEQUENCE: 267

Lys Ile Asp Pro Ala Asn Gly Asn Thr Lys Tyr Asp Pro Lys Phe Gln
1               5               10              15

Gly

<210> SEQ ID NO 268
<211> LENGTH: 11
<212> TYPE: PRT
<213> ORGANISM: Mus musculus

<400> SEQUENCE: 268

Thr Gly Asp Tyr Trp Gly Gln Gly Thr Thr Val
1               5               10

<210> SEQ ID NO 269
<211> LENGTH: 15
<212> TYPE: PRT
<213> ORGANISM: Mus musculus

<400> SEQUENCE: 269
```

```
Thr Met Ser Cys Lys Ser Ser Gln Ser Leu Leu Asn Ser Arg Thr
1               5                   10                  15

<210> SEQ ID NO 270
<211> LENGTH: 7
<212> TYPE: PRT
<213> ORGANISM: Mus musculus

<400> SEQUENCE: 270

Trp Ala Ser Thr Arg Glu Ser
1               5

<210> SEQ ID NO 271
<211> LENGTH: 9
<212> TYPE: PRT
<213> ORGANISM: Mus musculus

<400> SEQUENCE: 271

Arg Gln Ser Tyr Asn Leu Val Thr Phe
1               5

<210> SEQ ID NO 272
<211> LENGTH: 5
<212> TYPE: PRT
<213> ORGANISM: Mus musculus

<400> SEQUENCE: 272

Ser Tyr Val Met His
1               5

<210> SEQ ID NO 273
<211> LENGTH: 17
<212> TYPE: PRT
<213> ORGANISM: Mus musculus

<400> SEQUENCE: 273

Tyr Ile Asn Pro Tyr Asn Asp Gly Thr Lys Tyr Asn Glu Lys Phe Lys
1               5                   10                  15

Gly

<210> SEQ ID NO 274
<211> LENGTH: 11
<212> TYPE: PRT
<213> ORGANISM: Mus musculus

<400> SEQUENCE: 274

Arg Tyr Tyr Tyr Gly Ser Ser Gly Gly Tyr Phe
1               5                   10

<210> SEQ ID NO 275
<211> LENGTH: 15
<212> TYPE: PRT
<213> ORGANISM: Mus musculus

<400> SEQUENCE: 275

Arg Ala Ser Lys Ser Ile Ser Lys Tyr Leu Ala Trp Tyr Gln Glu
1               5                   10                  15

<210> SEQ ID NO 276
<211> LENGTH: 7
<212> TYPE: PRT
<213> ORGANISM: Mus musculus

<400> SEQUENCE: 276
```

-continued

```
Ser Gly Ser Thr Leu Gln Ser
1               5

<210> SEQ ID NO 277
<211> LENGTH: 9
<212> TYPE: PRT
<213> ORGANISM: Mus musculus

<400> SEQUENCE: 277

Gln Gln His Asn Glu Tyr Pro Tyr Thr
1               5

<210> SEQ ID NO 278
<211> LENGTH: 5
<212> TYPE: PRT
<213> ORGANISM: Mus musculus

<400> SEQUENCE: 278

Gly Tyr Phe Met Asn
1               5

<210> SEQ ID NO 279
<211> LENGTH: 17
<212> TYPE: PRT
<213> ORGANISM: Mus musculus

<400> SEQUENCE: 279

Arg Ile Asn Pro Tyr Asn Gly Asp Thr Phe Tyr Asn Gln Lys Phe Lys
1               5                   10                  15

Gly

<210> SEQ ID NO 280
<211> LENGTH: 11
<212> TYPE: PRT
<213> ORGANISM: Mus musculus

<400> SEQUENCE: 280

Arg Ile His Tyr Tyr Tyr Gly Ser Ser Tyr Tyr
1               5                   10

<210> SEQ ID NO 281
<211> LENGTH: 15
<212> TYPE: PRT
<213> ORGANISM: Mus musculus

<400> SEQUENCE: 281

Arg Ala Ser Lys Ser Ile Ser Lys Tyr Leu Ala Trp Tyr Gln Glu
1               5                   10                  15

<210> SEQ ID NO 282
<211> LENGTH: 7
<212> TYPE: PRT
<213> ORGANISM: Mus musculus

<400> SEQUENCE: 282

Ser Gly Ser Thr Leu Gln Ser
1               5

<210> SEQ ID NO 283
<211> LENGTH: 9
<212> TYPE: PRT
<213> ORGANISM: Mus musculus

<400> SEQUENCE: 283
```

-continued

```
Gln Gln His Asn Glu Tyr Pro Trp Thr
1               5

<210> SEQ ID NO 284
<211> LENGTH: 5
<212> TYPE: PRT
<213> ORGANISM: Mus musculus

<400> SEQUENCE: 284

Glu Tyr Ile Ile His
1               5

<210> SEQ ID NO 285
<211> LENGTH: 17
<212> TYPE: PRT
<213> ORGANISM: Mus musculus

<400> SEQUENCE: 285

Trp Phe Tyr Pro Gly Ser Gly Ser Ile Lys Tyr Asn Glu Lys Phe Lys
1               5               10              15

Asp

<210> SEQ ID NO 286
<211> LENGTH: 11
<212> TYPE: PRT
<213> ORGANISM: Mus musculus

<400> SEQUENCE: 286

His Glu Val Tyr Tyr Asp Tyr Asp Lys Ser Met
1               5               10

<210> SEQ ID NO 287
<211> LENGTH: 15
<212> TYPE: PRT
<213> ORGANISM: Mus musculus

<400> SEQUENCE: 287

Leu Tyr Ser Ser Asn Gln Lys Asn Tyr Leu Ala Trp Tyr Gln Gln
1               5               10              15

<210> SEQ ID NO 288
<211> LENGTH: 7
<212> TYPE: PRT
<213> ORGANISM: Mus musculus

<400> SEQUENCE: 288

Trp Ala Ser Thr Arg Glu Ser
1               5

<210> SEQ ID NO 289
<211> LENGTH: 9
<212> TYPE: PRT
<213> ORGANISM: Mus musculus

<400> SEQUENCE: 289

Gln Gln Tyr Tyr Ser Tyr Pro Tyr Thr
1               5

<210> SEQ ID NO 290
<211> LENGTH: 5
<212> TYPE: PRT
<213> ORGANISM: Mus musculus

<400> SEQUENCE: 290
```

-continued

```
Asn Tyr Leu Ile Glu
1               5

<210> SEQ ID NO 291
<211> LENGTH: 19
<212> TYPE: PRT
<213> ORGANISM: Mus musculus

<400> SEQUENCE: 291

Val Ile Asn Pro Lys Ser Gly Gly Thr Lys Tyr Asn Glu Lys Phe Arg
1               5                   10                  15

Gly Lys Ala

<210> SEQ ID NO 292
<211> LENGTH: 11
<212> TYPE: PRT
<213> ORGANISM: Mus musculus

<400> SEQUENCE: 292

Thr Gly Thr Asp Tyr Trp Gly Gln Gly Thr Thr
1               5                   10

<210> SEQ ID NO 293
<211> LENGTH: 10
<212> TYPE: PRT
<213> ORGANISM: Mus musculus

<400> SEQUENCE: 293

Val Thr Ile Ser Cys Ser Ala Ser Gln Gly
1               5                   10

<210> SEQ ID NO 294
<211> LENGTH: 7
<212> TYPE: PRT
<213> ORGANISM: Mus musculus

<400> SEQUENCE: 294

Tyr Thr Ser Ser Leu Arg Ser
1               5

<210> SEQ ID NO 295
<211> LENGTH: 9
<212> TYPE: PRT
<213> ORGANISM: Mus musculus

<400> SEQUENCE: 295

Gln Gln Tyr Ser Lys Leu Pro Arg Thr
1               5

<210> SEQ ID NO 296
<211> LENGTH: 12
<212> TYPE: PRT
<213> ORGANISM: Homo sapiens

<400> SEQUENCE: 296

Phe Thr Ser Gly Glu Lys Glu Gln Val Asp Glu Trp
1               5                   10

<210> SEQ ID NO 297
<211> LENGTH: 16
<212> TYPE: PRT
<213> ORGANISM: Homo sapiens

<400> SEQUENCE: 297
```

-continued

Ala Glu Gln Lys Arg Leu Lys Thr Val Leu Glu Leu Gln Tyr Val Leu
1               5                   10                  15

<210> SEQ ID NO 298
<211> LENGTH: 16
<212> TYPE: PRT
<213> ORGANISM: Homo sapiens

<400> SEQUENCE: 298

Val Glu Arg Val Phe Gln Ser Asn Tyr Phe Asp Ser Thr His Asn His
1               5                   10                  15

<210> SEQ ID NO 299
<211> LENGTH: 16
<212> TYPE: PRT
<213> ORGANISM: Homo sapiens

<400> SEQUENCE: 299

Phe Gln Ser Met Gln Thr Val Phe Asn Met Asn Ala Pro Val Pro Pro
1               5                   10                  15

<210> SEQ ID NO 300
<211> LENGTH: 5
<212> TYPE: PRT
<213> ORGANISM: Mus musculus

<400> SEQUENCE: 300

Thr Asn Ala Met Asn
1               5

<210> SEQ ID NO 301
<211> LENGTH: 17
<212> TYPE: PRT
<213> ORGANISM: Mus musculus

<400> SEQUENCE: 301

Arg Ile Arg Ser Lys Ser Asn Asn Tyr Ala Thr Tyr Tyr Ala Asp Ser
1               5                   10                  15

Val

<210> SEQ ID NO 302
<211> LENGTH: 11
<212> TYPE: PRT
<213> ORGANISM: Mus musculus

<400> SEQUENCE: 302

Asp Trp Asp Gly Phe Leu Tyr Phe Asp Tyr Trp
1               5                   10

<210> SEQ ID NO 303
<211> LENGTH: 112
<212> TYPE: PRT
<213> ORGANISM: Mus musculus

<400> SEQUENCE: 303

Gly Gly Gly Leu Val Gln Pro Lys Gly Ser Leu Lys Leu Ser Cys Ala
1               5                   10                  15

Ala Ser Gly Phe Thr Phe Asn Thr Asn Ala Met Asn Trp Val Arg Gln
            20                  25                  30

Ala Pro Gly Lys Gly Leu Glu Trp Val Ala Arg Ile Arg Ser Lys Ser
        35                  40                  45

Asn Asn Tyr Ala Thr Tyr Tyr Ala Asp Ser Val Lys Asp Arg Phe Thr

-continued

```
            50              55              60

Ile Ser Arg Asp Asp Ser Gln Ser Met Leu Tyr Leu Gln Met Asn Asn
65              70              75              80

Leu Lys Thr Glu Asp Thr Ala Met Tyr Tyr Cys Val Arg Asp Trp Asp
                85              90              95

Gly Phe Leu Tyr Phe Asp Tyr Trp Ala Lys His His Leu Thr Leu Phe
            100             105             110

<210> SEQ ID NO 304
<211> LENGTH: 15
<212> TYPE: PRT
<213> ORGANISM: Mus musculus

<400> SEQUENCE: 304

Ser Val Ser Thr Ser Gly Tyr Ser Tyr Met His Trp Asn Gln Gln
1               5               10              15

<210> SEQ ID NO 305
<211> LENGTH: 7
<212> TYPE: PRT
<213> ORGANISM: Mus musculus

<400> SEQUENCE: 305

Leu Val Ser Asn Leu Glu Ser
1               5

<210> SEQ ID NO 306
<211> LENGTH: 9
<212> TYPE: PRT
<213> ORGANISM: Mus musculus

<400> SEQUENCE: 306

Gln His Ile Arg Glu Leu Thr Arg Ser
1               5

<210> SEQ ID NO 307
<211> LENGTH: 104
<212> TYPE: PRT
<213> ORGANISM: Mus musculus

<400> SEQUENCE: 307

Thr Gln Ser Pro Ala Ser Leu Ala Val Ser Leu Gly Gln Arg Ala Thr
1               5               10              15

Ile Ser Tyr Arg Ala Ser Lys Ser Val Ser Thr Ser Gly Tyr Ser Tyr
                20              25              30

Met His Trp Asn Gln Gln Lys Pro Gly Gln Pro Arg Leu Leu Ile
            35              40              45

Tyr Leu Val Ser Asn Leu Glu Ser Gly Val Pro Ala Arg Phe Ser Gly
    50              55              60

Ser Gly Ser Gly Thr Asp Phe Thr Leu Asn Ile His Pro Val Glu Glu
65              70              75              80

Glu Asp Ala Ala Thr Tyr Tyr Cys Gln His Ile Arg Glu Leu Thr Arg
                85              90              95

Ser Glu Gly Gly Pro Ser Trp Lys
            100

<210> SEQ ID NO 308
<211> LENGTH: 14
<212> TYPE: PRT
<213> ORGANISM: Homo sapiens
```

```
<400> SEQUENCE: 308

Pro Pro Val Asn Glu Pro Glu Thr Leu Lys Gln Gln Asn Gln
1               5                   10

<210> SEQ ID NO 309
<211> LENGTH: 12
<212> TYPE: PRT
<213> ORGANISM: Homo sapiens

<400> SEQUENCE: 309

Glu Thr Leu Lys Gln Gln Asn Gln Tyr Gln Ala Ser
1               5                   10
```

METHODS FOR TREATING CAPRIN-1 EXPRESSING CANCERS

TECHNICAL FIELD

The present invention relates to a medicament for treatment and/or prevention of cancer, comprising an antibody against CAPRIN-1 protein, or a fragment thereof, and a pyrimidine-based drug and cisplatin.

BACKGROUND ART

Various antibody medicines targeting specific antigen proteins on cancer cells are applied as therapeutic agents for cancers with fewer side effects to cancer treatment because of their cancer specificity. For example, cytoplasmic-activation and proliferation-associated protein 1 (CAPRIN-1) is expressed on cell membrane surfaces of many solid cancers. Antibodies against this CAPRIN-1 protein are known to be promising in pharmaceutical uses for treatment and/or prevention of cancers (Patent Literature 1).

In recent years, treatment methods using combinations of pluralities of therapeutic agents for cancer have been clinically used as standard treatment methods in order to enhance the effectiveness of the therapeutic agents for cancers. It has been performed in common to treat using a plurality of anticancer agents, for example, colon cancer is treated by a treatment method using a combination of irinotecan, folinic acid, and fluorouracil; breast cancer is treated by a treatment method using a combination of doxorubicin and cyclophosphamide or a combination of paclitaxel, trastuzumab, and pertuzumab; and gastric cancer is treated using a plurality of anticancer agents such as cisplatin and fluorouracil. Therapeutic agents for cancers comprising anti-CAPRIN-1 antibodies as active ingredients have also been confirmed to have therapeutic effects on the cancers by combinations with chemotherapeutics (Patent Literature 2). However, treatment of a cancer by a combination of chemotherapeutics is not effective for every cancer to which the treatment is applied, and few combinations of chemotherapeutics synergistically drastically enhance therapeutic effects, though some combinations additively enhance therapeutic effects.

One specific example of the cancer treatment method using a combination of a plurality of therapeutic agents for cancer includes a combination of a pyrimidine-based drug (e.g., gemcitabine) and cisplatin.

The combination of gemcitabine and cisplatin is called GEM+CDDP therapy and is being attempted to treat biliary tract cancer, urinary bladder cancer such as urothelial carcinoma, non-small cell lung cancer (NSCLC), uterine cervical cancer, malignant mesothelioma, ovarian cancer and pancreatic cancer.

For urinary bladder cancer, M-VAC therapy (a combination of methotrexate, vinblastine, doxorubicin and cisplatin) has been used so far, whereas gemcitabine and cisplatin combination therapy with fewer side effects is now used. For example, for muscle invasive bladder cancer, gemcitabine+cisplatin therapy is reportedly standard treatment. However, there is a report stating that urinary bladder cancer patients who had undergone complete removal of the urinary bladder had a complete response rate of only 24.5% to gemcitabine+cisplatin combination therapy (Non Patent Literature 1).

In recent years, nab-paclitaxel combination therapy in addition to the conventional combination of gemcitabine and cisplatin has been tested for its efficacy on advanced biliary tract cancer patients by a phase 2 trial (NCT02392637). Although the first-line standard treatment of advanced biliary tract cancer patients is gemcitabine and cisplatin combination therapy, its overall survival (OS) is only less than 1 year. By contrast, in the clinical trial described above, which was constituted by 78% metastatic biliary tract cancer patients and 22% local advanced biliary tract cancer patients, the combination of nab-paclitaxel in addition to gemcitabine and cisplatin exhibited progression-free survival (PFS) of 11.8 months and objective response rate (ORR) of 45% with median overall survival (OS) of 19.2 months. Thus, this treatment produced a better outcome than that of the gemcitabine+cisplatin combination therapy (GEM+CDDP therapy) serving as standard therapy. However, adverse events (AE) of grade 3 or higher were also found in 50% or more of the cases, and 16% of the patients were forced to discontinue the treatment due to a treatment-related adverse event (TRAE) (Non Patent Literature 2).

CITATION LIST

Patent Literature

Patent Literature 1: WO2010/016526
Patent Literature 2: WO2011/096535

Non Patent Literature

Non Patent Literature 1: JAMA Oncol, 2018, 4 (11), 1535-1542
Non Patent Literature 2: JAMA Oncol. 2019, 5 (6), 824-830

SUMMARY OF INVENTION

Technical Problem

An object of the present invention is to provide a medicament for treatment and/or prevention of cancer specifically expressing CAPRIN-1 protein on a cell surface.

Solution to Problem

As mentioned above, for example, for advanced biliary tract cancer patients, a combination of gemcitabine and cisplatin has an overall survival (OS) of only less than 1 year, and even treatment method using a combination of gemcitabine, cisplatin, and further, nab-paclitaxel has an overall survival (OS) improved to only less than 2 years, in which no drastic improvement is found. As a result of intensive studies, the present inventors have found that a combination of an antibody against CAPRIN-1 protein, or a fragment thereof, having an immunological reactivity with cancer cells, and a pyrimidine-based drug (e.g., gemcitabine) and cisplatin exerts a very strong antitumor effect on a cancer patient, in particular, a cancer patient with a previous history of cancer treatment with a medicament other than this combination therapy. On the basis of these findings, the present invention has been completed.

Specifically, the present invention relates to the following embodiments (1) to (17):

(1) A medicament for treatment and/or prevention of cancer, comprising an antibody or a fragment thereof having an immunological reactivity with CAPRIN-1 protein, and a pyrimidine-based drug and cisplatin together or separately in combination, wherein a cancer patient with the cancer is a cancer patient with a previous history of cancer treatment with a medicament other than cancer treatment with a medicament comprising an antibody or a fragment thereof having an immunological reactivity with CAPRIN-1 protein, and a pyrimidine-based drug and cisplatin together or separately in combination.

(2) The medicament according to (1), wherein the cancer is cancer in a cancer patient with a previous history of cancer treatment with a pyrimidine-based drug and/or a platinum-containing drug.

(3) The medicament according to (1) or (2), wherein the cancer is cancer in a cancer patient who has not responded to cancer treatment with a medicament other than cancer treatment with a medicament comprising an antibody or a fragment thereof having an immunological reactivity with CAPRIN-1 protein, and a pyrimidine-based drug and cisplatin together or separately in combination.

(4) The medicament according to any of (1) to (3), wherein the cancer is cancer in a cancer patient who has not responded to cancer treatment with a pyrimidine-based drug and/or a platinum-containing drug.

(5) The medicament according to any of (1) to (4), wherein the pyrimidine-based drug is gemcitabine and/or a derivative of gemcitabine.

(6) The medicament according to any of (1) to (5), wherein the antibody or the fragment thereof has an immunological reactivity with CAPRIN-1 protein having an amino acid sequence shown in any one of the even numbered SEQ ID NOs: 2 to 30, or an amino acid sequence having 80% or more sequence identity with the amino acid sequence.

(7) The medicament according to any of (1) to (6), wherein the antibody or the fragment thereof has an immunological reactivity with an extracellular region of a CAPRIN-1 protein present on a cancer cell surface.

(8) The medicament according to any of (1) to (7), wherein the antibody or the fragment thereof has an immunological reactivity with a partial polypeptide of CAPRIN-1 protein, the partial polypeptide having an amino acid sequence represented by any one of SEQ ID NOs: 31 to 35, 296 to 299, 308 and 309, or an amino acid sequence having 80% or more sequence identity with the amino acid sequence.

(9) The medicament according to any of (1) to (8), wherein the antibody is a monoclonal antibody or a polyclonal antibody.

(10) The medicament according to any of (1) to (9), wherein the antibody or the fragment thereof is any one of the following (A) to (M):

(A) an antibody or a fragment thereof comprising a heavy-chain variable region comprising complementarity determining regions of SEQ ID NOs: 36, 37 and 38 (CDR1, CDR2 and CDR3, respectively) and a light-chain variable region comprising complementarity determining regions of SEQ ID NOs: 40, 41 and 42 (CDR1, CDR2 and CDR3, respectively), and having an immunological reactivity with CAPRIN-1 protein;

(B) an antibody or a fragment thereof comprising a heavy-chain variable region comprising complementarity determining regions of SEQ ID NOs: 44, 45 and 46 (CDR1, CDR2 and CDR3, respectively) and a light-chain variable region comprising complementarity determining regions of SEQ ID NOs: 48, 49 and 50 (CDR1, CDR2 and CDR3, respectively), and having an immunological reactivity with CAPRIN-1 protein;

(C) an antibody or a fragment thereof comprising a heavy-chain variable region comprising complementarity determining regions of SEQ ID NOs: 52, 53 and 54 (CDR1, CDR2 and CDR3, respectively) and a light-chain variable region comprising complementarity determining regions of SEQ ID NOs: 56, 57 and 58 (CDR1, CDR2 and CDR3, respectively), and having an immunological reactivity with CAPRIN-1 protein;

(D) an antibody or a fragment thereof comprising a heavy-chain variable region comprising complementarity determining regions of SEQ ID NOs: 60, 61 and 62 (CDR1, CDR2 and CDR3, respectively) and a light-chain variable region comprising complementarity determining regions of SEQ ID NOs: 64, 65 and 66 (CDR1, CDR2 and CDR3, respectively), and having an immunological reactivity with CAPRIN-1 protein;

(E) an antibody or a fragment thereof comprising a heavy-chain variable region comprising complementarity determining regions of SEQ ID NOs: 170, 171 and 172 (CDR1, CDR2 and CDR3, respectively) and a light-chain variable region comprising complementarity determining regions of SEQ ID NOs: 173, 174 and 175 (CDR1, CDR2 and CDR3, respectively), and having an immunological reactivity with CAPRIN-1 protein;

(F) an antibody or a fragment thereof comprising a heavy-chain variable region comprising complementarity determining regions of SEQ ID NOs: 176, 177 and 178 (CDR1, CDR2 and CDR3, respectively) and a light-chain variable region comprising complementarity determining regions of SEQ ID NOs: 179, 180 and 181 (CDR1, CDR2 and CDR3, respectively), and having an immunological reactivity with CAPRIN-1 protein;

(G) an antibody or a fragment thereof comprising a heavy-chain variable region comprising complementarity determining regions of SEQ ID NOs: 182, 183 and 184 (CDR1, CDR2 and CDR3, respectively) and a light-chain variable region comprising complementarity determining regions of SEQ ID NOs: 185, 186 and 187 (CDR1, CDR2 and CDR3, respectively), and having an immunological reactivity with CAPRIN-1 protein;

(H) an antibody or a fragment thereof comprising a heavy-chain variable region comprising complementarity determining regions of SEQ ID NOs: 188, 189 and 190 (CDR1, CDR2 and CDR3, respectively) and a light-chain variable region comprising complementarity determining regions of SEQ ID NOs: 191, 192 and 193 (CDR1, CDR2 and CDR3, respectively), and having an immunological reactivity with CAPRIN-1 protein;

(I) an antibody or a fragment thereof comprising a heavy-chain variable region comprising complementarity determining regions of SEQ ID NOs: 146, 147 and 148 (CDR1, CDR2 and CDR3, respectively) and a light-chain variable region comprising complementarity determining regions of SEQ ID NOs: 149, 150 and 151 (CDR1, CDR2 and CDR3, respectively), and having an immunological reactivity with CAPRIN-1 protein;

(J) an antibody or a fragment thereof comprising a heavy-chain variable region comprising complementarity determining regions of SEQ ID NOs: 272, 273 and 274 (CDR1, CDR2 and CDR3, respectively) and a light-chain variable region comprising complementarity determining regions of SEQ ID NOs: 275, 276 and 277 (CDR1, CDR2 and CDR3, respectively), and having an immunological reactivity with CAPRIN-1 protein;

(K) an antibody or a fragment thereof comprising a heavy-chain variable region comprising complementarity determining regions of SEQ ID NOs: 290, 291 and 292 (CDR1, CDR2 and CDR3, respectively) and a light-chain variable region comprising complementarity determining regions of SEQ ID NOs: 293, 294 and 295 (CDR1, CDR2 and CDR3, respectively), and having an immunological reactivity with CAPRIN-1 protein;

(L) an antibody or a fragment thereof comprising a heavy-chain variable region comprising complementarity determining regions of SEQ ID NOs: 300, 301, and 302 (CDR1, CDR2 and CDR3, respectively) and a light-chain variable region comprising complementarity determining regions of SEQ ID NOs: 304, 305, and 306 (CDR1, CDR2 and CDR3, respectively), and having an immunological reactivity with CAPRIN-1 protein; and (M) an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with CAPRIN-1 protein.

(11) The medicament according to any of (1) to (10), wherein the antibody or the fragment thereof is any one of the following (a) to (al):

(a) an antibody or a fragment thereof comprising a heavy-chain variable region comprising the amino acid sequence of SEQ ID NO: 39 and a light-chain variable region comprising the amino acid sequence of SEQ ID NO: 43;

(b) an antibody or a fragment thereof comprising a heavy-chain variable region comprising the amino acid sequence of SEQ ID NO: 47 and a light-chain variable region comprising the amino acid sequence of SEQ ID NO: 51;

(c) an antibody or a fragment thereof comprising a heavy-chain variable region comprising the amino acid sequence of SEQ ID NO: 55 and a light-chain variable region comprising the amino acid sequence of SEQ ID NO: 59;

(d) an antibody or a fragment thereof comprising a heavy-chain variable region comprising the amino acid sequence of SEQ ID NO: 63 and a light-chain variable region comprising the amino acid sequence of SEQ ID NO: 67;

(e) an antibody or a fragment thereof comprising a heavy-chain variable region comprising the amino acid sequence of SEQ ID NO: 68 and a light-chain variable region comprising the amino acid sequence of SEQ ID NO: 69;

(f) an antibody or a fragment thereof comprising a heavy-chain variable region comprising the amino acid sequence of SEQ ID NO: 70 and a light-chain variable region comprising the amino acid sequence of SEQ ID NO: 71;

(g) an antibody or a fragment thereof comprising a heavy-chain variable region comprising the amino acid sequence of SEQ ID NO: 72 and a light-chain variable region comprising the amino acid sequence of SEQ ID NO: 73;

(h) an antibody or a fragment thereof comprising a heavy-chain variable region comprising the amino acid sequence of SEQ ID NO: 74 and a light-chain variable region comprising the amino acid sequence of SEQ ID NO: 75;

(i) an antibody or a fragment thereof comprising a heavy-chain variable region comprising the amino acid sequence of SEQ ID NO: 76 and a light-chain variable region comprising the amino acid sequence of SEQ ID NO: 77;

(j) an antibody or a fragment thereof comprising a heavy-chain variable region comprising the amino acid sequence of SEQ ID NO: 78 and a light-chain variable region comprising the amino acid sequence of SEQ ID NO: 79;

(k) an antibody or a fragment thereof comprising a heavy-chain variable region comprising the amino acid sequence of SEQ ID NO: 80 and a light-chain variable region comprising the amino acid sequence of SEQ ID NO: 81;

(l) an antibody or a fragment thereof comprising a heavy-chain variable region comprising the amino acid sequence of SEQ ID NO: 82 and a light-chain variable region comprising the amino acid sequence of SEQ ID NO: 83;

(m) an antibody or a fragment thereof comprising a heavy-chain variable region comprising the amino acid sequence of SEQ ID NO: 84 and a light-chain variable region comprising the amino acid sequence of SEQ ID NO: 85;

(n) an antibody or a fragment thereof comprising a heavy-chain variable region comprising the amino acid sequence of SEQ ID NO: 86 and a light-chain variable region comprising the amino acid sequence of SEQ ID NO: 87;

(o) an antibody or a fragment thereof comprising a heavy-chain variable region comprising the amino acid sequence of SEQ ID NO: 88 and a light-chain variable region comprising the amino acid sequence of SEQ ID NO: 89;

(p) an antibody or a fragment thereof comprising a heavy-chain variable region comprising the amino acid sequence of SEQ ID NO: 90 and a light-chain variable region comprising the amino acid sequence of SEQ ID NO: 91;

(q) an antibody or a fragment thereof comprising a heavy-chain variable region comprising the amino acid sequence of SEQ ID NO: 92 and a light-chain variable region comprising the amino acid sequence of SEQ ID NO: 93;

(r) an antibody or a fragment thereof comprising a heavy-chain variable region comprising the amino acid sequence of SEQ ID NO: 94 and a light-chain variable region comprising the amino acid sequence of SEQ ID NO: 95;

(s) an antibody or a fragment thereof comprising a heavy-chain variable region comprising the amino acid sequence of SEQ ID NO: 96 and a light-chain variable region comprising the amino acid sequence of SEQ ID NO: 97;

(t) an antibody or a fragment thereof comprising a heavy-chain variable region comprising the amino acid sequence of SEQ ID NO: 98 and a light-chain variable region comprising the amino acid sequence of SEQ ID NO: 99;

(u) an antibody or a fragment thereof comprising a heavy-chain variable region comprising the amino acid sequence of SEQ ID NO: 100 and a light-chain variable region comprising the amino acid sequence of SEQ ID NO: 101;

(v) an antibody or a fragment thereof comprising a heavy-chain variable region comprising the amino acid sequence of SEQ ID NO: 102 and a light-chain variable region comprising the amino acid sequence of SEQ ID NO: 103;

(w) an antibody or a fragment thereof comprising a heavy-chain variable region comprising the amino acid sequence of SEQ ID NO: 104 and a light-chain variable region comprising the amino acid sequence of SEQ ID NO: 105;

(x) an antibody or a fragment thereof comprising a heavy-chain variable region comprising the amino acid sequence of SEQ ID NO: 106 and a light-chain variable region comprising the amino acid sequence of SEQ ID NO: 107;

(y) an antibody or a fragment thereof comprising a heavy-chain variable region comprising the amino acid sequence of SEQ ID NO: 108 and a light-chain variable region comprising the amino acid sequence of SEQ ID NO: 109;

(z) an antibody or a fragment thereof comprising a heavy-chain variable region comprising the amino acid sequence of SEQ ID NO: 110 and a light-chain variable region comprising the amino acid sequence of SEQ ID NO: 111;

(aa) an antibody or a fragment thereof comprising a heavy-chain variable region comprising the amino acid sequence of SEQ ID NO: 112 and a light-chain variable region comprising the amino acid sequence of SEQ ID NO: 113;

(ab) an antibody or a fragment thereof comprising a heavy-chain variable region comprising the amino acid sequence of SEQ ID NO: 114 and a light-chain variable region comprising the amino acid sequence of SEQ ID NO: 115;

(ac) an antibody or a fragment thereof comprising a heavy-chain variable region comprising the amino acid sequence of SEQ ID NO: 116 and a light-chain variable region comprising the amino acid sequence of SEQ ID NO: 117;

(ad) an antibody or a fragment thereof comprising a heavy-chain variable region comprising the amino acid sequence of SEQ ID NO: 118 and a light-chain variable region comprising the amino acid sequence of SEQ ID NO: 119;

(ae) an antibody or a fragment thereof comprising a heavy-chain variable region comprising the amino acid sequence of SEQ ID NO: 120 and a light-chain variable region comprising the amino acid sequence of SEQ ID NO: 121;

(af) an antibody or a fragment thereof comprising a heavy-chain variable region comprising the amino acid sequence of SEQ ID NO: 122 and a light-chain variable region comprising the amino acid sequence of SEQ ID NO: 123;

(ag) an antibody or a fragment thereof comprising a heavy-chain variable region comprising the amino acid sequence of SEQ ID NO: 124 and a light-chain variable region comprising the amino acid sequence of SEQ ID NO: 125;

(ah) an antibody or a fragment thereof comprising a heavy-chain variable region comprising the amino acid sequence of SEQ ID NO: 126 and a light-chain variable region comprising the amino acid sequence of SEQ ID NO: 127;

(ai) an antibody or a fragment thereof comprising a heavy-chain variable region comprising the amino acid sequence of SEQ ID NO: 128 and a light-chain variable region comprising the amino acid sequence of SEQ ID NO: 129;

(aj) an antibody or a fragment thereof comprising a heavy-chain variable region comprising the amino acid sequence of SEQ ID NO: 130 and a light-chain variable region comprising the amino acid sequence of SEQ ID NO: 131;

(ak) an antibody or a fragment thereof comprising a heavy-chain variable region comprising the amino acid sequence of SEQ ID NO: 132 and a light-chain variable region comprising the amino acid sequence of SEQ ID NO: 133; and (al) an antibody or a fragment thereof comprising a heavy-chain variable region comprising the amino acid sequence of SEQ ID NO: 303 and a light-chain variable region comprising the amino acid sequence of SEQ ID NO: 307.

(12) The medicament according to any of (1) to (11), wherein the antibody is a human antibody, a humanized antibody, a chimeric antibody or a single chain antibody.

(13) The medicament according to any of (1) to (12), wherein the cancer is cancer expressing CAPRIN-1 protein on a cell membrane surface.

(14) The medicament according to any of (1) to (13), wherein the cancer is bile duct cancer, breast cancer, kidney cancer, pancreatic cancer, colon cancer, melanoma, lung cancer, renal cell carcinoma, Hodgkin's lymphoma, head and neck cancer, gastric cancer, mesothelioma, colorectal cancer, esophageal cancer, gastroesophageal junction cancer, hepatocellular carcinoma, glioblastoma, urothelial carcinoma, ovarian cancer, urinary bladder cancer, uterine cancer, primary central nervous system lymphoma, primary testicular lymphoma, biliary tract cancer, brain tumor, prostate cancer, leukemia, lymphoma, liver cancer, sarcoma, fibrosarcoma, mastocytoma, adrenocortical carcinoma, Ewing's tumor, multiple myeloma, testicular cancer, thyroid cancer, basal cell carcinoma, Paget's disease or skin cancer.

(15) An agent increasing drug efficacy of a pharmaceutical composition for treatment and/or prevention of cancer comprising an antibody or a fragment thereof having an immunological reactivity with CAPRIN-1 protein as an active ingredient, wherein the agent comprises a pyrimidine-based drug and cisplatin as active ingredients and wherein a cancer patient with the cancer is a cancer patient with a previous history of cancer treatment with a medicament other than cancer treatment with a medicament comprising an antibody or a fragment thereof having an immunological reactivity with CAPRIN-1 protein, and a pyrimidine-based drug and cisplatin together or separately in combination.

(16) An agent increasing drug efficacy of a pharmaceutical composition for treatment and/or prevention of cancer comprising a pyrimidine-based drug and cisplatin as active ingredients, wherein the agent comprises an antibody or a fragment thereof having an immunological reactivity with CAPRIN-1 protein as an active ingredient and wherein a cancer patient with the cancer is a cancer patient with a previous history of cancer treatment with a medicament other than cancer treatment with a medicament comprising an antibody or a fragment thereof having an immunological reactivity with CAPRIN-1 protein, and a pyrimidine-based drug and cisplatin together or separately in combination.

(17) A method for treating and/or preventing cancer, comprising administering an antibody or a fragment thereof having an immunological reactivity with a CAPRIN-1 protein, and a pyrimidine-based drug and cisplatin together or separately to a subject, wherein a cancer patient with the cancer is a cancer patient with a previous history of cancer treatment with a medicament other than cancer treatment with a medicament comprising an antibody or a fragment thereof having an immunological reactivity with CAPRIN-1 protein, and a pyrimidine-based drug and cisplatin together or separately in combination.

The present specification encompasses the contents disclosed in Japanese Patent Application No. 2020-043019 on which the priority of the present application is based.

Advantageous Effects of Invention

The combination of an antibody against CAPRI-1 protein, or a fragment thereof, and a drug comprising a pyrimidine-based drug and cisplatin according to the present invention exerts a stronger antitumor effect than that of the antibody against CAPRIN-1 protein alone or an existing chemotherapeutic (a combination of a pyrimidine-based drug and a platinum-containing drug). The combination of an antibody against CAPRIN-1 protein, or a fragment thereof, and a drug comprising a pyrimidine-based drug and cisplatin according to the present invention exhibits a stronger antitumor effect than that of existing anticancer agent therapy or treatment with the antibody against CAPRIN-1 protein alone. Thus, the combination of the antibody against CAPRIN-1 protein, or the fragment thereof, and a pyrimidine-based drug and cisplatin is effective for treatment or prevention of cancer.

DESCRIPTION OF EMBODIMENTS

The antitumor activity of the combination of an antibody against CAPRIN-1 protein or a fragment thereof (hereinafter, referred to as an "anti-CAPRIN-1 antibody"), a pyrimidine-based drug, and cisplatin used in the present invention can be evaluated by examining in vivo the inhibition of tumor growth in tumor-bearing animals as mentioned later.

The term "comprising together or separately in combination" described herein refers to comprising a plurality of drugs in a form that allows the drugs to be administered simultaneously or separately to a patient. The form may be, for example, the form of a so-called mixed formulation in which a plurality of drugs is mixed, or may be the form of a so-called kit formulation comprising a plurality of drugs as individual formulations.

Such a kit formulation according to the present invention may be, for example, a kit formulation comprising a formulation (or a pharmaceutical composition) comprising the anti-CAPRIN-1 antibody and a formulation (or a pharmaceutical composition) comprising a pyrimidine-based drug and cisplatin. The kit formulation according to the present invention may comprise, in addition to the anti-CAPRIN-1 antibody, the pyrimidine-based drug and cisplatin, other formulations (other known antitumor agents or other pyrimidine-based drugs).

The term "combination" described herein refers to simultaneous administration or administration in a predetermined interval of the anti-CAPRIN-1 antibody, a pyrimidine-based drug, and cisplatin as independent active ingredients to the same organism. The interval may be simultaneous administration or may be 30 minutes later, 1 hour later, 3 hours later, 6 hours later, 12 hours later, 1 day later, 3 days later, 5 days later, 7 days later, 2 weeks later, 3 weeks later, or 4 weeks later. The anti-CAPRIN-1 antibody or a drug comprising a pyrimidine-based drug and cisplatin may be administered when another active ingredient exhibits its activity in vivo. The anti-CAPRIN-1 antibody may be administered first, or the drug comprising a pyrimidine-based drug and cisplatin may be administered first.

The anti-CAPRIN-1 antibody according to the present invention may be a monoclonal antibody or a polyclonal antibody and is preferably a monoclonal antibody. The antibody of the present invention may be any type of antibody, as long as it can exhibit antitumor activity. The antibody is a recombinant antibody, a human antibody, a humanized antibody, a chimeric antibody, or a non-human animal antibody.

Subjects in need of treatment and/or prevention of cancer according to the present invention are mammals such as human, pet animals, livestock animals, or sport animals. The preferred subject is a human.

Medicaments comprising an anti-CAPRIN-1 antibody, a pyrimidine-based drug and cisplatin as active ingredients, and methods for treating and/or preventing cancer, related to the present invention, will be explained below.

<Anti-CAPRIN-1 Antibody>

Among CAPRIN-1 proteins having an amino acid sequence shown in any one of the even numbered SEQ ID NOs: 2 to 30, which are specific examples of antigens having an immunological reactivity with the anti-CAPRIN-1 antibody used in the present invention, the amino acid sequences shown in SEQ ID NOs: 6, 8, 10, 12 and 14 are amino acid sequences of canine CAPRIN-1 proteins; the amino acid sequences shown in SEQ ID NOs: 2 and 4 are amino acid sequences of human CAPRIN-1 proteins; the amino acid sequence shown in SEQ ID NO: 16 is an amino acid sequence of a bovine CAPRIN-1 protein; the amino acid sequence shown in SEQ ID NO: 18 is an amino acid sequence of a horse CAPRIN-1 protein; the amino acid sequences shown in SEQ ID NOs: 20, 22, 24, 26 and 28 are amino acid sequences of mouse CAPRIN-1 proteins; and the amino acid sequence shown in SEQ ID NO: 30 is an amino acid sequence of a chicken CAPRIN-1 protein.

The anti-CAPRIN-1 antibody used in the present invention may have an immunological reactivity with a CAPRIN-1 protein variant having 80% or more, preferably 90% or more, more preferably 95% or more, and further preferably 99% or more sequence identity to the amino acid sequence shown in any one of the even numbered SEQ ID NOs: 2 to 30. The term "% sequence identity" as used herein means a percentage (%) of the number of identical amino acids (or nucleotides) to the total number of amino acids (or nucleotides) in the case that two sequences are aligned such that maximum similarity can be achieved with or without introduction of gaps.

In the present invention, the anti-CAPRIN-1 antibody refers to an antibody or a fragment (antigen binding fragment) thereof having an immunological reactivity with a full-length CAPRIN-1 protein or a fragment thereof. The term "immunological reactivity" used herein indicates the characteristics of an antibody specifically binding in vivo or in vitro to a CAPRIN-1 protein or a partial polypeptide thereof.

The anti-CAPRIN-1 antibody used in the present invention may be a monoclonal antibody or a polyclonal antibody.

Polyclonal antibodies having an immunological reactivity with a full-length CAPRIN-1 protein or a fragment thereof (anti-CAPRIN-1 polyclonal antibodies) can be obtained, for example, in a manner described below. Mice, human antibody-producing mice, rats, rabbits, chickens, or the like are immunized using a naturally occurring CAPRIN-1 protein or a protein fused with GST or the like, or a partial peptide thereof, followed by obtainment of serum, and then by purification from the obtained serum via ammonium sulfate precipitation, protein A, protein G, DEAE ion-exchange columns, affinity columns to which a CAPRIN-1 protein or a partial peptide is coupled, or the like.

Nucleotide sequences and amino acid sequences of CAP-RIN-1 and homologs thereof used in the immunization can be obtained by, for example, accessing the website of GenBank (NCBI, USA) and using the BLAST or FASTA algorithm (Karlin and Altschul, Proc. Natl. Acad. Sci. USA, 90: 5873-5877, 1993; and Altschul et al., Nucleic Acids Res. 25: 3389-3402, 1997). Methods for producing CAPRIN-1 protein can be obtained with reference to WO2014/012479 or may employ cells or the like expressing CAPRIN-1 protein.

Monoclonal antibodies having an immunological reactivity with a full-length CAPRIN-1 protein or a fragment thereof (anti-CAPRIN-1 monoclonal antibodies) can be obtained, for example, in a manner described below. Breast cancer cells SK-BR-3 expressing CAPRIN-1, a full-length CAPRIN-1 protein or a fragment thereof, or the like is administered to mice for immunization. Splenocytes separated from the mice are fused with myeloma cells. Clones capable of producing anti-CAPRIN-1 monoclonal antibodies can be selected from the obtained fusion cells (hybridomas) to obtain these antibodies. The antibodies produced from the selected hybridomas can be obtained in the same way as the aforementioned method for purifying polyclonal antibodies.

The antibody used in the present invention includes human antibodies, humanized antibodies, chimeric antibodies, and non-human animal antibodies.

For human antibodies, human lymphocytes infected with EB virus are sensitized with a protein, protein-expressing cells, or a lysate thereof. The sensitized lymphocytes are fused with human-derived myeloma cells such as U266 cells. Antibodies having an immunological reactivity with a full-length CAPRIN-1 protein or a fragment thereof can be obtained from the obtained fusion cells.

A humanized antibody is a modified antibody, and it is sometimes referred to as a reshaped human antibody. It is known that a humanized antibody is constructed by transplanting complementarity determining regions of an immunized animal-derived antibody into complementarity determining regions of a human antibody. In addition, a general gene recombinant technique therefor is well known. Specifically, a DNA sequence designed in a manner that allows complementarity determining regions of mouse or rabbit antibody to be ligated to human antibody framework regions is synthesized by the PCR method using several oligonucleotides prepared in such a manner that the oligonucleotides have portions overlapping each other at one end of each thereof. A humanized antibody can be obtained by ligating the above obtained DNA to DNA encoding a human antibody constant region, incorporating the resultant into an expression vector, and introducing the vector into a host for antibody production (see EP-A-239400 and WO96/02576). Framework regions of human antibody ligated to each other via complementarity determining regions are selected on the assumption that complementarity determining regions can form an effective antigen binding site. If necessary, amino acids in framework regions of an antibody variable region may be substituted in such a manner that complementarity determining regions in a reshaped human antibody form an appropriate antigen binding site (Sato K. et al., Cancer Research 1993, 53: 851-856). In addition, the framework regions may be substituted with framework regions from a different human antibody (see WO99/51743).

In general, antibodies are heteromultimeric glycoproteins each comprising at least two heavy chains and two light chains. Antibodies each comprise two identical light chains and two identical heavy chains. Each heavy chain has a heavy-chain variable region at one end thereof, to which some constant regions are bound in series. Each light chain has a light-chain variable region at one end thereof to which some constant regions are bound in series. Variable regions have a specific variable region, which is called complementarity determining region (CDR) and imparts binding specificity to an antibody. A relatively conserved portion in a variable region is called a framework region (FR). A complete heavy-chain or light-chain variable region comprises 4 FRs connected to each other via 3 CDRs (CDR1 to CDR3).

Sequences of human-derived heavy-chain and light-chain constant regions and variable regions can be obtained from, for example, NCBI (USA; GenBank, UniGene, etc.). For example, for a human IgG1 heavy-chain constant region, see registration No. J00228; for a human IgG2 heavy-chain constant region, see registration No. J00230; for a human light chain κ constant region, see sequences such as registration Nos. V00557, X64135, and X64133; and for a human light chain λ constant region, see sequences such as registration Nos. X64132 and X64134.

A chimeric antibody is an antibody produced by combining sequences from different animals. An example thereof is an antibody consisting of mouse antibody heavy-chain and light-chain variable regions and human antibody heavy-chain and light-chain constant regions. Such a chimeric antibody can be produced by a known method. For example, it can be obtained by ligating DNA encoding an antibody V region to DNA encoding a human antibody C region, incorporating the resultant into an expression vector, and introducing the vector into a host for antibody production.

Non-human animal antibodies are obtained by immunizing animals with sensitizing antigens according to a known method or by intraperitoneally, intracutaneously, or subcutaneously injecting sensitizing antigens into animals such as mice as a general method. For injecting sensitizing antigens, an appropriate amount of various adjuvants including CFA (complete Freund's adjuvant) is mixed therewith and the mixture is administered to animals several times. After immunization of animals and confirmation of an anti-CAPRIN-1 antibody contained in serum, the serum is obtained and a non-human animal antibody can be obtained by purification via ammonium sulfate precipitation, protein A, protein G, DEAE ion-exchange columns, affinity columns to which a CAPRIN-1 protein or a partial peptide is coupled, or the like, as mentioned above. In the case of obtaining monoclonal antibodies from non-human animals, a monoclonal antibody is obtained by collecting immune cells from the immunized animals and subjecting them to cell fusion with myeloma cells. The cell fusion of immune cells with myeloma cells can be carried out according to a known method (see Kohler, G. and Milstein, C. Methods Enzymol. (1981) 73, 3-46).

The antibody used in the present invention can also be obtained as a gene recombinant antibody produced by cloning an antibody gene from a hybridoma, incorporating the clone into an adequate vector, introducing the vector into a host, and producing the antibody by using a gene recombinant technique (see Carl, A. K. Borrebaeck, James, W. Larrick, THERAPEUTIC MONOCLONAL ANTIBODIES, Published in the United Kingdom by MACMILLAN PUBLISHERS LTD, 1990).

Amino acids in a variable region (e.g., FR) or a constant region in the anti-CAPRIN-1 antibody used in the present invention may be substituted with different amino acids. The amino acid substitution is a substitution of 1 or several, for example, less than 15, less than 10, not more than 8, not more than 6, not more than 5, not more than 4, not more than 3, or not more than 2 amino acids, preferably 1 to 9 amino acids. A substituted antibody should have characteristics of specifically binding to the antigen and binding affinity for the antigen equivalent to or higher than those of an unsubstituted antibody and should be an antibody that causes no rejection when applied to humans. The amino acid substitution is preferably a conservative amino acid substitution, which is a substitution between amino acids having similar characteristics in terms of charge, side chains, polarity, aromaticity, and the like. For example, characteristically similar amino acids can be classified into the following types: basic amino acids (arginine, lysine, and histidine); acidic amino acids (aspartic acid and glutamic acid); uncharged polar amino acids (glycine, asparagine, glutamine, serine, threonine, cysteine, and tyrosine); nonpolar amino acids (leucine, isoleucine, alanine, valine, proline, phenylalanine, tryptophan, and methionine); branched-chain amino acids (threonine, valine, isoleucine); and aromatic amino acids (phenylalanine, tyrosine, tryptophan, and histidine).

The anti-CAPRIN-1 antibody used in the present invention is expected to have a stronger antitumor effect when having higher binding affinity for CAPRIN-1 protein on the cancer cell surface. Association constant (affinity constant) Ka (kon/koff) is preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or at least $10^{13}$ $M^{-1}$.

The anti-CAPRIN-1 antibody used in the present invention may be chemically modified. Examples of such an antibody modifier can include antibodies bound to various molecules such as polyethylene glycol (PEG) and antitumor compounds (for example, antitumor agents listed below). Regarding antibody modifiers of the present invention, substances that bind to an antibody are not limited. Such an antibody modifier can be obtained by chemically modifying an obtained antibody. Methods of such modification have been already established in the field related to the present invention. The binding strength of the anti-CAPRIN-1 antibody used in the present invention against effector cells can be improved by substituting 1, 2 or several amino acids in the heavy-chain constant region of the antibody or by removing fucose bound to N-acetylglucosamine in a N-glycoside-linked sugar chain bound to the heavy-chain constant region. The anti-CAPRIN-1 antibody described above may have the amino acid substitution alone or may be a composition with an antibody bound to fucose.

Antibodies in which 1, 2 or several amino acids in the heavy-chain constant region have been substituted can be produced with reference to, for example, WO2004/063351, WO2011/120135, U.S. Pat. No. 8,388,955, WO2011/005481, U.S. Pat. No. 6,737,056, and WO2005/063351.

Antibodies in which fucose bound to N-acetylglucosamine in a N-glycoside-linked sugar chain in the heavy-chain constant region has been removed, or producing cells thereof can be produced with reference to U.S. Pat. No. 6,602,684, EP Patent No. 1914244, and U.S. Pat. No. 7,579,170. Compositions of antibodies in which fucose bound to N-acetylglucosamine in a N-glycoside-linked sugar chain bound to the heavy-chain constant region has been removed, with antibodies bound to fucose, or producing cells thereof can be produced with reference to, for example, U.S. Pat. No. 8,642,292.

The anti-CAPRIN-1 polyclonal antibody and the anti-CAPRIN-1 monoclonal antibody used in the present invention, methods for producing or purifying antibodies and methods for producing a CAPRIN-1 protein or partial polypeptide thereof used in immunization can be obtained with reference to WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125630, WO2013/125640, WO2013/147169, WO2013/147176 and WO2015/020212.

Specific examples of the anti-CAPRIN-1 antibody according to the present invention include anti-CAPRIN-1 antibodies described in WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125630, WO2013/125640, WO2013/147169, WO2013/147176 and WO2015/020212 mentioned above. Preferred examples of the anti-CAPRIN-1 antibody include the following.

An antibody or a fragment thereof having an immunological reactivity with a partial polypeptide of a CAPRIN-1 protein having the amino acid sequence shown in SEQ ID NO: 2 or SEQ ID NO: 4 or an amino acid sequence having 80% or more (preferably 85% or more, more preferably 90% or more, further preferably 95% or more, and still further preferably 99% or more) sequence identity to the amino acid sequence.

An antibody or a fragment thereof having an immunological reactivity with a partial polypeptide of CAPRIN-1 protein, the partial polypeptide having the amino acid sequence shown in SEQ ID NO: 31 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 36, 37 and 38 (CDR1, CDR2 and CDR3, respectively) and a light-chain variable region comprising complementarity determining regions of SEQ ID NOs: 40, 41 and 42 (CDR1, CDR2 and CDR3, respectively), and having an immunological reactivity with a CAPRIN-1 protein, an antibody or a fragment thereof comprising a heavy-chain variable region comprising complementarity determining regions of SEQ ID NOs: 140, 141 and 142 (CDR1, CDR2 and CDR3, respectively) and a light-chain variable region comprising complementarity determining regions of SEQ ID NOs: 143, 144 and 145 (CDR1, CDR2 and CDR3, respectively), and having an immunological reactivity with a CAPRIN-1 protein, or an antibody or a fragment thereof comprising a heavy-chain variable region comprising complementarity determining regions of SEQ ID NOs: 164, 165 and 166 (CDR1, CDR2 and CDR3, respectively) and a light-chain variable region comprising complementarity determining regions of SEQ ID NOs: 167, 168 and 169 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 39 and a light-chain variable region comprising the amino acid sequence of SEQ ID NO: 43, an antibody or a fragment thereof comprising a heavy-chain variable region comprising the amino acid sequence of SEQ ID NO: 70 and a light-chain variable region comprising the amino acid sequence of SEQ ID NO: 71, or an antibody or a fragment thereof comprising a heavy-chain variable region comprising the amino acid sequence of SEQ ID NO: 78 and a light-chain variable region comprising the amino acid sequence of SEQ ID NO: 79.

An antibody or a fragment thereof having an immunological reactivity with a partial polypeptide of CAPRIN-1 protein, the partial polypeptide having the amino acid sequence shown in SEQ ID NO: 33 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 60, 61 and 62 (CDR1, CDR2 and CDR3, respectively) and a light-chain variable region comprising complementarity determining regions of SEQ ID NOs: 64, 65 and 66 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 63 and a light-chain variable region comprising the amino acid sequence of SEQ ID NO: 67.

An antibody or a fragment thereof having an immunological reactivity with a partial polypeptide of CAPRIN-1 protein, the partial polypeptide having the amino acid sequence shown in SEQ ID NO: 32 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 52, 53 and 54 (CDR1, CDR2 and CDR3, respectively) and a light-chain variable region comprising complementarity determining regions of SEQ ID NOs: 56, 57 and 58 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 55 and a light-chain variable region comprising the amino acid sequence of SEQ ID NO: 59.

An antibody or a fragment thereof having an immunological reactivity with a partial polypeptide of CAPRIN-1 protein, the partial polypeptide having the amino acid sequence shown in SEQ ID NO: 34 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 170, 171 and 172 (CDR1, CDR2 and CDR3, respectively) and a light-chain variable region comprising complementarity determining regions of SEQ ID NOs: 173, 174 and 175 (CDR1, CDR2 and CDR3, respectively), and having an immunological reactivity with a CAPRIN-1 protein, or an antibody or a fragment thereof comprising a heavy-chain variable region comprising complementarity determining regions of SEQ ID NOs: 176, 177 and 178 (CDR1, CDR2 and CDR3, respectively) and a light-chain variable region comprising complementarity determining regions of SEQ ID NOs: 179, 180 and 181 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 80 and a light-chain variable region comprising the amino acid sequence of SEQ ID NO: 81, or an antibody or a fragment thereof comprising a heavy-chain variable region comprising the amino acid sequence of SEQ ID NO: 82 and a light-chain variable region comprising the amino acid sequence of SEQ ID NO: 83.

An antibody or a fragment thereof having an immunological reactivity with a partial polypeptide of CAPRIN-1 protein, the partial polypeptide having the amino acid sequence shown in SEQ ID NO: 35 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 182, 183 and 184 (CDR1, CDR2 and CDR3, respectively) and a light-chain variable region comprising complementarity determining regions of SEQ ID NOs: 185, 186 and 187 (CDR1, CDR2 and CDR3, respectively), and having an immunological reactivity with a CAPRIN-1 protein, or an antibody or a fragment thereof comprising a heavy-chain variable region comprising complementarity determining regions of SEQ ID NOs: 188, 189 and 190 (CDR1, CDR2 and CDR3, respectively) and a light-chain variable region comprising complementarity determining regions of SEQ ID NOs: 191, 192 and 193 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 84 and a light-chain variable region comprising the amino acid sequence of SEQ ID NO: 85, or an antibody or a fragment thereof comprising a heavy-chain variable region comprising the amino acid sequence of SEQ ID NO: 86 and a light-chain variable region comprising the amino acid sequence of SEQ ID NO: 87.

An antibody or a fragment thereof comprising a heavy-chain variable region comprising complementarity determining regions of SEQ ID NOs: 44, 45 and 46 (CDR1, CDR2 and CDR3, respectively) and a light-chain variable region comprising complementarity determining regions of SEQ ID NOs: 48, 49 and 50 (CDR1, CDR2 and CDR3, respectively), and having an immunological reactivity with a CAPRIN-1 protein, and preferably an antibody or a fragment thereof comprising a heavy-chain variable region comprising the amino acid sequence of SEQ ID NO: 47 and a light-chain variable region comprising the amino acid sequence of SEQ ID NO: 51.

An antibody or a fragment thereof having an immunological reactivity with a partial polypeptide of CAPRIN-1 protein, the partial polypeptide having the amino acid sequence shown in SEQ ID NO: 296 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 146, 147 and 148 (CDR1, CDR2 and CDR3, respectively) and a light-chain variable region comprising complementarity determining regions of SEQ ID NOs: 149, 150 and 151 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 72 and a light-chain variable region comprising the amino acid sequence of SEQ ID NO: 73.

An antibody or a fragment thereof having an immunological reactivity with a partial polypeptide of CAPRIN-1 protein, the partial polypeptide having the amino acid sequence shown in SEQ ID NO: 297 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 272, 273 and 274 (CDR1, CDR2 and CDR3, respectively) and a light-chain variable region comprising complementarity determining regions of SEQ ID NOs: 275, 276 and 277 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 114 and a light-chain variable region comprising the amino acid sequence of SEQ ID NO: 115.

An antibody or a fragment thereof having an immunological reactivity with a partial polypeptide of CAPRIN-1 protein, the partial polypeptide having the amino acid sequence shown in SEQ ID NO: 298 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 290, 291 and 292 (CDR1, CDR2 and CDR3, respectively) and a light-chain variable region comprising complementarity determining regions of SEQ ID NOs: 293, 294 and 295 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 120 and a light-chain variable region comprising the amino acid sequence of SEQ ID NO: 121.

An antibody or a fragment thereof having an immunological reactivity with a partial polypeptide of CAPRIN-1 protein, the partial polypeptide having the amino acid sequence shown in SEQ ID NO: 299 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 300, 301, and 302 303 (CDR1, CDR2 and CDR3, respectively) and a light-chain variable region comprising complementarity determining regions of SEQ ID NOs: 304, 305, and 306 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 303 and a light-chain variable region comprising the amino acid sequence of SEQ ID NO: 307.

An antibody or a fragment thereof having an immunological reactivity with a partial polypeptide of CAPRIN-1 protein, the partial polypeptide having the amino acid sequence shown in SEQ ID NO: 308 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 68 and a light-chain variable region comprising the amino acid sequence of SEQ ID NO: 69.

An antibody or a fragment thereof having an immunological reactivity with a partial polypeptide of CAPRIN-1 protein, the partial polypeptide having the amino acid sequence shown in SEQ ID NO: 309 or an amino acid sequence having 80% or more (preferably 85% or more, more preferably 90% or more, and further preferably 95% or more) sequence identity to the amino acid sequence, preferably an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with a CAPRIN-1 protein, and more preferably an antibody or a fragment thereof comprising a heavy-chain variable region comprising the amino acid sequence of SEQ ID NO: 68 and a light-chain variable region comprising the amino acid sequence of SEQ ID NO: 69.

In addition, the following anti-CAPRIN-1 antibodies are preferably used.

An antibody or a fragment thereof comprising a heavy-chain variable region comprising the amino acid sequence of SEQ ID NO: 68 and a light-chain variable region comprising the amino acid sequence of SEQ ID NO: 69.

An antibody or a fragment thereof comprising a heavy-chain variable region comprising the amino acid sequence of SEQ ID NO: 70 and a light-chain variable region comprising the amino acid sequence of SEQ ID NO: 71.

An antibody or a fragment thereof comprising a heavy-chain variable region comprising the amino acid sequence of SEQ ID NO: 72 and a light-chain variable region comprising the amino acid sequence of SEQ ID NO: 73.

An antibody or a fragment thereof comprising a heavy-chain variable region comprising the amino acid sequence of SEQ ID NO: 74 and a light-chain variable region comprising the amino acid sequence of SEQ ID NO: 75.

An antibody or a fragment thereof comprising a heavy-chain variable region comprising the amino acid sequence of SEQ ID NO: 76 and a light-chain variable region comprising the amino acid sequence of SEQ ID NO: 77.

An antibody or a fragment thereof comprising a heavy-chain variable region comprising the amino acid sequence of SEQ ID NO: 78 and a light-chain variable region comprising the amino acid sequence of SEQ ID NO: 79.

An antibody or a fragment thereof comprising a heavy-chain variable region comprising the amino acid sequence of SEQ ID NO: 80 and a light-chain variable region comprising the amino acid sequence of SEQ ID NO: 81.

An antibody or a fragment thereof comprising a heavy-chain variable region comprising the amino acid sequence of SEQ ID NO: 82 and a light-chain variable region comprising the amino acid sequence of SEQ ID NO: 83.

An antibody or a fragment thereof comprising a heavy-chain variable region comprising the amino acid sequence of SEQ ID NO: 84 and a light-chain variable region comprising the amino acid sequence of SEQ ID NO: 85.

An antibody or a fragment thereof comprising a heavy-chain variable region comprising the amino acid sequence of SEQ ID NO: 86 and a light-chain variable region comprising the amino acid sequence of SEQ ID NO: 87.

An antibody or a fragment thereof comprising a heavy-chain variable region comprising the amino acid sequence of SEQ ID NO: 88 and a light-chain variable region comprising the amino acid sequence of SEQ ID NO: 89.

An antibody or a fragment thereof comprising a heavy-chain variable region comprising the amino acid sequence of SEQ ID NO: 90 and a light-chain variable region comprising the amino acid sequence of SEQ ID NO: 91.

An antibody or a fragment thereof comprising a heavy-chain variable region comprising the amino acid sequence of SEQ ID NO: 92 and a light-chain variable region comprising the amino acid sequence of SEQ ID NO: 93.

An antibody or a fragment thereof comprising a heavy-chain variable region comprising the amino acid sequence of SEQ ID NO: 94 and a light-chain variable region comprising the amino acid sequence of SEQ ID NO: 95.

An antibody or a fragment thereof comprising a heavy-chain variable region comprising the amino acid sequence of SEQ ID NO: 96 and a light-chain variable region comprising the amino acid sequence of SEQ ID NO: 97.

An antibody or a fragment thereof comprising a heavy-chain variable region comprising the amino acid sequence of SEQ ID NO: 98 and a light-chain variable region comprising the amino acid sequence of SEQ ID NO: 99.

An antibody or a fragment thereof comprising a heavy-chain variable region comprising the amino acid sequence of SEQ ID NO: 100 and a light-chain variable region comprising the amino acid sequence of SEQ ID NO: 101.

An antibody or a fragment thereof comprising a heavy-chain variable region comprising the amino acid sequence of SEQ ID NO: 102 and a light-chain variable region comprising the amino acid sequence of SEQ ID NO: 103.

An antibody or a fragment thereof comprising a heavy-chain variable region comprising the amino acid sequence of SEQ ID NO: 104 and a light-chain variable region comprising the amino acid sequence of SEQ ID NO: 105.

An antibody or a fragment thereof comprising a heavy-chain variable region comprising the amino acid sequence of SEQ ID NO: 106 and a light-chain variable region comprising the amino acid sequence of SEQ ID NO: 107.

An antibody or a fragment thereof comprising a heavy-chain variable region comprising the amino acid sequence of SEQ ID NO: 108 and a light-chain variable region comprising the amino acid sequence of SEQ ID NO: 109.

An antibody or a fragment thereof comprising a heavy-chain variable region comprising the amino acid sequence of SEQ ID NO: 110 and a light-chain variable region comprising the amino acid sequence of SEQ ID NO: 111.

An antibody or a fragment thereof comprising a heavy-chain variable region comprising the amino acid sequence of SEQ ID NO: 112 and a light-chain variable region comprising the amino acid sequence of SEQ ID NO: 113.

An antibody or a fragment thereof comprising a heavy-chain variable region comprising the amino acid sequence of SEQ ID NO: 114 and a light-chain variable region comprising the amino acid sequence of SEQ ID NO: 115.

An antibody or a fragment thereof comprising a heavy-chain variable region comprising the amino acid sequence of SEQ ID NO: 116 and a light-chain variable region comprising the amino acid sequence of SEQ ID NO: 117.

An antibody or a fragment thereof comprising a heavy-chain variable region comprising the amino acid sequence of SEQ ID NO: 118 and a light-chain variable region comprising the amino acid sequence of SEQ ID NO: 119.

An antibody or a fragment thereof comprising a heavy-chain variable region comprising the amino acid sequence of SEQ ID NO: 120 and a light-chain variable region comprising the amino acid sequence of SEQ ID NO: 121.

An antibody or a fragment thereof comprising a heavy-chain variable region comprising the amino acid sequence of SEQ ID NO: 122 and a light-chain variable region comprising the amino acid sequence of SEQ ID NO: 123.

An antibody or a fragment thereof comprising a heavy-chain variable region comprising the amino acid sequence of SEQ ID NO: 124 and a light-chain variable region comprising the amino acid sequence of SEQ ID NO: 125.

An antibody or a fragment thereof comprising a heavy-chain variable region comprising the amino acid sequence of SEQ ID NO: 126 and a light-chain variable region comprising the amino acid sequence of SEQ ID NO: 127.

An antibody or a fragment thereof comprising a heavy-chain variable region comprising the amino acid sequence of SEQ ID NO: 128 and a light-chain variable region comprising the amino acid sequence of SEQ ID NO: 129.

An antibody or a fragment thereof comprising a heavy-chain variable region comprising the amino acid sequence of SEQ ID NO: 130 and a light-chain variable region comprising the amino acid sequence of SEQ ID NO: 131.

An antibody or a fragment thereof comprising a heavy-chain variable region comprising the amino acid sequence of SEQ ID NO: 132 and a light-chain variable region comprising the amino acid sequence of SEQ ID NO: 133.

An antibody or a fragment thereof comprising a heavy-chain variable region comprising the amino acid sequence of SEQ ID NO: 303 and a light-chain variable region comprising the amino acid sequence of SEQ ID NO: 307.

In Examples mentioned later, a polyclonal antibody or a monoclonal antibody against full-length CAPRIN-1 protein or a polypeptide of a portion of an extracellular region expressed on the cell membrane surface of cancer cells, combined with a drug comprising a pyrimidine-based drug and cisplatin, was confirmed to have its strong antitumor effect in tumor-bearing animals.

<Pyrimidine-Based Drug>

Examples of the pyrimidine-based drug include fluorouracil (5-FU), fluorouracil prodrugs tegafur (FT), and doxifluridine, cytarabine formulations, and derivatives thereof. Gemcitabine and/or a derivative of gemcitabine is preferred.

<Cisplatin>

The substance name of cisplatin is cis-diamminedichloroplatinum (II). The cisplatin described herein may comprise an appropriate tonicity agent or a pH adjusting agent, or an appropriate dosage form for administration to an organism.

<Other Drugs>

The anti-CAPRIN-1 antibody, and the drug comprising a pyrimidine-based drug and cisplatin serving as active ingredients in the medicament of the present invention may be combined with an antitumor agent known in literatures, etc. Specific examples of known antitumor agents include, but are not particularly limited to, paclitaxel, nab-paclitaxel, doxorubicin, daunorubicin, cyclophosphamide, methotrexate, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, dideoxyuridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, defofamine, demecolcine, diaziquone, eflornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel 6-thioguanine, mercaptopurine, oxaliplatin, vinblastine, etoposide, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, and pharmacologically acceptable (known) salts or (known) derivatives thereof.

Antitumor Effect of Present Invention

A combination of the anti-CAPRIN-1 antibody, a pyrimidine-based drug and cisplatin of the present invention has cytotoxic activity in vivo. Accordingly, the antitumor effect of the present invention can be determined by examining cytotoxic activity against cancer. The cytotoxic activity can be evaluated by administering the anti-CAPRIN-1 antibody and a drug comprising a pyrimidine-based drug and cisplatin to an organism having cancer, measuring the size of a tumor after the administration, and examining the size of the cancer over time. Also, the antitumor effect of the present invention can be evaluated by examining a survival rate. Alternatively, the antitumor effect of the present invention may be evaluated by examining the ability to produce cytokines or chemokines. The antitumor effect of the combination of the anti-CAPRIN-1 antibody and the drug comprising a pyrimidine-based drug and cisplatin according to the present invention can be further determined by examining prevention of cancer, prevention of metastasis or prevention of recurrence.

The anti-CAPRIN-1 antibody used in the present invention can be expected to have a stronger antitumor effect when having higher binding affinity for CAPRIN-1 protein on the cancer cell surface. Association constant (affinity constant) Ka (kon/koff) is preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ at least $10^{12}$ or at least $10^{13}$ $M^{-1}$.

An ability of an anti-CAPRIN-1 antibody used in the present invention to bind to CAPRIN-1 can be specified via binding assays using, for example, ELISA, Western blot, immunofluorescence, or flowcytometry analysis.

Administration of a combination of the anti-CAPRIN-1 antibody and a drug comprising a pyrimidine-based drug and cisplatin according to the present invention to an organism having cancer increases an antitumor effect as compared with an anti-CAPRIN-1 antibody alone, as mentioned above. The rate of increase is preferably 30% or more, more preferably 40% or more, further preferably 50% or more, still further preferably 55% or more, even further preferably 60% or more, even further preferably 65% or more, and most preferably 70% or more. The rate of increase in antitumor effect by administration of a combination of an anti-CAPRIN-1 antibody and a drug comprising a pyrimidine-based drug and cisplatin according to the present invention with respect to administration of the anti-CAPRIN-1 antibody alone can be calculated by administering their respective effective amounts to cancer-bearing mice under the same conditions and comparing tumor volumes on 7 days or later after the start of administration.

<Medicament for treatment and/or prevention of cancer>

A medicament of the present invention is aimed at treating and/or preventing cancer. A cancer targeted by the medicament of the present invention is not particularly limited as long as it is cancer (cells) expressing CAPRIN-1 protein.

The term "treatment" used herein refers to treatment of cancer based on an antitumor effect mentioned above. The term "prevention" used herein refers to not only prevention of development of cancer but prevention of metastasis or recurrence of cancer.

Both the terms "tumor" and "cancer" used herein refer to malignant neoplasm, and thus they are used in an exchangeable manner.

In the present invention, the cancer patient with a previous history of cancer treatment with a medicament other than cancer treatment with a medicament comprising an antibody or a fragment thereof having an immunological reactivity with CAPRIN-1 protein, and pyrimidine-based drug and cisplatin together or separately in combination can be any cancer patient who has undergone cancer treatment with a medicament other than the combination thereof, and also includes a patient treated with a chemotherapeutic, a molecular targeted drug, or hormone therapy in the past. Examples thereof include cancer patients who have undergone cancer treatment in accordance with "NCCN Clinical Practice Guidelines in Oncology", "ESMO Clinical Practice Guidelines" or "Clinical Practice Guideline". A cancer patient with a previous history of cancer treatment with a pyrimidine-based drug and/or a platinum-containing drug (cisplatin, carboplatin, oxaliplatin, or nedaplatin as a specific example) is preferred.

The patient is preferably a cancer patient who has not responded to cancer treatment with a medicament other than cancer treatment with a medicament comprising an anti-CAPRIN-1 antibody, and a pyrimidine-based drug and a platinum-containing drug together or separately in combination, and more preferably a cancer patient who has not responded to cancer treatment with a pyrimidine-based drug and/or a platinum-containing drug.

The patient is preferably a cancer patient with cancer resistant to cancer treatment with a medicament other than cancer treatment with a medicament comprising an anti-CAPRIN-1 antibody, and a pyrimidine-based drug and a platinum-containing drug together or separately in combination, and more preferably a cancer patient with cancer resistant to cancer treatment with a pyrimidine-based drug and/or a platinum-containing drug. The terms "having not responded to cancer treatment" and "resistant to cancer treatment" described herein are used to have the same meaning.

Cancer that can be a target in the present invention is any cancer as long as the cancer expresses CAPRIN-1 protein on a cell membrane surface. The cancer is preferably bile duct cancer, breast cancer, kidney cancer, pancreatic cancer, colon cancer, melanoma (including postoperative melanoma), lung cancer (including non-small cell lung cancer and small cell lung cancer), renal cell carcinoma, Hodgkin's lymphoma, head and neck cancer, gastric cancer, mesothelioma (including malignant pleural mesothelioma), colorectal cancer (e.g., MSI-high colorectal cancer), esophageal cancer, gastroesophageal junction cancer, hepatocellular carcinoma, glioblastoma, urothelial carcinoma, ovarian cancer, urinary bladder cancer, uterine cancer (including uterine cervical cancer and uterine body cancer), primary central nervous system lymphoma, primary testicular lymphoma, biliary tract cancer, brain tumor, prostate cancer, leukemia, lymphoma, liver cancer, sarcoma, fibrosarcoma, mastocytoma, adrenocortical carcinoma, Ewing's tumor, multiple myeloma, testicular cancer, thyroid cancer, basal cell carcinoma, Paget's disease or skin cancer. These cancers may be primary cancer, metastatic cancer, metastasized cancer or relapsed cancer, postoperative cancer, or unresectable cancer. Melanoma is often used to have the same meaning as malignant melanoma.

Other examples of the cancer that can be a target in the present invention include platinum/taxane-resistant relapsed ovarian cancer.

Other examples of the cancer that can be a target in the present invention include cancer resistant to known treatment methods. The resistant cancer is not particularly limited and can be cancer derived from a patient with any history of treatment. The resistant cancer is, for example, cancer that is derived from a patient with a history of treatment with 5-FU and has become resistant, has metastasized, or has relapsed after administration.

More specifically, examples of the cancer include, but are not limited to, for example, Bowen's disease, prickle cell carcinoma, extramammary Paget's disease, mycosis fungoides, Sezary's syndrome, cutaneous T/NK-cell lymphoma, T-cell leukemia or lymphoma having a lesion only in the skin, cutaneous B-cell lymphoma (indolent group), cutaneous T-cell lymphatic breast adenocarcinoma, composite type breast adenocarcinoma, malignant mammary mixed tumor, intraductal papillary adenocarcinoma, lung adenocarcinoma, squamous cell cancer, small cell cancer, large cell cancer, glioma that is a tumor of neuroepithelial tissue, glioblastoma, neuroblastoma, ependymoma, neuronal tumor, embryonal neuroectodermal tumor, schwannoma, neurofibroma, meningioma, chronic lymphocytic leukemia, lymphoma, gastrointestinal lymphoma, digestive lymphoma, small-cell-to-medium-cell lymphoma, cecal cancer, ascending colon cancer, descending colon cancer, transverse colon cancer, sigmoid colon cancer, rectal cancer, ovarian epithelial cancer, germ cell tumor, interstitial cell tumor, pancreatic duct cancer, invasive pancreatic duct cancer, adenocarcinoma of pancreatic cancer, acinar cell carcinoma, adenosquamous carcinoma, giant cell tumor, intraductal papillary mucinous neoplasm, mucinous adenocarcinoma, pancreatoblastoma, pancreatic islet cell tumor, Frantz tumor, serous cystadenocarcinoma, solid pseudopapillary cancer, gastrinoma, glucagonoma, insulinoma, multiple endocrine neoplasia type-1 (Wermer syndrome), nonfunctional islet cell tumor, somatostatinoma, VIPoma, uterine cervical cancer, uterine body cancer, fibrosarcoma, osteosarcoma, joint sarcoma, Ewing sarcoma, Wilms tumor, hepatoblastoma, soft tissue sarcoma, acute leukemia, chronic leukemia, spinal cord tumor, malignant soft tissue tumor, tumors of teratoma group, head and neck cancer including hypopharynx cancer, oropharynx cancer, tongue cancer, nasopharyngeal cancer, oral cavity cancer, lip cancer, nasal and sinus cancer, and laryngeal cancer, cancer of the renal pelvis and ureter, urinary bladder cancer, and urethra cancer. The cancer also includes a palpable cancer, a subcutaneously existing cancer, an intracutaneously existing cancer, a superficial cancer, cancer existing in the dermis and cancer existing in a non-parenchymal organ, advanced cancer, which originate from the cancers described above. The cancer also includes a palpable cancer, a subcutaneously existing cancer, an intracutaneously existing cancer, a superficial cancer, cancer existing in the dermis and cancer existing in a non-parenchymal organ, which originate from the cancers described above and have metastasized and recurred.

A preferable subject (patient) that can be a target is a mammal and is, for example, a mammal including primates, pet animals, livestock animals, and sport animals. Humans, dogs and cats are particularly preferable.

A medicament of the present invention can be formulated by a method known to persons skilled in the art. For instance, the medicament of the present invention can be parenterally used in the form of a parenteral injection of: an aseptic solution in water or a pharmacologically acceptable non-water solution; or a suspension liquid. In the medicament of the present invention, an active ingredient (at least one of an anti-CAPRIN-1 antibody, a pyrimidine-based drug and cisplatin) of each formulation or pharmaceutical composition may be combined with, for example, a pharmacologically acceptable carrier, medium, or additive, specifically, sterilized water, saline, an isotonic solution, a buffering agent (buffer solution, etc.), plant oil, oily liquid, an antioxidant, a dissolution aid, an emulsifier, a suspension, a surfactant, a stabilizer, a fragrance, an excipient, or a binder in an appropriate manner, and preferably, may be formulated by mixing with them in a unit dosage form required for a generally acceptable pharmaceutical formulation. An amount of an active ingredient in a formulation is determined such that an appropriate dosage within an indicated range can be achieved.

An aseptic composition for injection can be prepared in accordance with general formulation practice using a vehicle such as distilled water for injection. An aqueous solution for injection includes, for example, saline or isotonic solutions comprising glucose and other adjuvants such as D-sorbitol, D-mannose, D-mannitol, and sodium chloride. Such solution may be used with an appropriate dissolution aid. Such dissolution aid includes, for example, alcohols such as ethanol and polyalcohol, such as propylene glycol, polyethylene glycol, or nonionic surfactants such as polysorbate 80™ and HCO-60. Oily liquid includes, for example, sesame oil or soybean oil. Such oily liquid may be used in combination with a dissolution aid such as benzyl benzoate or benzyl alcohol. In addition, it may be mixed with a buffering agent such as a phosphate buffer solution or a sodium acetate buffer solution, a soothing agent such as procaine hydrochloride, a stabilizer such as benzyl alcohol or phenol, or an antioxidant. In general, a formulated injection solution is introduced into an adequate ample.

The above pharmaceutical composition is orally or parenterally administered. Preferably, it is parenterally administered. Specifically, dosage forms include injectable agents, intranasally-administered agents, transpulmonarily-administered agents, and percutaneously-administered agents. For example, injectable agents can be systemically or locally administered via intravenous injection, intramuscular injection, intraperitoneal injection, subcutaneous injection, or intratumoral injection. The percutaneously-administered agents include, for example, agents called liniments and external medicines. The external medicines include, for example, solid agents, solutions, sprays, ointments, creams, and gels.

The administration method can be appropriately determined depending on age, weight, gender, and symptoms of a patient. A single dose of a pharmaceutical composition comprising at least one of an anti-CAPRIN-1 antibody, a pyrimidine-based drug and cisplatin can be selected within a range of, for example, 0.0001 mg to 1000 mg per kg of body weight as an amount of each active ingredient. Alternatively, the dose of each active ingredient can be selected within a range of, for example, 0.001 to 100000 mg per patient's body or 1 mg to 30 mg per kg of patient's body weight; however, it is not necessarily limited thereto. The dose and the administration method are changed depending on patient age, weight, gender, and symptoms. However, persons skilled in the art can appropriately select the dose and the method.

<Administration Method>

Treatment and/or prevention of cancer with a medicament for treatment and/or prevention of cancer of the present invention includes various modes, in addition to administration as a medicament mentioned above. For example, respective active ingredients in a medicament of the present invention can be administered simultaneously, concurrently, or individually in a staggered manner. As a specific example, active ingredients can be administered within a time interval up to approximately 3 weeks, i.e., the second active ingredient can be administered from immediately up to approximately 3 weeks after administration of the first active ingredient. These administrations may be carried out subsequently to a surgical procedure, or a surgical procedure may be carried out between the administrations of the first and second drugs. In addition, the medicament for treatment and/or prevention of cancer of the present invention may be administered according to a plurality of administration cycles. For example, in the case of carrying out simultaneous administration of respective active ingredients in a medicament for treatment and/or prevention of cancer of the present invention, a pharmaceutical composition comprising the active ingredients of the present invention (an anti-CAPRIN-1 antibody of the present invention, a pyrimidine-based drug and cisplatin) is administered for approximately 2 days to approximately 3 weeks as one cycle. Then, this treatment cycle may be repeated, if necessary, according to the judgment of a physician in charge. Likewise, in the case of scheduling a formulation in a staggered manner, respective administration periods of individual agents are adjusted so as to span the same period. The interval between cycles can vary from 0 to 2 months. Respective doses of the active ingredients in the medicament for treatment and/or prevention of cancer of the present invention can be set in the same way as in the respective doses of the active ingredients in the pharmaceutical composition described above.

<Pharmaceutical Kit>

A medicament for treatment and/or prevention of cancer of the present invention may be in the form of a pharmaceutical kit. The pharmaceutical kit is a package for using active ingredients in the form of separate pharmaceutical compositions (formulations) in a method for treating and/or preventing cancer. The package may comprise an instruction for administering each of the active ingredients. The respective active ingredients in the pharmaceutical compositions for treatment and/or prevention of cancer contained in the pharmaceutical kit can be in the form of pharmaceutical compositions each formulated as described above such that the active ingredients can be administered together or separately. Further, the pharmaceutical kit comprises active ingredients in amounts sufficient for one or more doses such that the active ingredients can be administered according to the administration method described above.

<Treatment and/or Prevention Method>

On the basis of the contents specifically described above, the present invention provides a method for treating and/or preventing cancer, comprising administering the medicament of the present invention, or the anti-CAPRIN-1 antibody of the present invention, and a pyrimidine-based drug and cisplatin to a subject (patient). The present invention further provides, for example, a method for treating and/or preventing cancer, comprising administering the medicament of the present invention, etc. to a subject (patient) having cancer or suspected of having cancer. In the method of the present invention, in addition to the anti-CAPRIN-1 antibody of the present invention, the pyrimidine-based drug and cisplatin, other antitumor agents (known antitumor agents, etc.) may be administered to the subject (patient). In this embodiment, the anti-CAPRIN-1 antibody or the fragment thereof, the pyrimidine-based drug and cisplatin, and optionally, an antitumor agent contained in the medicament can be administered simultaneously or separately to the subject (patient).

EXAMPLES

The present invention is hereafter described in detail with reference to the following examples, although the scope of the present invention is not limited thereto.

(Example 1) Production of Anti-CAPRIN-1 Antibody

Anti-CAPRIN-1 antibodies having an immunological reactivity with CAPRIN-1 protein, used in the present invention were produced as described below for use.

(Polyclonal Antibody)

One (1) mg of a human CAPRIN-1 recombinant protein (SEQ ID NO: 2) produced according to Example 3 of WO2010/016526 was mixed with an incomplete Freund's adjuvant (IFA) solution in an amount equivalent to the recombinant protein. The mixture was subcutaneously administered to a rabbit 4 times every 2 weeks. Subsequently, blood was collected, so that an antiserum containing a polyclonal antibody was obtained. Furthermore, the antiserum was purified using a protein G carrier (GE Healthcare Bio-Sciences) and replaced with PBS(−) and then a polyclonal antibody against CAPRIN-1 protein (anti-CAPRIN-1 polyclonal antibody #1) was obtained.

(Monoclonal Antibody)

One hundred (100) μg of a human CAPRIN-1 recombinant protein produced according to Example 3 of WO2010/016526 was mixed with a MPL+TDM adjuvant (Sigma) in an amount equivalent to that of the recombinant protein. The mixture was used as an antigen solution per mouse. The antigen solution was administered intraperitoneally to 6-week-old Balb/c mice (Japan SLC Inc.) and then further administered 3 times and 24 times every week for completion of immunization. A spleen was removed on day 3 after the final immunization and then ground between two sterilized glass slides. Spleen cells were obtained by washing with PBS (−) (Nissui Pharmautheutical), centrifuging at 1500 rpm for 10 minutes, and removing supernatant, therein these were repeated 3 times. The obtained spleen cells were mixed with mouse myeloma cell SP2/0 (purchased from ATCC) at a ratio of 10:1. The PEG solution prepared by mixing 200 µl of RPMI1640 medium containing 10% FBS heated at 37° C. and 800 µl of PEG1500 (Boehringer) was added to the cells. The solution was incubated for 5 minutes for cell fusion. Centrifugation was performed at 1700 rpm for 5 minutes to remove supernatants. Cells were suspended in 150 ml of RPMI1640 medium (HAT selective medium) containing 15% FBS, to which 2% equivalent of HAT solution (Gibco) had been added and then seeded onto fifteen 96-well plates (Nunc) at 100 µl per well. Cells were cultured for 7 days under conditions of 37° C. and 5% $CO_2$, so that hybridomas resulting from fusion of spleen cells to myeloma cells were obtained. Hybridomas were selected using binding affinity to CAPRIN-1 protein of the antibody produced by the prepared hybridomas as an indicator. The CAPRIN-1 protein solution (1 µg/ml) was added at 100 µl per well of 96-well plates and then incubated at 4° C. for 18 hours. After each well was washed 3 times with PBS-T, 0.5% Bovine Serum Albumin (BSA) solution (Sigma) was added at 400 µl per well, and then the plates were incubated at room temperature for 3 hours. The solution was removed and then each well was washed 3 times with 400 µl of PBS-T. Each culture supernatant of the hybridomas obtained above was added at 100 µl per well and then incubated at room temperature for 2 hours. After each well was washed 3 times with PBS-T, an HRP-labeled anti-mouse IgG (H+L) antibody (Invitrogen) diluted 5000-fold with PBS was added at 100 µl per well and then incubated at room temperature for 1 hour. After each well was washed 3 times with PBS-T, a TMB substrate solution (Thermo) was added at 100 µl per well and then incubated for 15-30 minutes, so that a color reaction was performed. After color development, 1 N sulfuric acid was added at 100 µl per well to stop the reaction. Absorbance at 450 nm and absorbance at 595 nm were measured using an absorption spectrometer. As a result, a plurality of hybridomas producing antibodies with high absorbances were selected. The selected hybridomas were added at 0.5 hybridomas per well of 96-well plates and then cultured. After 1 week, hybridomas forming a single colony in wells were observed. Cells in these wells were further cultured. Hybridomas were selected using binding affinity to CAPRIN-1 protein of the antibody produced by cloned hybridomas as an indicator. The CAPRIN-1 protein solution (1 µg/ml) was added at 100 µl per well of 96-well plates and then incubated at 4° C. for 18 hours. Each well was washed 3 times with PBS-T, a 0.5% BSA solution was added at 400 µl per well, and then incubated at room temperature for 3 hours. The solution was removed and then each well was washed 3 times with 400 µl of PBS-T. Each culture supernatant of the hybridomas obtained above was added at 100 µl per well and then incubated at room temperature for 2 hours. Each well was washed 3 times with PBS-T, an HRP-labeled anti-mouse IgG (H+L) antibody (Invitrogen) diluted 5000-fold with PBS was added at 100 µl per well and then incubated at room temperature for 1 hour. Each well was washed 3 times with PBS-T, a TMB substrate solution (Thermo) was added at 100 µl per well and then incubated for 15-30 minutes, so that a color reaction was performed. After color development, 1 N sulfuric acid was added at 100 µl per well to stop the reaction. Absorbance at 450 nm and absorbance at 595 nm were measured using an absorption spectrometer. As a result, a plurality of mouse monoclonal antibodies exerting reactivity with CAPRIN-1 protein were obtained.

Reactivity of each monoclonal antibody with human cancer cells confirmed to express CAPRIN-1 protein on the cell membrane surface was further confirmed by flow cytometry. A mouse IgG control antibody exhibiting no reactivity with the cancer cells was used as a negative control. As a result of confirmation, several monoclonal antibodies were obtained which had stronger fluorescence intensity against the cancer cells than that of the mouse IgG control antibody and reacted strongly with the cell membrane surface of the cancer cells expressing CAPRIN-1 on the cell membrane surface. From among them, a monoclonal antibody against CAPRIN-1 described in WO2013/125630, which was an antibody comprising the amino acid sequence of a heavy-chain variable region shown in SEQ ID NO: 114 and the amino acid sequence of a light-chain variable region shown in SEQ ID NO: 115, was selected as a monoclonal antibody exhibiting reactivity with CAPRIN-1 protein.

CDR1 to CDR3 of the heavy-chain variable region of the antibody selected were identified. A nucleotide sequence was designed so as to be able to express a heavy-chain variable region in which framework regions comprising a human antibody sequence. This nucleotide sequence was inserted to a vector for mammalian expression having an insert of a human IgG1 heavy-chain constant region. Likewise, CDR1 to CDR3 of the light-chain variable region were identified. A nucleotide sequence was designed so as to be able to express a light-chain variable region in which framework regions comprised a human antibody sequence. This nucleotide sequence was inserted to a vector for mammalian expression having an insert of a human IgG1 light-chain constant region. These two recombinant expression vectors were introduced to mammalian cells according to a general method and then a culture supernatant containing humanized monoclonal antibody #1 (humanized antibody #1) against CAPRIN-1 was obtained.

The obtained culture supernatant containing the obtained humanized anti-CAPRIN-1 monoclonal antibody #1 was purified using Hitrap Protein A Sepharose FF (GE Healthcare Bio-Sciences) according to a general method, replaced with PBS(−), and filtered through a 0.22 µm filter (Millipore) for preparation of the filtrate.

The specific reactivity of the anti-CAPRIN-1 antibody to CAPRIN-1 protein was detected and confirmed by ELISA using CAPRIN-1 protein immobilized on a plate.

The reactivity of the anti-CAPRIN-1 antibody with cancer cells without permeation treatment of cell membrane was examined by flow cytometry to confirm that a portion of CAPRIN-1 was expressed on the cell membrane surface of cancer cells as shown in Examples given below.

It was confirmed by flow cytometry that, against all of breast cancer cells (BT-474), colon cancer cells (HT-29), lung cancer cells (QG56 and H1650), gastric cancer cells (NCI-N87), uterine cancer cells (HEC-1-A), prostate cancer cells (22Rv1), pancreatic cancer cells (Panc10.5), liver cancer cells (Hep3B), ovarian cancer cells (SKOV3), kidney cancer cells (Caki-2), brain tumor cells (U-87MG), urinary bladder cancer cells (T24), esophageal cancer cells (OE33), leukemia cells (OCI-AML5), lymphoma cells (Ramos), gallbladder cancer cells (TGBC14TKB), fibrosarcoma cells (HT-1080), and melanoma cells (G-361), which are human cancer cells confirmed to express CAPRIN-1 gene, and mouse kidney cancer cells (Renca) and mouse breast cancer cells (4T1) confirmed to express CAPRIN-1 gene, the humanized antibody #1 had stronger fluorescence intensity than that of a human IgG control antibody and rabbit IgG antibody serving as negative controls exhibiting no reactivity with the cancer cells and reacted strongly with the cell membrane surface of the cancer cells expressing CAPRIN-1.

Likewise, it was confirmed that the anti-CAPRIN-1 antibodies described in WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125640, WO2013/147169, WO2013/147176 and WO2015/020212 also reacted strongly with the cell membrane surface of the cancer cells.

(Example 2) Antitumor Effect of Combination of Anti-CAPRIN-1 Antibody, and Gemcitabine and Cisplatin in Human Cancer Cell-Bearing Mouse Model Next, in vivo antitumor effect in cancer-bearing mouse was evaluated by administering a combination of the anti-CAPRIN-1 antibody (anti-CAPRIN-1 humanized antibody #1) produced in Example 1, and gemcitabine and cisplatin.

Specifically, the antitumor effect of the combination of the anti-CAPRIN-1 antibody, and gemcitabine and cisplatin according to the present invention was studied using NOD-SCID mice in which human-derived cancer cells expressing CAPRIN-1 protein were subcutaneously transplanted. Human breast cancer cells BT474 were subcutaneously transplanted at $2 \times 10^7$ cells per mouse as a mixture with Matrigel (Sigma) and allowed to grow until a tumor became approximately 200 mm$^3$ to prepare cancer-bearing mice. The cancer cells BT474 express CAPRIN-1 protein on the cell membrane surface, and the anti-CAPRIN-1 antibodies produced in Example 1 were confirmed to react with a portion of CAPRIN-1 present on the cell membrane surface. Each anti-CAPRIN-1 antibody produced in Example 1 was administered at 10 mg/kg once a week to the tail veins of five cancer-bearing mice described above. To these mice, gemcitabine (5 mg/kg) and cisplatin (2 mg/kg) were administered once a week simultaneously with the administration of the anti-CAPRIN-1 antibody.

For a comparative control group, the same dose of the same anti-CAPRIN-1 antibody as above was administered once a week to cancer-bearing mice. For another comparative control group, gemcitabine (5 mg/kg) and cisplatin (2 mg/kg) were administered at the same administration intervals as above to other individuals of cancer-bearing mice. Cancer-bearing mice in a non-treatment group were used as negative controls. After the start of administration, the sizes of cancers in the cancer-bearing mice were measured over time using calipers. Tumor volumes were calculated according to a standard method using a calculation expression: (Length of the major axis of the tumor)×(Length of the minor axis of the tumor)×0.5.

As a result of evaluation, the tumor volume was 30% in the group given the anti-CAPRIN-1 humanized antibody #1 produced in Example 1, and 32% in the group given the combination of gemcitabine and cisplatin as the comparative control groups on day 46 after cancer bearing, when the tumor volume of the negative control was defined as 100%. On the other hand, the tumor volume was 15% in the group given the combination of the humanized antibody #1 produced in Example 1, and gemcitabine and cisplatin, and was thus reduced from that at the start of administration.

The results of this evaluation demonstrated that administration of a combination of the anti-CAPRIN-1 antibody, and gemcitabine and cisplatin has a much stronger antitumor effect than that of administration of the anti-CAPRIN-1 antibody alone or a combination of gemcitabine and cisplatin. Likewise, a similar antitumor effect was obtained in the anti-CAPRIN-1 antibodies described in WO2010/016526, WO2011/096517, WO2011/096528, WO2011/096519, WO2011/096533, WO2011/096534, WO2011/096535, WO2013/018886, WO2013/018894, WO2013/018892, WO2013/018891, WO2013/018889, WO2013/018883, WO2013/125636, WO2013/125654, WO2013/125640, WO2013/147169, WO2013/147176, and WO2015/020212.

(Example 3) Antitumor Effect of Combination of Anti-CAPRIN-1 Antibody, and Gemcitabine and Cisplatin A stage 4 bile duct cancer patient with a previous history of existing treatment (reduction mammoplasty and analgesic therapy with acetaminophen and a potent opioid analgesic oxycodone) was given "TRK-950" (anti-CAPRIN-1 antibody under clinical trial as a therapeutic agent for cancer) at a dose of 10 mg/kg in addition to the standard gemcitabine and cisplatin combination therapy. As a result of evaluation of the tumor sizes of metastatic foci in the patient by CT examination, the total tumor size was reduced by approximately 37% approximately 40 days after the start of administration and reduced by approximately 44% approximately 80 days after the start of administration and partial response was obtained as drug efficacy. Thus, treatment of cancer patients with a combination of an anti-CAPRIN-1 antibody, and gemcitabine and cisplatin was found to exert very strong efficacy.

All publications, patents and patent applications cited herein are incorporated herein by reference in their entirety.

The invention claimed is:

1. A method for treating cancer in a subject in need thereof, comprising administering a composition comprising an antibody or a fragment thereof specifically binding to an extracellular region of a CAPRIN-1 protein present on a cancer cell surface, gemcitabine, and cisplatin together or separately in combination;

wherein the cancer is cancer expressing CAPRIN-1 protein on a cell membrane surface; and wherein the subject is a cancer patient with a previous history of cancer treatment with a medicament other than cancer treatment with a medicament comprising an antibody or a fragment thereof having an immunological reactivity with CAPRIN-1 protein, and a pyrimidine-based drug and cisplatin together or separately in combination.

2. The method according to claim 1, wherein the antibody or the fragment thereof has an immunological reactivity with CAPRIN-1 protein having an amino acid sequence shown in any one of the even numbered SEQ ID NOs: 2 to 30, or an amino acid sequence having 80% or more sequence identity with the amino acid sequence.

3. The method according to claim 1, wherein the antibody or the fragment thereof has an immunological reactivity with a partial polypeptide of CAPRIN-1 protein, the partial polypeptide having an amino acid sequence represented by any one of SEQ ID NOs: 31 to 35, 296 to 299, 308 and 309, or an amino acid sequence having 80% or more sequence identity with the amino acid sequence.

4. The method according to claim 1, wherein the antibody is a monoclonal antibody or a polyclonal antibody.

5. The method according to claim 1, wherein the antibody or a fragment thereof is any one of the following (A) to (M):

(A) an antibody or a fragment thereof comprising a heavy-chain variable region comprising complementarity determining regions of SEQ ID NOs: 36, 37 and 38 (CDR1, CDR2 and CDR3, respectively) and a light-chain variable region comprising complementarity determining regions of SEQ ID NOs: 40, 41 and 42 (CDR1, CDR2 and CDR3, respectively), and having an immunological reactivity with CAPRIN-1 protein;

(B) an antibody or a fragment thereof comprising a heavy-chain variable region comprising complementarity determining regions of SEQ ID NOs: 44, 45 and 46 (CDR1, CDR2 and CDR3, respectively) and a light-chain variable region comprising complementarity determining regions of SEQ ID NOs: 48, 49 and 50 (CDR1, CDR2 and CDR3, respectively), and having an immunological reactivity with CAPRIN-1 protein;

(C) an antibody or a fragment thereof comprising a heavy-chain variable region comprising complementarity determining regions of SEQ ID NOs: 52, 53 and 54 (CDR1, CDR2 and CDR3, respectively) and a light-chain variable region comprising complementarity determining regions of SEQ ID NOs: 56, 57 and 58 (CDR1, CDR2 and CDR3, respectively), and having an immunological reactivity with CAPRIN-1 protein;

(D) an antibody or a fragment thereof comprising a heavy-chain variable region comprising complementarity determining regions of SEQ ID NOs: 60, 61 and 62 (CDR1, CDR2 and CDR3, respectively) and a light-chain variable region comprising complementarity determining regions of SEQ ID NOs: 64, 65 and 66 (CDR1, CDR2 and CDR3, respectively), and having an immunological reactivity with CAPRIN-1 protein;

(E) an antibody or a fragment thereof comprising a heavy-chain variable region comprising complementarity determining regions of SEQ ID NOs: 170, 171 and 172 (CDR1, CDR2 and CDR3, respectively) and a light-chain variable region comprising complementarity determining regions of SEQ ID NOs: 173, 174 and 175 (CDR1, CDR2 and CDR3, respectively), and having an immunological reactivity with CAPRIN-1 protein;

(F) an antibody or a fragment thereof comprising a heavy-chain variable region comprising complementarity determining regions of SEQ ID NOs: 176, 177 and 178 (CDR1, CDR2 and CDR3, respectively) and a light-chain variable region comprising complementarity determining regions of SEQ ID NOs: 179, 180 and 181 (CDR1, CDR2 and CDR3, respectively), and having an immunological reactivity with CAPRIN-1 protein;

(G) an antibody or a fragment thereof comprising a heavy-chain variable region comprising complementarity determining regions of SEQ ID NOs: 182, 183 and 184 (CDR1, CDR2 and CDR3, respectively) and a light-chain variable region comprising complementarity determining regions of SEQ ID NOs: 185, 186 and 187 (CDR1, CDR2 and CDR3, respectively), and having an immunological reactivity with CAPRIN-1 protein;

(H) an antibody or a fragment thereof comprising a heavy-chain variable region comprising complementarity determining regions of SEQ ID NOs: 188, 189 and 190 (CDR1, CDR2 and CDR3, respectively) and a light-chain variable region comprising complementarity determining regions of SEQ ID NOs: 191, 192 and 193 (CDR1, CDR2 and CDR3, respectively), and having an immunological reactivity with CAPRIN-1 protein;

(I) an antibody or a fragment thereof comprising a heavy-chain variable region comprising complementarity determining regions of SEQ ID NOs: 146, 147 and 148 (CDR1, CDR2 and CDR3, respectively) and a light-chain variable region comprising complementarity determining regions of SEQ ID NOs: 149, 150 and 151 (CDR1, CDR2 and CDR3, respectively), and having an immunological reactivity with CAPRIN-1 protein;

(J) an antibody or a fragment thereof comprising a heavy-chain variable region comprising complementarity determining regions of SEQ ID NOs: 272, 273 and 274 (CDR1, CDR2 and CDR3, respectively) and a light-chain variable region comprising complementarity determining regions of SEQ ID NOs: 275, 276 and 277 (CDR1, CDR2 and CDR3, respectively), and having an immunological reactivity with CAPRIN-1 protein;

(K) an antibody or a fragment thereof comprising a heavy-chain variable region comprising complementarity determining regions of SEQ ID NOs: 290, 291 and 292 (CDR1, CDR2 and CDR3, respectively) and a light-chain variable region comprising complementarity determining regions of SEQ ID NOs: 293, 294 and 295 (CDR1, CDR2 and CDR3, respectively), and having an immunological reactivity with CAPRIN-1 protein;

(L) an antibody or a fragment thereof comprising a heavy-chain variable region comprising complementarity determining regions of SEQ ID NOs: 300, 301, and 302 (CDR1, CDR2 and CDR3, respectively) and a light-chain variable region comprising complementarity determining regions of SEQ ID NOs: 304, 305, and 306 (CDR1, CDR2 and CDR3, respectively), and having an immunological reactivity with CAPRIN-1 protein; and (M) an antibody or a fragment thereof comprising a heavy-chain variable region comprising complementarity determining regions of SEQ ID NOs: 134, 135 and 136 (CDR1, CDR2 and CDR3, respectively) and a light-chain variable region comprising complementarity determining regions of SEQ ID NOs: 137, 138 and 139 (CDR1, CDR2 and CDR3, respectively), and having an immunological reactivity with CAPRIN-1 protein.

6. The method according to claim 1, wherein the antibody or the fragment thereof is any one of the following (a) to (al):

(a) an antibody or a fragment thereof comprising a heavy-chain variable region comprising the amino acid sequence of SEQ ID NO: 39 and a light-chain variable region comprising the amino acid sequence of SEQ ID NO: 43;

(b) an antibody or a fragment thereof comprising a heavy-chain variable region comprising the amino acid sequence of SEQ ID NO: 47 and a light-chain variable region comprising the amino acid sequence of SEQ ID NO: 51;

(c) an antibody or a fragment thereof comprising a heavy-chain variable region comprising the amino acid sequence of SEQ ID NO: 55 and a light-chain variable region comprising the amino acid sequence of SEQ ID NO: 59;

(d) an antibody or a fragment thereof comprising a heavy-chain variable region comprising the amino acid sequence of SEQ ID NO: 63 and a light-chain variable region comprising the amino acid sequence of SEQ ID NO: 67;

(e) an antibody or a fragment thereof comprising a heavy-chain variable region comprising the amino acid sequence of SEQ ID NO: 68 and a light-chain variable region comprising the amino acid sequence of SEQ ID NO: 69;

(f) an antibody or a fragment thereof comprising a heavy-chain variable region comprising the amino acid sequence of SEQ ID NO: 70 and a light-chain variable region comprising the amino acid sequence of SEQ ID NO: 71;

(g) an antibody or a fragment thereof comprising a heavy-chain variable region comprising the amino acid sequence of SEQ ID NO: 72 and a light-chain variable region comprising the amino acid sequence of SEQ ID NO: 73;

(h) an antibody or a fragment thereof comprising a heavy-chain variable region comprising the amino acid sequence of SEQ ID NO: 74 and a light-chain variable region comprising the amino acid sequence of SEQ ID NO: 75;

(i) an antibody or a fragment thereof comprising a heavy-chain variable region comprising the amino acid sequence of SEQ ID NO: 76 and a light-chain variable region comprising the amino acid sequence of SEQ ID NO: 77;

(j) an antibody or a fragment thereof comprising a heavy-chain variable region comprising the amino acid sequence of SEQ ID NO: 78 and a light-chain variable region comprising the amino acid sequence of SEQ ID NO: 79;

(k) an antibody or a fragment thereof comprising a heavy-chain variable region comprising the amino acid sequence of SEQ ID NO: 80 and a light-chain variable region comprising the amino acid sequence of SEQ ID NO: 81;

(l) an antibody or a fragment thereof comprising a heavy-chain variable region comprising the amino acid sequence of SEQ ID NO: 82 and a light-chain variable region comprising the amino acid sequence of SEQ ID NO: 83;

(m) an antibody or a fragment thereof comprising a heavy-chain variable region comprising the amino acid sequence of SEQ ID NO: 84 and a light-chain variable region comprising the amino acid sequence of SEQ ID NO: 85;

(n) an antibody or a fragment thereof comprising a heavy-chain variable region comprising the amino acid sequence of SEQ ID NO: 86 and a light-chain variable region comprising the amino acid sequence of SEQ ID NO: 87;

(o) an antibody or a fragment thereof comprising a heavy-chain variable region comprising the amino acid sequence of SEQ ID NO: 88 and a light-chain variable region comprising the amino acid sequence of SEQ ID NO: 89;

(p) an antibody or a fragment thereof comprising a heavy-chain variable region comprising the amino acid sequence of SEQ ID NO: 90 and a light-chain variable region comprising the amino acid sequence of SEQ ID NO: 91;

(q) an antibody or a fragment thereof comprising a heavy-chain variable region comprising the amino acid sequence of SEQ ID NO: 92 and a light-chain variable region comprising the amino acid sequence of SEQ ID NO: 93;

(r) an antibody or a fragment thereof comprising a heavy-chain variable region comprising the amino acid sequence of SEQ ID NO: 94 and a light-chain variable region comprising the amino acid sequence of SEQ ID NO: 95;

(s) an antibody or a fragment thereof comprising a heavy-chain variable region comprising the amino acid sequence of SEQ ID NO: 96 and a light-chain variable region comprising the amino acid sequence of SEQ ID NO: 97;

(t) an antibody or a fragment thereof comprising a heavy-chain variable region comprising the amino acid sequence of SEQ ID NO: 98 and a light-chain variable region comprising the amino acid sequence of SEQ ID NO: 99;

(u) an antibody or a fragment thereof comprising a heavy-chain variable region comprising the amino acid sequence of SEQ ID NO: 100 and a light-chain variable region comprising the amino acid sequence of SEQ ID NO: 101;

(v) an antibody or a fragment thereof comprising a heavy-chain variable region comprising the amino acid sequence of SEQ ID NO: 102 and a light-chain variable region comprising the amino acid sequence of SEQ ID NO: 103;

(w) an antibody or a fragment thereof comprising a heavy-chain variable region comprising the amino acid sequence of SEQ ID NO: 104 and a light-chain variable region comprising the amino acid sequence of SEQ ID NO: 105;

(x) an antibody or a fragment thereof comprising a heavy-chain variable region comprising the amino acid sequence of SEQ ID NO: 106 and a light-chain variable region comprising the amino acid sequence of SEQ ID NO: 107;

(y) an antibody or a fragment thereof comprising a heavy-chain variable region comprising the amino acid sequence of SEQ ID NO: 108 and a light-chain variable region comprising the amino acid sequence of SEQ ID NO: 109;

(z) an antibody or a fragment thereof comprising a heavy-chain variable region comprising the amino acid sequence of SEQ ID NO: 110 and a light-chain variable region comprising the amino acid sequence of SEQ ID NO: 111;

(aa) an antibody or a fragment thereof comprising a heavy-chain variable region comprising the amino acid sequence of SEQ ID NO: 112 and a light-chain variable region comprising the amino acid sequence of SEQ ID NO: 113;

(ab) an antibody or a fragment thereof comprising a heavy-chain variable region comprising the amino acid sequence of SEQ ID NO: 114 and a light-chain variable region comprising the amino acid sequence of SEQ ID NO: 115;

(ac) an antibody or a fragment thereof comprising a heavy-chain variable region comprising the amino acid sequence of SEQ ID NO: 116 and a light-chain variable region comprising the amino acid sequence of SEQ ID NO: 117;

(ad) an antibody or a fragment thereof comprising a heavy-chain variable region comprising the amino acid sequence of SEQ ID NO: 118 and a light-chain variable region comprising the amino acid sequence of SEQ ID NO: 119;

(ae) an antibody or a fragment thereof comprising a heavy-chain variable region comprising the amino acid sequence of SEQ ID NO: 120 and a light-chain variable region comprising the amino acid sequence of SEQ ID NO: 121;

(af) an antibody or a fragment thereof comprising a heavy-chain variable region comprising the amino acid sequence of SEQ ID NO: 122 and a light-chain variable region comprising the amino acid sequence of SEQ ID NO: 123;

(ag) an antibody or a fragment thereof comprising a heavy-chain variable region comprising the amino acid sequence of SEQ ID NO: 124 and a light-chain variable region comprising the amino acid sequence of SEQ ID NO: 125;

(ah) an antibody or a fragment thereof comprising a heavy-chain variable region comprising the amino acid sequence of SEQ ID NO: 126 and a light-chain variable region comprising the amino acid sequence of SEQ ID NO: 127;

(ai) an antibody or a fragment thereof comprising a heavy-chain variable region comprising the amino acid sequence of SEQ ID NO: 128 and a light-chain variable region comprising the amino acid sequence of SEQ ID NO: 129;

(aj) an antibody or a fragment thereof comprising a heavy-chain variable region comprising the amino acid sequence of SEQ ID NO: 130 and a light-chain variable region comprising the amino acid sequence of SEQ ID NO: 131;

(ak) an antibody or a fragment thereof comprising a heavy-chain variable region comprising the amino acid sequence of SEQ ID NO: 132 and a light-chain variable region comprising the amino acid sequence of SEQ ID NO: 133; and (al) an antibody or a fragment thereof comprising a heavy-chain variable region comprising the amino acid sequence of SEQ ID NO: 303 and a light-chain variable region comprising the amino acid sequence of SEQ ID NO: 307.

7. The method according to claim 1, wherein the antibody is a human antibody, a humanized antibody, a chimeric antibody or a single chain antibody.

8. The method according to claim 1, wherein the cancer is bile duct cancer, breast cancer, kidney cancer, pancreatic cancer, colon cancer, melanoma, lung cancer, renal cell carcinoma, Hodgkin's lymphoma, head and neck cancer, gastric cancer, mesothelioma, colorectal cancer, esophageal cancer, gastroesophageal junction cancer, hepatocellular carcinoma, glioblastoma, urothelial carcinoma, ovarian cancer, urinary bladder cancer, uterine cancer, primary central nervous system lymphoma, primary testicular lymphoma, biliary tract cancer, brain tumor, prostate cancer, leukemia, lymphoma, liver cancer, sarcoma, fibrosarcoma, mastocytoma, adrenocortical carcinoma, Ewing's tumor, multiple myeloma, testicular cancer, thyroid cancer, basal cell carcinoma, Paget's disease or skin cancer.

9. The method according to claim 1, wherein the cancer is cancer in a cancer patient who has not responded to cancer treatment with a pyrimidine-based drug and/or a platinum-containing drug.

10. The method according to claim 1, wherein the antibody or the fragment thereof, gemcitabine, and cisplatin are administered together.

11. The method according to claim 1, wherein the antibody or the fragment thereof, gemcitabine, and cisplatin are administered separately in combination.

\* \* \* \* \*